(12) United States Patent
Brodney et al.

(10) Patent No.: US 10,329,308 B2
(45) Date of Patent: *Jun. 25, 2019

(54) 1,1,1-TRIFLUORO-3-HYDROXYPROPAN-2-YL CARBAMATE DERIVATIVES AS MAGL INHIBITORS

(71) Applicant: PFIZER INC., New York, NY (US)

(72) Inventors: Michael Aaron Brodney, Newton, MA (US); Christopher Ryan Butler, Canton, MA (US); Laura Ann McAllister, Arlington, MA (US); Christopher John Helal, Mystic, CT (US); Steven Victor O'Neil, East Lyme, CT (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/874,987

(22) Filed: Jan. 19, 2018

(65) Prior Publication Data
US 2018/0208607 A1 Jul. 26, 2018

Related U.S. Application Data

(60) Provisional application No. 62/448,498, filed on Jan. 20, 2017.

(51) Int. Cl.
| | |
|---|---|
| *C07D 513/10* | (2006.01) |
| *C07D 221/20* | (2006.01) |
| *C07D 295/185* | (2006.01) |
| *C07D 401/08* | (2006.01) |
| *C07D 401/12* | (2006.01) |
| *C07D 491/10* | (2006.01) |

(52) U.S. Cl.
CPC ......... *C07D 513/10* (2013.01); *C07D 221/20* (2013.01); *C07D 295/185* (2013.01); *C07D 401/08* (2013.01); *C07D 401/12* (2013.01); *C07D 491/10* (2013.01)

(58) Field of Classification Search
CPC .. C07D 513/10; C07D 221/20; C07D 471/10; A61P 37/00; A61P 3/00
USPC ....................................................... 514/278
See application file for complete search history.

(56) References Cited

U.S. PATENT DOCUMENTS

| | | | |
|---|---|---|---|
| 4,804,665 A | 2/1989 | Goto et al. | |
| 5,854,268 A | 12/1998 | Baker et al. | |
| 6,106,864 A | 8/2000 | Dolan et al. | |
| 6,599,900 B2 | 7/2003 | Cai et al. | |
| 6,642,257 B2 | 11/2003 | Yamamoto et al. | |
| 6,696,443 B2 | 4/2004 | Mavunkel et al. | |
| 7,225,679 B2 | 6/2007 | Miyagawa et al. | |
| 7,241,770 B2 | 7/2007 | Mentzel et al. | |
| 7,786,046 B2 | 8/2010 | Witschel et al. | |
| 7,825,147 B2 | 11/2010 | Palle et al. | |
| 7,863,279 B2 | 1/2011 | Even et al. | |
| 7,879,761 B2 | 2/2011 | Witschel et al. | |
| 8,394,787 B2 | 3/2013 | Abouabdellah et al. | |
| 8,415,341 B2 | 4/2013 | Chevalier et al. | |
| 8,513,423 B2 | 8/2013 | Connolly et al. | |
| 8,748,417 B2 | 6/2014 | Zhang et al. | |
| 8,772,318 B2 | 7/2014 | Cravatt et al. | |
| 8,835,418 B2 | 9/2014 | Bartsch et al. | |
| 9,133,148 B2 | 9/2015 | Cisar et al. | |
| 9,845,301 B2* | 12/2017 | Butler | C07D 413/14 |
| 2002/0151712 A1 | 10/2002 | Lin et al. | |
| 2007/0179167 A1 | 8/2007 | Cottrell et al. | |
| 2007/0249648 A1 | 10/2007 | Bladh et al. | |
| 2009/0048247 A1 | 2/2009 | Palle et al. | |
| 2010/0035909 A1 | 2/2010 | Andres-Gil et al. | |

(Continued)

FOREIGN PATENT DOCUMENTS

| | | |
|---|---|---|
| WO | 9111172 | 8/1991 |
| WO | 9402518 | 2/1994 |

(Continued)

OTHER PUBLICATIONS

Almarsson, O and M. J. Zaworotko, Chem. Commun. 2004, 17, 1889-1896.
Bridgeman and N. C. O. Tomkinson, Synlett 2006, 243-246.
Finnin and Morgan, J. Pharm. Sci. 1999, 88, 955-958.
Flack, Acta Cryst. 1983, A39, 867-881.

(Continued)

*Primary Examiner* — Rita J Desai
(74) *Attorney, Agent, or Firm* — Feng Shao

(57) ABSTRACT

The present invention provides, in part, compounds of Formula I:

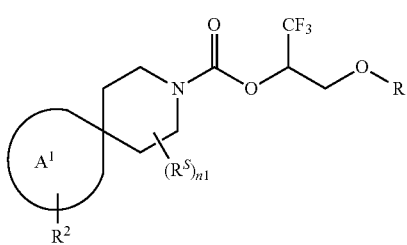

and pharmaceutically acceptable salts thereof; processes for the preparation of; intermediates used in the preparation of; and compositions containing such compounds or salts, and their uses for treating MAGL-mediated diseases and disorders including, e.g., pain, an inflammatory disorder, depression, anxiety, Alzheimer's disease, a metabolic disorder, stroke, or cancer.

23 Claims, No Drawings

(56) References Cited

U.S. PATENT DOCUMENTS

| | | |
|---|---|---|
| 2010/0063081 A1 | 3/2010 | Bradly |
| 2010/0113417 A1 | 5/2010 | Reich et al. |
| 2010/0190687 A1 | 7/2010 | Boyle et al. |
| 2010/0324011 A1 | 12/2010 | Bian et al. |
| 2011/0166165 A1 | 7/2011 | Neelamkavil et al. |
| 2012/0077797 A1 | 3/2012 | Connolly et al. |
| 2012/0264749 A1 | 10/2012 | Hadida-Ruah et al. |
| 2014/0017698 A1 | 1/2014 | Wang |
| 2017/0029390 A1* | 2/2017 | Butler .................. C07D 413/14 |
| 2018/0065943 A1 | 3/2018 | Butler et al. |
| 2018/0208608 A1* | 7/2018 | Brodney .................. A61P 3/00 |

FOREIGN PATENT DOCUMENTS

| | | |
|---|---|---|
| WO | 9855148 | 12/1998 |
| WO | 0035298 | 6/2000 |
| WO | 01011968 | 2/2001 |
| WO | 2008/130581 | 10/2008 |
| WO | 2009060030 | 5/2009 |
| WO | 2011142359 | 11/2011 |
| WO | 2012173174 | 12/2012 |
| WO | 2013/103973 | 7/2013 |
| WO | 2013131010 | 9/2013 |
| WO | 2014074715 | 5/2014 |

OTHER PUBLICATIONS

Freedman, T. B. et al., Absolute Configuration Determination of Chiral Molecules in the Solution State Using Vibrational Circular Dichroism. Chirality 2003, 15, 743-758.
Haleblian, J. K., J. Pharm. Sci. 1975, 64, 1269-1288.
Hooft, L. H. Straver, and A. L. Spek, J. Appl. Cryst. 2008, 41, 96-103.
Mechoulam, R. et al., "Identification of an endogenous 2-monoglyceride, present in canine gut, that binds to cannabinoid receptors" Biochem. Pharmacol., 50 (1995), 83-90.
C. F. Macrae, P. R. Edington, P. McCabe, E. Pidcock, G. P. Shields, R. Taylor, M. Towler, and J. van de Streek, J. Appl. Cryst. 2006, 39, 453-457.
O. V. Dolomanov, L. J. Bourhis, R. J. Gildea, J. A. K. Howard, and H. Puschmann, J. Appl. Cryst. 2009, 42, 339-341.
Patel, J. Z. et al., "Loratadine analogues as MAGL inhibitors," Bioorg. Med. Chem. Lett., 2015, 25(7):1436-42.
A. L. Spek, J. Appl. Cryst. 2003, 36, 7-13.
Senczyszyn, J. et. al, "Spirocyclic Dihydropyridines by Electrophile-Induced Dearomatizing Cyclization of N-Alkenyl Pyridinecarboxamides"; Organic Letters (2013), 15(8), 1922-1925.
Sugiura, T. et al., "2-Arachidonoylglycerol: a possible endogenous cannabinoid receptor ligand in brain," Biochem. Biophys. Res. Commun., 215 (1995), 89-97.
Verma et al., Pharmaceutical Technology On-line, 25(2), 1-14 (2001).
Wang, Y. et al., "A Fluorescence-Based Assay for Monoacylglycerol Lipase Compatible with Inhibitor Screening," Assay and Drug Development Technologies, 2008, vol. 6 (3) pp. 387-393.
Bioreversible Carriers in Drug Design, Pergamon Press, 1987 (Ed. E. B. Roche, American Pharmaceutical Association).
Crystals and the Polarizing Microscope by N. H. Hartshorne and A. Stuart, 4th Edition (Edward Arnold, 1970).
Design of Prodrugs by H. Bundgaard (Elsevier, 1985).
Greene and P. G. M. Wuts, Protective Groups in Organic Synthesis, 3rd Ed., Wiley & Sons, Inc., New York (1999).
Handbook of Pharmaceutical Salts: Properties, Selection, and Use by Stahl and Wermuth (Wiley-VCH, 2002).
Pro-drugs as Novel Delivery Systems, vol. 14, ACS Symposium Series (T. Higuchi and W. Stella).
Prodrugs: Challenges and Reward, 2007 edition, edited by Valentino Stella, Ronald Borchardt, Michael Hageman, Reza Oliyai, Hans Maag, Jefferson Tilley, 125-176 (Springer, 2007).
Remington's Pharmaceutical Sciences, 19th Edition (Mack Publishing Company, 1995).
Stereochemistry of Organic Compounds by E. L. Eliel and S. H. Wilen (Wiley, New York, 1994).
Bringmann, G. et al., Atroposelective Synthesis of Axially Chiral Biaryl Compounds. Angew. Chem., Int. Ed. 2005, 44, 5384-5427.
Liang and Chen, Expert Opinion in Therapeutic Patents, 2001, 11, 981-986.
Jae Won Chang et al: "Highly Selective Inhibitors of Monoacylglycerol Lipase Bearing a Reactive Group that is Bioisosteric with Endocannabinoid Substrates", Chemistry & Biology, vol. 19, No. 5, May 1, 2012 (May 1, 2012), pp. 579-588.
Pfizer Inc./Feng Shao, Notice of Co-Pending Application, Mar. 27, 2018.

* cited by examiner

1,1,1-TRIFLUORO-3-HYDROXYPROPAN-2-YL CARBAMATE DERIVATIVES AS MAGL INHIBITORS

This application claims the benefit of priority to U.S. Provisional Patent Application Ser. No. 62/448,498 filed Jan. 20, 2017, the disclosure of which is hereby incorporated by reference in its entirety.

FIELD OF THE INVENTION

The present invention relates to novel 1,1,1-trifluoro-3-hydroxypropan-2-yl carbamate derivatives, which are monoacylglycerol lipase (MAGL) inhibitors, pharmaceutical compositions thereof, and uses thereof in the treatment of MAGL-mediated disorders such as pain, an inflammatory disorder, depression, anxiety, Alzheimer's disease, a metabolic disorder, stroke, or cancer.

BACKGROUND OF THE INVENTION

MAGL is the principal enzyme responsible for the in vivo degradation of 2-arachidonoyl glycerol (2-AG), an endogenous ligand of the cannabinoid receptors (e.g., CB1 and CB2). See e.g., Patel, J. Z. et al., "Loratadine analogues as MAGL inhibitors," Bioorg. Med. Chem. Lett., 2015, 25(7): 1436-42; Mechoulam, R. et al., "Identification of an endogenous 2-monoglyceride, present in canine gut, that binds to cannabinoid receptors" Biochem. Pharmacol., 50 (1995), 83-90; Sugiura, T. et al., "2-Arachidonoylglycerol: a possible endogenous cannabinoid receptor ligand in brain," Biochem. Biophys. Res. Commun., 215 (1995), 89-97.

MAGL inhibitors are potentially useful for the treatment of a MAGL-mediated disease or disorder. Examples of MAGL-mediated diseases or disorders include a metabolic disorder (e.g., obesity); vomiting or emesis; nausea; an eating disorder (e.g., anorexia or bulimia); neuropathy (e.g., diabetic neuropathy, pellagric neuropathy, alcoholic neuropathy, Beriberi neuropathy); burning feet syndrome; a neurodegenerative disorder [multiple sclerosis (MS), Parkinson's disease (PD), Huntington's disease, Alzheimer's disease, amyotrophic lateral sclerosis (ALS), epilepsy, a sleep disorder, Creutzfeldt-Jakob disease (CJD), or prion disease]; a cardiovascular disease (e.g., hypertension, dyslipidemia, atherosclerosis, cardiac arrhythmias, or cardiac ischemia); osteoporosis; osteoarthritis; schizophrenia; depression; bipolar disease; tremor; dyskinesia; dystonia; spasticity; Tourette's syndrome; sleep apnea; hearing loss; an eye disease (e.g., glaucoma, ocular hypertension, macular degeneration, or a disease arising from elevated intraocular pressure); cachexia; insomnia; meningitis; sleeping sickness; progressive multifocal leukoencephalopathy; De Vivo disease; cerebral edema; cerebral palsy; withdrawal syndrome [alcohol withdrawal syndrome, antidepressant discontinuation syndrome, antipsychotic withdrawal syndrome, benzodiazepine withdrawal syndrome, cannabis withdrawal, neonatal withdrawal, nicotine withdrawal, or opioid withdrawal]; traumatic brain injury; spinal cord injury; seizures; excitotoxin exposure; ischemia [stroke, hepatic ischemia or reperfusion, CNS ischemia or reperfusion]; liver fibrosis, iron overload, cirrhosis of the liver; a lung disorder [asthma, allergies, COPD, chronic bronchitis, emphysema, cystic fibrosis, pneumonia, tuberculosis, pulmonary edema, lung cancers, acute respiratory distress syndrome, intersitital lung disease (ILD), sarcoidosis, idiopathic pulmonary fibrosis, pulmonary embolism, pleural effusion, or mesothelioma]; a liver disorder [acute liver failure, Alagille syndrome, hepatitis, enlarged liver, Gilbert's syndrome, liver cysts, liver hemangioma, fatty liver disease, steatohepatitis, primary sclerosing cholangitis, fascioliasis, primary bilary cirrhosis, Budd-Chiari syndrome, hemochromatosis, Wilson's disease, or transthyretin-related hereditary amyloidosis], stroke [e.g., ischemic stroke; hemorrhagic stroke]; subarachnoid hemorrhage; vasospasm; AIDS wasting syndrome; renal ischemia; a disorder associated with abnormal cell growth or proliferation [e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, bladder cancer, brain cancer, glioblastoma (GBM), gastrointestinal cancer, leukemia or blood cancer]; an autoimmune disease [e.g., psoriasis, lupus erythematosus, Sjögren's syndrome, ankylosing spondylitis, undifferentiated spondylitis, Behcet's disease, hemolytic anemia, graft rejection]; an inflammatory disorder [e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, IBS, pelvic inflammatory disease, sarcoidosis, HIV encephalitis, rabies, brain abscess, neuroinflammation, inflammation in the central nervous system (CNS)]; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome; pain [e.g., acute pain; chronic pain; inflammatory pain; visceral pain; post-operative pain; migraine; lower back pain; joint pain; abdominal pain; chest pain; postmastectomy pain syndrome; menstrual pain; endometriosis pain; pain due to physical trauma; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, irritable bowel syndrome (IBS), cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)]; a demyelinating disease [e.g., multiple sclerosis (MS), Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis]; and cognitive impairment [e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)]. See e.g., U.S. Pat. No. 8,415,341, 8,835,418, or 8,772,318.

There continues to be a need for alternative MAGL inhibitors.

SUMMARY OF THE INVENTION

The present invention provides, in part, a novel compound of Formula I:

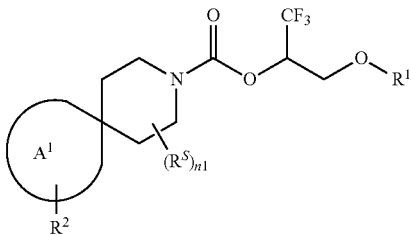

or a pharmaceutically acceptable salt thereof, wherein:

$R^1$ is H, —P(=O)(OR$^{81}$)(OR$^{82}$); or —S(=O)$_2$OR$^{90}$;

each of $R^{81}$, $R^{82}$, and $R^{90}$ is independently selected from the group consisting of H and $C_{1-6}$ alkyl, wherein each of the $C_{1-6}$ alkyl is optionally substituted with one or more (e.g., 0, 1, 2, 3, 4, 5, or 6) substituents each independently selected from the group consisting of —NH$_2$, —NH($C_{1-4}$ alkyl), and —N($C_{1-4}$ alkyl)$_2$;

each $R^S$ is independently selected from the group consisting of OH, oxo, halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy;

n1 is 0, 1, 2, 3, 4, 5, or 6;

the moiety of Formula M-1 of Formula I:

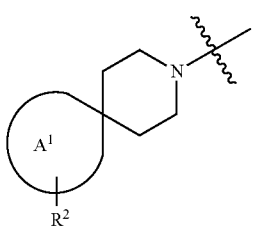

M-1 is a moiety of Formula M-1a, M-1b, or M-1c:

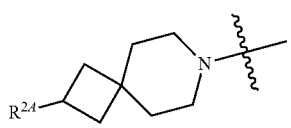

M-1a

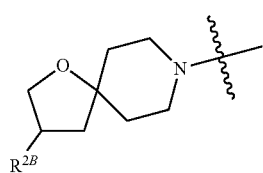

M-1b

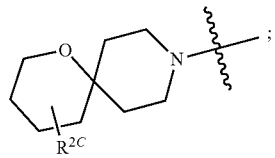

M-1c each of $R^{2A}$ and $R^{2C}$ is, independently, —NR$^3$S(=O)$_2$R$^4$, —NR$^3$C(=O)R$^4$; R$^5$, or —OR$^5$;

$R^{2B}$ is selected from the group consisting of [4-(trifluoromethyl)-1H-pyrazol-1-yl]methyl-, (cyclopentylcarbonyl)(methyl)amino-, (tert-butylsulfonyl)(methyl)amino-, (2,2-dimethylpropanoyl)(methyl)amino-, 4-(trifluoromethyl)-1H-pyrazol-1-yl-, 4-fluoro-1H-pyrazol-1-yl-, 3-cyanophenyl-, 6-(trifluoromethyl)pyridin-2-yl-, 5-fluoropyridin-2-yl-, 4-(difluoromethyl)-1H-pyrazol-1-yl-, 4-tert-butyl-1H-pyrazol-1-yl-, 4-chlorol-1H-pyrazol-1-yl-, 4-cyclopropyl-1H-pyrazol-1-yl-, 4-methyl-1H-pyrazol-1-yl-, 2-fluorophenyl-, 4-cyano-3-fluorophenyl-, 3-cyano-4-fluorophenyl-, 5-cyano-2-fluorophenyl-, 4-cyanophenyl-, 2,6-difluorophenyl-, 2,4-difluorophenyl-, 4-fluorophenyl-, 4-(difluoromethyl)pyridin-2-yl-, 6-(difluoromethyl)pyridin-3-yl-, 5-cyanopyridin-2-yl-, 5-(difluoromethyl)pyridin-2-yl-, 5-(trifluoromethyl)pyridin-2-yl-, pyridin-2-yl-, 3-tert-butyl-1H-pyrazol-1-yl-, 3-(trifluoromethyl)-1H-pyrazol-1-yl-, 3,4-dimethyl-1H-pyrazol-1-yl-, {[(3,3-difluorocyclobutyl)methyl]sulfonyl}(methyl)amino-, [(3,3-difluorocyclobutyl)carbonyl](methyl)amino-, 1H-indazol-1-yl-, 3-cyano-2-fluorophenyl-, and 4-cyano-2-fluorophenyl-;

each $R^3$ is independently $C_{1-3}$ alkyl;

each $R^4$ is independently selected from $C_{1-6}$ alkyl, $C_{3-7}$ cycloalkyl, ($C_{3-7}$ cycloalkyl)-$C_{1-2}$ alkyl-, ($C_{6-10}$ aryl)-$C_{1-2}$ alkyl-, (5- or 10-membered heteroaryl)-$C_{1-2}$ alkyl-, 5- or 10-membered heteroaryl, and $C_{6-10}$ aryl, wherein each of the selections is substituted with 0, 1, 2, or 3 halogen;

or $R^3$ and $R^4$, together with the intervening moiety of "—NS(=O)$_2$—" or "—NC(=O)—" to which they are attached, form a 4- to 10-membered heterocycloalkyl that is substituted with 0, 1, 2, 3, 4, or 5 substituents each independently selected from the group consisting of OH, oxo, halogen, $C_{1-4}$ alkyl, $C_{1-4}$ haloalkyl, $C_{1-4}$ alkoxy, and $C_{1-4}$ haloalkoxy, and wherein each of the ring-forming atoms of the 4- to 10-membered heterocycloalkyl is C, N, O, or S; and each $R^5$ is phenyl or 5- or 6-membered heteroaryl, wherein each of the phenyl or 5- or 6-membered heteroaryl is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy, and wherein each of the ring-forming atoms of the 5- or 6-membered heteroaryl is a carbon atom or a nitrogen atom.

In some embodiments, each $R^S$ is independently selected from the group consisting of halogen, $C_{1-4}$ alkyl, $C_{1-4}$ haloalkyl, $C_{1-4}$ alkoxy, and $C_{1-4}$ haloalkoxy. In some further embodiments, each $R^S$ is independently selected from the group consisting of halogen, $C_{1-2}$ alkyl, $C_{1-2}$ haloalkyl, $C_{1-2}$ alkoxy, and $C_{1-2}$ haloalkoxy.

In some embodiments, n1 is 0, 1, 2, 3, or 4. In some further embodiments, n1 is 0, 1, or 2. In some yet further embodiments, n1 is 0 or 1. In some still further embodiments, n1 is 0.

In some embodiments, each $R^3$ is independently $C_{1-3}$ alkyl; and each $R^4$ is independently selected from $C_{1-6}$ alkyl, $C_{3-7}$ cycloalkyl, ($C_{3-7}$ cycloalkyl)-$C_{1-2}$ alkyl-, ($C_{6-10}$ aryl)-

$C_{1-2}$ alkyl-, (5- or 10-membered heteroaryl)-$C_{1-2}$ alkyl-, 5- or 10-membered heteroaryl, and $C_{6-10}$ aryl, wherein each of the selections is substituted with 0, 1, 2, or 3 halogen. In some further embodiments, each $R^3$ is independently $C_{1-3}$ alkyl; and each $R^4$ is independently selected from $C_{1-6}$ alkyl, $C_{3-7}$ cycloalkyl, ($C_{3-7}$ cycloalkyl)-$C_{1-2}$ alkyl-, ($C_{6-10}$ aryl)-$C_{1-2}$ alkyl-, and $C_{6-10}$ aryl, wherein each of the selections is substituted with 0, 1, 2, or 3 halogen.

In some embodiments, the compound of Formula I or a pharmaceutically acceptable salt thereof is a compound of Formula I-1, I-2, or I-3:

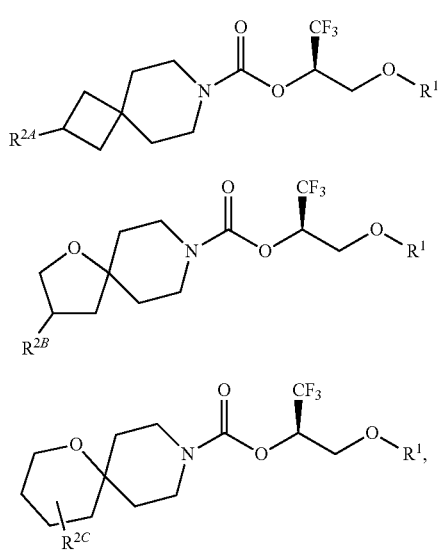

or a pharmaceutically acceptable salt thereof.

In some embodiments, $R^1$ is H or —P(=O)(OH)(OH). In some further embodiments, $R^1$ is H.

In some embodiments, the compound of Formula I or a pharmaceutically acceptable salt thereof is a compound of Formula I-1 or a pharmaceutically acceptable salt thereof.

In some embodiments, the compound of Formula I or a pharmaceutically acceptable salt thereof is a compound of Formula I-2 or a pharmaceutically acceptable salt thereof.

In some embodiments, the compound of Formula I or a pharmaceutically acceptable salt thereof is a compound of Formula I-3 or a pharmaceutically acceptable salt thereof.

In some embodiments of the compound of Formula I (e.g. a compound of Formula I-1) or a pharmaceutically acceptable salt thereof, $R^{2A}$ is $R^5$ or —$OR^5$. In some further embodiments, $R^5$ phenyl or 5- or 6-membered heteroaryl, wherein 1 or 2 of the ring-forming atoms of the 5- or 6-membered heteroaryl are nitrogen atoms, and the rest of the ring-forming atoms are carbon atoms; and the phenyl or 5- or 6-membered heteroaryl of $R^5$ is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-1) or a pharmaceutically acceptable salt thereof, $R^{2A}$ is $R^5$. In some further embodiments, $R^5$ is phenyl that is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-1) or a pharmaceutically acceptable salt thereof, $R^{2A}$ is $R^5$; and $R^5$ is 5- or 6-membered heteroaryl, wherein 1 or 2 of the ring-forming atoms of the 5- or 6-membered heteroaryl are nitrogen atoms, and the rest of the ring-forming atoms are carbon atoms; and the 5- or 6-membered heteroaryl of $R^5$ is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy. In some further embodiments, $R^5$ is selected from the group consisting of 1H-pyrazolyl (e.g. 1H-pyrazol-1-yl-) and pyridinyl (e.g. pyridin-2-yl- and pyridin-3-yl-), wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

In some embodiments of the compound of Formula I (e.g. a compound of Formula I-1) or a pharmaceutically acceptable salt thereof, $R^{2A}$ is $R^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy. In some further embodiments, $R^5$ is selected from the group consisting of phenyl, 1H-pyrazol-1-yl-, pyridin-2-yl-, pyridin-3-yl-, and pyridin-4-yl, wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

In some embodiments of the compound of Formula I (e.g. a compound of Formula I-1) or a pharmaceutically acceptable salt thereof, $R^{2A}$ is —$OR^5$. In some further embodiments, $R^5$ is phenyl that is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-1) or a pharmaceutically acceptable salt thereof, $R^{2A}$ is —$OR^5$; and $R^5$ is 5- or 6-membered heteroaryl, wherein 1 or 2 of the ring-forming atoms of the 5- or 6-membered heteroaryl are nitrogen atoms, and the rest of the ring-forming atoms are carbon atoms; and the 5- or 6-membered heteroaryl of $R^5$ is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-1) or a pharmaceutically acceptable salt thereof, $R^{2A}$ is —$OR^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy. In some further embodiments, $R^5$ is selected from the group consisting of phenyl, 1H-pyrazol-1-yl-, pyridin-2-yl-, and pyridin-3-yl-, and pyridin-4-yl, wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

In some embodiments of the compound of Formula I (e.g. a compound of Formula I-1) or a pharmaceutically acceptable salt thereof, $R^{2A}$ is —$NR^3S(=O)_2R^4$ or —$NR^3C(=O)R^4$; $R^3$ is methyl; each $R^4$ is independently selected from the group consisting of $C_{1-6}$ alkyl, $C_{3-7}$ cycloalkyl, ($C_{3-7}$ cycloalkyl)-$C_{1-2}$ alkyl-, (phenyl)-$C_{1-2}$ alkyl-, and phenyl.

In some embodiments of the compound of Formula I (e.g. a compound of Formula I-2) or a pharmaceutically acceptable salt thereof, $R^{2B}$ is 4-(trifluoromethyl)-1H-pyrazol-1-yl-, 4-fluoro-1H-pyrazol-1-yl-, 3-cyanophenyl-, 6-(trifluoromethyl)pyridin-2-yl-, 5-cyano-2-fluorophenyl-, or 4-(difluoromethyl)pyridin-2-yl-.

In some embodiments, the compound of Formula I or a pharmaceutically acceptable salt thereof is a compound of Formula I-3 or a pharmaceutically acceptable salt thereof, and the compound of Formula I-3 or a pharmaceutically acceptable salt thereof is a compound of Formula I-3a or Formula I-3b:

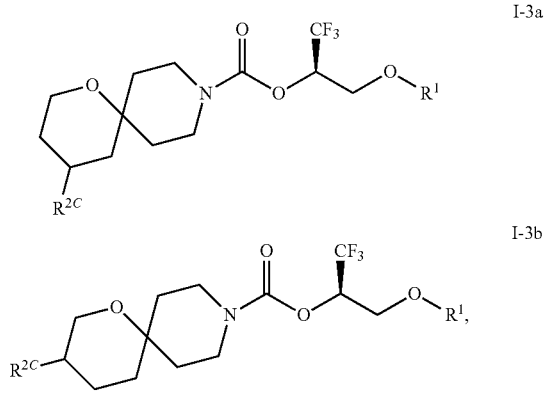

I-3a

I-3b or a pharmaceutically acceptable salt thereof.

In some embodiments, the compound of Formula I or a pharmaceutically acceptable salt thereof is a compound of Formula I-3a or a pharmaceutically acceptable salt thereof.

In some embodiments, the compound of Formula I or a pharmaceutically acceptable salt thereof is a compound of Formula I-3b or a pharmaceutically acceptable salt thereof.

In some embodiments of the compound of Formula I (e.g. a compound of Formula I-3, I-3a, or I-3b) or a pharmaceutically acceptable salt thereof, $R^{2C}$ is —$NR^3S(=O)_2R^4$ or $R^5$. In some further embodiments, $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-3, I-3a, or I-3b) or a pharmaceutically acceptable salt thereof, $R^{2C}$ is —$NR^3S(=O)_2R^4$. In some further embodiments, $R^3$ is methyl; and $R^4$ is selected from the group consisting of $C_{1-6}$ alkyl, $C_{3-7}$ cycloalkyl, and $(C_{3-7}$ cycloalkyl)-$C_{1-2}$ alkyl-. In some yet further embodiments, $R^4$ is selected from the group consisting of $C_{1-6}$ alkyl and $(C_{3-7}$ cycloalkyl)-$C_{1-2}$ alkyl-. In some still further embodiments, $R^4$ is $(C_{3-7}$ cycloalkyl)-$C_{1-2}$ alkyl-.

In some embodiments of the compound of Formula I (e.g. a compound of Formula I-3, I-3a, or I-3b) or a pharmaceutically acceptable salt thereof, $R^{2C}$ is $R^5$. In some further embodiments, $R^5$ is phenyl that is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

In some embodiments of the compound of Formula I (e.g. a compound of Formula I-3, I-3a, or I-3b) or a pharmaceutically acceptable salt thereof, $R^{2C}$ is $R^5$; and $R^5$ is 5- or 6-membered heteroaryl, wherein 1 or 2 of the ring-forming atoms of the 5- or 6-membered heteroaryl are nitrogen atoms, and the rest of the ring-forming atoms are carbon atoms; and the 5- or 6-membered heteroaryl of $R^5$ is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy. In some further embodiments, $R^5$ is selected from the group consisting of 1H-pyrazolyl (e.g. 1H-pyrazol-1-yl-) and pyridinyl (e.g. pyridin-2-yl-, pyridin-3-yl-, or pyridin-4-yl), wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

In some embodiments of the compound of Formula I (e.g. a compound of Formula I-3, I-3a, or I-3b) or a pharmaceutically acceptable salt thereof, $R^{2C}$ is $R^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy. In some further embodiments, $R^5$ is selected from the group consisting of phenyl, 1H-pyrazol-1-yl-, pyridin-2-yl-, pyridin-3-yl-, and pyridin-4-yl, wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

In some embodiments, the present invention provides a compound selected from Examples 1 to 90 in the EXAMPLES section or a pharmaceutically acceptable salt thereof (or the parent compound thereof where the exemplary compound, for example, is a salt) herein below.

In some embodiments, the present invention provides a compound selected from the group consisting of:
(2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 2;
(2R)-1,1,1-trifluoro-3-hydroxypropan-2-yl (3R)-3-(4-fluoro-1H-pyrazol-1-yl)-1-oxa-8-azaspiro[4.5]decane-8-carboxylate;
(2R)-1,1,1-trifluoro-3-hydroxypropan-2-yl (3S)-3-(3-cyanophenyl)-1-oxa-8-azaspiro[4.5]decane-8-carboxylate;
(2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 1;
(2R)-1,1,1-trifluoro-3-hydroxypropan-2-yl 2-{[6-(difluoromethyl)pyridin-3-yl]oxy}-7-azaspiro[3.5]nonane-7-carboxylate;
(2R)-1,1,1-trifluoro-3-hydroxypropan-2-yl 3-(5-cyano-2-fluorophenyl)-1-oxa-8-azaspiro[4.5]decane-8-carboxylate, DIAST 2;
(2R)-1,1,1-trifluoro-3-hydroxypropan-2-yl 3-[4-(difluoromethyl)pyridin-2-yl]-1-oxa-8-azaspiro[4.5]decane-8-carboxylate, DIAST 1;
(2R)-1,1,1-trifluoro-3-hydroxypropan-2-yl 2-[5-(difluoromethyl)pyridin-2-yl]-7-azaspiro[3.5]nonane-7-carboxylate;
(2R)-1,1,1-trifluoro-3-hydroxypropan-2-yl 2-(4-cyclopropyl-1H-pyrazol-1-yl)-7-azaspiro[3.5]nonane-7-carboxylate; and
(2R)-1,1,1-trifluoro-3-hydroxypropan-2-yl 2-(3-fluorophenoxy)-7-azaspiro[3.5]nonane-7-carboxylate,
or a pharmaceutically acceptable salt thereof.

The present invention includes any subset of any embodiment described herein.

The present invention includes combinations of two or more embodiments described hereinabove, or any subset thereof.

The present invention further provides the compound of Formula I or a pharmaceutically acceptable salt thereof (including all embodiments and combinations of two or more embodiments described herein or any subcombination thereof) for use in the treatment of a MAGL-mediated disease or disorder described herein.

The present invention further provides use of the compound of Formula I or a pharmaceutically acceptable salt thereof (including all embodiments and combinations of two or more embodiments described herein or any subcombination thereof) for treating a MAGL-mediated disease or disorder described herein.

The present invention further provides a method for treating a MAGL-mediated disease or disorder in a patient (e.g., a mammal such as a human) comprising administering to the patient a therapeutically effective amount of the compound of Formula I or a pharmaceutically acceptable salt thereof (including all embodiments and combinations of two or more embodiments described herein or any subcombination thereof).

The present invention further provides use of the compound of Formula I or a pharmaceutically acceptable salt thereof (including all embodiments and combinations of two or more embodiments described herein or any subcombination thereof) in the manufacture of a medicament for use in the treatment of a MAGL-mediated disease or disorder described herein.

The compound of Formula I or a pharmaceutically acceptable salt thereof of the present invention (or a metabolite thereof) is a MAGL inhibitor. Thus, the present invention further provides a method for inhibiting MAGL (i.e., an activity of MAGL either in vitro or in vivo), comprising contacting (including incubating) the MAGL with the compound of Formula I or a pharmaceutically acceptable salt thereof (such as one selected from Examples 1-90 herein) described herein.

As used herein, the term "contacting" refers to the bringing together of indicated moieties in an in vitro system or an in vivo system. For example, "contacting" MAGL with a compound of the invention includes the administration of a compound of the present invention to an individual or patient, such as a human, having the MAGL, as well as, for example, introducing a compound of the invention into a sample containing a cellular or purified preparation containing the MAGL.

The amount of the compound of Formula I or a pharmaceutically acceptable salt thereof used in any one of the methods (or uses) of the present invention is effective in inhibiting MAGL.

MAGL-mediated diseases or disorders include, for example, a metabolic disorder (e.g., obesity); vomiting or emesis; nausea; an eating disorder (e.g anorexia or bulimia); neuropathy (e.g., diabetic neuropathy, pellagric neuropathy, alcoholic neuropathy, Beriberi neuropathy); burning feet syndrome; a neurodegenerative disorder [multiple sclerosis (MS), Parkinson's disease (PD), Huntington's disease, Alzheimer's disease, amyotrophic lateral sclerosis (ALS), epilepsy, a sleep disorder, Creutzfeldt-Jakob disease (CJD), or prion disease]; a cardiovascular disease (e.g., hypertension, dyslipidemia, atherosclerosis, cardiac arrhythmias, or cardiac ischemia); osteoporosis; osteoarthritis; schizophrenia; depression; bipolar disease; tremor; dyskinesia; dystonia; spasticity; Tourette's syndrome; sleep apnea; hearing loss; an eye disease (e.g., glaucoma, ocular hypertension, macular degeneration, or a disease arising from elevated intraocular pressure); cachexia; insomnia; meningitis; sleeping sickness; progressive multifocal leukoencephalopathy; De Vivo disease; cerebral edema; cerebral palsy; withdrawal syndrome [alcohol withdrawal syndrome, antidepressant discontinuation syndrome, antipsychotic withdrawal syndrome, benzodiazepine withdrawal syndrome, cannabis withdrawal, neonatal withdrawal, nicotine withdrawal, or opioid withdrawal]; traumatic brain injury; spinal cord injury; seizures; excitotoxin exposure; ischemia [stroke, hepatic ischemia or reperfusion, CNS ischemia or reperfusion]; liver fibrosis, iron overload, cirrhosis of the liver; a lung disorder [asthma, allergies, COPD, chronic bronchitis, emphysema, cystic fibrosis, pneumonia, tuberculosis, pulmonary edema, lung cancers, acute respiratory distress syndrome, intersitital lung disease (ILD), sarcoidosis, idiopathic pulmonary fibrosis, pulmonary embolism, pleural effusion, or mesothelioma]; a liver disorder [acute liver failure, Alagille syndrome, hepatitis, enlarged liver, Gilbert's syndrome, liver cysts, liver hemangioma, fatty liver disease, steatohepatitis, primary sclerosing cholangitis, fascioliasis, primary bilary cirrhosis, Budd-Chiari syndrome, hemochromatosis, Wilson's disease, or transthyretin-related hereditary amyloidosis], stroke [e.g., ischemic stroke; hemorrhagic stroke]; subarachnoid hemorrhage; vasospasm; AIDS wasting syndrome; renal ischemia; a disorder associated with abnormal cell growth or proliferation [e.g., a benign tumor or cancer such as benign skin tumor, brain tumor, papilloma, prostate tumor, cerebral tumor (glioblastoma, medulloepithelioma, medulloblastoma, neuroblastoma, astrocytoma, astroblastoma, ependymoma, oligodendroglioma, plexus tumor, neuroepithelioma, epiphyseal tumor, ependymoblastoma, malignant meningioma, sarcomatosis, melanoma, schwannoma), melanoma, metastatic tumor, kidney cancer, bladder cancer, brain cancer, glioblastoma (GBM), gastrointestinal cancer, leukemia or blood cancer]; an autoimmune disease [e.g., psoriasis, lupus erythematosus, Sjogren's syndrome, ankylosing spondylitis, undifferentiated spondylitis, Behcet's disease, hemolytic anemia, graft rejection]; an inflammatory disorder [e.g., appendicitis, bursitis, colitis, cystitis, dermatitis, phlebitis, rhinitis, tendonitis, tonsillitis, vasculitis, acne vulgaris, chronic prostatitis, glomerulonephritis, hypersensitivities, IBS, pelvic inflammatory disease, sarcoidosis, HIV encephalitis, rabies, brain abscess, neuroinflammation, inflammation in the central nervous system (CNS)]; a disorder of the immune system (e.g., transplant rejection or celiac disease); post-traumatic stress disorder (PTSD); acute stress disorder; panic disorder; substance-induced anxiety; obsessive-compulsive disorder (OCD); agoraphobia; specific phobia; social phobia; anxiety disorder; attention deficit disorder (ADD); attention deficit hyperactivity disorder (ADHD); Asperger's syndrome; pain [e.g., acute pain; chronic pain; inflammatory pain; visceral pain; post-operative pain; migraine; lower back pain; joint pain; abdominal pain; chest pain; postmastectomy pain syndrome; menstrual pain; endometriosis pain; pain due to physical trauma; headache; sinus headache; tension headache arachnoiditis, herpes virus pain, diabetic pain; pain due to a disorder selected from: osteoarthritis, rheumatoid arthritis, osteoarthritis, spondylitis, gout, labor, musculoskeletal disease, skin disease, toothache, pyresis, burn, sunburn, snake bite, venomous snake bite, spider bite, insect sting, neurogenic bladder, interstitial cystitis, urinary tract infection (UTI), rhinitis, contact dermatitis/hypersensitivity, itch, eczema, pharyngitis, mucositis, enteritis, irritable bowel syndrome (IBS), cholecystitis, and pancreatitis; neuropathic pain (e.g., neuropathic low back pain, complex regional pain syndrome, post trigeminal neuralgia, causalgia, toxic neuropathy, reflex sympathetic dystrophy, diabetic neuropathy, chronic neuropathy from chemotherapeutic agent, or sciatica pain)]; a demyelinating disease [e.g., multiple sclerosis (MS), Devic's disease, CNS neuropathies, central pontine myelinolysis, syphilitic myelopathy, leukoencephalopathies, leukodystrophies, Guillain-Barre syndrome, chronic inflammatory demyelinating polyneuropathy, anti-myelin-associated glycoprotein (MAG) peripheral neuropathy, Charcot-Marie-Tooth disease, peripheral neuropathy, myelopathy, optic neuropathy, progressive inflammatory neuropathy, optic neuritis, transverse myelitis]; and cognitive impairment [e.g., cognitive impairment associated with Down's syndrome; cognitive impairment associated with Alzheimer's disease; cognitive impairment associated with PD; mild cognitive impairment (MCI), dementia, post-chemotherapy cognitive impairment (PCCI), postoperative cognitive dysfunction (POCD)].

The term "therapeutically effective amount" as used herein refers to that amount of the compound (including a pharmaceutically acceptable salt thereof) being administered which will relieve to some extent one or more of the symptoms of the disorder being treated. In reference to the treatment of a MAGL-mediated disease or disorder (e.g., Alzheimer's disease, inflammation, or pain), a therapeutically effective amount refers to that amount which has the effect of relieving to some extent (or, for example, eliminating) one or more symptoms associated with the MAGL-mediated disease or disorder (e.g., psychotic symptom of Alzheimer's disease).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

As used herein, the term "n-membered", where n is an integer, typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual sub-combination of the members of such groups and ranges.

For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 6 carbon atoms, 1 to 4 carbon atoms, 1 to 3 carbon atoms, or 1 to 2 carbon atoms. For example, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-4}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to methyl and/or ethyl; and the term "$C_1$ alkyl" refers to methyl. An alkyl group optionally can be substituted by one or more (e.g., 1 to 5) suitable substituents.

As used herein, the term "alkenyl" refers to aliphatic hydrocarbons having at least one carbon-carbon double bond, including straight chains and branched chains having at least one carbon-carbon double bond. In some embodiments, the alkenyl group has 2 to 6 carbon atoms, 3 to 6 carbon atoms, or 2 to 4 carbon atoms. For example, as used herein, the term "$C_{2-6}$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g., 1 to 5) suitable substituents. When the compounds of Formula I contain an alkenyl group, the alkenyl group may exist as the pure E form, the pure Z form, or any mixture thereof.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo[5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, bicyclo[1.1.1]pentan-1-yl, or bicyclo[1.1.1]pentan-2-yl). For another example, the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group optionally can be substituted by 1 or more (e.g., 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic ring radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 10 ring-forming atoms, including 1 to 9 carbon atoms, and 1 to 9 heteroatoms each independently selected from O, S, and N. In some embodiments, the heteroaryl group has 5 to 10 ring-forming atoms including one to four heteroatoms. The heteroaryl group can also contain one to three oxo or thiono (i.e., =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl (e.g., 1H-pyrazol-1-yl, pyrazol-3-yl, pyrazol-4-yl), tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group optionally can be substituted by 1 or more (e.g., 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 12-membered ring system, 4- to 10-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N (and optionally P or B when present). The heterocycloalkyl group can also optionally contain one or more oxo (i.e., =O) or thiono (i.e., =S) groups. For example, the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N; and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. The heterocycloalkyl group optionally can be substituted by 1 or more (e.g., 1 to 5) suitable substituents.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 2-oxaspiro[3.3]heptyl {e.g., 2-oxaspiro[3.3]hept-6-yl}, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-on-2-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, tetrahydropyranyl (e.g., tetrahydro-2H-pyran-4-yl), imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), 2-oxoazepan-3-yl, and the like. Some examples of aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); the term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e., methyl or ethyl) having one or more halogen substituents (up to perhaloalkyl, i.e., every hydrogen atom of the alkyl group has been replaced by a halogen atom). For yet another example, the term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-4}$ alkoxy" or "$C_{1-4}$ alkyloxy" refers to an —O—($C_{1-4}$ alkyl) group. For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used here, the term "haloalkoxy" refers to an —O-haloalkyl group. For another example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For another example, the term "$C_1$ haloalkoxy" refers to a methoxy group having one, two, or three halogen substituents. An example of haloalkoxy is —$OCF_3$ or —$OCHF_2$.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

As used herein, the point of attachment of a substituent can be specified to indicate the position where the substituent is attached to another moiety. For example, "($C_{3-7}$ cycloalkyl)-$C_{1-2}$ alkyl-" means the point of attachment occurs at the "$C_{1-2}$ alkyl" part of the "($C_{3-7}$ cycloalkyl)-$C_{1-2}$ alkyl-." For another example, "($C_{6-10}$ aryl)-$C_{1-2}$ alkyl-" means the point of attachment occurs at the "$C_{1-2}$ alkyl" part of the "($C_{6-10}$ aryl)-$C_{1-2}$ alkyl-."

As used herein, when a bond to a substituent is shown to cross a ring (or a bond connecting two atoms in a ring), then such substituent may be bonded to any of the ring-forming atoms in that ring that are substitutable (i.e., bonded to one or more hydrogen atoms), unless otherwise specified or otherwise implicit from the context. For example, as shown in Formula M-1 below, $R^2$ may be bonded to any of ring-forming atoms of ring $A^1$ (e.g. a nitrogen or carbon) that bears a hydrogen atom (e.g. NH or $CH_2$). For another example, as shown in Moiety M-1c below, an $R^{2C}$ may be bonded to any ring-forming atom of the tetrahydropyran ring that is substitutable (i.e., one of the carbon atoms of the —$CH_2$—$CH_2$—$CH_2$— groups of the tetrahydropyran ring); but not on the piperidine ring of Moiety M-1c because the bond does not cross the piperidine ring. For yet another example, as shown in the structure of M-100, $R^{55}$ may be bonded to the nitrogen of (the NH) or one of the carbon atoms.

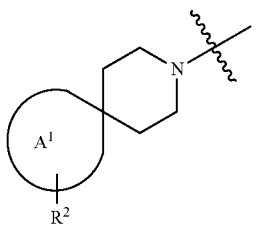

M-1

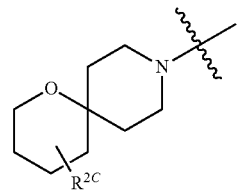

M-1c

M-100

When a substituted or optionally substituted moiety is described without indicating the atom via which such moiety is bonded to a substituent, then the substituent may be bonded via any appropriate atom in such moiety. For example in a substituted arylalkyl, a substituent on the arylalkyl [e.g., ($C_{6-10}$ aryl)-$C_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I" or "Formula I or a pharmaceutically acceptable salt thereof" are defined to include all forms of the compound of Formula I or pharmaceutically salt thereof, including hydrates, solvates, isomers (including for example rotational stereoisomers), crystalline and non-crystalline forms, isomorphs, polymorphs, metabolites, and prodrugs thereof.

As is known to the person skilled in the art, amine compounds (i.e., those comprising one or more nitrogen atoms), for example tertiary amines, can form N-oxides (also known as amine oxides). An N-oxide has the formula of $(R^{100})(R^{200})(R^{300})N^+$—$O^-$ wherein the parent amine $(R^{100})(R^{200})(R^{300})N$ can be, for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100})(R^{200})(R^{300})N$ together forms 1-alkylpiperidine, 1-alkylpyrrolidine, 1-benzylpyrrolidine, or pyridine]. For instance, an imine nitrogen, especially a heterocyclic or heteroaromatic imine nitrogen, or pyridine-type nitrogen

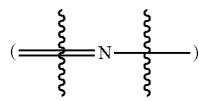 [SMILES: *N=*]

atom [such as a nitrogen atom in pyridine, pyridazine, or pyrazine], can be N-oxidized to form the N-oxide comprising the group

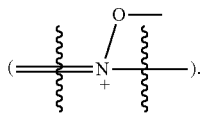

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

Compounds of Formula I and their salts described herein further include N-oxides thereof.

In the description herein below, unless otherwise specified, compounds of Formula I (or compounds of the invention) include salts of the compounds and the N-oxides of the compounds or the salts.

As is also known to the person skilled in the art, tertiary amine compounds (i.e., those comprising one or more tertiary amine nitrogen atoms) can form quaternary ammonium salts.

In the description herein below, unless otherwise specified, compounds of Formula I (or compounds of the invention) further include their quaternary ammonium salts.

Compounds of Formula I may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, Chem. Commun. 2004, 17, 1889-1896. For a general review of multi-component complexes, see J. K. Haleblian, J. Pharm. Sci. 1975, 64, 1269-1288.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO⁻Na⁺, —COO⁻K⁺, or —SO₃⁻Na⁺) or non-ionic (such as —N⁻N⁺(CH₃)₃) polar head group. For more information, see Crystals and the Polarizing Microscope by N. H. Hartshorne and A. Stuart, 4th Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of Formula I may themselves act as prodrugs of other compounds of Formula I.

Also included within the scope of the invention are metabolites of compounds of Formula I, that is, compounds formed in vivo upon administration of the drug.

The compounds of Formula I include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I (including salts thereof) may have asymmetric carbon atoms. The carbon-carbon bonds of the compounds of Formula I may be depicted herein using a solid line (—), a wavy line (⁓), a solid wedge (◥), or a dotted wedge (⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. The use of a wavy line to depict bonds to asymmetric carbon atoms is meant to indicate that the stereochemistry is unknown (unless otherwise specified). It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I may exhibit the phenomena of tautomerism and structural isomerism. For example, the compounds of Formula I may exist in several tautomeric forms, including the enol and imine form, the amide and imidic acid form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates. Even though one tautomer may be described, the present invention includes all tautomers of the compounds of Formula I. For example, when one of the following two tautomers (wherein R can be, for example, phenyl that is further substituted) is disclosed, those skilled in the art would readily recognize the other tautomer.

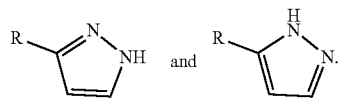

The present invention includes all pharmaceutically acceptable isotopically labelled compounds of Formula I or salts thereof wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and $^{13}$N, can be useful in Positron Emission Topography (PET) studies for examining substrate receptor occupancy.

Isotopically labeled compounds of Formula I can generally be prepared by conventional techniques known to those skilled in the art or by processes analogous to those described in the accompanying Examples and Preparations using an appropriate isotopically labeled reagent in place of the non-labeled reagent previously employed.

The present invention also provides compositions (e.g., pharmaceutical compositions) comprising a novel compound of Formula I. Accordingly, in one embodiment, the invention provides a pharmaceutical composition comprising (a therapeutically effective amount of) a novel compound of Formula I or a pharmaceutically acceptable salt thereof and optionally comprising a pharmaceutically acceptable carrier. In one further embodiment, the invention provides a pharmaceutical composition comprising (a therapeutically effective amount of) a compound of Formula I or a pharmaceutically acceptable salt thereof, optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I or salt thereof and a pharmaceutically acceptable carrier.

Compounds of Formula I (including salts thereof) are MAGL inhibitors. In some embodiments, the IC$_{50}$ of a compound of Formula I (or its metabolite) is less than about 10 µM, 5 µM, 2 µM, 1 µM, 500 nM, 200 nM, 100 nM, 50, 40, 30, 20, 10, 5, 2, or 1 nM as determined by the method in Example AA described herein below.

Administration of the compounds of Formula I (including salts thereof) may be effected by any method that enables delivery of the compounds to the site of action. These methods include, for example, enteral routes (e.g., oral routes, buccal routes, sublabial routes, sublingual routes), oral routes, intranasal routes, inhaled routes, intraduodenal routes, parenteral injection (including intravenous, subcutaneous, intramuscular, intravascular or infusion), intrathecal routes, epidural routes, intracerebral routes, intracerbroventricular routes, topical, and rectal administration.

In one embodiment of the present invention, the compounds of Formula I may be administered/effected by parenteral injection routes (e.g., intravenous injection route).

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with an at least one additional pharmaceutical or medicinal agent (e.g., an anti-schizophrenia agent), either sequentially or simultaneously.

The present invention includes the use of a combination of a compound of Formula I (including a salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including a pharmaceutically acceptable salt thereof); (b) a second pharmaceutically active agent; and (c) a pharmaceutically acceptable carrier, vehicle or diluent.

Various pharmaceutically active agents may be selected for use in conjunction with the compounds of Formula I, depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-ß (or fragments thereof), such as Aß$_{1-15}$ conjugated to pan HLA DR-binding epitope (PADRE) and ACC-001 (Elan/Wyeth);

(iii) antibodies to amyloid-ß (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 or M4 subtype) agonists such as bethanechol chloride (DUVOID, URECHOLINE);

(xxvi) neuroprotective drugs such as 2,3,4,9-tetrahydro-1H-carbazol-3-one oxime;

(xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g., PDE10A) inhibitors such as papaverine;

(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));

(xxxi) quinolines such as quinine (including its hydrochloride, dihydrochloride, sulfate, bisulfate and gluconate salts);

(xxxii) β-secretase inhibitors such as WY-25105;

(xxxiii) γ-secretase inhibitors such as LY-411575 (Lilly);

(xxxiv) serotonin (5-hydroxytryptamine) 1A (5-HT$_{1A}$) receptor antagonists such as spiperone;

(xxxv) serotonin (5-hydroxytryptamine) 4 (5-HT$_4$) receptor agonists such as PRX-03140 (Epix);

(xxxvi) serotonin (5-hydroxytryptamine) 6 (5-HT$_6$) receptor antagonists such as mianserin (TORVOL, BOLVIDON, NORVAL);

(xxxvii) serotonin (5-HT) reuptake inhibitors such as alaproclate, citalopram (CELEXA, CIPRAMIL);

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline; (xxxix) antihemorrhagic (i.e., hemostatic) agents such as rivaroxaban or apixaban; and the like.

The compound of Formula I (including a salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a MAGL-mediated disease or disorder in a mammal, comprising administering to the mammal an effective amount of a compound of Formula I (including a pharmaceutically acceptable salt thereof) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's, anti-anxiety, and antihemorrhagic agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical antidepressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone. Some additional "another active agent" examples include rivastigmine (Exelon), Clozapine, Levodopa, Rotigotine, Aricept, Methylphenidate, memantine. milnacipran, guanfacine, bupropion, and atomoxetine. Examples of antihemorrhagic agents (including, e.g., coagulation factors, activators, or stabilizers) include Factor Xa inhibitors (e.g., rivaroxaban or apixaban) and recombinant Coagulation Factor VIIa (e.g., NovoSeven®).

As noted above, the compounds of Formula I or salts thereof may be used in combination with one or more additional anti-Alzheimer's agents which are described herein. When a combination therapy is used, the one or more additional anti-Alzheimer's agents may be administered sequentially or simultaneously with the compound of the invention. In one embodiment, the additional anti-Alzheimer's agent(s) is(are) administered to a mammal (e.g., a human) prior to administration of the compound of the invention. In another embodiment, the additional anti-Alzheimer's agent(s) is(are) administered to the mammal after administration of the compound of the invention. In another embodiment, the additional anti-Alzheimer's agent(s) is(are) administered to the mammal (e.g., a human) simultaneously with the administration of the compound of the invention (or a pharmaceutically acceptable salt thereof).

The invention also provides a pharmaceutical composition for the treatment of an inflammatory disorder (e.g., nueroinflammation) in a mammal, including a human, which comprises an amount of a compound of Formula I (including a salt thereof), as defined above (including hydrates, solvates and polymorphs of said compound or pharmaceutically acceptable salts thereof), in combination with one or more (for example one to three) anti-inflammation agents, wherein the amounts of the active agent and the combination when taken as a whole are therapeutically effective for treating the inflammatory disorder.

The invention also provides a pharmaceutical composition for treating a MAGL-mediated disease or disorder in a mammal, including a human, which comprises an amount of a compound of Formula I (including a salt thereof), as defined above (including hydrates, solvates and polymorphs of said compound or a salt thereof), in combination with one or more (for example one to three) other agents for treating the MAGL-mediated disease or disorder, wherein the amount of the active agents and the combination when taken as a whole are therapeutically effective for treating the MAGL-mediated disease or disorder.

It will be understood that the compounds of Formula I depicted above are not limited to a particular stereoisomer (e.g., enantiomer or diasteroisomer) shown, but also include all stereoisomers and mixtures thereof.

DETAILED DESCRIPTION OF THE INVENTION

Compounds of the invention, including salts of the compounds, can be prepared using known organic synthesis techniques and can be synthesized according to any of numerous possible synthetic routes. The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC) or thin layer chromatography (TLC).

Compounds of Formula I, salts, and intermediates thereof may be prepared according to the following reaction schemes and accompanying discussion. Unless otherwise indicated, $R^1$, $R^2$, $R^{2A}$, $R^S$, $R^3$, $R^4$, $R^5$, ring $A^1$, n1 and structural Formula I (including, e.g., I-1, I-2, I-3) in the reaction schemes and discussion that follow are as defined above. In general, the compounds of this invention may be made by processes which include processes analogous to those known in the chemical arts, particularly in light of the description contained herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

Scheme 1 refers to the synthesis of compounds of Formula I. A compound of Formula 1-3 [wherein Pg$^1$ is an alcohol protecting group such as p-methoxbenzyl(PMB) or tert-butyldimethyl silyl (TBDMS)] can be prepared by reacting an amine of Formula 1-1 with a compound of Formula 1-2 using standard methods of carbamate formation well known to those skilled in the art [for example, in the presence of phosgene, triphosgene, or a suitably activated carbonate reagent such as bis(pentafluorophenyl)carbonate or N,N'-disuccinimidyl carbonate]. Carbamate formation may be accomplished in the presence of a base (such as triethylamine or hunigs base). Alternatively, the compound of Formula 1-3 may be obtained by reaction of an amine of Formula 1-1 with a compound of Formula 1-2a [wherein Lg$^1$ is a leaving group such as pentafluorophenoxy] in the presence of a base such as trimethylamine, in a suitable aprotic solvent such as acetonitrile. Amines of Formula 1-1 may be obtained commercially, synthesized by methods described herein, or made by other methods well known to those skilled in the art. A compound of Formula 1-4 may be obtained by deprotecting the compounds of Formula 1-3, using appropriate conditions depending on the selection of the Pg$^1$ group. For example, where Pg$^1$ is PMB or TBDMS, treatment with an acid such as trifluoroacetic acid in aprotic solvent such as dichloromethane may be employed. The compound of Formula 1-4 (which is a compound of Formula I wherein R$^1$ is H) may optionally be converted to a compound of Formula I wherein R$^1$ is other than H. For example, reaction of the alcohol of Formula 1-4 with diphosphoryl tetrachloride in a suitable solvent such as acetonitrile affords compounds of Formula I where R$^1$ is —P(=O)(OH)$_2$ or a salt thereof. For another example, reaction of the alcohol of Formula 1-4 with a sulfating agent [e.g. SO$_3$, sulfamic acid H$_2$N—S(=O)$_2$(OH), chlorosulfonic acid HO—S(=O)$_2$(Cl)] under suitable conditions can afford a compound of Formula I wherein R$^1$ is —S(=O)$_2$(OH) or a salt thereof.

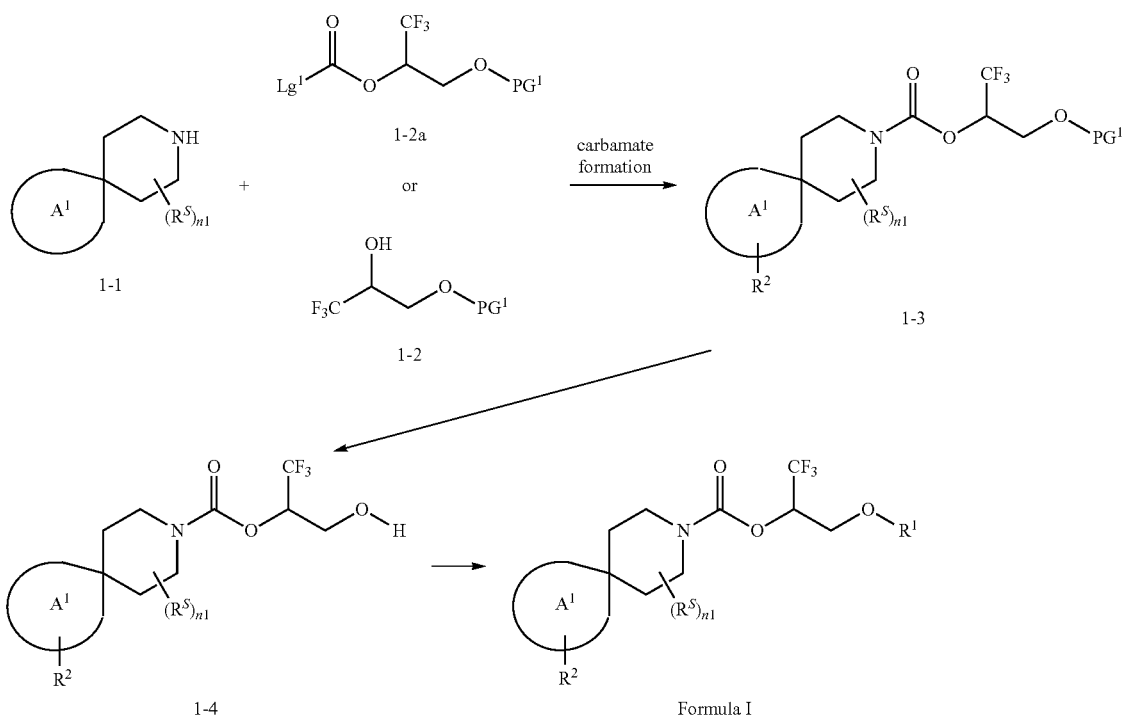

Scheme 2 refers to a synthesis of a compound of Formula 2-3 [wherein $Pg^1$ is an alcohol protecting group such p-methoxybenzyl] and/or a compound of formula 2-4 [where $Lg^1$ is a leaving group such as pentafluorophenoxy]. Referring to Scheme 2, reaction of an epoxide of Formula 2-1 with an alcohol of Formula 2-2, in the presence of a base (e.g. sodium hydroxide) in a in non-protic solvent (e.g. THF or DMF), affords a compound of Formula 2-3, which can be used as a compound of Formula 1-2 in Scheme 1. The compound of Formula 2-3 can subsequently be converted to a compound of Formula 2-4 wherein where $Lg^1$ is a leaving group. For example, where $Lg^1$ is pentafluorophenoxy, reaction of the compound of formula 2-3 with a compound such as bis(pentafluorophenyl) carbonate in the presence of a base such as trimethylamine affords a compound of Formula 2-4. The compound of Formula 2-4 can be used as a compound of Formula 1-2a in Scheme 1.

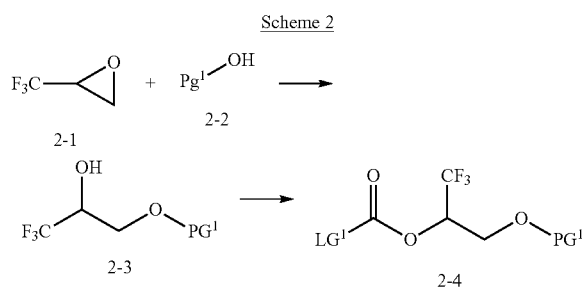

Scheme 3 refers to the synthesis of a compound of formula 3-5 [where $R^{2A}$ is, for example, $R^5$ such as 1H-pyrazolyl or 5- or 6-membered heteroaryl (e.g. pyridinyl) that is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy]. Referring to Scheme 3, an amine of Formula 3-1 may undergo carbamate formation with a compound of Formula 3-2 (which can be the same as the compound of Formula 2-4) in the presence of a base (e.g. trimethylamine) and a suitable solvent, to afford bromide intermediate of Formula 3-3. The bromide intermediate of Formula 3-3 can undergo further transformations to give a bromide compound of Formula 3-4. For example, treatment of bromide intermediate of Formula 3-3 with a 1H-pyrazole compound (which is un-substituted on the 1-position, but is optionally substituted on the 3-, 4-, and/or 5-position) in the presence of an appropriate base (e.g. $Cs_2CO_3$) in a solvent such as dimethylformamide at elevated temperature (e.g. 80° C.) affords a compound of Formula 3-4 wherein $R^{2A}$ is an optionally substituted 1H-pyrazol-1-yl. For another example, a compound of Formula 3-4 (wherein $R^{2A}$ is $R^5$ such as an optionally substituted 5- or 6-membered heteroaryl) may be prepared by coupling an aryl- or heteroaryl-halide ($R^5$—$X^1$, wherein $X^1$ is a halogen such as Cl or Br) with bromide intermediate of Formula 3-3 using a catalytic system such as Nickel(II) chloride 1,2-dimethoxyethane, phenanthroline, sodium tetrafluoroborate and powdered manganese, in a solvent such as ethyl pyridine in an inert atmosphere at 60° C.

Alternatively, the compound of Formula 3-4 may be obtained by coupling an aryl- or heteoroaryl-halide with a boronate compound such as a boronate compound of Formula 3-6 (which may be prepared by standard methods known to those skilled in the art) to give an alkene of Formula 3-7, followed by reduction of the alkene of Formula 3-7 to give the compound of Formula 3-4. Some example conditions of coupling include a catalyst such as [1,1'-bis (diphenylphosphino)ferrocene]dichloropalladium(II), with base such as cesium fluoride, in a solvent such as 1,4-dioxane in the presence of water. Reduction of the alkene group of the compound of Formula 3-7 can be effected by hydrogenation, for example, $H_2$ in the presence of a metal catalyst such as palladium on carbon in a solvent such as ethyl acetate, to give a compound of Formula 3-4.

The compound of Formula 3-4 can be deprotected to afford a compound of Formula 3-5 under appropriate conditions depending on the selection of $Pg^1$. For example, where $Pg^1$ is p-methyoxybenzyl deprotection may be effected by treatment with acid such as trifluoroacetic acid; alternatively, by hydrogenolysis of the compound of Formula 3-4, with $H_2$ at elevated pressure, and using a catalyst such as palladium on carbon.

1-position, but is optionally substituted on the 3-, 4-, and/or 5-position; wherein t1 is 0, 1, 2, or 3; and each $R^{30}$ is independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy) in the presence of a base such as cesium carbonate, in an aprotic solvent (e.g. DMF). Deprotection of the Compound of Formula 4-4 then affords the amine compound Formula 4-5 depending on the choice of protecting group $Pg^2$. For example, where $Pg^2$ is BOC, deprotection can be achieved by treatment with trifluoroacetic acid.

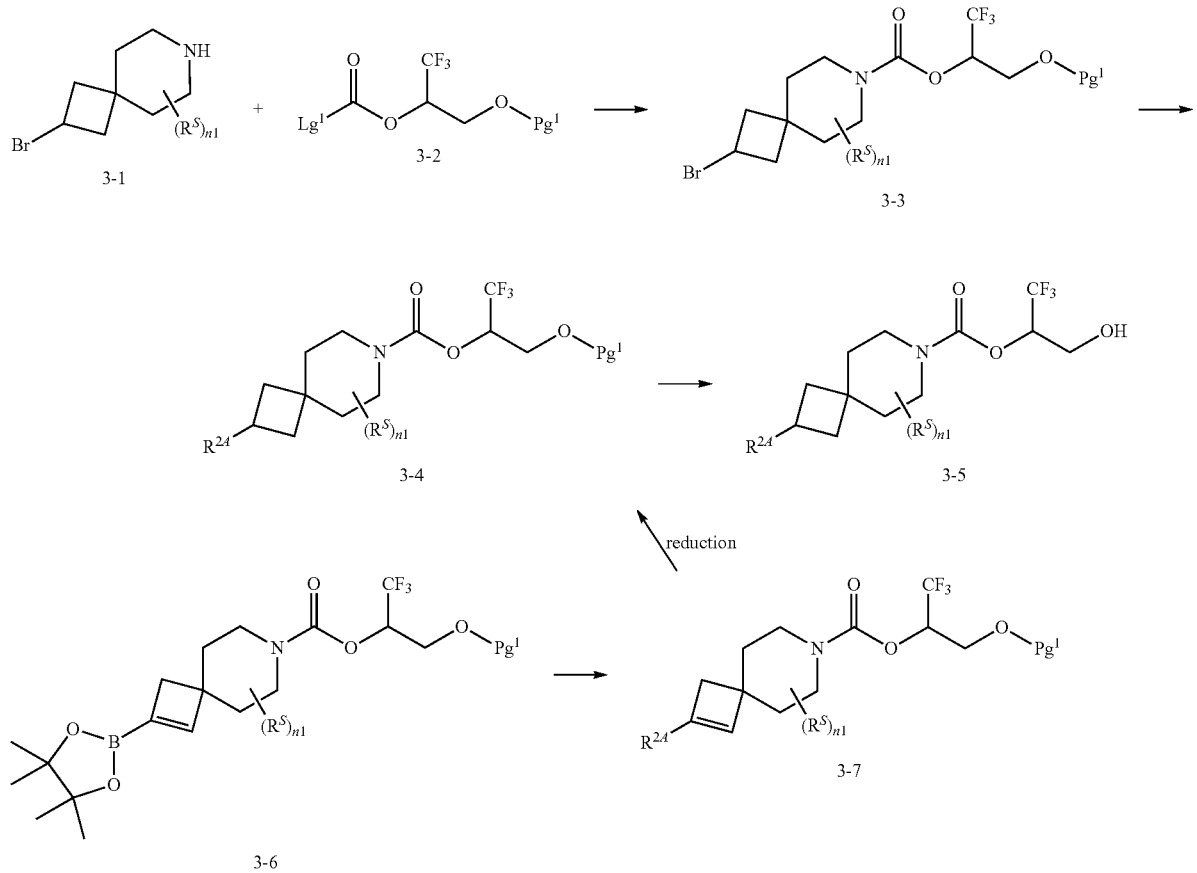

Scheme 3

Scheme 4 refers to the preparation of an amine of Formula 4-5, which may be used as a compound of Formula 1-1 in Scheme 1. A compound of formula 4-1 (wherein $Pg^2$ is a protecting group such as BOC) can be converted to a compound of Formula 4-2 [where $Lg^2$ is a leaving group such as tosylate], by treatment with a reagent such a tosyl chloride in the presence of a catalyst such as dimethylaminopyridine, in an appropriate solvent (e.g. dichloromethane). The compound of Formula 4-2 can be converted to a compound of Formula 4-4 by reacting with a 1H-pyrazole compound of Formula 4-3 (which is un-substituted on the

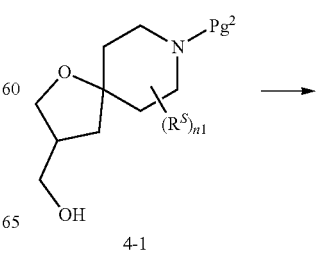

Scheme 4

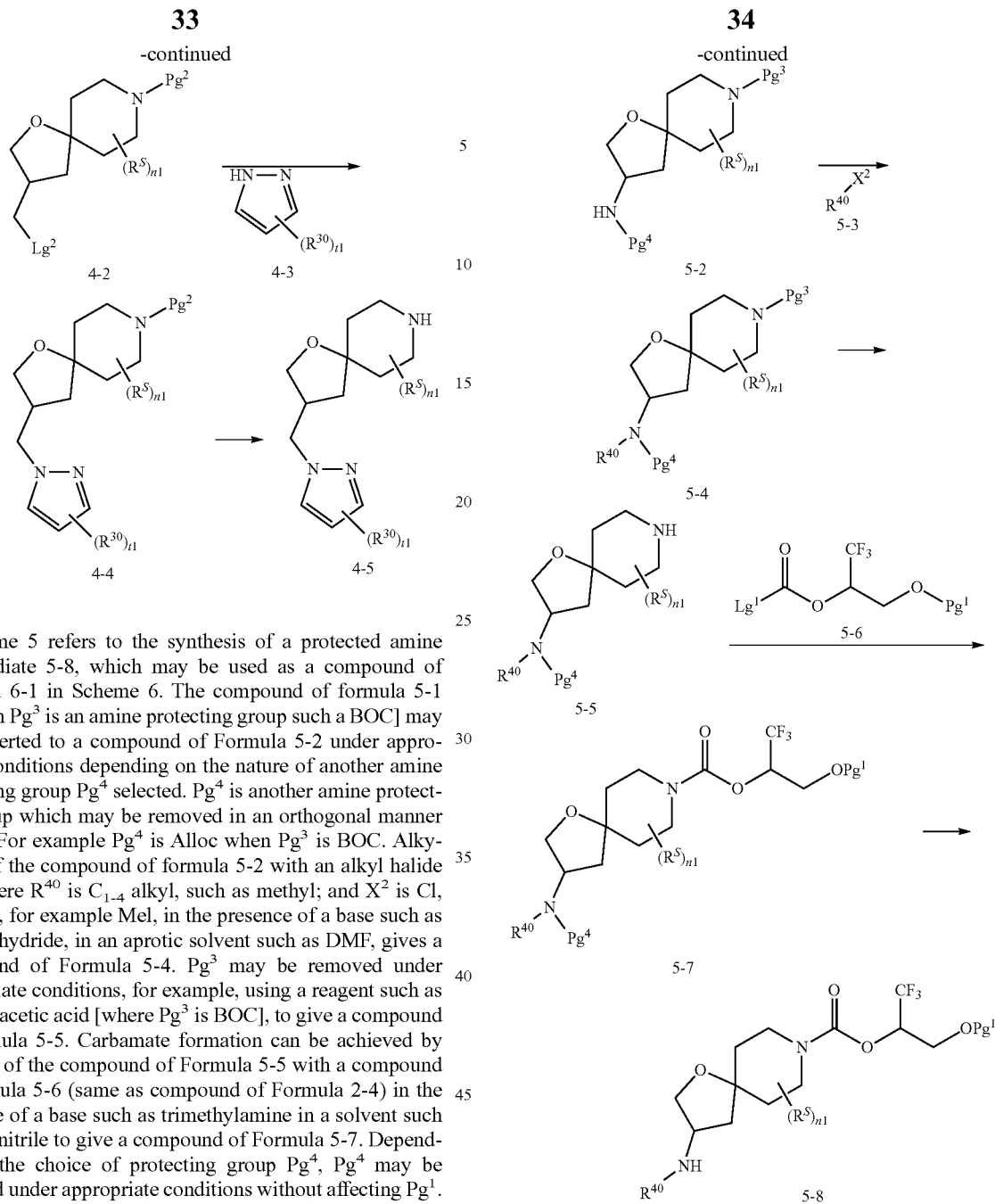

Scheme 5 refers to the synthesis of a protected amine intermediate 5-8, which may be used as a compound of Formula 6-1 in Scheme 6. The compound of formula 5-1 [wherein $Pg^3$ is an amine protecting group such a BOC] may be converted to a compound of Formula 5-2 under appropriate conditions depending on the nature of another amine protecting group $Pg^4$ selected. $Pg^4$ is another amine protecting group which may be removed in an orthogonal manner to $Pg^3$. For example $Pg^4$ is Alloc when $Pg^3$ is BOC. Alkylation of the compound of formula 5-2 with an alkyl halide 5-3 (where $R^{40}$ is $C_{1-4}$ alkyl, such as methyl; and $X^2$ is Cl, Br, or I), for example MeI, in the presence of a base such as sodium hydride, in an aprotic solvent such as DMF, gives a compound of Formula 5-4. $Pg^3$ may be removed under appropriate conditions, for example, using a reagent such as trifluoroacetic acid [where $Pg^3$ is BOC], to give a compound of Formula 5-5. Carbamate formation can be achieved by reaction of the compound of Formula 5-5 with a compound of Formula 5-6 (same as compound of Formula 2-4) in the presence of a base such as trimethylamine in a solvent such as acetonitrile to give a compound of Formula 5-7. Depending on the choice of protecting group $Pg^4$, $Pg^4$ may be removed under appropriate conditions without affecting $Pg^1$. For example, where $Pg^4$ is Alloc (and $Pg^1$ is PMB), the compound of formula 5-7 may be treated with Tetrakis(triphenylphosphine)palladium(0) in the presence of 1,3-dimethylpyrimidine-2,4,6(1H,3H,5H)-trione, in a solvent such as THF to give a compound of Formula 5-8.

Scheme 5

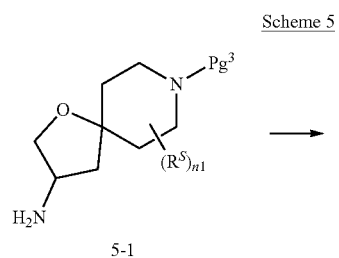

As shown in Scheme 6, a method for preparing a compound of Formula 6-6 or 6-7 (wherein each of $R^{41}$ and $R^{42}$ can be, for example, alkyl, cycloalkyl, aryl, heteroaryl, cycloalkylalkyl, arylalkyl, or heteroarylalkyl) is provided. Sulfonylation of the compound of Formula 6-1 with a reagent of Formula 6-2 (where $Lg^3$ is a leaving group such as chloride) in the presence of a base such as hunig's base, gives a sulfonamide of Formula 6-3. Deprotection of $Pg^1$ using a method appropriate for the protecting group affords a compound of Formula 6-7. Similarly, coupling of a compound of Formula 6-1 with a compound of Formula 6-4 [where $Lg^4$ is OH or a leaving group such as chloride], for example, where $Lg^4$ is OH, using a standard coupling reagent such as HATU in the presence of an organic base (e.g. diisopropyl ethylamine) provides an amide of Formula 6-5. An alternative method for generating the compound of Formula 6-5 is acylation with an acyl chloride such as a compound of formula 6-4, where Lg⁴ is a halide such as chloride. Removal of the protecting group Pg$^1$ from the compound of Formula 6-5 under appropriate conditions known to those skilled in the art affords a compound of Formula 6-6.

tosylate; and m is 1 or 2] with a 1H-pyrazole compound of Formula 7-2 (which is un-substituted on the 1-position, but is optionally substituted on the 3-, 4-, and/or 5-position; wherein t1 is 0, 1, 2, or 3; and each $R^{30}$ is independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ Scheme 6

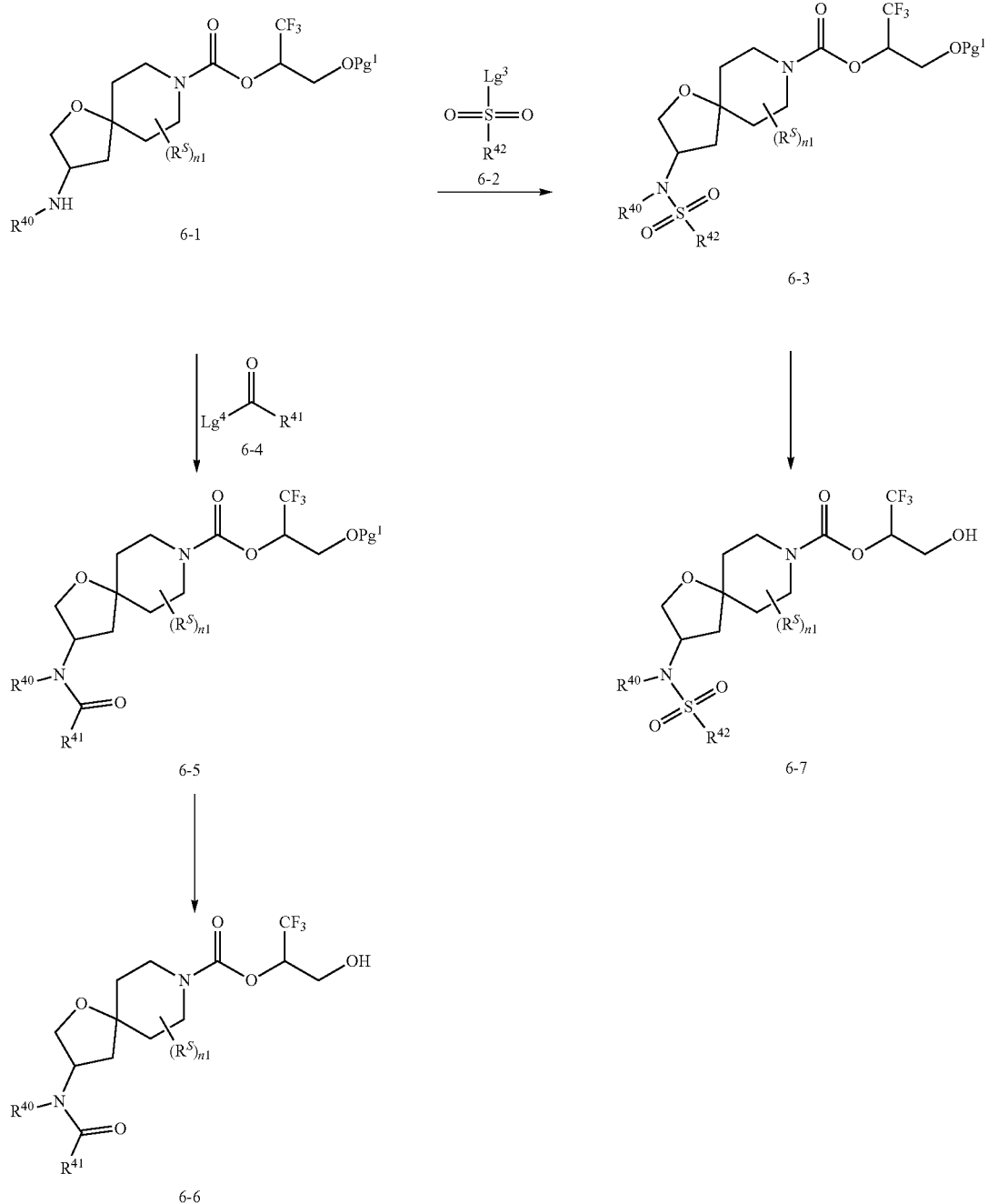

Scheme 7 refers to a method of preparation of an amine of Formula 7-4, which may be used as a compound of Formula 1-1 in Scheme 1. Treatment of a compound of Formula 7-1 [where Pg$^5$ is an amine protecting group such as BOC; $Y^1$ is a leaving group such as Br, mesylate, or tosylate] haloalkoxy) in the presence of a base such as cesium carbonate, in a solvent such as DMF at an appropriate temperature (e.g. 80° C.) affords a compound of Formula 7-3. The protecting group Pg$^5$ may be cleaved using standard conditions to give the amine of Formula 7-4.

Scheme 7

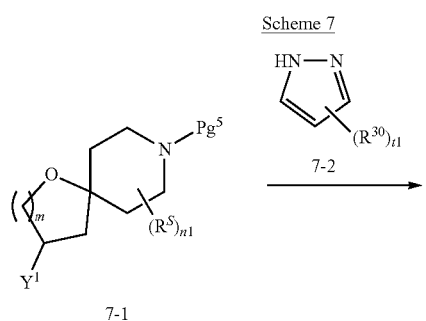

substituted aryl or heteroaryl] to the bromide of Formula 8-3 to give a compound of Formula 8-5 can be accomplished using a catalyst such as nickel iodide and a strong base such as sodium bis(trimethylsilyl)amide, in the presence of a ligand such as trans-2-aminocyclohexanol. The reaction can be carried out in protic solvent such as 2-propanol at an elevated temperature (e.g. about 60° C.). The protecting group $Pg^1$ of the compound of Formula 8-5 can be removed to form a compound of Formula 8-6 under appropriate conditions, for example, where $Pg^1$ is PMB, by treatment with an organic acid such as trifluoroacetic acid.

Scheme 8

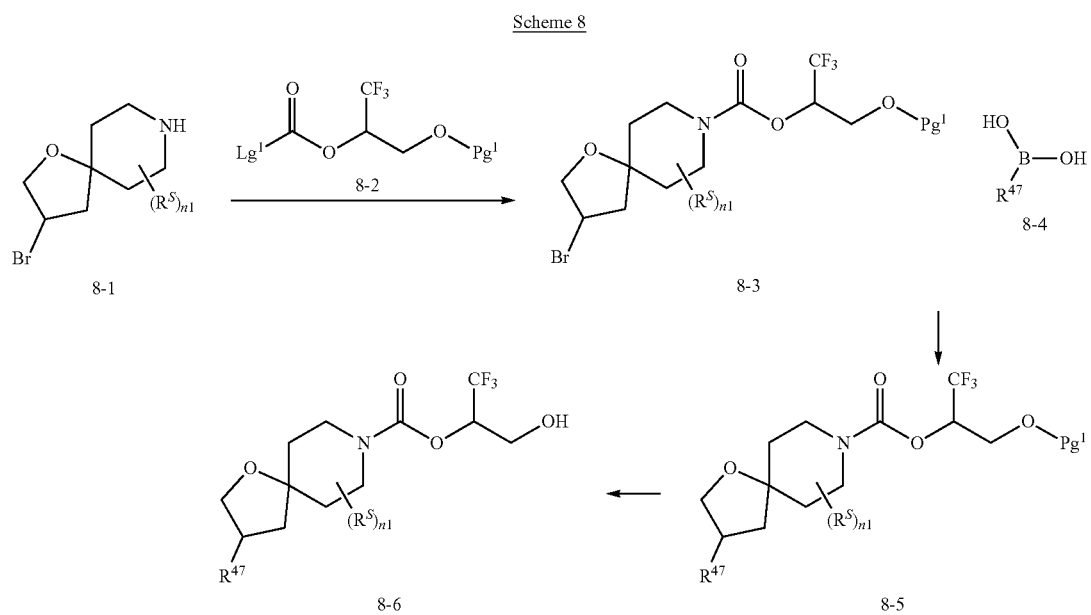

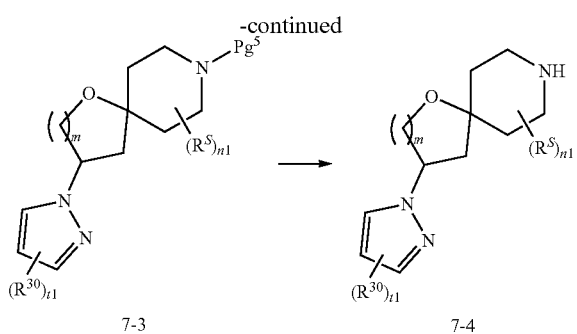

Scheme 8 refers to a synthesis of a compound of Formula 8-6. A carbamate of Formula 8-3 can be prepared by reaction of a compound of Formula 8-1 with a compound of Formula 8-2 [same as the compound of Formula 2-4, for example, where $Lg^1$ is pentafluorophenoxy] in the presence of base such as trimethylamine. Coupling of a boronic acid of Formula 8-4 [where $R^{47}$ can be, for example, optionally Scheme 9 refers to preparation of a compound of Formula 9-7. A compound of Formula 9-2 wherein $-O-Z^1$ is a leaving group such as a triflate group (i.e. $Z^1$ is $-SO_2CF_3$) can be synthesized by treatment of a ketone of Formula 9-1 [wherein $Pg^4$ is a amine protecting group such as BOC; and m is 1 or 2] with a strong base such as potassium bis(trimethylsilyl)amide and triflating reagent such as 1,1,1-trifluoro-N-phenyl-N-[(trifluoromethyl)sulfonyl]-methanesulfonamide. The reaction can be carried out in an aprotic solvent such as THF at an appropriate temperature (e.g. about −70° C.). The triflate such as that of Formula 9-2 may be converted into an boronic ester such as that in the compound of Formula 9-3 by coupling with 4,4,4',4',5,5,5',5'-octamethyl-2,2'-bi-1,3,2-dioxaborolane via a palladium catalyzed coupling with an appropriate catalyst system. Some example conditions include, treatment with [1,1'-bis(diphenylphosphino)-ferrocene]dichloropalladium(II) catalyst and 1,1'-bis(diphenylphosphino)-ferrocene ligand, in a solvent such as 1,4-dioxane at an appropriate temperature (e.g. about 80° C.). Boronic ester of Formula 9-3 may be coupled with aryl- or heteroaryl-bromide of Formula 9-4 [where $R^{47}$ can be, e.g., optionally substituted aryl or heteroaryl; and $X^3$ is a halogen such as Br or Cl] using standard palladium catalyzed coupling conditions to give a compound of Formula 9-5. Some example conditions include a catalyst such as [1,1'-bis(diphenylphosphino)ferrocene]dichloropalladium(II), with base such as cesium fluoride, in a solvent such as 1,4-dioxane in the presence of water. Reduction of the alkene group of the compound of Formula 9-5 can be effected by hydrogenation, for example, at 1-6 atm of $H_2$ in the presence of a metal catalyst such as palladium on carbon or Raney nickel in a protic solvent such as MeOH or EtOH to give a compound of Formula 9-6. Deprotection of compound of Formula 9-6 can be achieved by standard methods depending on the protecting group. The compound of Formula 9-7 can be used as a compound of Formula 1-1 in Scheme 1.

Scheme 10 refers to a preparation of an amine of Formula 10-8, which may be used as an amine of Formula 1-1 in Scheme 1. A compound of Formula 10-4 [wherein $Pg^5$ is an amine protecting group such as Cbz and $Pg^6$ is an orthogonally cleavable amine protecting group such as BOC] can be obtained by alkylation of a compound of Formula 10-2 with an alkyl halide of Formula 10-3 [wherein $X^4$ is halogen such as Cl, Br or I] such as methyl iodide, in the presence of a base such as sodium hydride in a polar aprotic solvent such as DMF. Removal of $Pg^6$ can be achieved using methods known to those skilled in the art. For example, where $Pg^6$ is a BOC then treatment with organic acid such as trifluoroacetic acid in a solvent such as dicloromethane affords an amine of Formula 10-5. Treatment of the amine of Formula 10-5 with a reagent such as a sulfonyl chloride, or alternatively activated sulfonylating reagent of formula 10-6 (wherein $Lg^5$ is a leaving group) affords a sulfonamide of formula 10-7. Subsequently, $Pg^5$ may be removed using methods well known to those skilled in the art. For example, where $Pg^5$ is a Cbz group, it can be cleaved by hydrogenolysis.

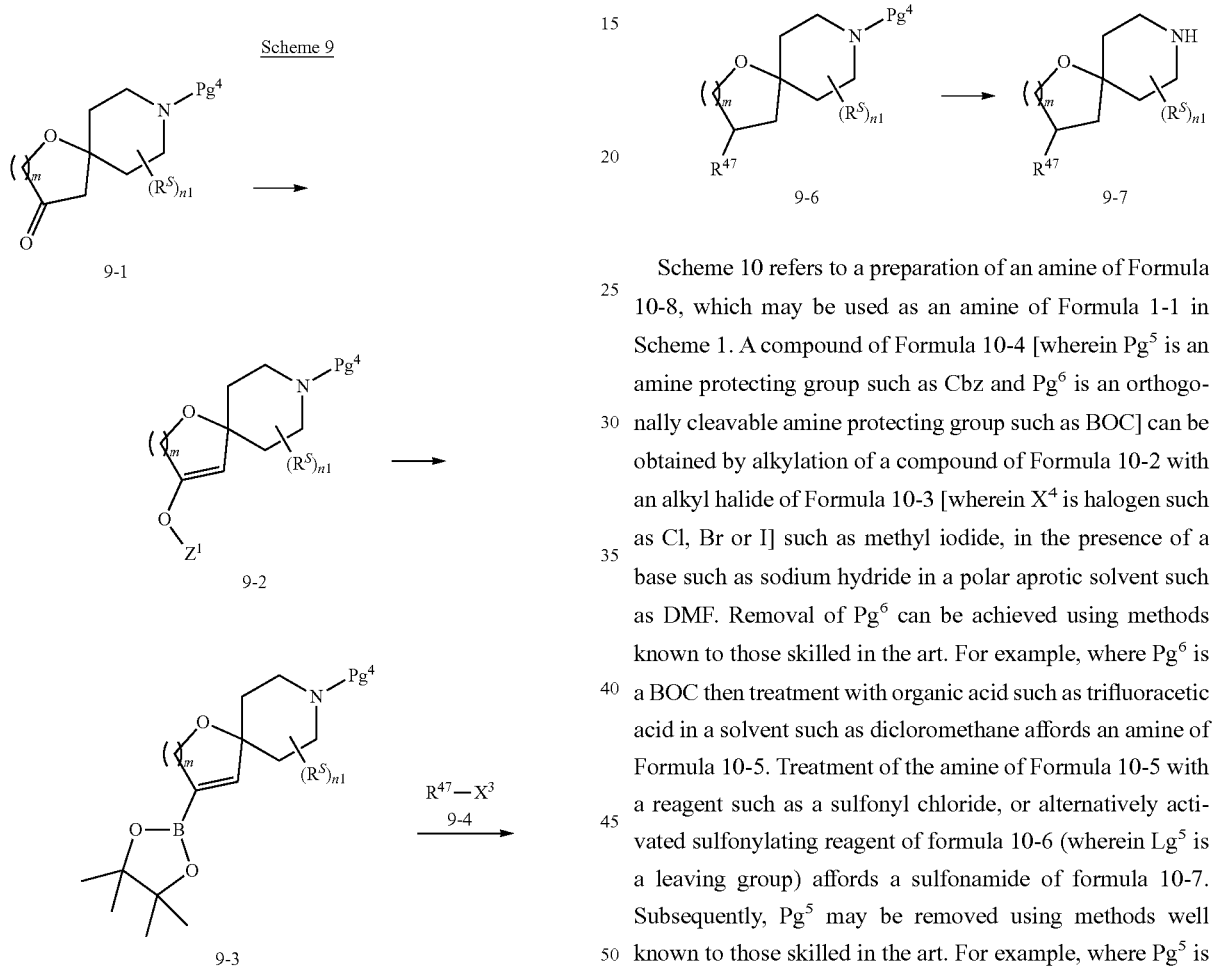

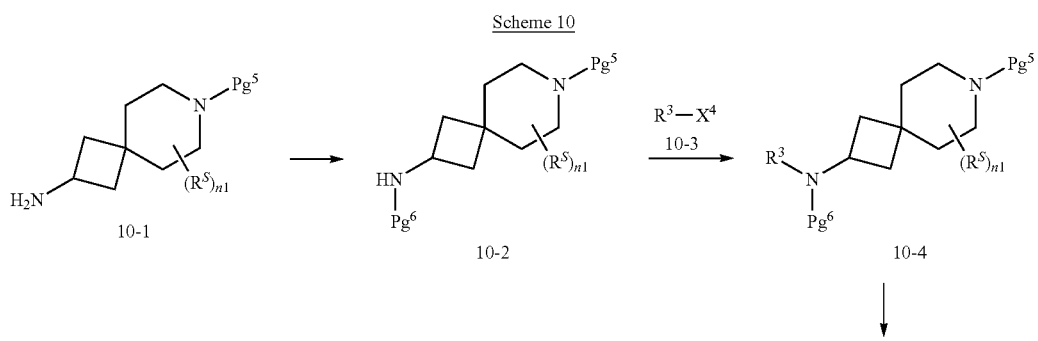

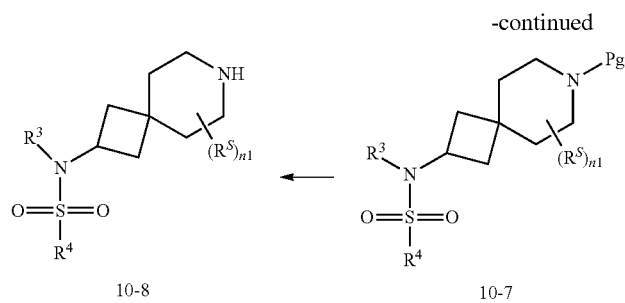
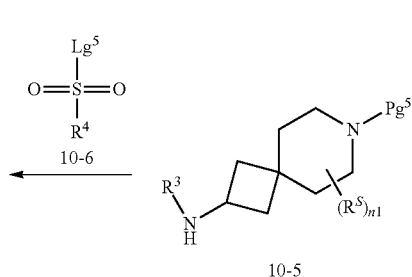

Scheme 11 refers to a synthesis of a heteroaryl ether or aryl ether of Formula 11-4. Mitsunobu reaction of an aryl or heteroaryl alcohol of Formula 11-2 with an alcohol of Formula 11-1 affords a compound of Formula 11-3 (wherein $Pg^7$ is an amine protecting group, e.g. BOC). Example Mitsonobu conditions include treatment with diisopropyl azodicarboxylate and triphenylphospine in an aprotic solvent such as THF, at room temperature. An alternative method for preparation of the compound of Formula 11-3 involves coupling a compound of Formula 11-1 with a compound of Formula 11-2a [where $X^5$ is a leaving group such as halide, for example chloride or bromide], using a palladium catalyst and suitable ligand. Example conditions include use of Tris(dibenzylideneacetone)dipalladium(0) and Josiphos ligand in the presence of a base such cesium carbonate in solvent such as toluene at an elevated temperature (e.g. 80° C.). Another additional method for preparation of a compound of Formula 11-3 involves halide displacement of a compound of Formula 11-2a [where $X^5$ is for example bromide or fluoride], in the presence of a base such as sodium hydride in an aprotic polar solvent such as DMF.

Removal of $Pg^7$ from the compound Formula 11-3 then results in formation of the compound of Formula 11-4.

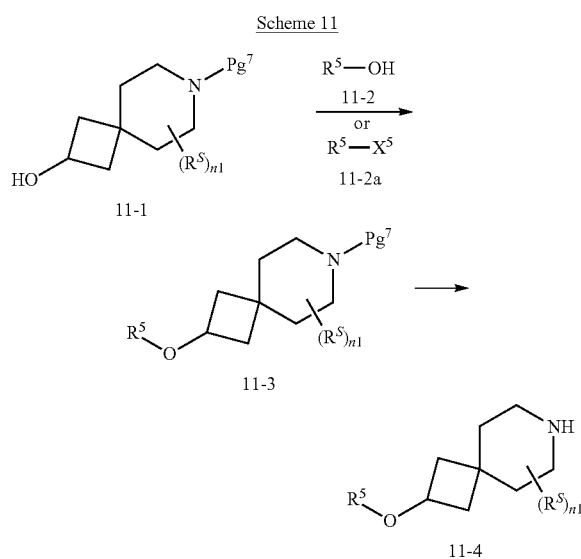

Scheme 11

Additional starting materials and intermediates useful for making the compounds of the present invention can be obtained from chemical vendors such as Sigma-Aldrich or can be made according to methods described in the chemical art.

Those skilled in the art can recognize that in all of the schemes described herein, if there are functional (reactive) groups present on a part of the compound structure such as a substituent group, for example $R^1$, $R^2$, $R^S$, $R^{2A}$, $R^3$, $R^4$, $R^5$, etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion (CN—). For another example, an —S— can be oxidized to —S(=O)— and/or —S(=O)$_2$—. For yet another example, an unsaturated bond such as C=C or C≡C can be reduced to a saturated bond by hydrogenation. For yet another example, an amino group can be converted to an amide or sulfonamide group. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^1$, $R^2$, $R^3$, $R^4$, $R^5$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an NH$_2$ group can be protected by a benzyloxycarbonyl (Cbz) or BOC group; conversion back to the NH$_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high-performance liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., Stereochemistry of Organic Compounds by E. L. Eliel and S. H. Wilen (Wiley, New York, 1994), the disclosure of which is incorporated herein by reference in its entirety. Suitable stereoselective techniques are well known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula I-a or I-b) may be prepared by, e.g., one or more of three methods:
(i) by reacting the compound of Formula I with the desired acid or base;
(ii) by removing an acid- or base-labile protecting group from a suitable precursor of the compound of Formula I or by ring-opening a suitable cyclic precursor, for example, a lactone or lactam, using the desired acid or base; or
(iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in Remington's Pharmaceutical Sciences, 19th Edition (Mack Publishing Company, 1995).

The compounds of the invention (including pharmaceutically acceptable salts thereof) may be administered orally. Oral administration may involve swallowing, so that the compound enters the gastrointestinal tract, and/or buccal, lingual, or sublingual administration by which the compound enters the bloodstream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast-dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form. Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line*, 25(2), 1-14 (2001). The use of chewing gum to achieve controlled release is described in WO 00/35298.

The compounds of the invention (including pharmaceutically acceptable salts thereof) may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 μg to 200 mg, which may be administered in a single dose or, more usually, as divided doses throughout the day.

The compounds of the invention (including pharmaceutically acceptable salts thereof) may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I, a prodrug thereof, or a salt of such compound or prodrug; and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen on which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXAMPLES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers or diastereomers of certain compounds of the invention or their precursors/intermediates. In some examples, the separated enantiomers are designated as ENT-1 and ENT-2, according to their order of elution. In some examples, the separated diastereomers are designated as DIAST 1 and DIAST 2, according to their order of elution; and where desigations are determined for some precursors/intermediates, these designations are carried over to their subsequent products respectively. In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Abbreviations

BOC (or Boc)—tert-butoxycarbonyl
HPLC—high-performance liquid chromatography
PMB—para-methoxybenzyl (or 4-methoxybenzyl)
psi—pounds per square inch

Example 1

(2R)-1,1,1-Trifluoro-3-hydroxypropan-2-yl 2-[4-(trifluoromethyl)-1H-pyrazol-1-yl]-7-azaspiro[3.5]nonane-7-carboxylate (1)

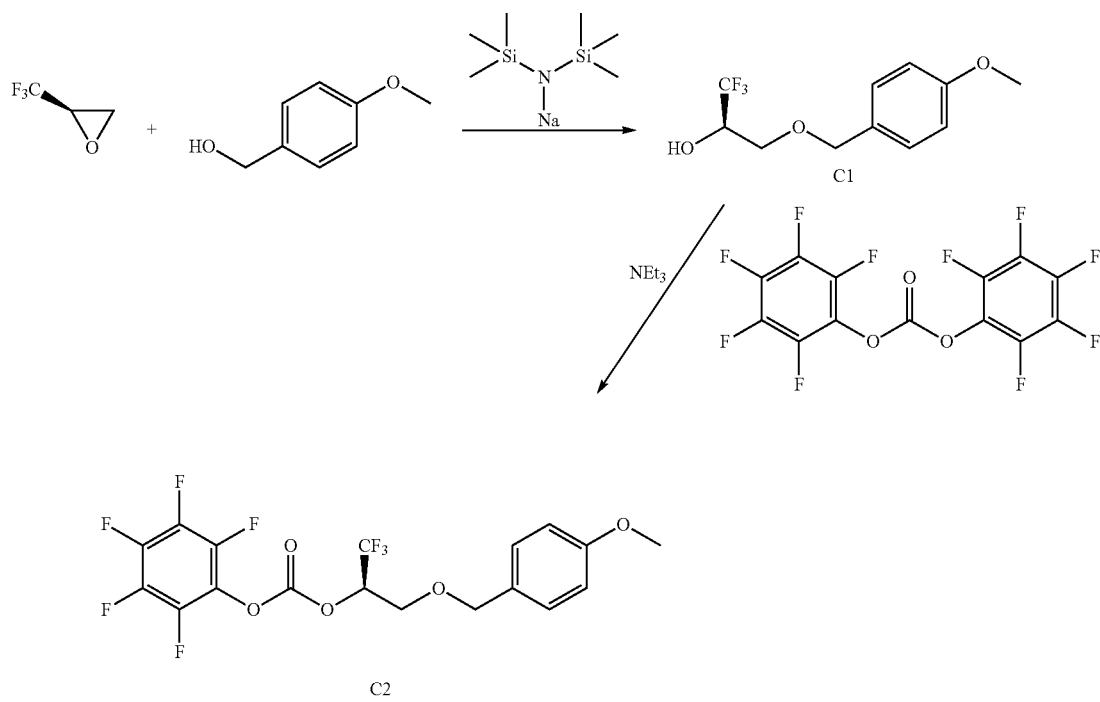

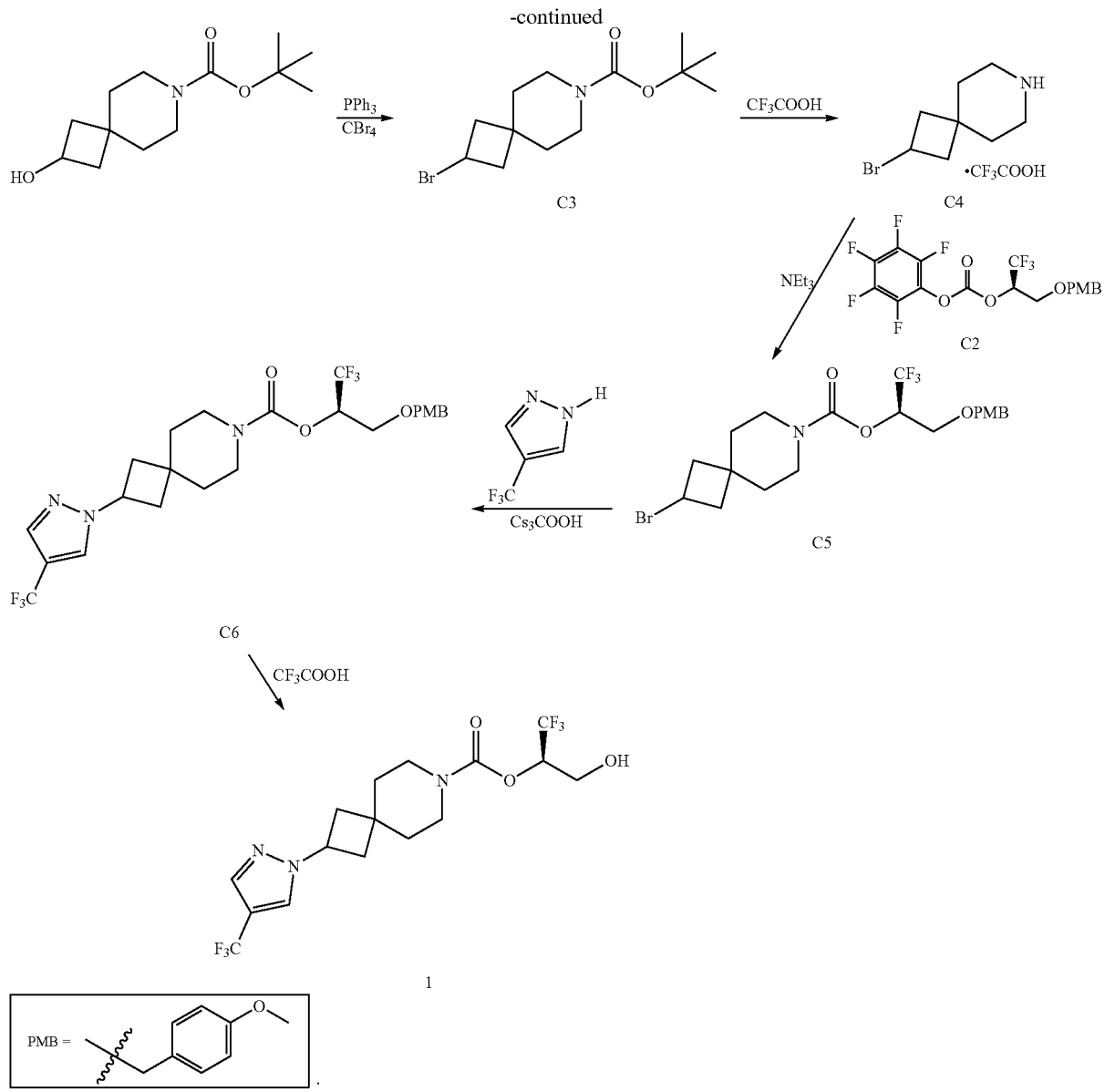

Step 1. Synthesis of (2R)-1,1,1-trifluoro-3-[(4-methoxybenzyl)oxy]propan-2-ol (C1)

(4-Methoxyphenyl)methanol (98%, 1.14 mL, 8.96 mmol) was slowly added to a 0° C. solution of sodium bis(trimethylsilyl)amide in tetrahydrofuran (1.0 M, 8.9 mL, 8.9 mmol) in a microwave vial. After the reaction mixture had stirred at 0° C. for 45 minutes, (2R)-2-(trifluoromethyl)oxirane (500 mg, 4.46 mmol) in tetrahydrofuran (2 mL) was added via syringe, and the vial was sealed and heated at 100° C. for 18 hours. The reaction mixture was then cooled to room temperature and diluted with water; the mixture was extracted twice with tert-butyl methyl ether and the combined organic layers were washed with saturated aqueous sodium chloride solution, dried over sodium sulfate, filtered, and concentrated in vacuo. Purification via chromatography on silica gel (Gradient: 0% to 60% ethyl acetate in heptane) afforded the product as a pale yellow oil. Yield: 1.09 g, 4.36 mmol, 98%. GCMS m/z 250.1 [M+]. $^1$H NMR (400 MHz, DMSO-$d_6$) δ 7.26 (d, J=8.5 Hz, 2H), 6.91 (d, J=8.5 Hz, 2H), 6.36 (d, J=6.7 Hz, 1H), 4.46 (s, 2H), 4.21-4.09 (m, 1H), 3.74 (s, 3H), 3.58 (dd, half of ABX pattern, J=10.6, 4.5 Hz, 1H), 3.48 (dd, half of ABX pattern, J=10.5, 6.3 Hz, 1H).

Step 2. Synthesis of pentafluorophenyl (2R)-1,1,1-trifluoro-3-[(4-methoxybenzyl)oxy]propan-2-yl carbonate (C2)

Bis(pentafluorophenyl) carbonate (9.44 g, 24.0 mmol) was added to a 0° C. solution of C1 (5.99 g, 23.9 mmol) in acetonitrile (100 mL). Triethylamine (12.8 mL, 91.8 mmol) was added, and the reaction mixture was allowed to warm to 25° C. and stirred for 1 hour. The resulting solution of C2 was used directly in Step 5. For subsequent syntheses described herein that utilize C2, this material was generated at the appropriate scale, and the reaction solution of C2 was used directly in the coupling reaction

Step 3. Synthesis of tert-butyl 2-bromo-7-azaspiro[3.5]nonane-7-carboxylate (C3)

A solution of tert-butyl 2-hydroxy-7-azaspiro[3.5]nonane-7-carboxylate (4.87 g, 20.2 mmol) in tetrahydrofuran (65 mL) was cooled to 0° C. and treated with triphenylphosphine (6.35 g, 24.2 mmol), followed by tetrabromomethane (8.03 g, 24.2 mmol). After 30 minutes, the reaction mixture was warmed to room temperature and allowed to stir for 3.5 hours, whereupon it was concentrated in vacuo to afford a light brown solid. This material was combined with the crude material from a similar reaction carried out using tert-butyl 2-hydroxy-7-azaspiro[3.5]nonane-7-carboxylate (1.12 g, 4.64 mmol) and subjected to silica gel chromatography (Gradient: 5% to 10% ethyl acetate in heptane), affording the product as a white solid. Combined yield: 5.62 g, 18.5 mmol, 74%. GCMS m/z 303.0 (bromine isotope pattern observed) [M+]. $^1$H NMR (400 MHz, CDCl$_3$) δ 4.49 (quint, J=7.8 Hz, 1H), 3.36-3.27 (m, 4H), 2.65-2.57 (m, 2H), 2.34-2.26 (m, 2H), 1.68-1.62 (m, 2H), 1.57-1.51 (m, 2H), 1.45 (s, 9H).

Step 4. Synthesis of 2-bromo-7-azaspiro[3.5]nonane, trifluoroacetate salt (C4)

Trifluoroacetic acid (25 mL) was added to a 0° C. solution of C3 (5.60 g, 18.4 mmol) in dichloromethane (100 mL). The reaction mixture was stirred at room temperature for 1 hour, whereupon it was concentrated in vacuo, providing the product as an oil. Yield: 5.86 g, 18.4 mmol, quantitative. GCMS m/z 203.0 (bromine isotope pattern observed) [M+]. $^1$H NMR (400 MHz, CDCl$_3$) δ 4.47 (quint, J=7.7 Hz, 1H), 3.25-3.13 (m, 4H), 2.75-2.66 (m, 2H), 2.44-2.35 (m, 2H), 2.07-1.99 (m, 2H), 1.93-1.85 (m, 2H).

Step 5. Synthesis of (2R)-1,1,1-trifluoro-3-[(4-methoxybenzyl)oxy]propan-2-yl 2-bromo-7-azaspiro[3.5]nonane-7-carboxylate (C5)

Triethylamine (12.8 mL, 91.8 mmol) was added to a 0° C. solution of C4 (5.86 g, 18.4 mmol) in acetonitrile (100 mL) and the mixture was stirred at 0° C. for few minutes. Compound C2 [from step 2, as the crude reaction mixture in acetonitrile (100 mL); 23.9 mmol] was added, and the reaction mixture was stirred at 0° C. for few minutes, whereupon it was allowed to warm to room temperature and stir overnight. The reaction mixture was then concentrated in vacuo, and the residue was dissolved in ethyl acetate and washed sequentially with 1 M aqueous hydrochloric acid, saturated aqueous sodium bicarbonate solution, and saturated aqueous sodium chloride solution. The organic layer was dried over sodium sulfate, filtered, and concentrated under reduced pressure. Silica gel chromatography (Gradient: 75% to 100% dichloromethane in heptane) afforded the product as a thick, opaque oil. Yield: 5.08 g, 10.6 mmol, 58%. $^1$H NMR (400 MHz, CDCl$_3$) δ 7.24 (br d, J=8.8 Hz, 2H), 6.88 (br d, J=8.6 Hz, 2H), 5.51-5.42 (m, 1H), 4.54-4.44 (m, 1H), 4.50 (AB quartet, J$_{AB}$=11.7 Hz, Δv$_{AB}$=28.5 Hz, 2H), 3.82 (s, 3H), 3.75 (dd, half of ABX pattern, J=11.2, 4.0 Hz, 1H), 3.68 (dd, half of ABX pattern, J=11.1, 7.0 Hz, 1H), 3.48-3.33 (br m, 4H), 2.67-2.56 (m, 2H), 2.36-2.26 (m, 2H), 1.75-1.63 (br m, 2H), 1.63-1.51 (br m, 2H).

Step 6. Synthesis of (2R)-1,1,1-trifluoro-3-[(4-methoxybenzyl)oxy]propan-2-yl 2-[4-(trifluoromethyl)-1H-pyrazol-1-yl]-7-azaspiro[3.5]nonane-7-carboxylate (C6)

To a room temperature solution of C5 (100 mg, 0.208 mmol) in N,N-dimethylformamide (2 mL) was added cesium carbonate (170 mg, 0.522 mmol), followed by 4-(trifluoromethyl)-1H-pyrazole (42.5 mg, 0.312 mmol), and the reaction mixture was stirred at 80° C. overnight. It was then partitioned between water and ethyl acetate, and the aqueous layer was extracted with ethyl acetate (3×15 mL). The combined organic layers were dried over magnesium sulfate, filtered, and concentrated in vacuo. Silica gel chromatography (Gradient: 0% to 25% ethyl acetate in heptane) provided the product as an oil. Yield: 71 mg, 0.13 mmol, 62%. LCMS m/z 536.4 [M+H]+. $^1$H NMR (400 MHz, CDCl$_3$) δ 7.74 (s, 1H), 7.69 (s, 1H), 7.25 (br d, J=8.6 Hz, 2H), 6.88 (br d, J=8.6 Hz, 2H), 5.54-5.44 (m, 1H), 4.78 (quint, J=8.4 Hz, 1H), 4.51 (AB quartet, J$_{AB}$=11.7 Hz, Δv$_{AB}$=28.5 Hz, 2H), 3.81 (s, 3H), 3.76 (dd, half of ABX pattern, J=11.3, 3.9 Hz, 1H), 3.69 (br dd, half of ABX pattern, J=10.9, 7.0 Hz, 1H), 3.55-3.47 (br m, 2H), 3.47-3.38 (br m, 2H), 2.52-2.42 (m, 2H), 2.38 (dd, half of ABX pattern, J=12.5, 8.6 Hz, 2H), 1.76-1.62 (br m, 4H).

Step 7. Synthesis of (2R)-1,1,1-trifluoro-3-hydroxypropan-2-yl 2-[4-(trifluoromethyl)-1H-pyrazol-1-yl]-7-azaspiro[3.5]nonane-7-carboxylate (1)

Trifluoroacetic acid (1.2 mL, 15.6 mmol) was added to a 0° C. solution of C6 (71 mg, 0.13 mmol) in dichloromethane (6.6 mL). The reaction mixture was stirred at 0° C. for 1.5 hours, whereupon it was diluted with saturated aqueous sodium chloride solution and extracted with ethyl acetate (3×5 mL). The combined organic layers were dried over magnesium sulfate, filtered, concentrated in vacuo, and purified via chromatography on silica gel (Gradient: 10% to 55% ethyl acetate in heptane) to provide the product as an oil. Yield: 49 mg, 0.12 mmol, 92%. LCMS m/z 416.5 [M+H]+. $^1$H NMR (400 MHz, CDCl$_3$) δ 7.74 (s, 1H), 7.69 (s, 1H), 5.31-5.21 (m, 1H), 4.79 (quint, J=8.3 Hz, 1H), 4.00 (dd, half of ABX pattern, J=12.5, 3.5 Hz, 1H), 3.87 (dd, half of ABX pattern, J=12.5, 6.6 Hz, 1H), 3.63-3.34 (m, 4H), 2.54-2.44 (m, 2H), 2.39 (dd, half of ABX pattern, J=12, 8.4 Hz, 2H), 2.43-2.27 (m, 1H), 1.79-1.67 (br m, 4H).

Example 2

(2R)-1,1,1-Trifluoro-3-hydroxypropan-2-yl 2-(5-fluoropyridin-2-yl)-7-azaspiro[3.5]nonane-7-carboxylate (2)

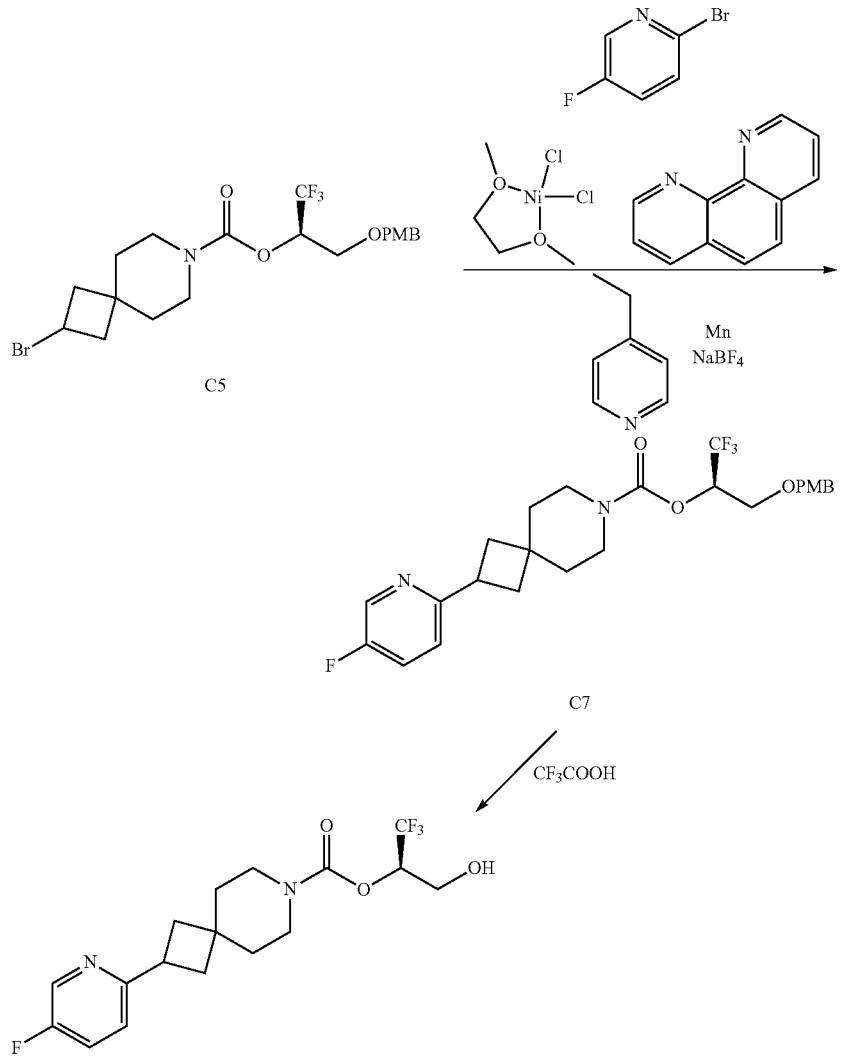

Step 1. Synthesis of (2R)-1,1,1-trifluoro-3-[(4-methoxybenzyl)oxy]propan-2-yl 2-(5-fluoropyridin-2-yl)-7-azaspiro[3.5]nonane-7-carboxylate (C7)

Nickel(II) chloride 1,2-dimethoxyethane complex (14.0 mg, 63.7 μmol), 1,10-phenanthroline (23.0 mg, 0.128 mmol), sodium tetrafluoroborate (95%, 36.1 mg, 0.312 mmol), and powdered manganese (68.6 mg, 1.25 mmol) were combined in a vial, which was then evacuated and charged with nitrogen. This evacuation cycle was repeated twice. In a separate vial, a solution of 4-ethylpyridine (36 μL, 0.32 mmol), C5 (300 mg, 0.625 mmol), and 2-bromo-5-fluoropyridine (110 mg, 0.625 mmol) in methanol (4.0 mL) was purged with nitrogen and then evacuated; this cycle was repeated twice and the vial was again purged with nitrogen. The solution containing C5 was added to the nickel-containing vial, and the reaction mixture was heated at 60° C. for 17 hours. It was then allowed to cool to room temperature and filtered through a 0.45 μm membrane filter. The filter was rinsed with methanol, and the combined filtrates were concentrated in vacuo and subjected to two rounds of silica gel chromatography (Column #1: Eluents, 0% followed by 5%, 10%, 15%, 20%, and 25% ethyl acetate in heptane. Column #2: Eluent, 5% methanol in dichloromethane), providing the product as a colorless oil, which was impure by LCMS analysis. This material was taken directly into the following step.

Yield: 146 mg, 50.294 mmol, <47%. LCMS m/z 497.5 [M+H]$^+$.

Step 2. Synthesis of (2R)-1,1,1-trifluoro-3-hydroxypropan-2-yl 2-(5-fluoropyridin-2-yl)-7-azaspiro[3.5]nonane-7-carboxylate (2)

Trifluoroacetic acid (1.0 mL, 13 mmol) was added to a 0° C. solution of C7 (from the previous step; 146 mg, 50.294 mmol) in dichloromethane (4 mL). The reaction mixture was stirred for 1 hour at room temperature, whereupon it was concentrated in vacuo and partitioned between dichloromethane and saturated aqueous sodium bicarbonate solution. The aqueous layer was extracted twice with dichloromethane, and the combined organic layers were dried over sodium sulfate, filtered, and concentrated under reduced pressure. Silica gel chromatography (Eluents: 10% followed by 20%, 30%, and 40% ethyl acetate in heptane) afforded the slightly impure product as an off-white gum (35 mg). LCMS m/z 377.4 [M+H]+. 1H NMR (400 MHz, CDCl3) δ 8.42 (d, J=2.7 Hz, 1H), 7.32 (ddd, J=8.6, 8.2, 3.1 Hz, 1H), 7.13 (dd, J=8.6, 4.3 Hz, 1H), 5.30-5.20 (m, 1H), 4.00 (dd, half of ABX pattern, J=12, 3 Hz, 1H), 3.87 (dd, half of ABX pattern, J=12, 7 Hz, 1H), 3.63 (quint, J=9.0 Hz, 1H), 3.6-3.28 (m, 4H), 2.29 (dd, J=11.5, 9.2 Hz, 2H), 2.12 (dd, J=11.9, 9.2 Hz, 2H), 1.82-1.72 (m, 2H), 1.67-1.57 (m, 2H). This material was repurified using reversed-phase HPLC (Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 5.0% to 100% B), affording the product. Yield: 30.1 mg, 80.0 μmol, 13% over two steps. LCMS m/z 377.3 [M+H]+.

Examples 3 and 4

(2R)-1,1,1-Trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 1 [From C13, DIAST 1] (3) and (2R)-1,1,1-Trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 2 [From C14, DIAST 2] (4)

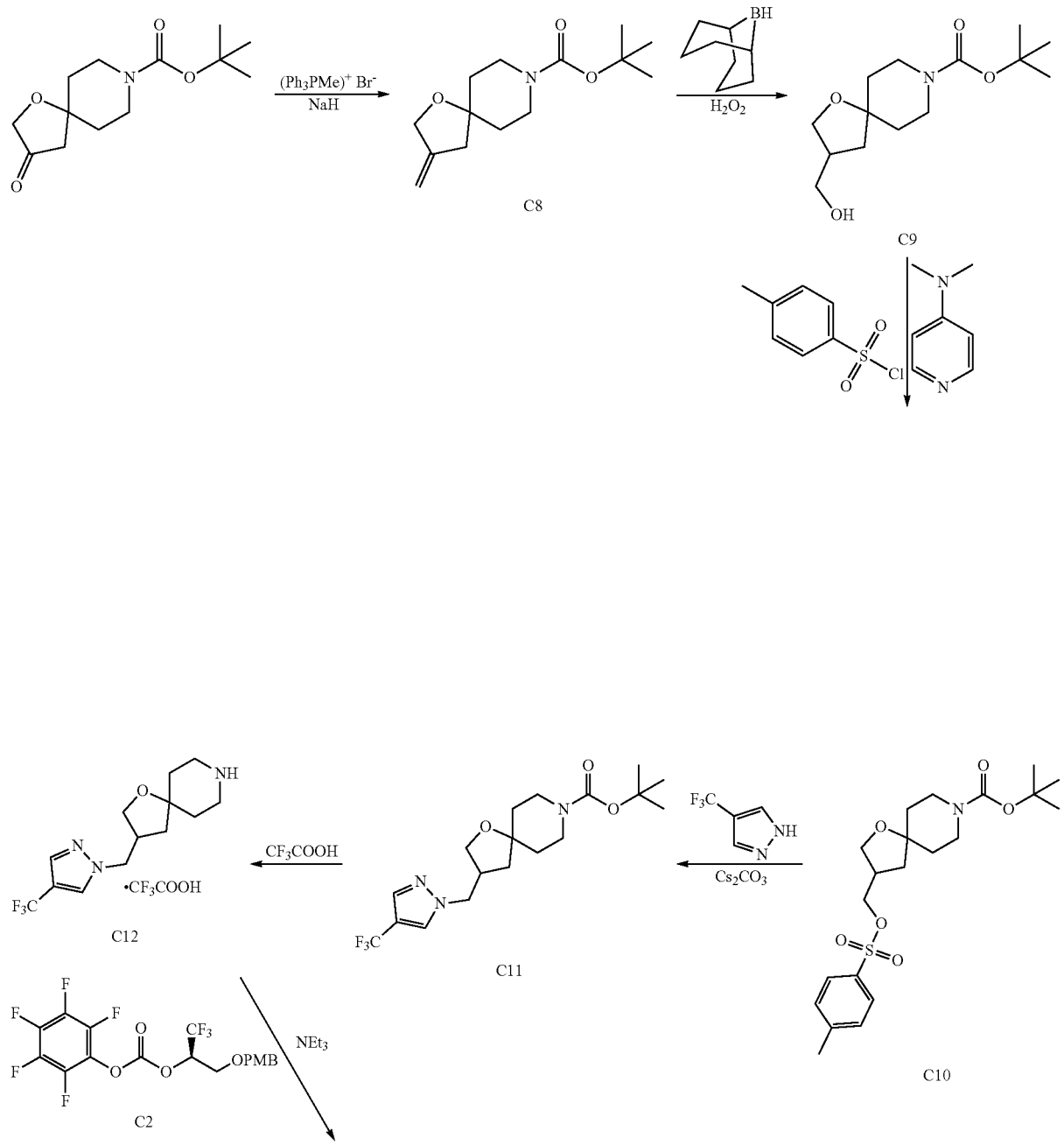

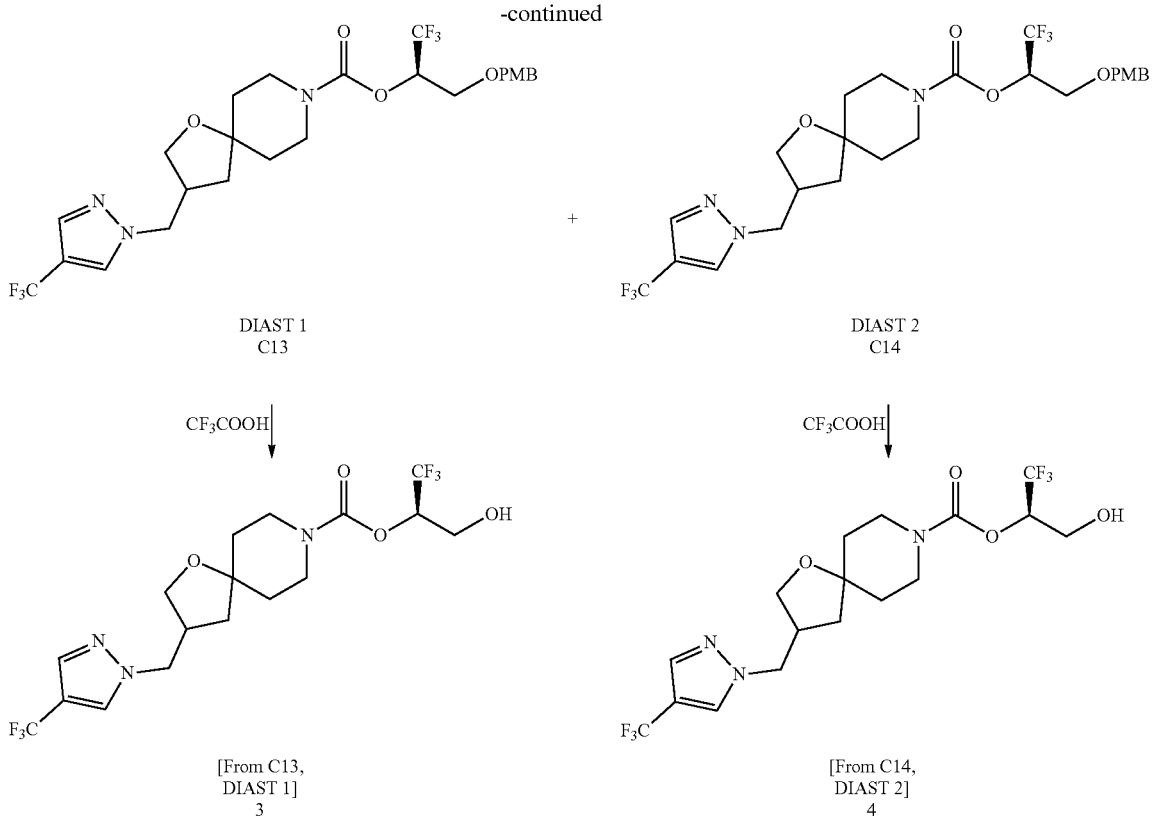

Step 1. Synthesis of tert-butyl 3-methylidene-1-oxa-8-azaspiro[4.5]decane-8-carboxylate (C8)

Methyltriphenylphosphonium bromide (8.4 g, 24 mmol) was added portion-wise to a mixture of sodium hydride (60% dispersion in mineral oil; 940 mg, 23.5 mmol) in dimethyl sulfoxide (40 mL), and the reaction mixture was stirred for 30 minutes at room temperature. A solution of tert-butyl 3-oxo-1-oxa-8-azaspiro[4.5]decane-8-carboxylate (2.0 g, 7.8 mmol) in dimethyl sulfoxide (18 mL) was then added drop-wise, and the reaction mixture was allowed to continue stirring at room temperature for 72 hours. The reaction was then carefully quenched with water (250 mL), and extracted with diethyl ether (5×50 mL). The combined organic layers were washed with water (2×25 mL), dried over magnesium sulfate, filtered, and concentrated in vacuo. The residue was triturated three times with heptane to afford an off-white solid, which proved to be largely triphenylphosphine oxide on analysis. The combined heptane portions from the triturations were concentrated in vacuo and subjected to silica gel chromatography (Eluents: 0% followed by 10% and 20% ethyl acetate in heptane), which afforded the product as a colorless oil. Yield: 1.77 g, 6.99 mmol, 90%. GCMS m/z 253.1 [M+]. $^1$H NMR (400 MHz, CDCl$_3$) δ 5.02-4.98 (m, 1H), 4.95-4.91 (m, 1H), 4.37-4.33 (m, 2H), 3.60 (ddd, J=13, 5, 5 Hz, 2H), 3.34 (ddd, J=13.3, 9.9, 3.3 Hz, 2H), 2.42-2.38 (m, 2H), 1.70-1.63 (m, 2H), 1.55 (ddd, J=13.3, 10.0, 4.5 Hz, 2H), 1.46 (s, 9H).

Step 2. Synthesis of tert-butyl 3-(hydroxymethyl)-1-oxa-8-azaspiro[4.5]decane-8-carboxylate (C9)

A mixture of C8 (2.30 g, 9.08 mmol) and 9-borabicyclo[3.3.1]nonane (0.5 M solution in tetrahydrofuran; 54.5 mL, 27.2 mmol) was stirred at 70° C. for 15 hours. After the reaction mixture had cooled, water (54.5 mL) was added, followed by 30% hydrogen peroxide (aqueous; 5.15 g, 45.4 mmol), and stirring was continued at 30° C. for 15 hours. The oxidant was quenched via addition of saturated aqueous sodium sulfite solution (~150 mL), until the mixture tested negative with potassium iodide-starch test paper. The resulting mixture was extracted with ethyl acetate (2×100 mL), and the combined organic layers were dried over sodium sulfate, filtered, and concentrated in vacuo. Purification via silica gel chromatography (Gradient: 0% to 50% ethyl acetate in petroleum ether) provided the product as a colorless oil. Yield: 1.75 g, 6.45 mmol, 71%. LCMS m/z 216.1 [(M−2-methylprop-1-ene)+H]+. $^1$H NMR (400 MHz, CDCl$_3$) δ 3.97 (dd, J=9.0, 7.5 Hz, 1H), 3.70-3.54 (m, 5H), 3.37-3.27 (m, 2H), 2.62-2.50 (m, 1H), 1.92 (dd, J=12.6, 8.5 Hz, 1H), 1.91-1.84 (m, 1H), 1.69-1.58 (m, 2H, assumed; partially obscured by water peak), 1.53-1.39 (m, 3H), 1.46 (s, 9H).

Step 3. Synthesis of tert-butyl 3-({[(4-methylphenyl)sulfonyl]oxy}methyl)-1-oxa-8-azaspiro[4.5]decane-8-carboxylate (C10)

4-(Dimethylamino)pyridine (1.08 g, 8.84 mmol) was added to a suspension of C9 (1.20 g, 4.42 mmol) in dichloromethane (45 mL). p-Toluenesulfonyl chloride (927 mg, 4.86 mmol) was added, and the reaction mixture was stirred at 30° C. for 18 hours, whereupon it was concentrated in vacuo and purified via chromatography on silica gel (Gradient: 0% to 30% ethyl acetate in petroleum ether). The product was combined with the material from a similar reaction carried out on C9 (400 mg, 1.47 mmol) to afford C10 as a colorless gum. Combined yield: 2.0 g, 4.7 mmol, 80%. LCMS m/z 370.0 [(M−2-methylprop-1-ene)+H]$^+$. $^1$H NMR (400 MHz, CDCl$_3$) δ 7.79 (br d, J=8.5 Hz, 2H), 7.36 (br d, J=8.0 Hz, 2H), 4.02-3.92 (m, 2H), 3.88 (dd, J=9.3, 7.3 Hz, 1H), 3.63-3.49 (m, 3H), 3.31-3.20 (m, 2H), 2.73-2.61 (m, 1H), 2.46 (s, 3H), 1.88 (dd, J=12.8, 8.8 Hz, 1H), 1.63-1.55 (m, 1H), 1.55-1.49 (m, 2H), 1.45 (s, 9H), 1.49-1.40 (m, 1H), 1.35 (dd, J=12.8, 7.3 Hz, 1H).

Step 4. Synthesis of tert-butyl 3-{[4-(trifluoromethyl)-1H-pyrazol-1-yl]methyl}-1-oxa-8-azaspiro[4.5]decane-8-carboxylate (C11)

A mixture of 4-(trifluoromethyl)-1H-pyrazole (150 mg, 1.1 mmol), C10 (516 mg, 1.21 mmol), and cesium carbonate (1.08 g, 3.31 mmol) in N,N-dimethylformamide (5 mL) was stirred at 40° C. for 15 hours, whereupon the reaction mixture was partitioned between ethyl acetate (15 mL) and saturated aqueous sodium chloride solution (15 mL). The organic layer was washed with saturated aqueous sodium chloride solution (2×15 mL), dried over sodium sulfate, filtered, and concentrated under reduced pressure. The residue was purified via silica gel chromatography (Gradient: 0% to 30% ethyl acetate in petroleum ether) to provide the product (500 mg) as a colorless oil. $^1$H NMR analysis indicated that this material contained N,N-dimethylformamide and ethyl acetate. Yield, corrected for solvents: 420 mg, 1.08 mmol, 98%.

LCMS m/z 290.1 {[M−(2-methylprop-1-ene and carbon dioxide)]+H}$^+$. $^1$H NMR (400 MHz, CDCl$_3$) δ 7.71 (s, 1H), 7.67 (s, 1H), 4.20-4.15 (m, 1H), 4.15-4.09 (m, 1H), 3.92 (dd, J=9.2, 7.0 Hz, 1H), 3.68-3.54 (br m, 2H), 3.62 (dd, J=9.2, 6.2 Hz, 1H), 3.35-3.22 (m, 2H), 2.98-2.86 (m, 1H), 1.93 (dd, J=12.8, 8.4 Hz, 1H), 1.73-1.58 (m, 4H), 1.49-1.42 (m, 1H), 1.45 (s, 9H).

Step 5. Synthesis of 3-{[4-(trifluoromethyl)-1H-pyrazol-1-yl]methyl}-1-oxa-8-azaspiro[4.5]decane, trifluoroacetate salt (C12)

Trifluoroacetic acid (1 mL) was added to a 0° C. solution of C11 (from the previous step, 420 mg, 1.08 mmol) in dichloromethane (4 mL), and the reaction mixture was stirred at 28° C. for 2 hours. Concentration in vacuo provided the product as a yellow gum, which was taken directly to the following step. LCMS m/z 289.9 [M+H]$^+$.

Step 6. Synthesis of (2R)-1,1,1-trifluoro-3-[(4-methoxybenzyl)oxy]propan-2-yl 3-{[4-(trifluoromethyl)-1H-pyrazol-1-yl]methyl}-1-oxa-8-azaspiro[4.5]decane-8-carboxylate, DIAST 1 (C13) and (2R)-1,1,1-trifluoro-3-[(4-methoxybenzyl)oxy]propan-2-yl 3-{[4-(trifluoromethyl)-1H-pyrazol-1-yl]methyl}-1-oxa-8-azaspiro[4.5]decane-8-carboxylate, DIAST 2 (C14)

Triethylamine (334 mg, 3.30 mmol) was added to a 0° C. solution of C12 (from the previous step; ≤1.08 mmol) in acetonitrile (3 mL). After the mixture had been stirred at 0° C. for a few minutes, C2 (reaction solution in acetonitrile, containing 1.76 mmol) was added drop-wise; stirring was continued at 0° C. for a few minutes, and then the reaction mixture was allowed to stir at 28° C. for 15 hours. Volatiles were removed via concentration in vacuo, and the residue was purified using silica gel chromatography (Gradient: 0% to 40% ethyl acetate in petroleum ether) to afford a mixture of C13 and C14 as a yellow gum. Yield of diastereomeric mixture: 483 mg, 0.854 mmol, 79% over 2 steps. LCMS m/z 588.1 [M+Na$^+$]. $^1$H NMR (400 MHz, CDCl$_3$) δ 7.72 (s, 1H), 7.67 (s, 1H), 7.24 (br d, J=8.5 Hz, 2H), 6.88 (br d, J=8.5 Hz, 2H), 5.53-5.42 (m, 1H), 4.51 (AB quartet, upfield doublet is broadened, $J_{AB}$=11.5 Hz, $\Delta v_{AB}$=28.4 Hz, 2H), 4.19-4.12 (m, 2H), 3.93 (dd, J=9.3, 6.8 Hz, 1H), 3.88-3.60 (m, 5H), 3.81 (s, 3H), 3.41-3.24 (m, 2H), 2.99-2.87 (m, 1H), 2.00-1.85 (m, 1H), 1.76-1.38 (m, 5H, assumed; partially obscured by water peak).

This material was separated into its component diastereomers via supercritical fluid chromatography [Column: Chiral Technologies Chiralpak AD, 10 μm; Mobile phase: 85:15 carbon dioxide/(methanol containing 0.1% ammonium hydroxide)], affording C13, the first-eluting diastereomer, as a colorless gum. Yield: 200 mg, 0.354 mmol, 41% for the separation.

LCMS m/z 588.1 [M+Na$^+$].

Compound C14 was the second-eluting diastereomer, isolated as a light yellow gum. Yield: 211 mg, 0.373 mmol, 44% for the separation. LCMS m/z 588.1 [M+Na$^+$].

Step 7. Synthesis of (2R)-1,1,1-trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 1 [From C13, DIAST 1](3)

Trifluoroacetic acid (1 mL) was added to a 10° C. solution of C13 (200 mg, 0.354 mmol) in dichloromethane (4 mL), and the reaction mixture was stirred at 30° C. for 1 hour. It was then washed with saturated aqueous sodium bicarbonate solution (2×3 mL), concentrated in vacuo, and purified via reversed-phase HPLC (Column: Agela Durashell, 5 μm; Mobile phase A: 0.225% formic acid in water; Mobile phase B: acetonitrile; Gradient: 39% to 59% B), providing the product as a colorless gum. Yield: 43.7 mg, 98.1 μmol, 28%. LCMS m/z 446.2 [M+H]$^+$. $^1$H NMR (400 MHz, CDCl$_3$) δ 7.72 (s, 1H), 7.67 (s, 1H), 5.30-5.20 (br m, 1H), 4.16 (d, J=7.5 Hz, 2H), 4.00 (br dd, half of ABX pattern, J=12.6, 3.0 Hz, 1H), 3.93 (dd, J=9.3, 6.8 Hz, 1H), 3.90-3.70 (br m, 3H), 3.65 (dd, J=9.0, 6.5 Hz, 1H), 3.42-3.23 (m, 2H), 3.00-2.87 (m, 1H), 2.6-2.2 (v br s, 1H), 1.95 (dd, J=12.8, 8.3 Hz, 1H), 1.76-1.52 (m, 4H, assumed; partially obscured by water peak), 1.49 (dd, J=12.8, 7.8 Hz, 1H).

Step 8. Synthesis of (2R)-1,1,1-trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 2 [From C14, DIAST 2] (4)

Conversion of C14 to the product was effected using the method employed for synthesis of 3 from C13, affording the product as a colorless gum. Yield: 37.7 mg, 84.6 μmol, 23%. LCMS m/z 446.2 [M+H]$^+$. $^1$H NMR (400 MHz, CDCl$_3$) δ 7.72 (s, 1H), 7.67 (s, 1H), 5.31-5.19 (br m, 1H), 4.16 (d, J=7.0 Hz, 2H), 4.04-3.73 (m, 5H), 3.64 (dd, J=9.0, 6.5 Hz, 1H), 3.45-3.26 (m, 2H), 3.00-2.87 (m, 1H), 2.5-2.2 (v br s, 1H), 1.95 (dd, J=12.8, 8.3 Hz, 1H), 1.77-1.44 (m, 4H, assumed; partially obscured by water peak), 1.50 (dd, J=12.6, 7.5 Hz, 1H).

Example 5
(2R)-1,1,1-Trifluoro-3-hydroxypropan-2-yl (3R)-3-[(cyclopentylcarbonyl)(methyl)amino]-1-oxa-8-azaspiro[4.5]decane-8-carboxylate (5)
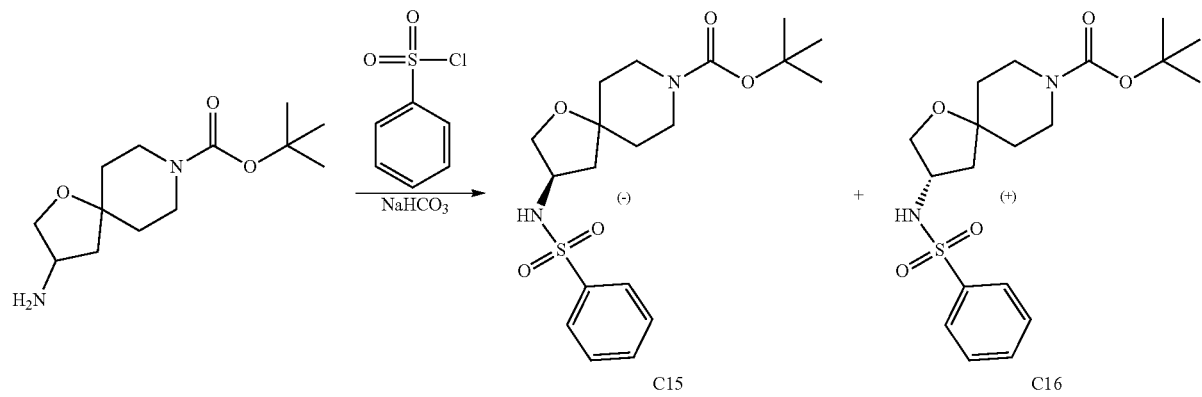
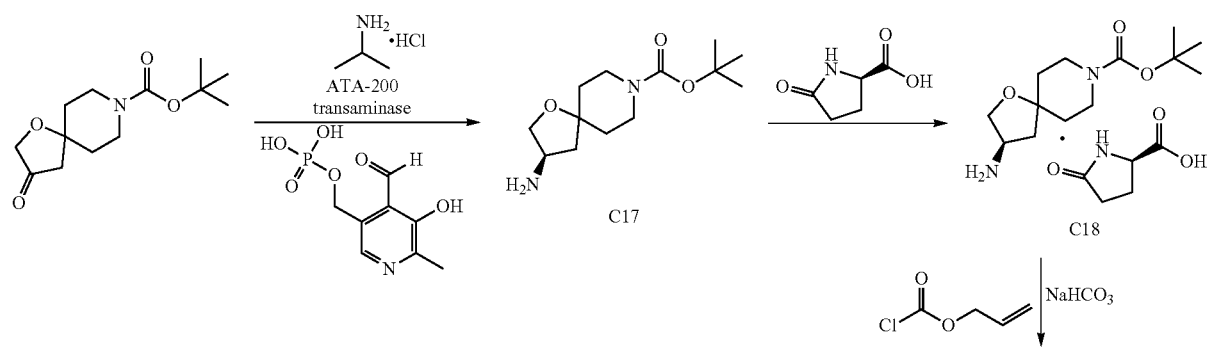
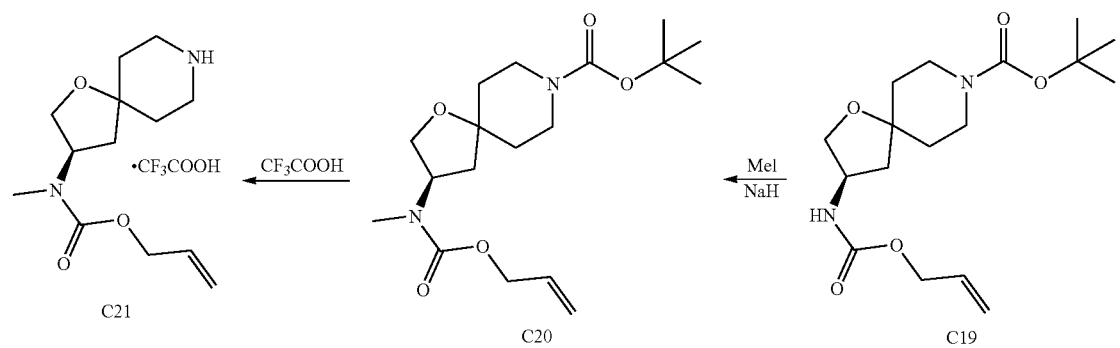
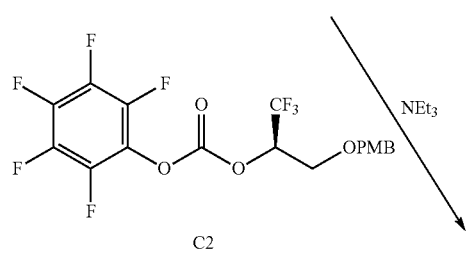

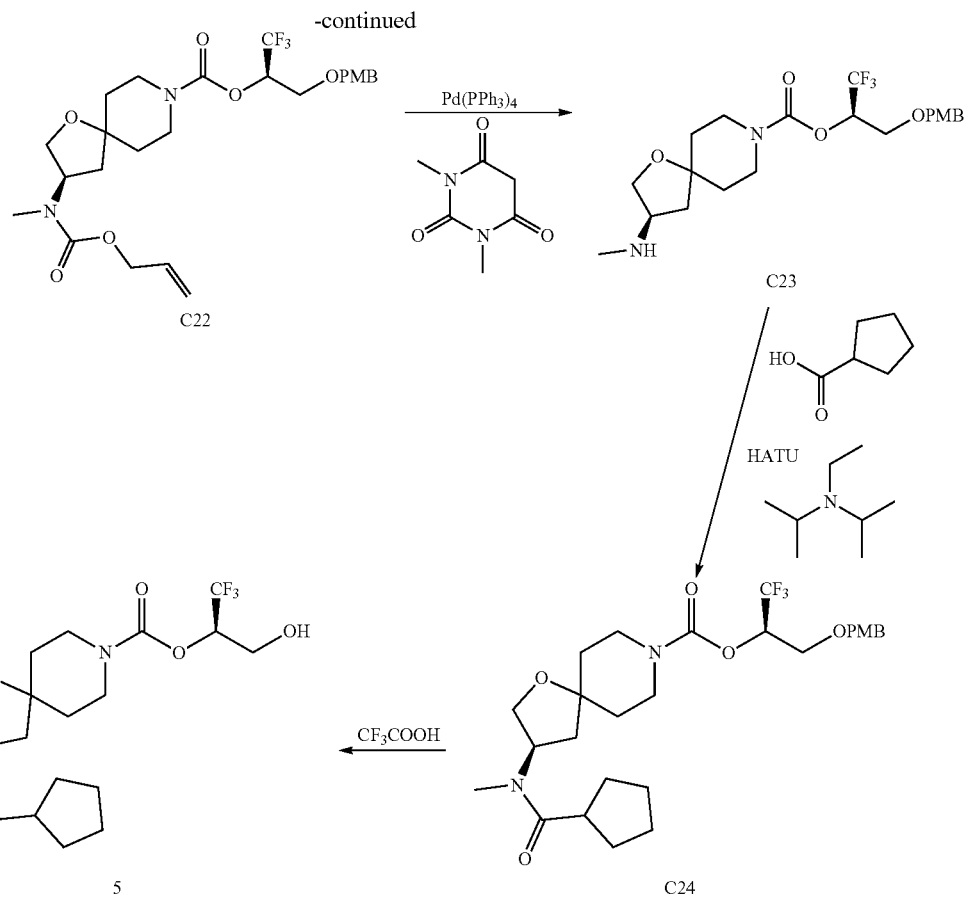

Step 1. Synthesis of tert-butyl (3R)-3-[(phenylsulfonyl)amino]-1-oxa-8-azaspiro[4.5]decane-8-carboxylate (C15) and tert-butyl (3S)-3-[(phenylsulfonyl)amino]-1-oxa-8-azaspiro[4.5]decane-8-carboxylate (C16)

A solution of tert-butyl 3-amino-1-oxa-8-azaspiro[4.5]decane-8-carboxylate (1.98 g, 7.72 mmol) in dichloromethane (80 mL) was treated with saturated aqueous sodium bicarbonate solution (20 mL). Benzenesulfonyl chloride (1.49 mL, 11.7 mmol) was added drop-wise, and the reaction mixture was stirred for 23 hours at room temperature. The aqueous layer was extracted with dichloromethane, and the combined organic layers were washed with saturated aqueous sodium chloride solution, dried over sodium sulfate, filtered, and concentrated in vacuo. This racemic product was purified using silica gel chromatography (Gradient: 20% to 50% ethyl acetate in heptane) to afford a white solid (2.88 g), which was then separated into its component enantiomers via supercritical fluid chromatography [Column: Phenomenex Lux Cellulose-3, 5 μm; Mobile phase: 7.5% (1:1 methanol/acetonitrile) in carbon dioxide]. The first-eluting product, obtained as a tacky white solid that exhibited a negative (−) rotation, was designated as C15. Yield: 1.35 g, 3.40 mmol, 45%. LCMS m/z 395.5 [M−H+]. $^1$H NMR (400 MHz, CDCl$_3$) δ 7.90-7.86 (m, 2H), 7.64-7.59 (m, 1H), 7.57-7.52 (m, 2H), 4.81 (d, J=7.9 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.48-1.38 (m, 1H), 1.44 (s, 9H).

The second-eluting product, obtained as a tacky white solid that exhibited a positive (+) rotation, was designated as C16. Yield: 1.15 g, 2.90 mmol, 38%. LCMS m/z 395.5 [M−H+]. $^1$H NMR (400 MHz, CDCl$_3$) δ 7.90-7.86 (m, 2H), 7.64-7.59 (m, 1H), 7.57-7.52 (m, 2H), 4.79 (d, J=8.0 Hz, 1H), 4.00-3.91 (m, 1H), 3.81 (dd, J=9.7, 5.7 Hz, 1H), 3.59-3.48 (m, 3H), 3.30-3.19 (m, 2H), 1.97 (dd, J=13.4, 7.7 Hz, 1H), 1.67-1.49 (m, 4H), 1.47-1.38 (m, 1H), 1.44 (s, 9H).

The absolute configurations shown were established as follows: a portion of this batch of C15 was recrystallized from dichloromethane/tert-butyl methyl ether, and its absolute configuration was determined via single crystal X-ray structure determination:

Single-Crystal X-Ray Structural Determination of C15

Single Crystal X-Ray Analysis
Data collection was performed on a Bruker APEX diffractometer at room temperature. Data collection consisted of omega and phi scans.
The structure was solved by direct methods using SHELX software suite in the space group P2$_1$2$_1$2$_1$. The structure was subsequently refined by the full-matrix least squares method. All non-hydrogen atoms were found and refined using anisotropic displacement parameters.
The hydrogen atom located on nitrogen was found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft, 2008) was performed using PLATON (Spek, 2010). The results indicate that the absolute structure has been correctly assigned. The method calculates that the probability that the structure is correct is 100.0. The Hooft parameter is reported as 0.015 with an esd of 0.09.

The final R-index was 4.2%. A final difference Fourier revealed no missing or misplaced electron density.

Pertinent crystal, data collection and refinement information is summarized in Table 1. Atomic coordinates, bond lengths, bond angles, and displacement parameters are listed in Tables 2-5.

SOFTWARE AND REFERENCES

SHELXTL, Version 5.1, Bruker AXS, 1997.

PLATON, A. L. Spek, *J. Appl. Cryst.* 2003, 36, 7-13.

MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.

OLEX2, O. V. Dolomanov, L. J. Bourhis, R. J. Gildea, J. A. K. Howard, and H. Puschmann, *J. Appl. Cryst.* 2009, 42, 339-341.

R. W. W. Hooft, L. H. Straver, and A. L. Spek, *J. Appl. Cryst.* 2008, 41, 96-103.

H. D. Flack, *Acta Cryst.* 1983, A39, 867-881.

TABLE 1

Crystal data and structure refinement for C15.

| | |
|---|---|
| Empirical formula | $C_{19}H_{28}N_2O_5S$ |
| Formula weight | 396.50 |
| Temperature | 276(2) K |
| Wavelength | 1.54178 Å |
| Crystal system | Orthorhombic |
| Space group | $P2_12_12_1$ |
| Unit cell dimensions | a = 9.79150(10) Å, $\alpha = 90°$ |
| | b = 11.11580(10) Å, $\beta = 90°$ |
| | c = 18.6694(2) Å, $\gamma = 90°$ |
| Volume | 2031.98(4) Å$^3$ |
| Z | 4 |
| Density (calculated) | 1.296 Mg/m$^3$ |
| Absorption coefficient | 1.686 mm$^{-1}$ |
| F(000) | 848 |
| Crystal size | 0.260 × 0.180 × 0.140 mm$^3$ |
| Theta range for data collection | 4.630 to 68.568° |
| Index ranges | $-11 \leq h \leq 11, -13 \leq k \leq 13, -20 \leq l \leq 22$ |
| Reflections collected | 9404 |
| Independent reflections | 3633 [$R_{int}$ = 0.0247] |
| Completeness to theta = 70.31° | 99.3% |
| Absorption correction | None |
| Refinement method | Full-matrix least-squares on F$^2$ |
| Data/restraints/parameters | 3633/1/251 |
| Goodness-of-fit on F$^2$ | 1.067 |
| Final R indices [I > 2sigma(I)] | R1 = 0.0418, wR2 = 0.1074 |
| R indices (all data) | R1 = 0.0441, wR2 = 0.1098 |
| Absolute structure parameter | 0.017(9) |
| Extinction coefficient | n/a |
| Largest diff. peak and hole | 0.428 and −0.457 e · Å$^{-3}$ |

TABLE 2

Atomic coordinates (×10$^4$) and equivalent isotropic displacement parameters (Å$^2$ × 10$^3$) for C15. U(eq) is defined as one-third of the trace of the orthogonalized U$^{ij}$ tensor.

| | x | y | z | U(eq) |
|---|---|---|---|---|
| S(1) | −3733(1) | 10920(1) | 849(1) | 53(1) |
| N(1) | −3045(3) | 9602(2) | 839(2) | 59(1) |
| N(2) | 3033(2) | 7292(2) | 1366(2) | 52(1) |
| O(1) | −5113(3) | 10761(2) | 1075(1) | 74(1) |
| O(2) | −2848(3) | 11724(2) | 1218(1) | 68(1) |
| O(3) | 29(3) | 8787(2) | 1780(1) | 68(1) |
| O(4) | 5295(2) | 7383(2) | 1100(1) | 53(1) |
| O(5) | 4386(2) | 5806(2) | 1709(1) | 55(1) |
| C(1) | −4868(3) | 11071(3) | −483(2) | 63(1) |
| C(2) | −4920(4) | 11465(4) | −1195(2) | 76(1) |
| C(3) | −3910(5) | 12188(4) | −1452(2) | 77(1) |
| C(4) | −2853(5) | 12532(4) | −1029(2) | 80(1) |
| C(5) | −2775(3) | 12136(3) | −315(2) | 64(1) |
| C(6) | −3796(3) | 11406(2) | −54(2) | 49(1) |
| C(7) | −1575(3) | 9468(3) | 927(2) | 49(1) |
| C(8) | −1069(4) | 9583(4) | 1697(2) | 77(1) |
| C(9) | 248(3) | 8100(3) | 1135(2) | 48(1) |
| C(10) | −1087(3) | 8216(3) | 724(2) | 51(1) |
| C(11) | 601(3) | 6821(3) | 1356(2) | 62(1) |
| C(12) | 1914(4) | 6735(3) | 1772(2) | 67(1) |
| C(13) | 2776(3) | 8526(3) | 1137(2) | 55(1) |
| C(14) | 1463(3) | 8609(3) | 722(2) | 49(1) |
| C(15) | 4329(3) | 6873(2) | 1372(2) | 46(1) |
| C(16) | 5650(3) | 5100(3) | 1749(2) | 50(1) |
| C(17) | 6713(4) | 5783(4) | 2169(2) | 69(1) |
| C(18) | 6126(5) | 4758(4) | 1005(2) | 82(1) |
| C(19) | 5191(4) | 3991(3) | 2158(2) | 62(1) |

TABLE 3

Bond lengths [Å] and angles [°] for C15.

| | |
|---|---|
| S(1)—O(2) | 1.423(3) |
| S(1)—O(1) | 1.426(2) |
| S(1)—N(1) | 1.613(2) |
| S(1)—C(6) | 1.772(3) |
| N(1)—C(7) | 1.456(4) |
| N(2)—C(15) | 1.353(4) |
| N(2)—C(13) | 1.459(4) |
| N(2)—C(12) | 1.468(4) |
| O(3)—C(8) | 1.400(4) |
| O(3)—C(9) | 1.441(4) |
| O(4)—C(15) | 1.214(4) |
| O(5)—C(15) | 1.344(3) |
| O(5)—C(16) | 1.467(3) |
| C(1)—C(6) | 1.372(5) |
| C(1)—C(2) | 1.400(5) |
| C(2)—C(3) | 1.362(6) |
| C(3)—C(4) | 1.358(6) |
| C(4)—C(5) | 1.405(5) |
| C(5)—C(6) | 1.376(4) |
| C(7)—C(10) | 1.520(4) |
| C(7)—C(8) | 1.525(5) |
| C(9)—C(11) | 1.520(4) |
| C(9)—C(10) | 1.521(4) |
| C(9)—C(14) | 1.526(4) |
| C(11)—C(12) | 1.506(5) |
| C(13)—C(14) | 1.503(4) |
| C(16)—C(17) | 1.508(5) |
| C(16)—C(18) | 1.514(5) |
| C(16)—C(19) | 1.518(4) |
| O(2)—S(1)—O(1) | 120.73(17) |
| O(2)—S(1)—N(1) | 108.79(15) |
| O(1)—S(1)—N(1) | 106.64(15) |
| O(2)—S(1)—C(6) | 106.86(14) |
| O(1)—S(1)—C(6) | 106.70(15) |
| N(1)—S(1)—C(6) | 106.29(15) |
| C(7)—N(1)—S(1) | 120.3(2) |
| C(15)—N(2)—C(13) | 119.2(2) |
| C(15)—N(2)—C(12) | 123.4(2) |
| C(13)—N(2)—C(12) | 114.8(3) |

TABLE 3-continued

Bond lengths [Å] and angles [°] for C15.

| | |
|---|---|
| C(8)—O(3)—C(9) | 110.9(2) |
| C(15)—O(5)—C(16) | 122.1(2) |
| C(6)—C(1)—C(2) | 119.8(3) |
| C(3)—C(2)—C(1) | 119.6(4) |
| C(4)—C(3)—C(2) | 120.9(4) |
| C(3)—C(4)—C(5) | 120.4(4) |
| C(6)—C(5)—C(4) | 118.7(3) |
| C(1)—C(6)—C(5) | 120.6(3) |
| C(1)—C(6)—S(1) | 119.9(2) |
| C(5)—C(6)—S(1) | 119.4(3) |
| N(1)—C(7)—C(10) | 112.1(3) |
| N(1)—C(7)—C(8) | 114.8(3) |
| C(10)—C(7)—C(8) | 102.1(3) |
| O(3)—C(8)—C(7) | 107.5(3) |
| O(3)—C(9)—C(11) | 107.7(3) |
| O(3)—C(9)—C(10) | 104.4(2) |
| C(11)—C(9)—C(10) | 114.3(3) |
| O(3)—C(9)—C(14) | 109.9(3) |
| C(11)—C(9)—C(14) | 107.9(2) |
| C(10)—C(9)—C(14) | 112.6(2) |
| C(7)—C(10)—C(9) | 102.8(2) |
| C(12)—C(11)—C(9) | 113.1(3) |
| N(2)—C(12)—C(11) | 110.1(3) |
| N(2)—C(13)—C(14) | 110.9(3) |
| C(13)—C(14)—C(9) | 112.6(2) |
| O(4)—C(15)—O(5) | 125.2(3) |
| O(4)—C(15)—N(2) | 124.5(3) |
| O(5)—C(15)—N(2) | 110.3(2) |
| O(5)—C(16)—C(17) | 109.8(3) |
| O(5)—C(16)—C(18) | 110.3(3) |
| C(17)—C(16)—C(18) | 113.0(3) |
| O(5)—C(16)—C(19) | 102.1(2) |
| C(17)—C(16)—C(19) | 110.6(3) |
| C(18)—C(16)—C(19) | 110.4(3) |

Symmetry transformations used to generate equivalent atoms.

TABLE 4

Anisotropic displacement parameters (Å$^2$ × 10$^3$) for C15. The anisotropic displacement factor exponent takes the form: $-2\pi^2[h^2 a^{*2}U^{11} + \ldots + 2 h k a^* b^* U^{12}]$.

| | U$^{11}$ | U$^{22}$ | U$^{33}$ | U$^{23}$ | U$^{13}$ | U$^{12}$ |
|---|---|---|---|---|---|---|
| S(1) | 48(1) | 42(1) | 69(1) | 2(1) | 10(1) | 8(1) |
| N(1) | 44(1) | 42(1) | 91(2) | 9(1) | 4(1) | 3(1) |
| N(2) | 41(1) | 49(1) | 67(2) | 17(1) | 2(1) | 2(1) |
| O(1) | 57(1) | 69(1) | 95(2) | 19(1) | 28(1) | 18(1) |
| O(2) | 80(1) | 52(1) | 70(1) | −7(1) | −6(1) | 9(1) |
| O(3) | 66(2) | 88(2) | 49(1) | −8(1) | −5(1) | 24(1) |
| O(4) | 43(1) | 49(1) | 68(1) | 7(1) | 4(1) | 0(1) |
| O(5) | 46(1) | 46(1) | 73(1) | 16(1) | 1(1) | 4(1) |
| C(1) | 45(2) | 51(2) | 92(2) | 0(2) | −4(2) | −4(1) |
| C(2) | 66(2) | 78(2) | 84(2) | −6(2) | −20(2) | 2(2) |
| C(3) | 85(3) | 77(2) | 69(2) | 6(2) | −1(2) | 2(2) |
| C(4) | 77(2) | 83(3) | 81(2) | 12(2) | 15(2) | −22(2) |
| C(5) | 53(2) | 65(2) | 75(2) | 1(2) | 2(2) | −18(2) |
| C(6) | 40(1) | 36(1) | 70(2) | −2(2) | 5(1) | 4(1) |
| C(7) | 42(1) | 44(1) | 60(2) | 2(1) | 4(1) | 4(1) |
| C(8) | 78(2) | 83(2) | 70(2) | −22(2) | −9(2) | 27(2) |
| C(9) | 47(2) | 49(2) | 48(2) | −1(1) | 3(1) | 6(1) |
| C(10) | 46(1) | 49(1) | 57(2) | −5(2) | 1(1) | 7(1) |
| C(11) | 44(2) | 54(2) | 91(2) | 21(2) | 9(2) | 1(1) |
| C(12) | 50(2) | 69(2) | 83(2) | 35(2) | 10(2) | 9(2) |
| C(13) | 48(2) | 48(2) | 68(2) | 10(2) | −2(2) | 0(1) |
| C(14) | 51(2) | 45(1) | 51(2) | 5(1) | 1(1) | 5(1) |
| C(15) | 44(1) | 43(1) | 50(1) | 2(1) | −1(1) | 2(1) |
| C(16) | 51(2) | 51(2) | 48(2) | 5(1) | 1(1) | 13(1) |
| C(17) | 56(2) | 80(2) | 70(2) | 17(2) | −7(2) | −6(2) |
| C(18) | 120(4) | 71(2) | 56(2) | 4(2) | 14(2) | 37(2) |
| C(19) | 71(2) | 51(2) | 64(2) | 12(1) | −4(2) | 10(2) |

TABLE 5

Hydrogen coordinates (×10$^4$) and isotropic displacement parameters (Å$^2$ × 10$^3$) for C15.

| | x | y | z | U(eq) |
|---|---|---|---|---|
| H(1X) | −3660(30) | 8980(20) | 932(17) | 57(9) |
| H(1) | −5558 | 10584 | −302 | 75 |
| H(2) | −5639 | 11234 | −1490 | 91 |
| H(3) | −3946 | 12450 | −1925 | 92 |
| H(4) | −2177 | 13033 | −1212 | 96 |
| H(5) | −2047 | 12362 | −25 | 77 |
| H(7) | −1107 | 10063 | 628 | 59 |
| H(8A) | −776 | 10401 | 1791 | 92 |
| H(8B) | −1794 | 9380 | 2029 | 92 |
| H(10A) | −938 | 8151 | 212 | 61 |
| H(10B) | −1738 | 7606 | 872 | 61 |
| H(11A) | −137 | 6501 | 1645 | 75 |
| H(11B) | 674 | 6326 | 929 | 75 |
| H(12A) | 1811 | 7141 | 2229 | 81 |
| H(12B) | 2127 | 5898 | 1865 | 81 |
| H(13A) | 3526 | 8801 | 840 | 66 |
| H(13B) | 2726 | 9045 | 1554 | 66 |
| H(14A) | 1562 | 8173 | 275 | 59 |
| H(14B) | 1285 | 9446 | 607 | 59 |
| H(17A) | 7038 | 6448 | 1888 | 103 |
| H(17B) | 7462 | 5258 | 2281 | 103 |
| H(17C) | 6316 | 6080 | 2605 | 103 |
| H(18A) | 5376 | 4423 | 741 | 124 |
| H(18B) | 6844 | 4173 | 1040 | 124 |
| H(18C) | 6460 | 5461 | 763 | 124 |
| H(19A) | 4803 | 4229 | 2609 | 93 |
| H(19B) | 5962 | 3476 | 2242 | 93 |
| H(19C) | 4519 | 3565 | 1883 | 93 |

Step 2. Synthesis of tert-butyl (3R)-3-amino-1-oxa-8-azaspiro[4.5]decane-8-carboxylate (C17)

A pH 8.0 buffer solution was prepared, containing 0.1 M aqueous potassium phosphate and 2 mM magnesium chloride. A stock solution of substrate was prepared as follows: tert-butyl 3-oxo-1-oxa-8-azaspiro[4.5]decane-8-carboxylate (18.0 g, 70.5 mmol) was dissolved in water containing 4% dimethyl sulfoxide (14.4 mL). Warming and stirring were required for dissolution, and the resulting solution was maintained at 40° C.
Propan-2-amine, hydrochloride salt (16.8 g, 176 mmol) was added to a mixture of pyridoxal 5'-phosphate monohydrate (1.87 g, 7.05 mmol) and the pH 8.0 buffer (300 mL). The resulting pH was approximately 6.5; the pH was adjusted to 8 via addition of aqueous potassium hydroxide solution (6 M; approximately 4 mL). The stock solution of substrate was added via syringe, in 5 mL portions, resulting in a suspension, still at pH 8. Codex® ATA-200 transaminase (batch 899; 1.4 g) was almost completely dissolved in pH 8 buffer (20 mL), and poured into the reaction mixture. Additional pH 8 buffer (25.6 mL) was used to ensure complete transfer of the enzyme. The reaction mixture was stirred at 35° C. with a nitrogen sweep (32 mL/minute) through a needle placed approximately 0.5 cm above the reaction surface. Due to difficulties in stirring, vacuum (220 Torr, 300 mbar) was applied after 3 hours, to remove the acetone generated by the transamination reaction. The suspended solids were broken up manually, which improved the stirring of the reaction mixture. After 26 hours, the reaction mixture was allowed to cool to room temperature, and aqueous hydrochloric acid (6 M, 5 mL) was added, to bring the pH from 8 to 6.5. After addition of ethyl acetate (200 mL), the mixture was vigorously stirred for 5 minutes and then filtered through diatomaceous earth (43 g; this filter aid had been slurried in water prior to being introduced into the filter funnel. The water was then removed, providing a tightly packed bed). The filter pad was washed sequentially with water (120 mL) and ethyl acetate (100 mL), and the aqueous layer of the combined filtrates was adjusted to pH 9-9.5 with aqueous potassium hydroxide solution (6 M; approximately 10 mL). The aqueous layer was then treated with dichloromethane (200 mL), and the resulting mixture was vigorously stirred for 5 minutes before being filtered through a pad of diatomaceous earth. The filter pad was washed with dichloromethane (100 mL), and the aqueous layer of the combined filtrates was extracted twice with dichloromethane, in the same manner as that described above, with adjustment of the pH to 9-10 (this required approximately 2 mL of the 6 M aqueous potassium hydroxide solution in both cases). All of the dichloromethane extracts were combined and dried over sodium sulfate with vigorous stirring. Filtration and concentration in vacuo afforded the product as an oily yellow solid (14.76 g). A fourth extraction was carried out in the same manner, but in this case the aqueous layer was adjusted to a pH of >10. The product obtained from this extraction was a white solid (1.9 g). Combined yield: 16.61 g, 64.79 mmol, 92%. $^1$H NMR (500 MHz, CDCl$_3$) δ 3.95 (dd, J=9.0, 5.6 Hz, 1H), 3.69-3.63 (m, 1H), 3.62-3.52 (m, 3H), 3.38-3.27 (m, 2H), 2.6-2.2 (v br s, 2H), 2.07 (dd, J=13.0, 7.6 Hz, 1H), 1.78-1.71 (m, 1H), 1.69-1.56 (m, 2H), 1.55-1.47 (m, 2H), 1.45 (s, 9H).

Step 3. Synthesis of tert-butyl (3R)-3-amino-1-oxa-8-azaspiro[4.5]decane-8-carboxylate, (2R)-5-oxopyrrolidine-2-carboxylate salt (C18)

A solution of C17 (16.61 g, 64.79 mmol) in ethanol (400 mL) was heated to 63° C. and treated portion-wise with (2R)-5-oxopyrrolidine-2-carboxylic acid (7.78 g, 60.3 mmol). The reaction mixture was then removed from the heating bath, and allowed to cool overnight. The mixture was cooled to 12° C. in an ice bath, and filtered. The collected solids were washed with cold ethanol (2×50 mL) and then with diethyl ether (100 mL), affording the product as a pale yellow solid (19.2 g). The combined filtrates were concentrated in vacuo, with removal of approximately 400 mL of solvents. A thin line of solid formed around the inner surface of the flask. This was swirled back into the remaining solvents; diethyl ether (100 mL) was added, and the mixture was cooled in an ice bath with stirring. After approximately 15 minutes, the mixture was filtered and the collected solids were washed with diethyl ether (100 mL), affording additional product as a yellow solid (1.5 g). Combined yield: 20.7 g, 53.7 mmol, 89%. $^1$H NMR (500 MHz, D$_2$O) δ 4.16 (dd, J=8.9, 5.9 Hz, 1H), 4.11 (dd, half of ABX pattern, J=10.4, 5.8 Hz, 1H), 4.09-4.03 (m, 1H), 3.93 (dd, J=10.3, 3.1 Hz, 1H), 3.61-3.46 (m, 2H), 3.46-3.30 (m, 2H), 2.53-2.36 (m, 4H), 2.06-1.97 (m, 1H), 1.85 (dd, J=14.1, 4.6 Hz, 1H), 1.82-1.72 (m, 2H), 1.72-1.65 (m, 1H), 1.59 (ddd, half of ABXY pattern, J=18, 9, 4.5 Hz, 1H), 1.43 (s, 9H).

Conversion of C18 to C15, for Confirmation of Absolute Stereochemistry

A small sample of C18 was derivatized via reaction with benzenesulfonyl chloride and saturated aqueous sodium bicarbonate solution for 1 hour at 40° C. The reaction mixture was extracted with ethyl acetate, and the solvent was removed from the extract under a stream of nitrogen. Supercritical fluid chromatographic analysis (Column: Chiral Technologies Chiralcel OJ-H, 5 μm; Mobile phase A: carbon dioxide; Mobile phase B: methanol; Gradient: 5% to 60% B) revealed the product to have an enantiomeric excess of >99%. Injection, under the same conditions, of samples of C15 and C16 established the derivatization product as identical to C15, the absolute configuration of which was determined via X-ray crystallographic analysis (see above).

Step 4. Synthesis of tert-butyl (3R)-3-{[(prop-2-en-1-yloxy)carbonyl]amino}-1-oxa-8-azaspiro[4.5]decane-8-carboxylate (C19)

Prop-2-en-1-yl carbonochloridate (7.13 g, 59.2 mmol) was added drop-wise to a 0° C. solution of C18 (15.2 g, 39.4 mmol) in saturated aqueous sodium bicarbonate solution (160 mL) and tetrahydrofuran (40 mL). The reaction mixture was stirred at 10° C. for 14 hours, whereupon it was extracted with ethyl acetate (3×100 mL). The combined organic layers were dried over sodium sulfate, filtered, and concentrated in vacuo to afford the product as a pale yellow gum (13.6 g). This material was used directly in the following step. $^1$H NMR (400 MHz, CDCl$_3$) δ 5.98-5.85 (m, 1H), 5.31 (apparent br dd, J=17.2, 1.4 Hz, 1H), 5.23 (br d, J=10.3 Hz, 1H), 4.95-4.84 (m, 1H), 4.62-4.51 (m, 2H), 4.39-4.27 (m, 1H), 4.00 (dd, J=9.4, 5.6 Hz, 1H), 3.73-3.52 (m, 3H), 3.38-3.24 (m, 2H), 2.13 (dd, J=13.3, 7.8 Hz, 1H), 1.74-1.57 (m, 4H, assumed; partially obscured by water peak), 1.56-1.46 (m, 1H), 1.46 (s, 9H).

Step 5. Synthesis of tert-butyl (3R)-3-{methyl[(prop-2-en-1-yloxy)carbonyl]amino}-1-oxa-8-azaspiro[4.5]decane-8-carboxylate (C20)

Sodium hydride (60% dispersion in mineral oil; 2.36 g, 59.0 mmol) was added to a 0° C. solution of C19 (from the previous step; 13.4 g, 538.8 mmol) in tetrahydrofuran (200 mL), and the reaction mixture was stirred at 0° C. for 30 minutes. Iodomethane (16.8 g, 118 mmol) was added drop-wise, and stirring was continued for 16 hours at 0° C. to 5° C. Sodium hydride (60% dispersion in mineral oil; 2.36 g, 59.0 mmol) was again added, and the reaction mixture was stirred at 25° C. for 16 hours, whereupon it was poured into saturated aqueous ammonium chloride solution (200 mL) and extracted with ethyl acetate (3×300 mL). The combined organic layers were washed with saturated aqueous sodium chloride solution (600 mL), dried over sodium sulfate, filtered, and concentrated under reduced pressure to afford the product as a brown gum (16 g). This was used in the following step without additional purification. $^1$H NMR (400 MHz, CDCl$_3$) δ 5.99-5.89 (m, 1H), 5.34-5.27 (m, 1H), 5.24-5.19 (m, 1H), 5.09-4.85 (br m, 1H), 4.59 (ddd, J=5.5, 1.5, 1.4 Hz, 2H), 3.94 (dd, half of ABX pattern, J=9.7, 7.6 Hz, 1H), 3.76 (dd, half of ABX pattern, J=9.9, 5.4 Hz, 1H), 3.69-3.52 (m, 2H), 3.38-3.23 (m, 2H), 2.87 (s, 3H), 2.09 (dd, J=13.1, 9.0 Hz, 1H), 1.75-1.60 (m, 4H, assumed; partially obscured by water peak), 1.51-1.41 (m, 1H), 1.46 (s, 9H).

Step 6. Synthesis of prop-2-en-1-yl methyl[(3R)-1-oxa-8-azaspiro[4.5]dec-3-yl]carbamate, trifluoroacetate salt (C21)

Trifluoroacetic acid (20 mL) was added to a solution of C20 (from the previous step; 16 g, ≤38.8 mmol) in dichloromethane (100 mL), and the reaction mixture was stirred at 15° C. for 2 hours. Removal of volatiles in vacuo afforded Step 7. Synthesis of (2R)-1,1,1-trifluoro-3-[(4-methoxybenzyl)oxy]propan-2-yl (3R)-3-{methyl [(prop-2-en-1-yloxy) carbonyl]amino}-1-oxa-8-azaspiro[4.5]decane-8-carboxylate (C22)

Triethylamine (19.9 g, 197 mmol) was slowly added to a 0° C. solution of C21 (from the previous step; 20 g, ≤38.8 mmol) in acetonitrile (250 mL). The reaction mixture was stirred at 0° C. for 30 minutes, whereupon C2 [reaction solution in acetonitrile (80 mL) containing 40 mmol], was added, and stirring was continued at 13° C. for 18 hours. The reaction mixture was concentrated in vacuo, and the residue was purified via silica gel chromatography (Gradient: 9% to 50% ethyl acetate in petroleum ether) to provide the product as a pale yellow gum. Yield: 16.67 g, 31.4 mmol, 81% over 4 steps. LCMS m/z 553.1 [M+Na$^+$]. $^1$H NMR (400 MHz, CDCl$_3$) δ 7.24 (br d, J=8.8 Hz, 2H), 6.88 (br d, J=8.8 Hz, 2H), 6.01-5.89 (m, 1H), 5.53-5.43 (m, 1H), 5.35-5.27 (m, 1H), 5.26-5.20 (m, 1H), 5.08-4.86 (br m, 1H), 4.60 (ddd, J=5.5, 1.5, 1.2 Hz, 2H), 4.51 (AB quartet, J$_{AB}$=11.5 Hz, Δν$_{AB}$=28.3 Hz, 2H), 3.94 (dd, J=9.8, 7.5 Hz, 1H), 3.81 (s, 3H), 3.80-3.64 (m, 5H), 3.43-3.25 (m, 2H), 2.88 (s, 3H), 2.13-2.00 (m, 1H), 1.80-1.60 (m, 4H), 1.47 (ddd, J=13.6, 10.8, 4.3 Hz, 1H).

Step 8. Synthesis of (2R)-1,1,1-trifluoro-3-[(4-methoxybenzyl)oxy]propan-2-yl (3R)-3-(methylamino)-1-oxa-8-azaspiro[4.5]decane-8-carboxylate (C23)

Tetrakis(triphenylphosphine)palladium(0) (2.12 g, 1.83 mmol) was added to a 10° C. solution of C22 (6.50 g, 12.2 mmol) and 1,3-dimethylpyrimidine-2,4,6(1H,3H,5H)-trione (2.87 g, 18.4 mmol) in tetrahydrofuran (100 mL). After the reaction mixture had been stirred at 25° C. for 2 hours, solid sodium carbonate (65 mg, 0.61 mmol) was added, and stirring was continued at 10° C. for 20 minutes. The reaction mixture was filtered, and the filtrate was concentrated in vacuo. The residue was purified twice by silica gel chromatography (Gradient: 0% to 10% methanol in dichloromethane) to afford the product as a yellow gum. Yield: 3.8 g, 8.5 mmol, 70%. LCMS m/z 447.3 [M+H]$^+$. $^1$H NMR (400 MHz, CDCl$_3$) δ 7.24 (br d, J=8.7 Hz, 2H), 6.88 (br d, J=8.7 Hz, 2H), 5.53-5.42 (m, 1H), 4.51 (AB quartet, J$_{AB}$=11.6 Hz, Δν$_{AB}$=28.0 Hz, 2H), 3.96 (dd, J=9.2, 6.0 Hz, 1H), 3.81 (s, 3H), 3.8-3.64 (m, 5H), 3.43-3.28 (m, 3H), 2.43 (s, 3H), 2.08-1.97 (m, 1H), 1.85-1.46 (m, 5H, assumed; partially obscured by water peak).

Step 9. Synthesis of (2R)-1,1,1-trifluoro-3-[(4-methoxybenzyl)oxy]propan-2-yl (3R)-3-[(cyclopentylcarbonyl)(methyl)amino]-1-oxa-8-azaspiro[4.5]decane-8-carboxylate (C24)

To an 18° C. suspension of C23 (110 mg, 0.246 mmol) in dichloromethane (1 mL) were added cyclopentanecarboxylic acid (33.7 mg, 0.295 mmol), O-(7-azabenzotriazol-1-yl)-N,N,N',N'-tetramethyluronium hexafluorophosphate (HATU; 281 mg, 0.739 mmol), and N,N-diisopropylethylamine (159 mg, 1.23 mmol). The reaction mixture was stirred at 18° C. for 2 hours, whereupon it was combined with a similar reaction mixture derived from C23 (20 mg, 45 μmol), concentrated in vacuo, and purified via silica gel chromatography (Gradient: 0% to 80% ethyl acetate in petroleum ether). The product was isolated as a colorless gum. Yield: 158 mg, 0.291 mmol, 100%. LCMS m/z 565.1 [M+Na$^+$].

Step 10. Synthesis of (2R)-1,1,1-trifluoro-3-hydroxypropan-2-yl (3R)-3-[(cyclopentylcarbonyl)(methyl)amino]-1-oxa-8-azaspiro[4.5]decane-8-carboxylate (5)

Trifluoroacetic acid (3 mL) was added drop-wise to a 0° C. solution of C24 (158 mg, 0.291 mmol) in dichloromethane (10 mL). The reaction mixture was stirred at 18° C. for 2 hours, whereupon it was diluted with saturated aqueous sodium chloride solution and extracted with dichloromethane (3×15 mL). The combined organic layers were dried over sodium sulfate, filtered, and concentrated in vacuo. Purification via reversed-phase HPLC (Column: YMC-Actus Triart C18, 5 μm; Mobile phase A: water containing 0.225% formic acid; Mobile phase B: acetonitrile; Gradient: 40% to 60% B) afforded the product as a white gum. Variable temperature $^1$H NMR (DMSO-d$_6$, 80° C.) was used to establish that the product exists as a mixture of rotamers. Yield: 45.1 mg, 0.107 mmol, 37%. LCMS m/z 423.1 [M+H]$^+$. $^1$H NMR (400 MHz, CDCl$_3$) δ [5.47-5.36 (m) and 4.82-4.71 (m), total 1H], 5.31-5.19 (br m, 1H), 4.02-3.89 (m, 2H), 3.89-3.67 (m, 4H), 3.47-3.25 (m, 2H), [2.98 (s) and 2.85 (s), total 3H], 2.96-2.79 (m, 1H), [2.16-2.02 (m), 1.88-1.67 (m), and 1.64-1.41 (m), total 14H].

Example 6

(2R)-1,1,1-Trifluoro-3-hydroxypropan-2-yl (3R)-3-[(tert-butylsulfonyl) (methyl)amino]-1-oxa-8-azaspiro[4.5]decane-8-carboxylate (6)

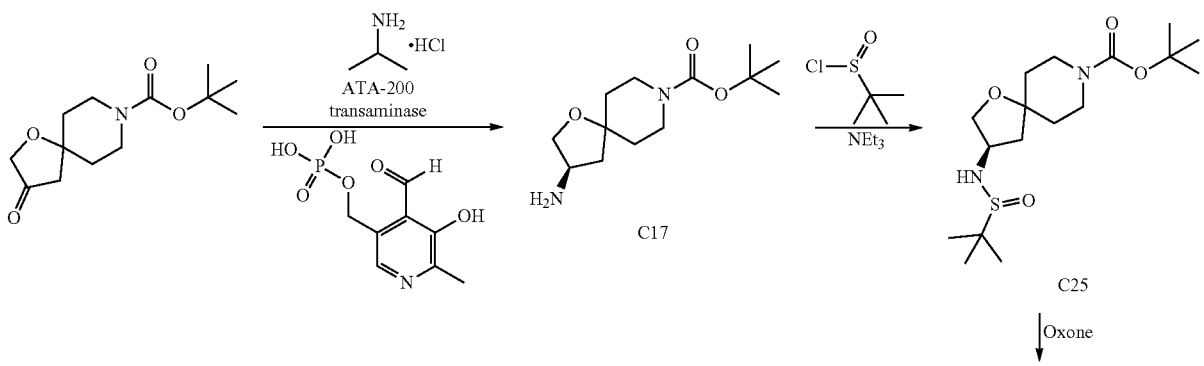

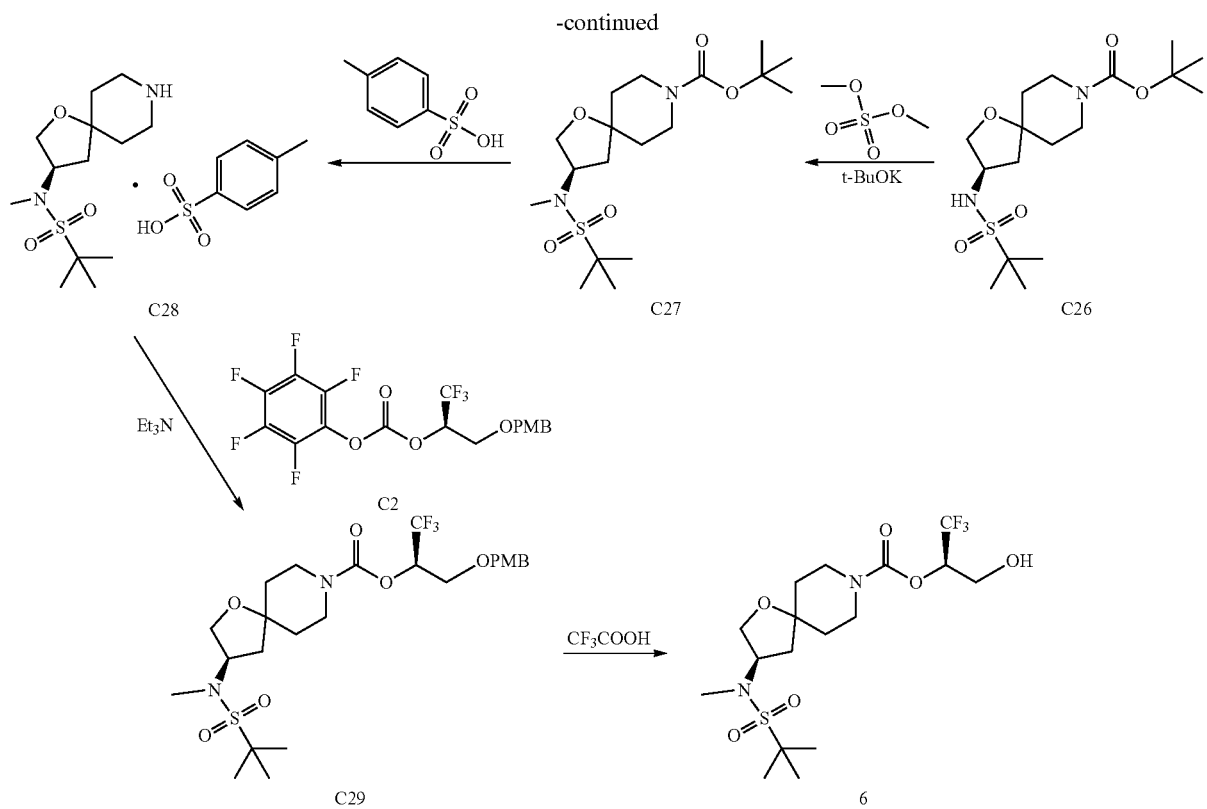

Step 1. Improved synthesis of tert-butyl (3R)-3-amino-1-oxa-8-azaspiro[4.5]decane-8-carboxylate (C17)

A pH 8.0 buffer solution was prepared, containing 0.1 M aqueous potassium phosphate. A stock solution of substrate was prepared as follows: tert-butyl 3-oxo-1-oxa-8-azaspiro[4.5]decane-8-carboxylate (4.00 g, 15.7 mmol) was dissolved in dimethyl sulfoxide (4 mL); some warming was required to effect dissolution.

An aqueous solution of propan-2-amine, hydrochloride salt (4.0 M; 9.80 mL, 39.2 mmol) was combined with the potassium phosphate buffer (63.8 mL). The substrate solution was then added slowly, over 2 minutes. After this mixture had stirred overnight, Codex® ATA-200 transaminase (batch D11099; 320 mg) and pyridoxal 5′-phosphate monohydrate (40 mg, 0.16 mmol) were added, and the reaction mixture was stirred for 24 hours at 35° C. with a nitrogen sweep (50 mL/minute) through a needle placed above the reaction surface. The pH was then adjusted to 3.2 by addition of aqueous hydrochloric acid (12 M, approximately 500 µL), and the resulting mixture was treated with diatomaceous earth (2.6 g) and ethyl acetate (50 mL), and stirred for 30 minutes. The mixture was filtered through a pad of diatomaceous earth (previously wetted with 1.3 g water), and the aqueous layer of the filtrate was adjusted to pH 10.2 by addition of aqueous sodium hydroxide solution (25%; approximately 3.5 mL). This was repeatedly extracted with tert-butyl methyl ether (50 mL), with the aqueous layer being readjusted to pH 10.2 between extractions. After 4 extractions, the organic layers were combined, dried over sodium sulfate, and filtered. {Solutions of this type, either in tert-butyl methyl ether or 2-methyltetrahydrofuran, were normally utilized directly in subsequent reactions; the concentration of C17 was determined via solvent removal from a specific volume of solution and determination of the mass of the residue.} Concentration in vacuo afforded the product as a white solid. Yield: 1.85 g, 7.22 mmol, 46%. $^1$H NMR (400 MHz, CDCl$_3$) δ 3.94 (dd, J=8.8, 5.7 Hz, 1H), 3.67-3.51 (m, 3H), 3.49 (dd, J=8.8, 5.3 Hz, 1H), 3.39-3.26 (m, 2H), 2.06 (dd, J=12.9, 7.4 Hz, 1H), 1.77-1.42 (m, 5H), 1.45 (s, 9H).

Step 2. Synthesis of tert-butyl (3R)-3-[(tert-butylsulfinyl)amino]-1-oxa-8-azaspiro[4.5]decane-8-carboxylate (C25)

A solution of C17 in 2-methyltetrahydrofuran (134 mg/mL; 7.5 mL, 1.0 g, 3.9 mmol) was cooled to 0° C. and treated with 2-methylpropane-2-sulfinyl chloride (0.48 mL, 3.9 mmol). After the mixture had been allowed to stir at 0° C. for 1 minute, triethylamine (0.54 mL, 3.9 mmol) was added, and stirring was continued at 0° C. for 5 minutes. The reaction mixture was then allowed to warm to room temperature and stir for 1 hour, whereupon it was filtered through a pad of diatomaceous earth, and the pad was rinsed with 2-methyltetrahydrofuran. The combined filtrates were concentrated in vacuo and purified via silica gel chromatography (Gradient: 50% to 100% ethyl acetate in heptane), affording the product as a solid, white foam. From analysis of the $^1$H NMR, this material was presumed to exist as a mixture of diastereomers, due to the stereochemistry around the sulfinamide. Yield: 1.26 g, 3.49 mmol, 89%. LCMS m/z 361.5 [M+H]$^+$. $^1$H NMR (400 MHz, CDCl$_3$) δ 4.11-3.99 (m, 2H), 3.77-3.69 (m, 1H), 3.68-3.52 (br m, 2H), [3.38-3.25 (m) and 3.18 (d, J=5.8 Hz), total 3H], [2.21 (dd, J=13.1, 7.2 Hz) and 2.15-2.06 (m), total 1H], 1.81-1.48 (m, 5H, assumed; partially obscured by water peak), 1.46 (s, 9H), [1.22 (s) and 1.22 (s), total 9H].

Step 3. Synthesis of tert-butyl (3R)-3-[(tert-butylsulfonyl)amino]-1-oxa-8-azaspiro[4.5]decane-8-carboxylate (C26)

A solution of potassium peroxymonosulfate (Oxone®, 98%; 4.35 g, 6.93 mmol) in water (18 mL) was added in a drop-wise manner over 5 minutes to a 0° C. solution of C25 (1.25 g, 3.47 mmol) in methanol (18 mL). The reaction mixture was stirred at 0° C. for 1 minute, and subsequently allowed to warm to room temperature and stir for 17 hours. It was then cooled to 0° C., and slowly made basic by addition of saturated aqueous sodium bicarbonate solution. The resulting mixture was extracted three times with dichloromethane, and the combined organic layers were washed with saturated aqueous sodium chloride solution, dried over sodium sulfate, filtered, and concentrated in vacuo to provide the product as a white solid. Yield: 1.16 g, 3.08 mmol, 89%. LCMS m/z 375.6 [M–H+]. $^1$H NMR (400 MHz, CDCl$_3$) δ 4.17-4.08 (m, 1H), 4.06-3.99 (m, 2H), 3.70 (dd, J=9.4, 4.7 Hz, 1H), 3.68-3.54 (br m, 2H), 3.38-3.25 (m, 2H), 2.20 (dd, J=13.5, 7.6 Hz, 1H), 1.75-1.46 (m, 5H, assumed; partially obscured by water peak), 1.46 (s, 9H), 1.40 (s, 9H).

Step 4. Synthesis of tert-butyl (3R)-3-[(tert-butylsulfonyl) (methyl)amino]-1-oxa-8-azaspiro[4.5]decane-8-carboxylate (C27)

Potassium tert-butoxide (1 M solution in tetrahydrofuran; 4.58 mL, 4.58 mmol) was added in a drop-wise manner to a 0° C. solution of C26 (1.15 g, 3.05 mmol) in tetrahydrofuran (25 mL). Stirring was continued at 0° C. for 30 minutes, whereupon dimethyl sulfate (867 μL, 9.16 mmol) was added drop-wise to the reaction mixture, which was subsequently allowed to warm to room temperature and stir for 2 hours. It was then cooled to 0° C., quenched by addition of saturated aqueous ammonium chloride solution, and extracted three times with ethyl acetate. The combined organic layers were washed with saturated aqueous sodium chloride solution, dried over sodium sulfate, filtered, and concentrated in vacuo. The residue was stirred in heptane (100 mL) for 1 hour and filtered; the collected solid was rinsed with heptane to afford the product as a white solid (988 mg). The filtrate was concentrated in vacuo to provide additional product as a white solid (138 mg). Combined yield: 1.126 g, 2.883 mmol, 94%. LCMS m/z 291.5 {[M–(2-methylprop-1-ene and carbon dioxide)]+H}+. $^1$H NMR (400 MHz, CDCl$_3$) δ 4.71-4.61 (m, 1H), 3.96 (dd, half of ABX pattern, J=10.0, 7.6 Hz, 1H), 3.83 (dd, half of ABX pattern, J=10.0, 5.3 Hz, 1H), 3.70-3.52 (br m, 2H), 3.38-3.21 (m, 2H), 2.91 (s, 3H), 2.10 (dd, half of ABX pattern, J=13.3, 9.4 Hz, 1H), 1.77 (dd, half of ABX pattern, J=13.5, 7.2 Hz, 1H), 1.74-1.60 (m, 3H), 1.50-1.40 (m, 1H), 1.46 (s, 9H), 1.37 (s, 9H).

Step 5. Synthesis of N,2-dimethy-N-[(3R)-1-oxa-8-azaspiro[4.5]dec-3-yl]propane-2-sulfonamide, p-toluenesulfonate salt (C28)

To a solution of C27 (1.12 g, 2.87 mmol) in ethyl acetate (25 mL) was added p-toluenesulfonic acid monohydrate (1.09 g, 5.73 mmol) and the reaction mixture was stirred at 50° C. for 1.5 hours. It was then cooled to 0° C.; the solids were collected via filtration and rinsed with cold ethyl acetate, affording the product as a white solid. Yield: 1.07 g, 2.31 mmol, 80%. LCMS m/z 291.5 [M+H]+. $^1$H NMR (400 MHz, CDCl$_3$) δ 8.97-8.83 (br m, 1H), 8.64-8.49 (br m, 1H), 7.74 (br d, J=8.2 Hz, 2H), 7.23 (br d, J=7.8 Hz, 2H), 4.68-4.57 (m, 1H), 3.89 (dd, half of ABX pattern, J=10.2, 7.4 Hz, 1H), 3.78 (dd, half of ABX pattern, J=10.0, 5.6 Hz, 1H), 3.41-3.07 (m, 4H), 2.86 (s, 3H), 2.39 (s, 3H), 2.19-2.08 (m, 1H), 2.05 (dd, half of ABX pattern, J=13.5, 9.2 Hz, 1H), 1.90-1.73 (m, 4H), 1.35 (s, 9H).

Step 6. Synthesis of (2R)-1,1,1-trifluoro-3-[(4-methoxybenzyl)oxy]propan-2-yl (3R)-3-[(tert-butylsulfonyl) (methyl)amino]-1-oxa-8-azaspiro[4.5]decane-8-carboxylate (C29)

Conversion of C28 to C29 was carried out using the method described for synthesis of C5 from C4 in Example 1. In this case, silica gel chromatography was carried out using eluents of 20% followed by 40% and 60% ethyl acetate in heptane, affording the product as a thick, colorless oil. Yield: 974 mg, 1.72 mmol, 91%. $^1$H NMR (400 MHz, CDCl$_3$) δ 7.24 (br d, J=8.6 Hz, 2H), 6.88 (br d, J=8.6 Hz, 2H), 5.54-5.42 (br m, 1H), 4.72-4.61 (m, 1H), 4.51 (AB quartet, J$_{AB}$=11.7 Hz, Δv$_{AB}$=28.1 Hz, 2H), 3.96 (dd, half of ABX pattern, J=10.2, 7.4 Hz, 1H), 3.90-3.64 (m, 5H), 3.82 (s, 3H), 3.43-3.24 (m, 2H), 2.91 (s, 3H), 2.14-1.99 (m, 1H), 1.86-1.62 (m, 4H), 1.45 (ddd, J=13.7, 10.9, 4.3 Hz, 1H), 1.37 (s, 9H).

Step 7. Synthesis of (2R)-1,1,1-trifluoro-3-hydroxypropan-2-yl (3R)-3-[(tert-butylsulfonyl) (methyl)amino]-1-oxa-8-azaspiro[4.5]decane-8-carboxylate (6)

Trifluoroacetic acid (5.0 mL) was added to a 0° C. solution of C29 (972 mg, 1.72 mmol) in dichloromethane (20 mL). The reaction mixture was allowed to stir at room temperature for 70 minutes, whereupon it was concentrated in vacuo, and the residue was partitioned between dichloromethane and saturated aqueous sodium bicarbonate solution. The aqueous layer was extracted twice with dichloromethane, and the combined organic layers were dried over sodium sulfate, filtered, and concentrated in vacuo. Silica gel chromatography (Eluents: 10% followed by 25%, 50%, and 75% ethyl acetate in heptane) provided the product as a white solid. Yield: 697 mg, 1.56 mmol, 91%. LCMS m/z 447.6 [M+H]+. $^1$H NMR (400 MHz, CDCl$_3$) δ 5.31-5.20 (br m, 1H), 4.72-4.63 (m, 1H), 4.04-3.92 (m, 2H), 3.92-3.72 (m, 4H), 3.47-3.27 (m, 2H), 2.91 (s, 3H), 2.16-2.05 (m, 1H), 1.86-1.42 (m, 6H, assumed; partially obscured by water peak), 1.38 (s, 9H).

Example 7
(2R)-1,1,1-Trifluoro-3-hydroxypropan-2-yl (3R)-3-[(2,2-dimethylpropanoyl)(methyl)amino]-1-oxa-8-azaspiro[4.5]decane-8-carboxylate (7)
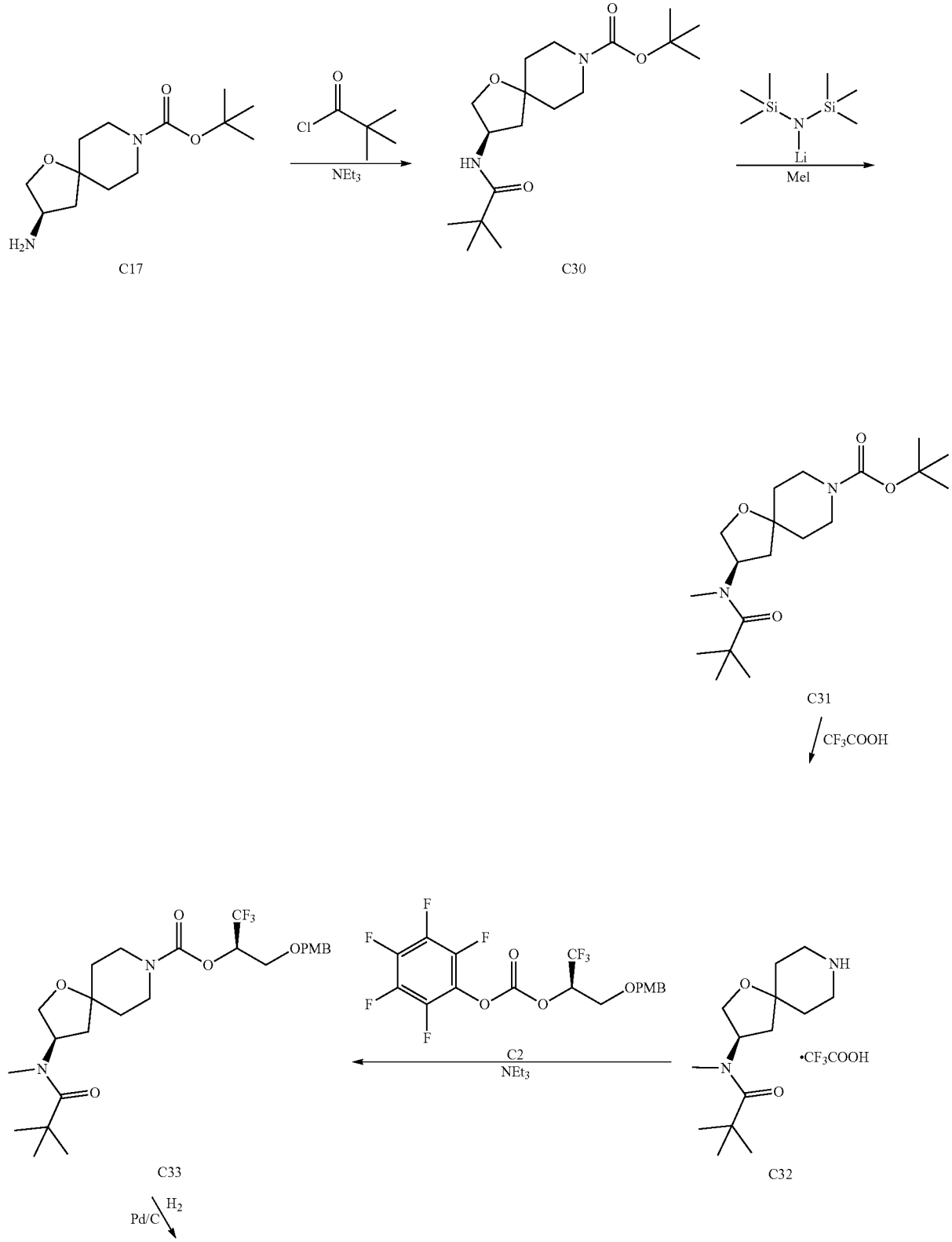

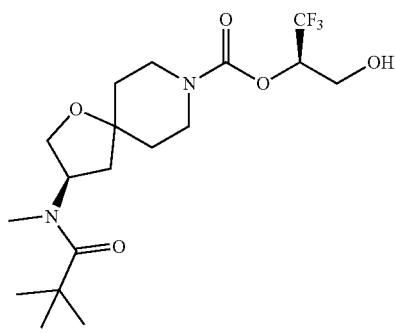

7

Step 1. Synthesis of tert-butyl (3R)-3-[(2,2-dimethylpropanoyl)amino]-1-oxa-8-azaspiro[4.5]decane-8-carboxylate (C30)

A solution of C17 in 2-methyltetrahydrofuran (428 mg/mL; 114 mL, 48.8 g, 190 mmol) was diluted with 2-methyltetrahydrofuran (250 mL), cooled to 0° C. and treated with triethylamine (31.8 mL, 228 mmol), followed by 2,2-dimethylpropanoyl chloride (25.0 mL, 203 mmol). After the reaction mixture had stirred at 0° C. for 30 minutes, it was allowed to slowly warm to room temperature and stir for 75 minutes. It was then filtered through a pad of diatomaceous earth, which was subsequently rinsed with 2-methyltetrahydrofuran (500 mL). The combined filtrates were concentrated in vacuo and subjected to two rounds of trituration with diethyl ether, affording the product as a solid. Yield: 65 g, 190 mmol, quantitative. LCMS m/z 341.5 [M+H]$^+$. $^1$H NMR (400 MHz, CDCl$_3$) δ 5.78 (br d, J=7.0 Hz, 1H), 4.55-4.46 (m, 1H), 4.02 (dd, J=9.8, 5.5 Hz, 1H), 3.65 (br dd, J=9.8, 3.5 Hz, 1H), 3.65-3.55 (m, 2H), 3.38-3.27 (m, 2H), 2.16 (dd, J=13.3, 7.4 Hz, 1H), 1.7-1.58 (m, 4H, assumed; partially obscured by water peak), 1.56-1.47 (m, 1H), 1.46 (s, 9H), 1.19 (s, 9H).

Step 2. Synthesis of tert-butyl (3R)-3-[(2, 2-dimethylpropanoyl)(methyl)amino]-1-oxa-8-azaspiro[4.5]decane-8-carboxylate (C31)

A 0° C. solution of lithium bis(trimethylsilyl)amide (1.5 M; 253 mL, 380 mmol) was added via cannula to a 0° C. solution of C30 (65 g, 190 mmol) in tetrahydrofuran (1 L). The reaction mixture was stirred at 0° C. for 1.5 hours, whereupon iodomethane (41.4 mL, 665 mmol) was added and the reaction mixture was allowed to stir at room temperature for 3 hours. It was then partitioned between saturated aqueous ammonium chloride solution (400 mL) and ethyl acetate (250 mL), and the aqueous layer was extracted twice with ethyl acetate (total of 2.5 L). The combined organic layers were dried over magnesium sulfate, filtered, and concentrated in vacuo. The resulting gummy material was divided in half for processing; each half was admixed with diethyl ether (600 mL), followed by heptane (200 mL), and the flask was swirled until the solids adhered to the sides of the flask. The supernatant was filtered through a small plug of diatomaceous earth, and the filtrate was concentrated in vacuo to afford the product as a light yellow solid. Total yield: 37 g, 100 mmol, 53%. LCMS m/z 355.6 [M+H]$^+$. $^1$H NMR (400 MHz, CDCl$_3$) δ 5.23-5.12 (m, 1H), 3.95 (dd, half of ABX pattern, J=9.8, 7.8 Hz, 1H), 3.77 (dd, half of ABX pattern, J=10.0, 5.3 Hz, 1H), 3.68-3.55 (m, 2H), 3.39-3.24 (m, 2H), 2.95 (s, 3H), 2.09 (dd, J=13.3, 9.0 Hz, 1H), 1.75-1.60 (m, 4H), 1.53-1.43 (m, 1H), 1.46 (s, 9H), 1.30 (s, 9H).

Step 3. Synthesis of N,2,2-trimethyl-N-[(3R)-1-oxa-8-azaspiro[4.5]dec-3-yl]propanamide, trifluoroacetate salt (C32)

Trifluoroacetic acid (84 mL) was added to a 0° C. solution of C31 (20.0 g, 56.4 mmol) in dichloromethane (280 mL) and the reaction mixture was stirred at 0° C. After 30 minutes, it was concentrated in vacuo, and the residue was azeotroped three times with heptane, affording the product as a highly viscous oil. This material was used in the following step without further purification. LCMS m/z 255.5 [M+H]$^+$. $^1$H NMR (400 MHz, CDCl$_3$), characteristic product peaks: δ 8.35-8.05 (br s, 2H), 5.25-5.15 (m, 1H), 3.97 (dd, half of ABX pattern, J=10.2, 7.4 Hz, 1H), 3.83 (dd, half of ABX pattern, J=10.3, 5.3 Hz, 1H), 3.44-3.23 (m, 4H), 3.02 (s, 3H), 2.21 (dd, J=13.3, 9.0 Hz, 1H), 1.31 (s, 9H).

Step 4. Synthesis of (2R)-1,1,1-trifluoro-3-[(4-methoxybenzyl)oxy]propan-2-yl (3R)-3-[(2,2-dimethylpropanoyl)(methyl)amino]-1-oxa-8-azaspiro[4.5]decane-8-carboxylate (C33)

A solution of C32 (from the previous step; ≤56.4 mmol) in acetonitrile (140 mL) was cooled to 0° C. and treated with triethylamine (78 mL, 560 mmol). Compound C2 (reaction solution in acetonitrile, at 0° C., containing 72.7 mmol) was added via cannula, and the reaction mixture was allowed to slowly warm to room temperature overnight. It was then concentrated in vacuo; the residue was dissolved in ethyl acetate (600 ml) and washed sequentially with aqueous hydrochloric acid (1 M; 100 mL), saturated aqueous ammonium chloride solution (125 mL), and saturated aqueous sodium chloride solution (100 mL). The organic layer was dried, filtered, and concentrated in vacuo, whereupon non-polar impurities were removed by loading the resulting material on a 4 inch pad of silica gel and eluting with ethyl acetate in heptane (4 L of 20%, followed by 1 L of 40%). Subsequent elution with 1:1 ethyl acetate/heptane afforded partially purified product (25 g), which was subjected to silica gel chromatography (Eluent: 1:1 ethyl acetate/heptane) to provide the product as a viscous oil. Yield: 19.0 g, 35.8 mmol, 63% over two steps. LCMS m/z 531.5 [M+H]$^+$. $^1$H NMR (400 MHz, CDCl$_3$) δ 7.24 (br d, J=8.6 Hz, 2H), 6.88 (br d, J=8.6 Hz, 2H), 5.53-5.43 (br m, 1H), 5.23-5.12 (br m, 1H), 4.51 (AB quartet, J$_{AB}$=1.7 Hz, Δv$_{AB}$=28.5 Hz, 2H), 3.95 (dd, J=10.0, 7.6 Hz, 1H), 3.89-3.64 (m, 4H), 3.81

(s, 3H), 3.77 (dd, J=10.0, 5.3 Hz, 1H), 3.44-3.26 (m, 2H), 2.96 (br s, 3H), 2.13-1.99 (br m, 1H), 1.82-1.62 (br m, 4H), 1.48 (ddd, J=13.3, 11.1, 4.5 Hz, 1H), 1.30 (s, 9H).

Step 5. Synthesis of (2R)-1,1,1-trifluoro-3-hydroxypropan-2-yl (3R)-3-[(2,2-dimethylpropanoyl)(methyl)amino]-1-oxa-8-azaspiro[4.5]decane-8-carboxylate (7)

Hydrogenation of C33 (30.8 g, 58.0 mmol) was carried out in ethanol (620 mL), using palladium on carbon [10% Pd (50% wet with water); 3.08 g] and hydrogen at 50 psi. The reaction took less than 3 hours to go to completion, at which time the catalyst was removed via filtration through diatomaceous earth. The filter pad was rinsed with ethanol and the combined filtrates were concentrated in vacuo. The resulting gummy material was treated with ethyl acetate (100 mL), followed by heptane (300 mL), and the mixture was vigorously stirred under a flow of nitrogen. The resulting solid was isolated via filtration using a nylon filter, to provide the product as a white solid. Yield: 16 g, 39 mmol, 68%. LCMS m/z 411.5 [M+H]$^+$. $^1$H NMR (400 MHz, CDCl$_3$) δ 5.31-5.13 (m, 2H), 4.04-3.92 (m, 2H), 3.92-3.73 (m, 4H), 3.48-3.28 (m, 2H), 2.96 (s, 3H), 2.15-2.05 (m, 1H), 1.82-1.66 (m, 4H), 1.6-1.44 (m, 1H, assumed; partially obscured by water peak), 1.30 (s, 9H). A sample of 7 was stirred in heptane overnight and filtered, affording a white solid (melting point 105.2° C.) that proved to be crystalline via powder X-ray diffraction.

Examples 8 and 9

(2R)-1,1,1-Trifluoro-3-hydroxypropan-2-yl 3-[4-(trifluoromethyl)-1H-pyrazol-1-yl]-1-oxa-8-azaspiro[4.5]decane-8-carboxylate, DIAST 1 [From C39, DIAST 1] (8) and (2R)-1,1,1-Trifluoro-3-hydroxypropan-2-yl 3-[4-(trifluoromethyl)-1H-pyrazol-1-yl]-1-oxa-8-azaspiro[4.5]decane-8-carboxylate, DIAST 2 [From C40, DIAST 2] (9)

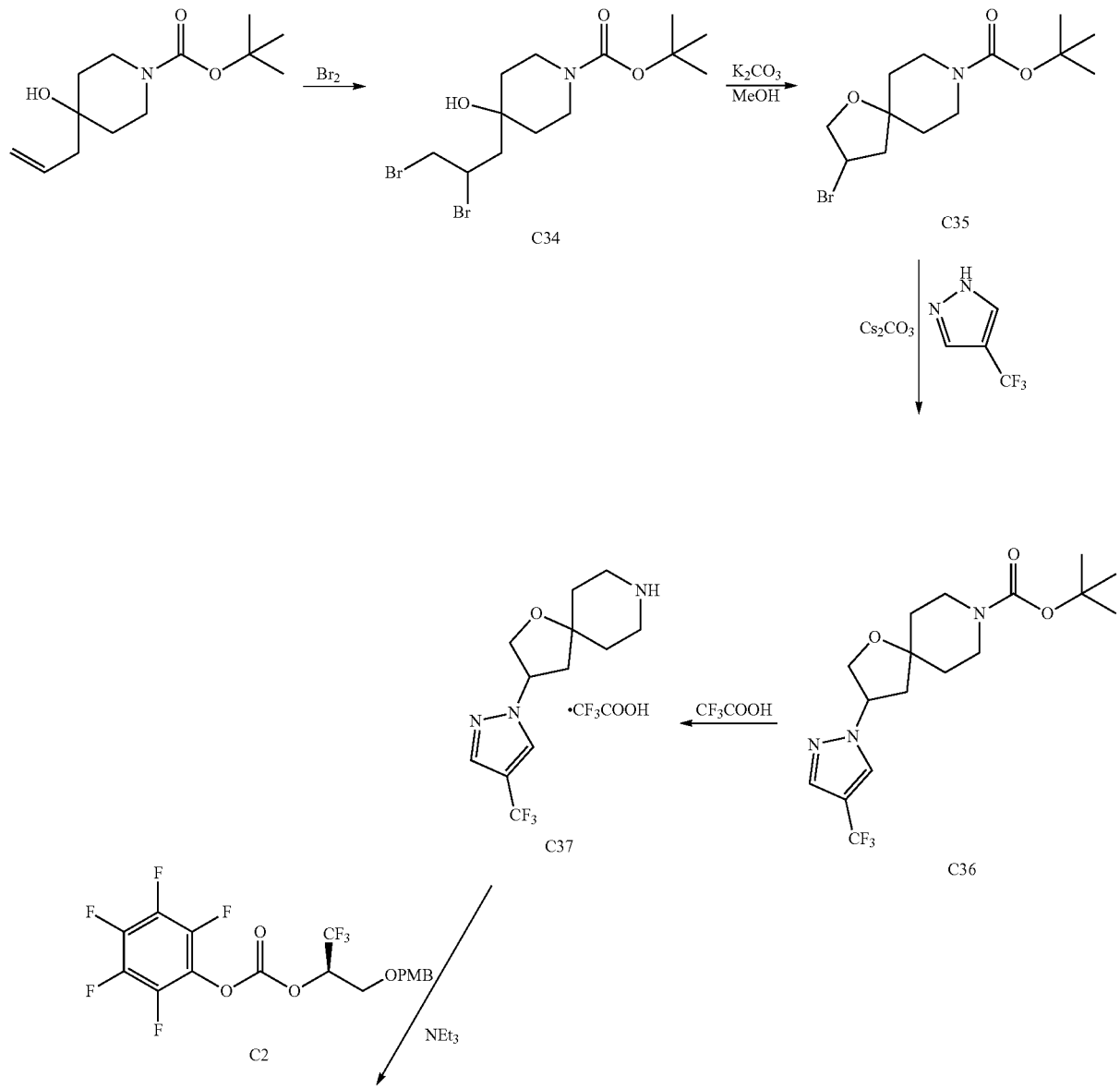

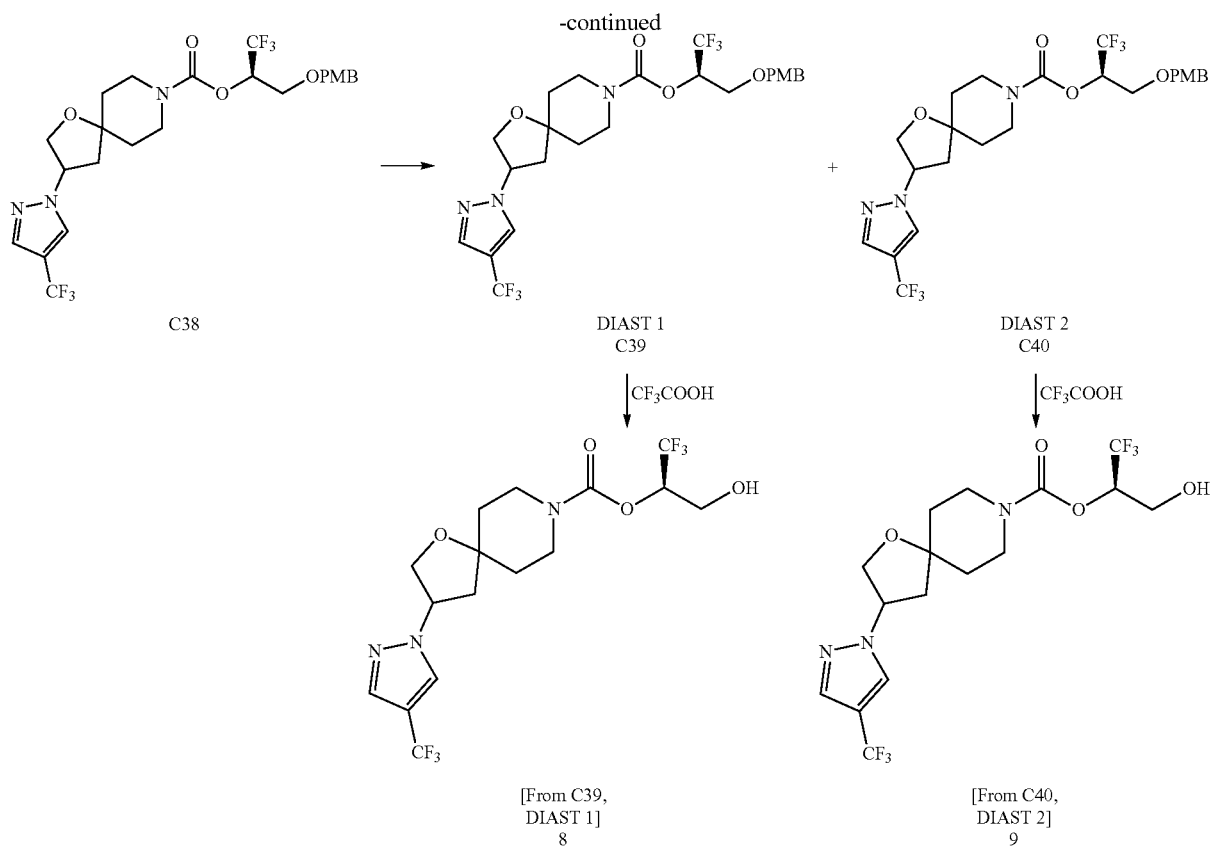

Step 1. Synthesis of tert-butyl 4-(2, 3-dibromopropyl)-4-hydroxypiperidine-1-carboxylate (C34)

This reaction was carried out in two identical batches. A solution of tert-butyl 4-hydroxy-4-(prop-2-en-1-yl)piperidine-1-carboxylate (209 g, 0.866 mol) in dichloromethane (1.2 L) was cooled in a cold water bath. A solution of bromine (152 g, 0.951 mol) in dichloromethane (250 mL) was added at such a rate that the color of the reaction mixture did not become intense. At the conclusion of the addition, an aqueous solution containing sodium thiosulfate and sodium bicarbonate was added to the reaction mixture, and stirring was continued until the mixture had completely decolorized. At this point, the two batches were combined. The aqueous layer was extracted with dichloromethane (3×400 mL), and the combined organic layers were washed with saturated aqueous sodium chloride solution (2×200 mL), dried over sodium sulfate, and concentrated in vacuo to afford the product as a red gum. Yield: 600 g, 1.5 mol, 87%. $^1$H NMR (400 MHz, CDCl$_3$) δ 4.43-4.33 (m, 1H), 3.96-3.74 (m, 2H), 3.91 (dd, J=10.3, 4.0 Hz, 1H), 3.66 (dd, J=10.0, 9.8 Hz, 1H), 3.27-3.13 (m, 2H), 2.47 (dd, half of ABX pattern, J=15.8, 2.8 Hz, 1H), 2.13 (dd, half of ABX pattern, J=15.7, 8.9 Hz, 1H), 1.78-1.68 (m, 2H), 1.65-1.53 (m, 2H, assumed; partially obscured by water peak), 1.47 (s, 9H).

Step 2. Synthesis of tert-butyl 3-bromo-1-oxa-8-azaspiro[4.5]decane-8-carboxylate (C35)

Potassium carbonate (119 g, 861 mmol) was added to a cooled solution of C34 (230 g, 573 mmol) in methanol (1.5 L), and the reaction mixture was stirred at 10° C. to 15° C. for 16 hours. The crude reaction mixture was combined with the crude reaction mixtures from two similar reactions using C34 (350 g, 873 mmol; and 20 g, 50 mmol) and filtered. The filtrate was concentrated in vacuo, and the resulting red oil was recrystallized from petroleum ether (150 mL) at 0° C. to provide a light yellow solid (360 g). This was subjected to silica gel chromatography (Eluent: dichloromethane), and the purified material was recrystallized from petroleum ether (120 mL) and washed with petroleum ether (3×40 mL) to afford the product as a white solid (180 g). The mother liquors from recrystallization were concentrated under reduced pressure and purified by silica gel chromatography (Gradient: 0% to 20% ethyl acetate in petroleum ether). The resulting material was recrystallized from petroleum ether (100 mL) and washed with petroleum ether (3×40 mL), affording additional product as a white solid (95 g). Combined yield: 275 g, 0.859 mol, 57%. $^1$H NMR (400 MHz, DMSO-d$_6$) δ 4.71-4.63 (m, 1H), 4.12 (dd, J=10.4, 4.9 Hz, 1H), 3.90 (dd, J=10.5, 3.8 Hz, 1H), 3.52-3.40 (m, 2H), 3.3-3.15 (m, 2H), 2.41 (dd, J=14.3, 7.3 Hz, 1H), 2.10 (dd, J=14.0, 4.0 Hz, 1H), 1.79-1.71 (m, 1H), 1.65 (br ddd, half of ABXY pattern, J=13, 10, 4 Hz, 1H), 1.55-1.41 (m, 2H), 1.39 (s, 9H).

Step 3. Synthesis of tert-butyl 3-[4-(trifluoromethyl)-1H-pyrazol-1-yl]-1-oxa-8-azaspiro[4.5]decane-8-carboxylate (C36)

A mixture of C35 (3.39 g, 10.6 mmol), 4-(trifluoromethyl)-1H-pyrazole (1.20 g, 8.82 mmol), and cesium carbonate (8.62 g, 26.5 mmol) in N,N-dimethylformamide (10 mL) was stirred at 80° C. for 2 hours, whereupon it was partitioned between ethyl acetate (50 mL) and water (50 mL). The aqueous layer was extracted with ethyl acetate (2×50 mL), and the combined organic layers were washed with saturated aqueous sodium chloride solution (3×50 mL), dried over sodium sulfate, filtered, and concentrated in vacuo. Purification via silica gel chromatography (Gradient: 0% to 20% ethyl acetate in petroleum ether) provided the product as a white solid. Yield: 2.90 g, 7.73 mmol, 88%. LCMS m/z 320.0 [(M−2-methylprop-1-ene)+H]$^+$. $^1$H NMR (400 MHz, CDCl$_3$) δ 7.79 (s, 1H), 7.72 (s, 1H), 5.03-4.94 (m, 1H), 4.23 (dd, half of ABX pattern, J=10.0, 6.5 Hz, 1H), 4.17 (dd, half of ABX pattern, J=10.0, 4.5 Hz, 1H), 3.72-3.60 (br m, 2H), 3.40-3.28 (m, 2H), 2.36 (dd, half of ABX pattern, J=13.6, 8.5 Hz, 1H), 2.24 (dd, half of ABX pattern, J=13.6, 5.5 Hz, 1H), 1.84-1.64 (m, 3H), 1.64-1.54 (m, 1H), 1.47 (s, 9H).

Step 4. Synthesis of 3-[4-(trifluoromethyl)-1H-pyrazol-1-yl]-1-oxa-8-azaspiro[4.5]decane, trifluoroacetate salt (C37)

Trifluoroacetic acid (4 mL) was added to a 0° C. solution of C36 (2.90 g, 7.73 mmol) in dichloromethane (16 mL). The reaction mixture was stirred at 25° C. for 2 hours, whereupon it was concentrated in vacuo to provide the product as a yellow oil. This material was taken directly to the following step. LCMS m/z 276.0 [M+H]$^+$.

Step 5. Synthesis of (2R)-1,1,1-trifluoro-3-[(4-methoxybenzyl)oxy]propan-2-yl 3-[4-(trifluoromethyl)-1H-pyrazol-1-yl]-1-oxa-8-azaspiro[4.5]decane-8-carboxylate (C38)

Conversion of C37 to C38 was carried out using the method described for synthesis of the mixture of C13 and C14 from C12 in Examples 3 and 4. The product was isolated as a colorless gum, which contained some ethyl acetate. Yield of diastereomeric mixture over 2 steps, corrected for solvent: 3.20 g, 5.80 mmol, 75%. $^1$H NMR (400 MHz, CDCl$_3$) δ 7.78 (s, 1H), 7.73 (s, 1H), 7.24 (d, J=8.5 Hz, 2H), 6.88 (br d, J=8.0 Hz, 2H), 5.54-5.43 (br m, 1H), 5.03-4.93 (br m, 1H), 4.51 (AB quartet, upfield doublet is broad, J$_{AB}$=11.5 Hz, Δv$_{AB}$=28 Hz, 2H), 4.26-4.15 (m, 2H), 3.91-3.65 (m, 4H), 3.81 (br s, 3H), 3.45-3.29 (br m, 2H), 2.41-2.16 (m, 2H), 1.91-1.52 (m, 4H).

Step 6. Isolation of (2R)-1,1,1-trifluoro-3-[(4-methoxybenzyl)oxy]propan-2-yl 3-[4-(trifluoromethyl)-1H-pyrazol-1-yl]-1-oxa-8-azaspiro[4.5]decane-8-carboxylate, DIAST 1 (C39) and (2R)-1,1,1-trifluoro-3-[(4-methoxybenzyl)oxy]propan-2-yl 3-[4-(trifluoromethyl)-1H-pyrazol-1-yl]-1-oxa-8-azaspiro[4.5]decane-8-carboxylate, DIAST 2 (C40)

Separation of C38 (from the previous step; 2.0 g, 3.6 mmol) into its component diastereomers was carried out via supercritical fluid chromatography [Column: Chiral Technologies Chiralpak AD, 10 µm; Mobile phase: 65:35 carbon dioxide/(methanol containing 0.1% ammonium hydroxide)]. The first eluting diastereomer was C39, obtained as a yellow oil.

Yield: 830 mg, 1.51 mmol, 42%. LCMS m/z 574.0 [M+Na$^+$].

The second-eluting diastereomer was C40, also isolated as a yellow oil. Yield: 920 mg, 1.67 mmol, 46%. LCMS m/z 574.1 [M+Na$^+$].

Step 7. Synthesis of (2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 1 [From C39, DIAST 1] (8)

Trifluoroacetic acid (2.5 mL) was added to a solution of C39 (830 mg, 1.51 mmol) in dichloromethane (10 mL) at room temperature. The reaction mixture was stirred at 30° C. for 2 hours, whereupon it was washed with saturated aqueous sodium bicarbonate solution (2×3 mL) and concentrated in vacuo. Reversed-phase HPLC (Column: Agela Durashell, 5 µm; Mobile phase A: 0.225% formic acid in water; Mobile phase B: acetonitrile; Gradient: 51% to 71% B) afforded the product as a yellow gum. Yield: 248 mg, 0.575 mmol, 38%. LCMS m/z 432.0 [M+H]$^+$. $^1$H NMR (400 MHz, CDCl$_3$) δ 7.78 (s, 1H), 7.73 (s, 1H), 5.31-5.20 (br m, 1H), 5.03-4.95 (m, 1H), 4.24 (dd, half of ABX pattern, J=10.0, 6.5 Hz, 1H), 4.22-4.16 (m, 1H), 4.04-3.97 (m, 1H), 3.93-3.76 (m, 3H), 3.48-3.28 (m, 2H), 2.36 (dd, half of ABX pattern, J=13.8, 8.3 Hz, 1H), 2.28 (dd, half of ABX pattern, J=13.8, 5.3 Hz, 1H), 1.93-1.84 (br m, 1H), 1.83-1.5 (br m, 4H, assumed; partially obscured by water peak).

Step 8. Synthesis of (2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 2 [From C40, DIAST 2] (9)

Conversion of C40 to the product was effected using the method employed for synthesis of 8 from C39. The product was obtained as a colorless gum. Yield: 356 mg, 0.825 mmol, 49%. LCMS m/z 432.0 [M+H]$^+$. $^1$H NMR (400 MHz, CDCl$_3$) δ 7.78 (s, 1H), 7.73 (s, 1H), 5.31-5.20 (br m, 1H), 5.03-4.95 (m, 1H), 4.24 (dd, half of ABX pattern, J=10.0, 6.5 Hz, 1H), 4.19 (dd, half of ABX pattern, J=10.0, 5.0 Hz, 1H), 4.01 (dd, half of ABX pattern, J=12.8, 3.3 Hz, 1H), 3.93-3.76 (m, 3H), 3.49-3.30 (m, 2H), 2.36 (dd, half of ABX pattern, J=13.6, 8.5 Hz, 1H), 2.28 (br dd, half of ABX pattern, J=13.8, 5.3 Hz, 1H), 1.94-1.83 (br m, 1H), 1.83-1.5 (br m, 4H).

Examples 10 and 11

(2R)-1,1,1-Trifluoro-3-hydroxypropan-2-yl (3S)-3-(4-fluoro-1H-pyrazol-1-yl)-1-oxa-8-azaspiro[4.5]decane-8-carboxylate (10) and (2R)-1,1,1-Trifluoro-3-hydroxypropan-2-yl (3R)-3-(4-fluoro-1H-pyrazol-1-yl)-1-oxa-8-azaspiro[4.5]decane-8-carboxylate (11)

Step 1. Synthesis of tert-butyl 3-(4-fluoro-1H-pyrazol-1-yl)-1-oxa-8-azaspiro[4.5]decane-8-carboxylate (C41)

To a suspension of 4-fluoro-1H-pyrazole (40 mg, 0.46 mmol) in N,N-dimethylformamide (1.5 mL) was added C35 (223 mg, 0.696 mmol), followed by cesium carbonate (454 mg, 1.39 mmol). The reaction mixture was stirred at 80° C.

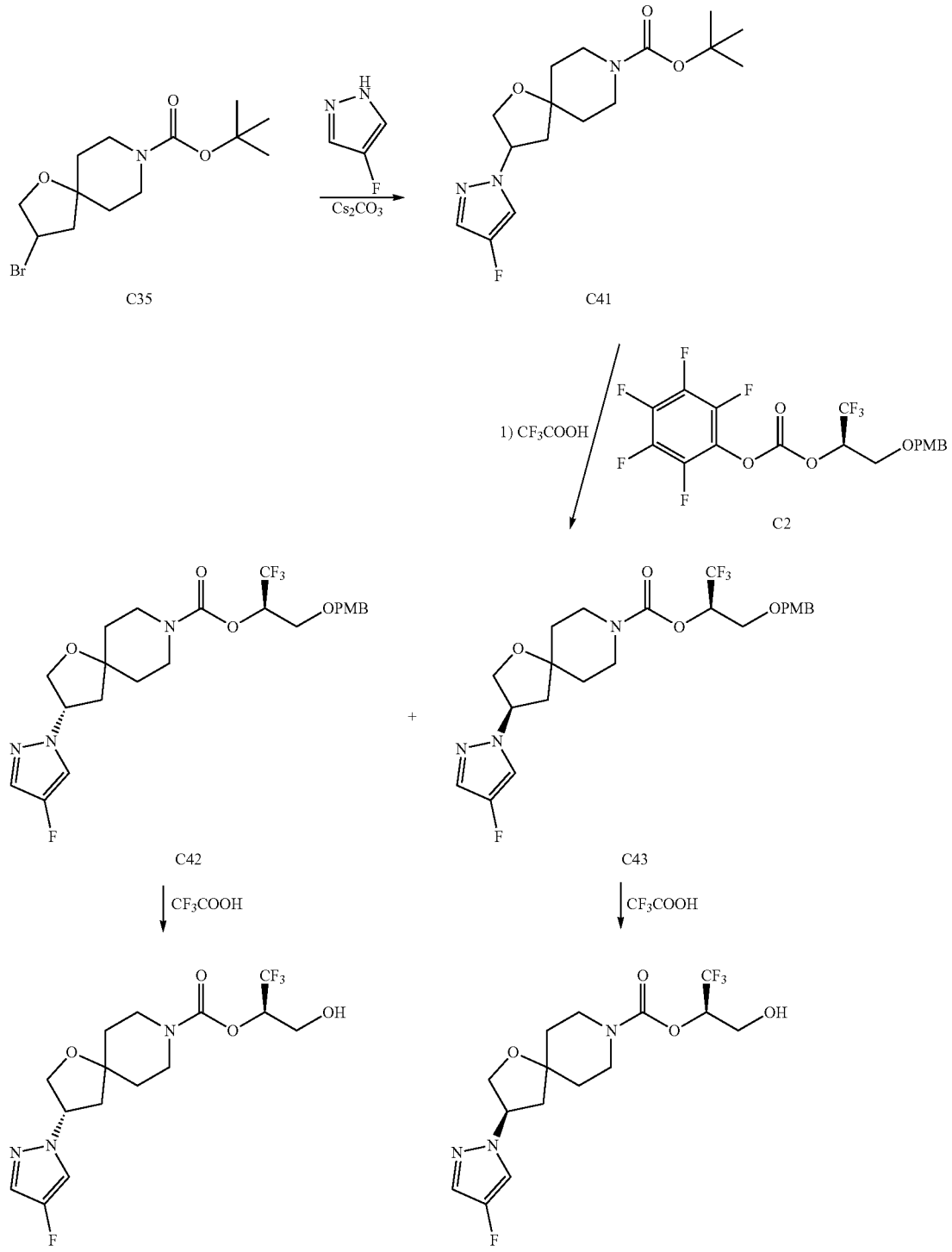

for 2 hours, whereupon it was diluted with water (40 mL) and extracted with ethyl acetate (3×25 mL). The combined organic layers were dried over sodium sulfate, filtered, concentrated in vacuo, and purified via chromatography on silica gel (Gradient: 0% to 40% ethyl acetate in petroleum ether) to afford the product as a white solid. Yield: 133 mg, 0.409 mmol, 89%. LCMS m/z 269.9 [(M−2-methylprop-1-ene)+H]$^+$. $^1$H NMR (400 MHz, CDCl$_3$) δ 7.39 (d, J=4.5 Hz, 1H), 7.35 (d, J=4.5 Hz, 1H), 4.90-4.82 (m, 1H), 4.17 (dd, half of ABX pattern, J=10.0, 6.5 Hz, 1H), 4.12 (dd, half of ABX pattern, J=10.0, 5.0 Hz, 1H), 3.71-3.57 (br m, 2H), 3.39-3.28 (m, 2H), 2.31 (dd, half of ABX pattern, J=13.6, 8.5 Hz, 1H), 2.19 (dd, half of ABX pattern, J=13.6, 5.0 Hz, 1H), 1.82-1.63 (m, 3H), 1.61-1.52 (m, 1H), 1.46 (s, 9H).

Step 2. Synthesis of (2R)-1,1, 1-trifluoro-3-[(4-methoxybenzyl)oxy]propan-2-yl (3S)-3-(4-fluoro-1H-pyrazol-1-yl)-1-oxa-8-azaspiro[4.5]decane-8-carboxylate (C42) and (2R)-1,1, 1-trifluoro-3-[(4-methoxybenzyl)oxy]propan-2-yl (3R)-3-(4-fluoro-1H-pyrazol-1-yl)-1-oxa-8-azaspiro[4.5]decane-8-carboxylate (C43)

Trifluoroacetic acid (3 mL) was added to a 0° C. solution of C41 (273 mg, 0.839 mmol) in dichloromethane (10 mL). The reaction mixture was stirred at 20° C. for 2 hours, whereupon it was concentrated in vacuo. The resulting material was dissolved in acetonitrile (5 mL), cooled to 0° C., and slowly treated with C2 (reaction solution in acetonitrile, containing 1.01 mmol), followed by triethylamine (679 mg, 6.71 mmol). The reaction mixture was stirred at 20° C. for 16 hours, whereupon it was concentrated under reduced pressure and purified via silica gel chromatography (Gradient: 0% to 30% ethyl acetate in petroleum ether), providing a mixture of C42 and C43 as a yellow gum. Yield of diastereomeric mixture: 269 mg, 0.536 mmol, 64%. LCMS m/z 524.0 [M+Na$^+$]. $^1$H NMR (400 MHz, CDCl$_3$) δ 7.38 (d, J=4.5 Hz, 1H), 7.36 (d, J=4.0 Hz, 1H), 7.25 (d, J=9.0 Hz, 2H), 6.88 (br d, J=8 Hz, 2H), 5.53-5.43 (br m, 1H), 4.91-4.81 (br m, 1H), 4.51 (AB quartet, upfield doublet is broad, J$_{AB}$=12 Hz, Δv$_{AB}$=29 Hz, 2H), 4.22-4.10 (m, 2H), 3.90-3.65 (m, 4H), 3.81 (s, 3H), 3.43-3.31 (br m, 2H), 2.35-2.13 (m, 2H), 1.88-1.5 (m, 4H, assumed; partially obscured by water peak).

The component diastereomers were separated using supercritical fluid chromatography [Column: Chiral Technologies Chiralpak AD, 5 μm; Mobile phase: 3:2 carbon dioxide/(methanol containing 0.1% ammonium hydroxide)]. The first-eluting diastereomer was C42, obtained as a colorless gum. Yield: 110 mg, 0.219 mmol, 41% for the separation. LCMS m/z 524.1 [M+Na$^+$]. The second-eluting diastereomer was C43, also isolated as a colorless gum. Yield: 116 mg, 0.231 mmol, 43% for the separation. LCMS m/z 524.1 [M+Na$^+$]. The indicated absolute stereochemistries of C42 and C43 were assigned on the basis of a single crystal X-ray structure determination carried out on the derived product 11 (see below).

Step 3. Synthesis of (2R)-1,1, 1-trifluoro-3-hydroxypropan-2-yl (3S)-3-(4-fluoro-1H-pyrazol-1-yl)-1-oxa-8-azaspiro[4.5]decane-8-carboxylate (10)

Trifluoroacetic acid (3 mL) was added to a 0° C. solution of C42 (110 mg, 0.219 mmol) in dichloromethane (10 mL), and the reaction mixture was stirred at 20° C. for 1 hour. It was then diluted with saturated aqueous sodium chloride solution and extracted with dichloromethane (15 mL) and ethyl acetate (2×20 mL). The combined organic layers were dried over sodium sulfate, filtered, and concentrated in vacuo. Purification was effected via reversed-phase HPLC (Column: Agela Durashell, 5 μm; Mobile phase A: 0.225% formic acid in water; Mobile phase B: acetonitrile; Gradient: 26% to 46% B), providing the product as a colorless gum. Yield: 36.4 mg, 95.4 μmol, 44%. LCMS m/z 382.2 [M+H]$^+$. $^1$H NMR (400 MHz, CDCl$_3$) δ 7.38 (d, J=4.8 Hz, 1H), 7.35 (d, J=4.3 Hz, 1H), 5.31-5.20 (br m, 1H), 4.91-4.82 (m, 1H), 4.22-4.11 (m, 2H), 4.04-3.96 (m, 1H), 3.92-3.73 (m, 3H), 3.48-3.28 (m, 2H), 2.31 (dd, half of ABX pattern, J=13.6, 8.3 Hz, 1H), 2.24 (dd, half of ABX pattern, J=13.7, 5.1 Hz, 1H), 1.91-1.54 (br m, 4H, assumed; partially obscured by water peak).

Step 4. Synthesis of (2R)-1,1, 1-trifluoro-3-hydroxypropan-2-yl (3R)-3-(4-fluoro-1H-pyrazol-1-yl)-1-oxa-8-azaspiro[4.5]decane-8-carboxylate (11)

Conversion of C43 to the product was effected using the method employed for synthesis of 10 from C42. The product was isolated as a white solid. Yield: 40.7 mg, 0.107 mmol, 46%. LCMS m/z 382.2 [M+H]$^+$. $^1$H NMR (400 MHz, CDCl$_3$) δ 7.38 (d, J=4.8 Hz, 1H), 7.35 (d, J=4.3 Hz, 1H), 5.31-5.20 (br m, 1H), 4.91-4.82 (m, 1H), 4.19 (dd, half of ABX pattern, J=10.0, 6.3 Hz, 1H), 4.15 (dd, half of ABX pattern, J=10.0, 5.0 Hz, 1H), 4.00 (br dd, half of ABX pattern, J=12.4, 3.1 Hz, 1H), 3.91-3.74 (br m, 3H), 3.49-3.30 (m, 2H), 2.52-2.36 (v br s, 1H), 2.31 (dd, half of ABX pattern, J=13.6, 8.3 Hz, 1H), 2.28-2.20 (br m, 1H), 1.91-1.53 (br m, 4H, assumed; partially obscured by water peak).

A sample of 11 was crystallized from ethyl acetate/pentane via vapor diffusion and used to determine the absolute configuration via X-ray crystallography:

Single-crystal X-ray structural determination of 11

Single Crystal X-Ray Analysis

Data collection was performed on a Bruker APEX diffractometer at room temperature. Data collection consisted of omega and phi scans.

The structure was solved by direct methods using SHELX software suite in the orthorhombic class space group P2$_1$2$_1$2$_1$. The structure was subsequently refined by the full-matrix least squares method. All non-hydrogen atoms were found and refined using anisotropic displacement parameters.

The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). Assuming the sample submitted is enantiopure, the results indicate that the absolute structure has been correctly assigned. The method calculates that the probability that the structure is correctly assigned is 100.0. The Hooft parameter is reported as −0.04 with an esd of 0.005.

The final R-index was 4.2%. A final difference Fourier revealed no missing or misplaced electron density.

Pertinent crystal, data collection, and refinement information is summarized in Table 6. Atomic coordinates, bond lengths, bond angles, and displacement parameters are listed in Tables 7-9.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE 6

Crystal data and structure refinement for 11.

| | |
|---|---|
| Empirical formula | $C_{15}H_{19}F_4N_3O_4$ |
| Formula weight | 381.33 |
| Temperature | 296(2) K |
| Wavelength | 1.54178 Å |
| Crystal system | Orthorhombic |
| Space group | $P2_12_12_1$ |
| Unit cell dimensions | a = 6.3960(18) Å    α = 90° |
| | b = 8.117(2) Å    β = 90° |
| | c = 32.957(9) Å    γ = 90° |
| Volume | 1711.0(8) Å$^3$ |
| Z | 4 |
| Density (calculated) | 1.480 Mg/m$^3$ |
| Absorption coefficient | 1.189 mm$^{-1}$ |
| F(000) | 792 |
| Crystal size | 0.460 × 0.260 × 0.200 mm$^3$ |
| Theta range for data collection | 2.681 to 70.547° |
| Index ranges | −6 <= h <= 7, −9 <= k <= 9, −40 <= l <= 40 |
| Reflections collected | 57846 |
| Independent reflections | 3264 [R$_{int}$ = 0.1126] |
| Completeness to theta = 67.679° | 99.6% |
| Absorption correction | Empirical |
| Refinement method | Full-matrix least-squares on F$^2$ |
| Data/restraints/parameters | 3264/1/239 |
| Goodness-of-fit on F$^2$ | 1.113 |
| Final R indices [I > 2σ(I)] | R1 = 0.0421, wR2 = 0.1026 |
| R indices (all data) | R1 = 0.0428, wR2 = 0.1033 |
| Absolute structure parameter | −0.06(5) |
| Extinction coefficient | 0.053(3) |
| Largest diff. peak and hole | 0.253 and −0.373 e · Å$^{-3}$ |

TABLE 7

Atomic coordinates (×10$^4$) and equivalent isotropic displacement parameters (Å$^2$ × 10$^3$) for 11. U(eq) is defined as one-third of the trace of the orthogonalized U$^{ij}$ tensor.

| | x | y | z | U(eq) |
|---|---|---|---|---|
| F(1) | 6134(4) | 11893(3) | 4343(1) | 96(1) |
| F(2) | 3255(4) | −114(3) | 2304(1) | 97(1) |
| F(3) | 213(4) | −538(4) | 2540(1) | 100(1) |
| F(4) | 2359(4) | −2513(3) | 2480(1) | 99(1) |
| N(1) | 2128(4) | 10013(3) | 4908(1) | 58(1) |
| N(2) | 2418(3) | 8982(3) | 4593(1) | 48(1) |
| N(3) | 786(4) | 3029(3) | 3396(1) | 50(1) |
| O(1) | 637(3) | 6907(2) | 3856(1) | 48(1) |
| O(2) | −313(3) | 382(2) | 3414(1) | 55(1) |
| O(3) | 2712(3) | 1045(2) | 3102(1) | 53(1) |
| O(4) | 5870(3) | −1140(4) | 3446(1) | 86(1) |
| C(1) | 3501(5) | 11229(4) | 4846(1) | 60(1) |
| C(2) | 4599(5) | 10944(4) | 4496(1) | 58(1) |
| C(3) | 3902(4) | 9510(4) | 4335(1) | 58(1) |
| C(4) | 1047(4) | 7551(3) | 4545(1) | 50(1) |
| C(5) | −388(4) | 7754(3) | 4178(1) | 53(1) |
| C(6) | 1507(4) | 5422(3) | 4031(1) | 43(1) |
| C(7) | 2256(5) | 5967(3) | 4453(1) | 56(1) |
| C(8) | −199(4) | 4096(3) | 4056(1) | 46(1) |

TABLE 7-continued

Atomic coordinates (×10$^4$) and equivalent isotropic displacement parameters (Å$^2$ × 10$^3$) for 11. U(eq) is defined as one-third of the trace of the orthogonalized U$^{ij}$ tensor.

| | x | y | z | U(eq) |
|---|---|---|---|---|
| C(9) | −962(4) | 3618(3) | 3639(1) | 50(1) |
| C(10) | 2454(5) | 4252(3) | 3341(1) | 58(1) |
| C(11) | 3244(4) | 4848(3) | 3750(1) | 52(1) |
| C(12) | 948(4) | 1417(3) | 3315(1) | 43(1) |
| C(13) | 3012(4) | −654(3) | 3005(1) | 45(1) |
| C(14) | 2178(5) | −951(3) | 2582(1) | 59(1) |
| C(15) | 5313(4) | −1042(3) | 3035(1) | 57(1) |

TABLE 8

Bond lengths [Å] and angles [°] for 11.

| | |
|---|---|
| F(1)—C(2) | 1.346(3) |
| F(2)—C(14) | 1.333(4) |
| F(3)—C(14) | 1.308(4) |
| F(4)—C(14) | 1.317(3) |
| N(1)—C(1) | 1.336(4) |
| N(1)—N(2) | 1.347(3) |
| N(2)—C(3) | 1.342(3) |
| N(2)—C(4) | 1.464(3) |
| N(3)—C(12) | 1.340(3) |
| N(3)—C(9) | 1.456(3) |
| N(3)—C(10) | 1.468(3) |
| O(1)—C(5) | 1.423(3) |
| O(1)—C(6) | 1.447(3) |
| O(2)—C(12) | 1.209(3) |
| O(3)—C(12) | 1.362(3) |
| O(3)—C(13) | 1.429(3) |
| O(4)—C(15) | 1.403(4) |
| O(4)—H(4X) | 0.97(2) |
| C(1)—C(2) | 1.373(4) |
| C(1)—H(1) | 0.9300 |
| C(2)—C(3) | 1.354(4) |
| C(3)—H(3) | 0.9300 |
| C(4)—C(5) | 1.527(4) |
| C(4)—C(7) | 1.531(4) |
| C(4)—H(4A) | 0.9800 |
| C(5)—H(5A) | 0.9700 |
| C(5)—H(5B) | 0.9700 |
| C(6)—C(11) | 1.518(3) |
| C(6)—C(8) | 1.535(3) |
| C(6)—C(7) | 1.537(3) |
| C(7)—H(7A) | 0.9700 |
| C(7)—H(7B) | 0.9700 |
| C(8)—C(9) | 1.510(4) |
| C(8)—H(8A) | 0.9700 |
| C(8)—H(8B) | 0.9700 |
| C(9)—H(9A) | 0.9700 |
| C(9)—H(9B) | 0.9700 |
| C(10)—C(11) | 1.520(4) |
| C(10)—H(10A) | 0.9700 |
| C(10)—H(10B) | 0.9700 |
| C(11)—H(11A) | 0.9700 |
| C(11)—H(11B) | 0.9700 |
| C(13)—C(15) | 1.508(4) |
| C(13)—C(14) | 1.513(4) |
| C(13)—H(13) | 0.9800 |
| C(15)—H(15A) | 0.9700 |
| C(15)—H(15B) | 0.9700 |
| C(1)—N(1)—N(2) | 104.6(2) |
| C(3)—N(2)—N(1) | 112.7(2) |
| C(3)—N(2)—C(4) | 127.5(2) |
| N(1)—N(2)—C(4) | 119.6(2) |
| C(12)—N(3)—C(9) | 119.3(2) |
| C(12)—N(3)—C(10) | 125.4(2) |
| C(9)—N(3)—C(10) | 113.9(2) |
| C(5)—O(1)—C(6) | 106.50(18) |
| C(12)—O(3)—C(13) | 116.14(17) |
| C(15)—O(4)—H(4X) | 109(3) |
| N(1)—C(1)—C(2) | 109.8(2) |
| N(1)—C(1)—H(1) | 125.1 |

TABLE 8-continued

Bond lengths [Å] and angles [°] for 11.

| | |
|---|---|
| C(2)—C(1)—H(1) | 125.1 |
| F(1)—C(2)—C(3) | 125.9(3) |
| F(1)—C(2)—C(1) | 126.3(3) |
| C(3)—C(2)—C(1) | 107.8(3) |
| N(2)—C(3)—C(2) | 105.2(2) |
| N(2)—C(3)—H(3) | 127.4 |
| C(2)—C(3)—H(3) | 127.4 |
| N(2)—C(4)—C(5) | 111.0(2) |
| N(2)—C(4)—C(7) | 112.7(2) |
| C(5)—C(4)—C(7) | 103.7(2) |
| N(2)—C(4)—H(4A) | 109.7 |
| C(5)—C(4)—H(4A) | 109.7 |
| C(7)—C(4)—H(4A) | 109.7 |
| O(1)—C(5)—C(4) | 105.1(2) |
| O(1)—C(5)—H(5A) | 110.7 |
| C(4)—C(5)—H(5A) | 110.7 |
| O(1)—C(5)—H(5B) | 110.7 |
| C(4)—C(5)—H(5B) | 110.7 |
| H(5A)—C(5)—H(5B) | 108.8 |
| O(1)—C(6)—C(11) | 107.20(19) |
| O(1)—C(6)—C(8) | 109.42(19) |
| C(11)—C(6)—C(8) | 109.76(19) |
| O(1)—C(6)—C(7) | 103.87(19) |
| C(11)—C(6)—C(7) | 114.3(2) |
| C(8)—C(6)—C(7) | 111.9(2) |
| C(4)—C(7)—C(6) | 105.3(2) |
| C(4)—C(7)—H(7A) | 110.7 |
| C(6)—C(7)—H(7A) | 110.7 |
| C(4)—C(7)—H(7B) | 110.7 |
| C(6)—C(7)—H(7B) | 110.7 |
| H(7A)—C(7)—H(7B) | 108.8 |
| C(9)—C(8)—C(6) | 111.1(2) |
| C(9)—C(8)—H(8A) | 109.4 |
| C(6)—C(8)—H(8A) | 109.4 |
| C(9)—C(8)—H(8B) | 109.4 |
| C(6)—C(8)—H(8B) | 109.4 |
| H(8A)—C(8)—H(8B) | 108.0 |
| N(3)—C(9)—C(8) | 109.7(2) |
| N(3)—C(9)—H(9A) | 109.7 |
| C(8)—C(9)—H(9A) | 109.7 |
| N(3)—C(9)—H(9B) | 109.7 |
| C(8)—C(9)—H(9B) | 109.7 |
| H(9A)—C(9)—H(9B) | 108.2 |
| N(3)—C(10)—C(11) | 110.3(2) |
| N(3)—C(10)—H(10A) | 109.6 |
| C(11)—C(10)—H(10A) | 109.6 |
| N(3)—C(10)—H(10B) | 109.6 |
| C(11)—C(10)—H(10B) | 109.6 |
| H(10A)—C(10)—H(10B) | 108.1 |
| C(6)—C(11)—C(10) | 113.3(2) |
| C(6)—C(11)—H(11A) | 108.9 |
| C(10)—C(11)—H(11A) | 108.9 |
| C(6)—C(11)—H(11B) | 108.9 |
| C(10)—C(11)—H(11B) | 108.9 |
| H(11A)—C(11)—H(11B) | 107.7 |
| O(2)—C(12)—N(3) | 125.0(2) |
| O(2)—C(12)—O(3) | 122.5(2) |
| N(3)—C(12)—O(3) | 112.48(19) |
| O(3)—C(13)—C(15) | 108.6(2) |
| O(3)—C(13)—C(14) | 108.3(2) |
| C(15)—C(13)—C(14) | 111.8(2) |
| O(3)—C(13)—H(13) | 109.4 |
| C(15)—C(13)—H(13) | 109.4 |

TABLE 8-continued

Bond lengths [Å] and angles [°] for 11.

| | |
|---|---|
| C(14)—C(13)—H(13) | 109.4 |
| F(3)—C(14)—F(4) | 107.7(3) |
| F(3)—C(14)—F(2) | 107.0(3) |
| F(4)—C(14)—F(2) | 105.7(3) |
| F(3)—C(14)—C(13) | 113.3(3) |
| F(4)—C(14)—C(13) | 111.0(2) |
| F(2)—C(14)—C(13) | 111.8(2) |
| O(4)—C(15)—C(13) | 108.8(2) |
| O(4)—C(15)—H(15A) | 109.9 |
| C(13)—C(15)—H(15A) | 109.9 |
| O(4)—C(15)—H(15B) | 109.9 |
| C(13)—C(15)—H(15B) | 109.9 |
| H(15A)—C(15)—H(15B) | 108.3 |

Symmetry transformations used to generate equivalent atoms.

TABLE 9

Anisotropic displacement parameters (Å² × 10³) for 11. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 99(2) | 105(2) | 85(1) | 14(1) | 2(1) | −59(1) |
| F(2) | 130(2) | 107(2) | 54(1) | 0(1) | 10(1) | −14(2) |
| F(3) | 75(1) | 145(2) | 82(1) | −25(1) | −26(1) | 33(1) |
| F(4) | 124(2) | 66(1) | 106(2) | −42(1) | −28(1) | 4(1) |
| N(1) | 67(1) | 63(1) | 45(1) | −16(1) | 7(1) | −7(1) |
| N(2) | 53(1) | 53(1) | 39(1) | −10(1) | 6(1) | −9(1) |
| N(3) | 51(1) | 45(1) | 55(1) | −10(1) | 16(1) | −12(1) |
| O(1) | 53(1) | 43(1) | 47(1) | 0(1) | −5(1) | 2(1) |
| O(2) | 47(1) | 49(1) | 69(1) | −3(1) | 11(1) | −15(1) |
| O(3) | 55(1) | 40(1) | 63(1) | −11(1) | 22(1) | −12(1) |
| O(4) | 50(1) | 144(2) | 63(1) | 20(1) | −6(1) | −33(1) |
| C(1) | 76(2) | 50(1) | 56(1) | −9(1) | −7(1) | −10(1) |
| C(2) | 58(2) | 60(2) | 55(1) | 10(1) | −6(1) | −18(1) |
| C(3) | 58(2) | 70(2) | 46(1) | −9(1) | 8(1) | −14(1) |
| C(4) | 49(1) | 55(1) | 45(1) | −4(1) | 3(1) | −13(1) |
| C(5) | 45(1) | 50(1) | 63(1) | −11(1) | −3(1) | 2(1) |
| C(6) | 42(1) | 39(1) | 48(1) | 2(1) | −3(1) | −3(1) |
| C(7) | 61(2) | 52(1) | 56(1) | 2(1) | −18(1) | −5(1) |
| C(8) | 46(1) | 46(1) | 48(1) | −2(1) | 8(1) | −6(1) |
| C(9) | 42(1) | 52(1) | 55(1) | −9(1) | 6(1) | −7(1) |
| C(10) | 65(2) | 44(1) | 64(2) | −8(1) | 26(1) | −14(1) |
| C(11) | 41(1) | 40(1) | 74(2) | 0(1) | 7(1) | −7(1) |
| C(12) | 39(1) | 46(1) | 42(1) | −3(1) | 3(1) | −10(1) |
| C(13) | 44(1) | 39(1) | 52(1) | −5(1) | 4(1) | −7(1) |
| C(14) | 62(2) | 53(1) | 61(2) | −10(1) | −5(1) | 2(1) |
| C(15) | 47(1) | 66(2) | 58(1) | −4(1) | 4(1) | −5(1) |

Examples 12 and 13

(2R)-1,1,1-Trifluoro-3-hydroxypropan-2-yl (3R)-3-(3-cyanophenyl)-1-oxa-8-azaspiro[4.5]decane-8-carboxylate (12) and (2R)-1,1,1-Trifluoro-3-hydroxypropan-2-yl (3S)-3-(3-cyanophenyl)-1-oxa-8-azaspiro[4.5]decane-8-carboxylate (13)

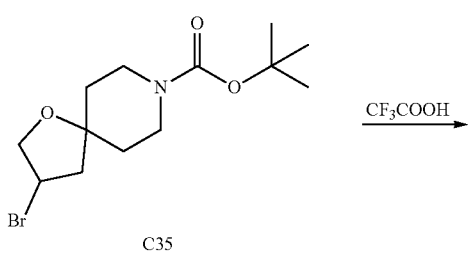

C35

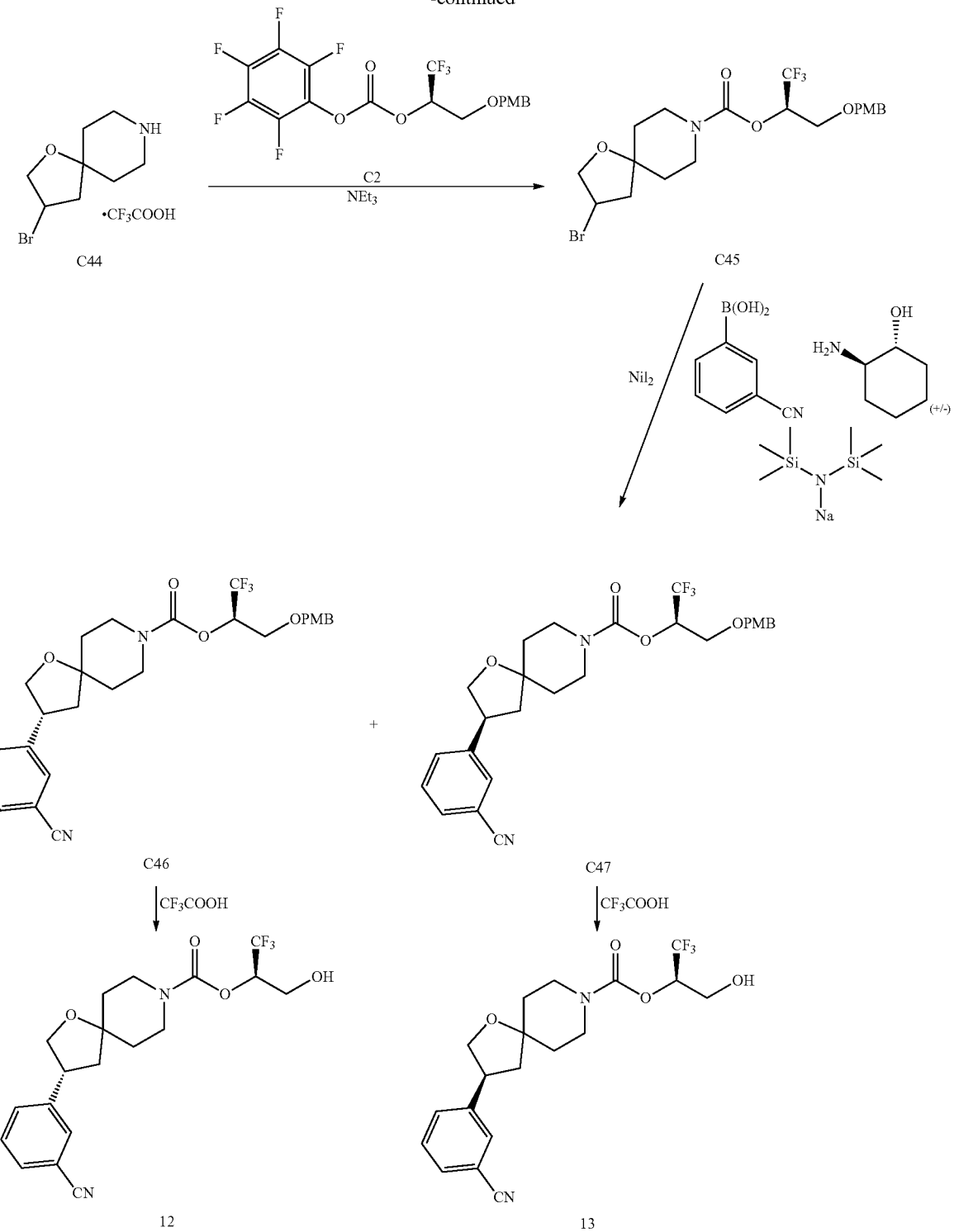

Step 1. Synthesis of 3-bromo-1-oxa-8-azaspiro[4.5]decane, trifluoroacetate salt (C44)

Trifluoroacetic acid (100 mL) was added drop-wise to a 0° C. solution of C35 (25.0 g, 78.1 mmol) in dichloromethane (400 mL). After the reaction mixture had been stirred at 13° C. for 15 hours, it was concentrated in vacuo to afford the product as a brown oil (30 g). This material was used in the next step without additional purification. $^1$H NMR (400 MHz, CD$_3$OD) δ 4.63-4.55 (m, 1H), 4.20 (dd, half of ABX pattern, J=10.5, 4.5 Hz, 1H), 4.04 (dd, half of ABX pattern, J=10.5, 3.5 Hz, 1H), 3.3-3.21 (m, 4H), 2.50 (dd, half of ABX pattern, J=14.6, 7.0 Hz, 1H), 2.30-2.18 (m, 2H), 1.97 (ddd, J=14, 10, 6.5 Hz, 1H), 1.91-1.77 (m, 2H).

Step 2. Synthesis of (2R)-1,1, 1-trifluoro-3-[(4-methoxybenzyl)oxy]propan-2-yl 3-bromo-1-oxa-8-azaspiro[4.5]decane-8-carboxylate (C45)

Triethylamine (39.5 g, 390 mmol) was added to a 15° C. solution of C44 (from the previous step; ≤78.1 mmol) in acetonitrile (400 mL). The resulting solution was stirred at 15° C. for 1 hour, whereupon it was cooled to 0° C. and treated with C2 [reaction solution in acetonitrile (400 mL) containing 85.9 mmol]. After the reaction mixture had been stirred at 13° C. for 15 hours, it was concentrated in vacuo and purified twice via silica gel chromatography (Gradient: 5% to 9% ethyl acetate in petroleum ether). A final chromatographic purification on silica gel (Gradient: 0% to 9% ethyl acetate in petroleum ether) afforded the product as a colorless gum. Yield: 20.3 g, 40.9 mmol, 52% over 2 steps. LCMS m/z 519.8 (bromine isotope pattern observed) [M+Na$^+$]. $^1$H NMR (400 MHz, CDCl$_3$) δ 7.25 (d, J=8.5 Hz, 2H), 6.89 (d, J=8.7 Hz, 2H), 5.54-5.43 (m, 1H), 4.51 (AB quartet, upfield doublet is broadened, $J_{AB}$=11.7 Hz, $\Delta v_{AB}$=29.1 Hz, 2H), 4.44-4.36 (m, 1H), 4.19 (dd, J=10.4, 5.3 Hz, 1H), 4.07-3.99 (m, 1H), 3.91-3.63 (m, 4H), 3.82 (s, 3H), 3.44-3.27 (m, 2H), 2.42-2.25 (m, 1H), 2.24-2.08 (m, 1H), 2.04-1.89 (m, 1H), 1.81-1.47 (m, 3H).

Step 3. Synthesis of (2R)-1,1,1-trifluoro-3-[(4-methoxybenzyl)oxy]propan-2-yl (3R)-3-(3-cyanophenyl)-1-oxa-8-azaspiro[4.5]decane-8-carboxylate (C46) and (2R)-1,1,1-trifluoro-3-[(4-methoxybenzyl)oxy]propan-2-yl (3S)-3-(3-cyanophenyl)-1-oxa-8-azaspiro[4.5]decane-8-carboxylate (C47)

Sodium bis(trimethylsilyl)amide (1 M solution in tetrahydrofuran; 1.81 mL, 1.81 mmol) was added to a mixture of C45 (450 mg, 0.907 mmol), (3-cyanophenyl)boronic acid (266 mg, 1.81 mmol), trans-2-aminocyclohexanol (20.9 mg, 0.181 mmol), and nickel iodide (56.7 mg, 0.181 mmol) in 2-propanol (dried over molecular sieves; 5 mL). The reaction mixture was stirred at 60° C. for 14 hours, whereupon it was filtered through diatomaceous earth. The filtrate was concentrated in vacuo, and the residue was purified using chromatography on silica gel (Gradient: 0% to 20% ethyl acetate in petroleum ether), affording a mixture of C46 and C47 as a colorless oil. Yield of diastereomeric mixture: 320 mg, 0.617 mmol, 68%.

This material was separated into its component diastereomers via supercritical fluid chromatography [Column: Chiral Technologies Chiralpak AD, 5 μm; Mobile phase: 3:1 carbon dioxide/(ethanol containing 0.1% ammonium hydroxide)]. The first-eluting diastereomer was C46, which was isolated as a light yellow oil. Yield: 154 mg, 0.297 mmol, 48% for the separation. LCMS m/z 541.1 [M+Na$^+$].

The second-eluting diastereomer was C47, also obtained as a light yellow oil. Yield: 138 mg, 0.266 mmol, 43% for the separation. LCMS m/z 541.1 [M+Na$^+$]. The indicated absolute stereochemistries of C46 and C47 were assigned on the basis of a single crystal X-ray structure determination carried out on the derived product 13 (see below).

Step 4. Synthesis of (2R)-1,1, 1-trifluoro-3-hydroxypropan-2-yl (3R)-3-(3-cyanophenyl)-1-oxa-8-azaspiro[4.5]decane-8-carboxylate (12)

Trifluoroacetic acid (1 mL) was added to a 10° C. solution of C46 (154 mg, 0.297 mmol) in dichloromethane (4 mL), and the reaction mixture was stirred at 30° C. for 1 hour. It was then washed with saturated aqueous sodium bicarbonate solution (2×3 mL) and concentrated under reduced pressure. Purification via reversed-phase HPLC (Column: Agela Durashell, 5 μm; Mobile phase A: 0.225% formic acid in water; Mobile phase B: acetonitrile; Gradient: 53% to 73% B) afforded the product as a yellow gum. Yield: 59.7 mg, 0.150 mmol, 50%. LCMS m/z 399.2 [M+H]$^+$. $^1$H NMR (400 MHz, CDCl$_3$) δ 7.56-7.52 (m, 2H), 7.51-7.41 (m, 2H), 5.32-5.21 (br m, 1H), 4.25 (dd, J=8.4, 7.9 Hz, 1H), 4.05-3.97 (m, 1H), 3.93-3.77 (m, 4H), 3.61-3.50 (m, 1H), 3.48-3.29 (m, 2H), 2.50-2.35 (br s, 1H), 2.30 (dd, J=12.8, 8.4 Hz, 1H), 1.87-1.70 (m, 4H), 1.70-1.6 (m, 1H, assumed; partially obscured by water peak).

Step 5. Synthesis of (2R)-1,1, 1-trifluoro-3-hydroxypropan-2-yl (3S)-3-(3-cyanophenyl)-1-oxa-8-azaspiro[4.5]decane-8-carboxylate (13)

Trifluoroacetic acid (1 mL) was added to a 30° C. solution of C47 (138 mg, 0.266 mmol) in dichloromethane (4 mL), and the reaction mixture was stirred at 30° C. for 1.5 hours. It was then washed with saturated aqueous sodium bicarbonate solution (2×3 mL) and concentrated under reduced pressure. Purification via reversed-phase HPLC (Column: Agela Durashell, 5 μm; Mobile phase A: 0.225% formic acid in water; Mobile phase B: acetonitrile; Gradient: 53% to 73% B) afforded the product as a white gum. Yield: 58.6 mg, 0.147 mmol, 55%. LCMS m/z 399.1 [M+H]$^+$. $^1$H NMR (400 MHz, CDCl$_3$) δ 7.56-7.52 (m, 2H), 7.51-7.41 (m, 2H), 5.32-5.21 (br m, 1H), 4.25 (dd, J=7.9, 7.9 Hz, 1H), 4.05-3.97 (m, 1H), 3.94-3.76 (m, 4H), 3.61-3.50 (m, 1H), 3.50-3.32 (m, 2H), 2.50-2.35 (br s, 1H), 2.30 (br dd, J=12.1, 8.6 Hz, 1H), 1.87-1.73 (m, 4H), 1.70-1.55 (m, 1H, assumed; largely obscured by water peak).

A sample of 13 was crystallized from chloroform via vapor diffusion and used to determine the absolute configuration via X-ray crystallography:

Single-crystal X-ray structural determination of 13

Single Crystal X-Ray Analysis

Data collection was performed on a Bruker APEX diffractometer at room temperature. Data collection consisted of omega and phi scans.

The structure was solved by direct methods using SHELX software suite in the monoclinic class space group P2$_1$. The structure was subsequently refined by the full-matrix least squares method. All non-hydrogen atoms were found and refined using anisotropic displacement parameters.

The hydrogen atoms located on oxygen were found from the Fourier difference map and refined with distances restrained. The remaining hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). Assuming the sample submitted is enantiopure, the results indicate that the absolute structure has been correctly assigned. The method calculates that the probability that the structure is correctly assigned is 1.000. The Hooft parameter is reported as 0.01 with an esd of 0.009.

The final R-index was 4.4%. A final difference Fourier revealed no missing or misplaced electron density.

Pertinent crystal, data collection and refinement information is summarized in Table 10. Atomic coordinates, bond lengths, bond angles, and displacement parameters are listed in Tables 11-13.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, J. Appl. Cryst. 2008, 41, 96-103.
H. D. Flack, *Acta Cryst.* 1983, A39, 867-881.

TABLE 10

Crystal data and structure refinement for 13.

| | |
|---|---|
| Empirical formula | $C_{19}H_{21}F_3N_2O_4$ |
| Formula weight | 398.38 |
| Temperature | 296(2) K |
| Wavelength | 1.54178 Å |
| Crystal system | Monoclinic |
| Space group | $P2_1$ |
| Unit cell dimensions | a = 5.7877(3) Å  α = 90° |
| | b = 8.6611(4) Å  β = 94.000(3)° |
| | c = 19.3480(9) Å  γ = 90° |
| Volume | 967.51(8) Å$^3$ |
| Z | 2 |
| Density (calculated) | 1.367 Mg/m$^3$ |
| Absorption coefficient | 0.988 mm$^{-1}$ |
| F(000) | 416 |
| Crystal size | 0.480 × 0.300 × 0.080 mm$^3$ |
| Theta range for data collection | 4.582 to 70.530° |
| Index ranges | −7 <= h <= 7, −10 <= k <= 10, −23 <= l <= 23 |
| Reflections collected | 27143 |
| Independent reflections | 3684 [R$_{int}$ = 0.0687] |
| Completeness to theta = 67.679° | 99.9% |
| Absorption correction | Empirical |
| Refinement method | Full-matrix least-squares on F$^2$ |
| Data/restraints/parameters | 3684/2/256 |
| Goodness-of-fit on F$^2$ | 1.074 |
| Final R indices [I > 2σ(I)] | R1 = 0.0442, wR2 = 0.0865 |
| R indices (all data) | R1 = 0.0671, wR2 = 0.0959 |
| Absolute structure parameter | 0.01(10) |
| Extinction coefficient | n/a |
| Largest diff. peak and hole | 0.167 and −0.152 e · Å$^{-3}$ |

TABLE 11

Atomic coordinates (×10$^4$) and equivalent isotropic displacement parameters (Å$^2$ × 10$^3$) for 13. U(eq) is defined as one-third of the trace of the orthogonalized U$^{ij}$ tensor.

| | x | y | z | U(eq) |
|---|---|---|---|---|
| F(1) | 10539(6) | 91(6) | 5163(2) | 135(1) |
| F(2) | 8307(7) | −1740(4) | 5403(2) | 127(1) |
| F(3) | 7183(6) | 538(4) | 5460(1) | 118(1) |
| N(1) | 10121(9) | 10767(8) | −357(2) | 129(2) |
| N(2) | 8258(5) | 2468(3) | 3146(1) | 51(1) |
| O(1) | 5682(4) | 4904(3) | 1949(1) | 62(1) |
| O(2) | 10239(4) | 228(3) | 3326(1) | 65(1) |
| O(3) | 7593(5) | 998(3) | 4056(1) | 67(1) |
| O(4) | 4385(6) | −1267(5) | 3576(2) | 118(2) |
| C(1) | 4069(7) | 10231(5) | 1563(2) | 67(1) |
| C(2) | 4076(9) | 11546(5) | 1169(3) | 83(1) |
| C(3) | 5638(9) | 11721(5) | 676(2) | 81(1) |
| C(4) | 7226(7) | 10548(5) | 583(2) | 65(1) |
| C(5) | 8862(9) | 10684(7) | 62(2) | 88(2) |
| C(6) | 7216(7) | 9219(5) | 979(2) | 58(1) |
| C(7) | 5652(6) | 9044(4) | 1483(2) | 50(1) |
| C(8) | 5600(6) | 7598(4) | 1912(2) | 52(1) |
| C(9) | 4987(6) | 6138(4) | 1508(2) | 55(1) |
| C(10) | 7529(6) | 5392(4) | 2442(2) | 49(1) |

TABLE 11-continued

Atomic coordinates (×10$^4$) and equivalent isotropic displacement parameters (Å$^2$ × 10$^3$) for 13. U(eq) is defined as one-third of the trace of the orthogonalized U$^{ij}$ tensor.

| | x | y | z | U(eq) |
|---|---|---|---|---|
| C(11) | 7894(7) | 7115(4) | 2284(2) | 60(1) |
| C(12) | 9625(7) | 4410(5) | 2343(2) | 62(1) |
| C(13) | 9230(7) | 2719(4) | 2476(2) | 58(1) |
| C(14) | 6233(7) | 3407(4) | 3278(2) | 65(1) |
| C(15) | 6717(7) | 5103(4) | 3160(2) | 64(1) |
| C(16) | 8798(6) | 1163(4) | 3485(2) | 49(1) |
| C(17) | 7500(7) | −496(4) | 4351(2) | 58(1) |
| C(18) | 8373(8) | −388(5) | 5094(2) | 74(1) |
| C(19) | 5035(8) | −1051(6) | 4279(3) | 88(1) |

TABLE 12

Bond lengths [Å] and angles [°] for 13.

| | |
|---|---|
| F(1)—C(18) | 1.318(5) |
| F(2)—C(18) | 1.317(5) |
| F(3)—C(18) | 1.299(5) |
| N(1)—C(5) | 1.131(6) |
| N(2)—C(16) | 1.333(4) |
| N(2)—C(14) | 1.464(4) |
| N(2)—C(13) | 1.464(4) |
| O(1)—C(9) | 1.409(4) |
| O(1)—C(10) | 1.445(4) |
| O(2)—C(16) | 1.217(4) |
| O(3)—C(16) | 1.354(4) |
| O(3)—C(17) | 1.417(4) |
| O(4)—C(19) | 1.398(6) |
| O(4)—H(4X) | 0.97(3) |
| C(1)—C(2) | 1.371(6) |
| C(1)—C(7) | 1.393(5) |
| C(1)—H(1) | 0.9300 |
| C(2)—C(3) | 1.369(7) |
| C(2)—H(2) | 0.9300 |
| C(3)—C(4) | 1.390(6) |
| C(3)—H(3) | 0.9300 |
| C(4)—C(6) | 1.383(5) |
| C(4)—C(5) | 1.434(6) |
| C(6)—C(7) | 1.385(5) |
| C(6)—H(6) | 0.9300 |
| C(7)—C(8) | 1.504(5) |
| C(8)—C(9) | 1.516(5) |
| C(8)—C(11) | 1.524(5) |
| C(8)—H(8) | 0.9800 |
| C(9)—H(9A) | 0.9700 |
| C(9)—H(9B) | 0.9700 |
| C(10)—C(12) | 1.505(5) |
| C(10)—C(15) | 1.518(5) |
| C(10)—C(11) | 1.540(5) |
| C(11)—H(11A) | 0.9700 |
| C(11)—H(11B) | 0.9700 |
| C(12)—C(13) | 1.507(6) |
| C(12)—H(12A) | 0.9700 |
| C(12)—H(12B) | 0.9700 |
| C(13)—H(13A) | 0.9700 |
| C(13)—H(13B) | 0.9700 |
| C(14)—C(15) | 1.515(5) |
| C(14)—H(14A) | 0.9700 |
| C(14)—H(14B) | 0.9700 |
| C(15)—H(15A) | 0.9700 |
| C(15)—H(15B) | 0.9700 |
| C(17)—C(18) | 1.493(6) |
| C(17)—C(19) | 1.503(6) |
| C(17)—H(17) | 0.9800 |
| C(19)—H(19A) | 0.9700 |
| C(19)—H(19B) | 0.9700 |
| C(16)—N(2)—C(14) | 123.3(3) |
| C(16)—N(2)—C(13) | 118.0(3) |
| C(14)—N(2)—C(13) | 115.7(3) |
| C(9)—O(1)—C(10) | 110.1(3) |
| C(16)—O(3)—C(17) | 117.5(3) |
| C(19)—O(4)—H(4X) | 108(3) |

TABLE 12-continued

Bond lengths [Å] and angles [°] for 13.

| | |
|---|---|
| C(2)—C(1)—C(7) | 121.6(4) |
| C(2)—C(1)—H(1) | 119.2 |
| C(7)—C(1)—H(1) | 119.2 |
| C(3)—C(2)—C(1) | 120.5(4) |
| C(3)—C(2)—H(2) | 119.7 |
| C(1)—C(2)—H(2) | 119.7 |
| C(2)—C(3)—C(4) | 119.0(4) |
| C(2)—C(3)—H(3) | 120.5 |
| C(4)—C(3)—H(3) | 120.5 |
| C(6)—C(4)—C(3) | 120.5(4) |
| C(6)—C(4)—C(5) | 119.1(4) |
| C(3)—C(4)—C(5) | 120.4(4) |
| N(1)—C(5)—C(4) | 178.3(6) |
| C(4)—C(6)—C(7) | 120.6(4) |
| C(4)—C(6)—H(6) | 119.7 |
| C(7)—C(6)—H(6) | 119.7 |
| C(6)—C(7)—C(1) | 117.8(3) |
| C(6)—C(7)—C(8) | 121.3(3) |
| C(1)—C(7)—C(8) | 120.9(3) |
| C(7)—C(8)—C(9) | 115.0(3) |
| C(7)—C(8)—C(11) | 116.1(3) |
| C(9)—C(8)—C(11) | 100.3(3) |
| C(7)—C(8)—H(8) | 108.3 |
| C(9)—C(8)—H(8) | 108.3 |
| C(11)—C(8)—H(8) | 108.3 |
| O(1)—C(9)—C(8) | 105.9(3) |
| O(1)—C(9)—H(9A) | 110.6 |
| C(8)—C(9)—H(9A) | 110.6 |
| O(1)—C(9)—H(9B) | 110.6 |
| C(8)—C(9)—H(9B) | 110.6 |
| H(9A)—C(9)—H(9B) | 108.7 |
| O(1)—C(10)—C(12) | 108.5(3) |
| O(1)—C(10)—C(15) | 107.1(3) |
| C(12)—C(10)—C(15) | 109.0(3) |
| O(1)—C(10)—C(11) | 105.0(3) |
| C(12)—C(10)—C(11) | 113.6(3) |
| C(15)—C(10)—C(11) | 113.3(3) |
| C(8)—C(11)—C(10) | 103.4(3) |
| C(8)—C(11)—H(11A) | 111.1 |
| C(10)—C(11)—H(11A) | 111.1 |
| C(8)—C(11)—H(11B) | 111.1 |
| C(10)—C(11)—H(11B) | 111.1 |
| H(11A)—C(11)—H(11B) | 109.0 |
| C(13)—C(12)—C(10) | 113.2(3) |
| C(13)—C(12)—H(12A) | 108.9 |
| C(10)—C(12)—H(12A) | 108.9 |
| C(13)—C(12)—H(12B) | 108.9 |
| C(10)—C(12)—H(12B) | 108.9 |
| H(12A)—C(12)—H(12B) | 107.7 |
| N(2)—C(13)—C(12) | 111.6(3) |
| N(2)—C(13)—H(13A) | 109.3 |
| C(12)—C(13)—H(13A) | 109.3 |
| N(2)—C(13)—H(13B) | 109.3 |
| C(12)—C(13)—H(13B) | 109.3 |
| H(13A)—C(13)—H(13B) | 108.0 |
| N(2)—C(14)—C(15) | 110.7(3) |
| N(2)—C(14)—H(14A) | 109.5 |
| C(15)—C(14)—H(14A) | 109.5 |
| N(2)—C(14)—H(14B) | 109.5 |
| C(15)—C(14)—H(14B) | 109.5 |
| H(14A)—C(14)—H(14B) | 108.1 |
| C(14)—C(15)—C(10) | 111.7(3) |
| C(14)—C(15)—H(15A) | 109.3 |
| C(10)—C(15)—H(15A) | 109.3 |
| C(14)—C(15)—H(15B) | 109.3 |
| C(10)—C(15)—H(15B) | 109.3 |
| H(15A)—C(15)—H(15B) | 107.9 |
| O(2)—C(16)—N(2) | 125.5(3) |
| O(2)—C(16)—O(3) | 122.5(3) |
| N(2)—C(16)—O(3) | 112.0(3) |
| O(3)—C(17)—C(18) | 108.1(3) |
| O(3)—C(17)—C(19) | 108.5(3) |
| C(18)—C(17)—C(19) | 111.4(4) |
| O(3)—C(17)—H(17) | 109.6 |
| C(18)—C(17)—H(17) | 109.6 |
| C(19)—C(17)—H(17) | 109.6 |
| F(3)—C(18)—F(2) | 105.5(4) |
| F(3)—C(18)—F(1) | 106.7(5) |
| F(2)—C(18)—F(1) | 106.9(4) |
| F(3)—C(18)—C(17) | 114.1(4) |
| F(2)—C(18)—C(17) | 111.3(4) |
| F(1)—C(18)—C(17) | 111.9(4) |
| O(4)—C(19)—C(17) | 108.8(4) |
| O(4)—C(19)—H(19A) | 109.9 |
| C(17)—C(19)—H(19A) | 109.9 |
| O(4)—C(19)—H(19B) | 109.9 |
| C(17)—C(19)—H(19B) | 109.9 |
| H(19A)—C(19)—H(19B) | 108.3 |

Symmetry transformations used to generate equivalent atoms.

TABLE 13

Anisotropic displacement parameters (Å$^2$ × 10$^3$) for 13. The anisotropic displacement factor exponent takes the form: $-2\pi^2[h^2 a^{*2} U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| F(1) | 100(2) | 219(4) | 84(2) | −7(2) | −8(2) | −16(3) |
| F(2) | 182(3) | 101(2) | 97(2) | 47(2) | 2(2) | 44(2) |
| F(3) | 171(3) | 116(2) | 70(2) | −7(2) | 24(2) | 57(2) |
| N(1) | 110(3) | 198(6) | 80(3) | 42(3) | 8(3) | −45(4) |
| N(2) | 55(2) | 46(2) | 54(2) | 7(1) | 15(1) | 11(2) |
| O(1) | 68(2) | 45(1) | 70(2) | 8(1) | −14(1) | −9(1) |
| O(2) | 62(2) | 58(2) | 76(2) | 6(1) | 13(1) | 22(1) |
| O(3) | 102(2) | 42(1) | 60(2) | 11(1) | 27(1) | 18(1) |
| O(4) | 93(2) | 141(4) | 117(3) | −46(3) | −24(2) | 49(2) |
| C(1) | 74(3) | 53(2) | 73(3) | −1(2) | 8(2) | 10(2) |
| C(2) | 108(4) | 52(3) | 88(3) | 4(2) | 0(3) | 16(3) |
| C(3) | 109(4) | 55(3) | 75(3) | 20(2) | −22(2) | −13(3) |
| C(4) | 71(3) | 68(3) | 54(2) | 14(2) | −5(2) | −18(2) |
| C(5) | 84(3) | 120(4) | 61(3) | 32(3) | −5(2) | −32(3) |
| C(6) | 61(2) | 58(2) | 58(2) | 9(2) | 9(2) | 0(2) |
| C(7) | 53(2) | 44(2) | 54(2) | 0(2) | 7(2) | 3(2) |
| C(8) | 57(2) | 49(2) | 52(2) | 3(2) | 16(2) | 4(2) |
| C(9) | 52(2) | 56(2) | 58(2) | 8(2) | 2(2) | −2(2) |
| C(10) | 48(2) | 49(2) | 51(2) | 4(2) | 0(2) | −2(2) |
| C(11) | 75(3) | 47(2) | 56(2) | 5(2) | −5(2) | −9(2) |
| C(12) | 52(2) | 65(2) | 71(2) | 14(2) | 16(2) | 0(2) |
| C(13) | 57(2) | 60(2) | 60(2) | 6(2) | 20(2) | 14(2) |
| C(14) | 67(3) | 57(2) | 74(3) | 18(2) | 30(2) | 21(2) |
| C(15) | 83(3) | 53(2) | 57(2) | 7(2) | 14(2) | 17(2) |
| C(16) | 55(2) | 42(2) | 51(2) | −3(2) | 4(2) | 2(2) |
| C(17) | 68(2) | 43(2) | 63(2) | 10(2) | 10(2) | 13(2) |
| C(18) | 80(3) | 73(3) | 70(3) | 13(2) | 10(2) | 19(3) |
| C(19) | 83(3) | 78(3) | 104(4) | 7(3) | 11(3) | 3(3) |

Examples 14 and 15
(2R)-1,1,1-Trifluoro-3-hydroxypropan-2-yl 3-[6-(trifluoromethyl)pyridin-2-yl]-1-oxa-8-azaspiro[4.5]decane-8-carboxylate, DIAST 1 [From C54, DIAST 1] (14) and (2R)-1,1,1-Trifluoro-3-hydroxypropan-2-yl 3-[6-(trifluoromethyl)pyridin-2-yl]-1-oxa-8-azaspiro[4.5]decane-8-carboxylate, DIAST 2 [From C55, DIAST 2] (15)
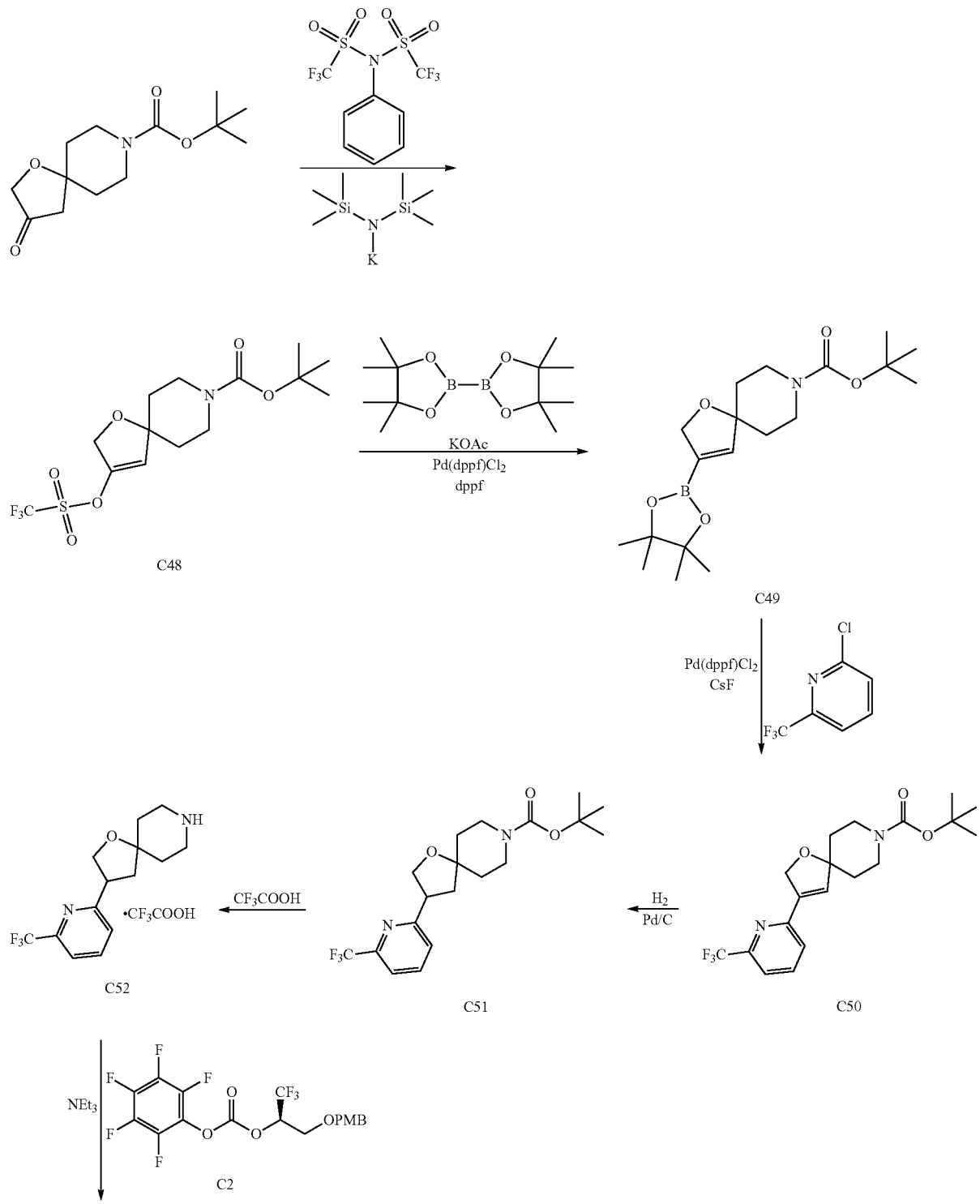

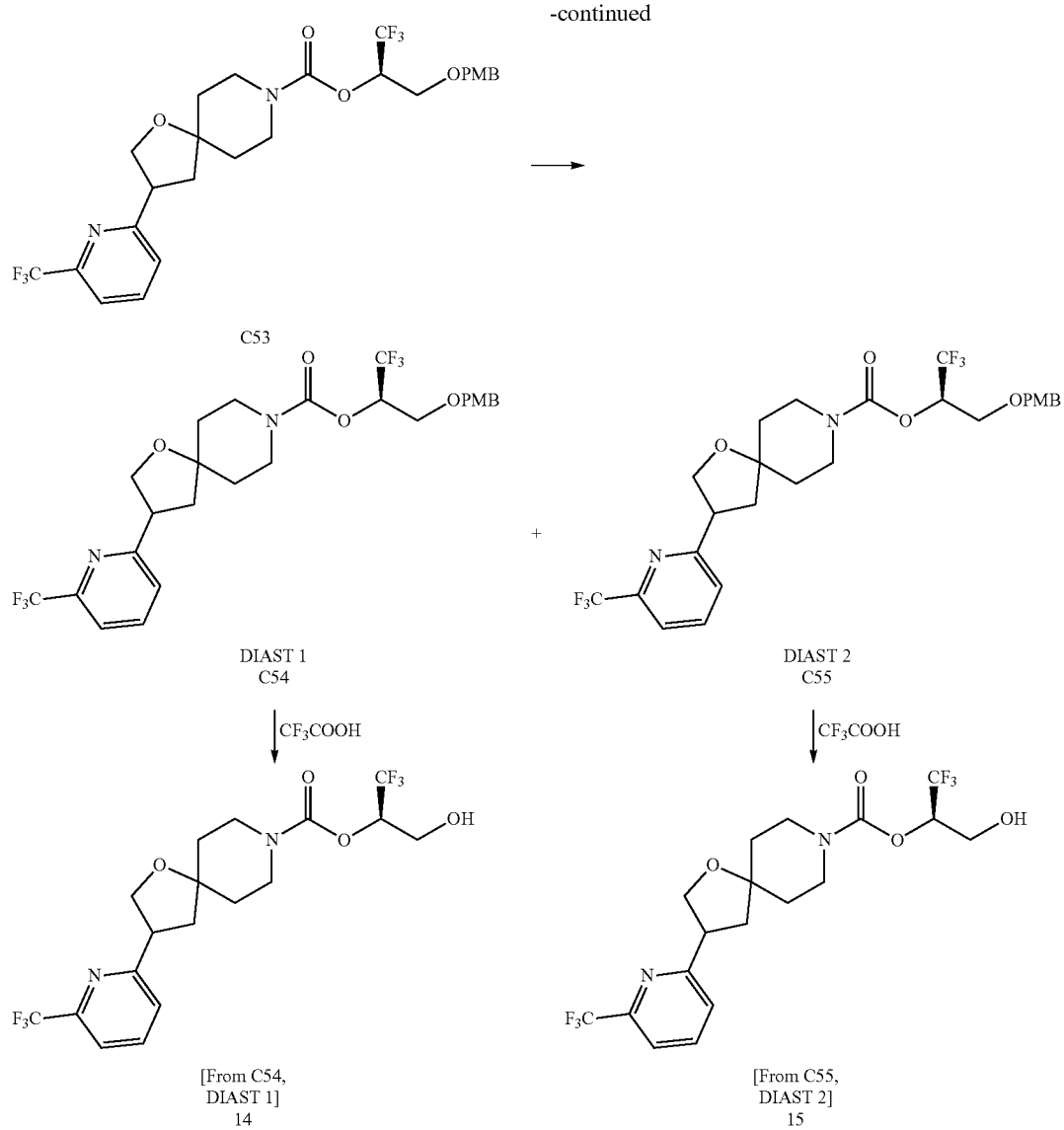

Step 1. Synthesis of tert-butyl 3-{[(trifluoromethyl)sulfonyl]oxy}-1-oxa-8-azaspiro[4.5]dec-3-ene-8-carboxylate (C48)

Potassium bis(trimethylsilyl)amide (1 M solution in tetrahydrofuran; 58.8 mL, 58.8 mmol) was added drop-wise to a −70° C. solution of tert-butyl 3-oxo-1-oxa-8-azaspiro[4.5]decane-8-carboxylate (10.0 g, 39.2 mmol) in tetrahydrofuran (250 mL). After the reaction mixture had been stirred at −70° C. for 30 minutes, a solution of 1,1,1-trifluoro-N-phenyl-N-[(trifluoromethyl)sulfonyl]methanesulfonamide (18.2 g, 50.9 mmol) in tetrahydrofuran (100 mL) was slowly added. The reaction mixture was then warmed to 20° C. and stirred for 1 hour, whereupon it was quenched, via addition of saturated aqueous ammonium chloride solution (200 mL), and diluted with water (300 mL). The resulting mixture was extracted with ethyl acetate (3×300 mL), and the combined organic layers were dried over sodium sulfate, filtered, and concentrated in vacuo. Repeated silica gel chromatography (Gradient: 0% to 10% ethyl acetate in petroleum ether), followed by final chromatographic purifications on silica gel (Gradient: 0% to 2% ethyl acetate in petroleum ether, followed by 100% ethyl acetate) afforded the product as a white solid. Yield: 12.2 g, 31.5 mmol, 80%. LCMS m/z 332.0 [(M−2-methylprop-1-ene)+H]$^+$. $^1$H NMR (400 MHz, CDCl$_3$) δ 5.75 (t, J=2.2 Hz, 1H), 4.65 (d, J=2.0 Hz, 2H), 3.84-3.69 (br m, 2H), 3.32-3.20 (m, 2H), 1.74-1.66 (m, 4H), 1.47 (s, 9H).

Step 2. Synthesis of tert-butyl 3-(4, 4, 5, 5-tetramethyl-1, 3, 2-dioxaborolan-2-yl)-1-oxa-8-azaspiro[4.5]dec-3-ene-8-carboxylate (C49)

This experiment was carried out in two identical batches. To a solution of C48 (2.45 g, 6.32 mmol) in 1,4-dioxane (30 mL) were added 4,4,4',4',5,5,5',5'-octamethyl-2,2'-bi-1,3,2-dioxaborolane (1.69 g, 6.65 mmol), potassium acetate (1.86 g, 19.0 mmol), [1,1'-bis(diphenylphosphino)ferrocene]dichloropalladium(II) (463 mg, 0.633 mmol), and 1,1'-bis(diphenylphosphino)ferrocene (351 mg, 0.633 mmol). The reaction mixture was stirred at 80° C. for 16 hours, whereupon it was combined with the second batch and diluted with ethyl acetate (100 mL). After filtration, the filtrate was concentrated in vacuo, diluted with heptane (150 mL), and stirred at 75° C. for 50 minutes. The resulting mixture was filtered, and the filtrate was concentrated under reduced pressure until ⅓ of the added heptane remained. Upon cooling to 0° C., a yellow solid precipitated; this was removed via filtration and the filtrate was concentrated in vacuo. The resulting gum was treated with petroleum ether (5 mL) and cooled in an ice bath. The product, which slowly precipitated, was isolated via filtration as a yellow solid. Combined yield: 2.38 g, 6.52 mmol, 52%. LCMS m/z 310.1 [(M−2-methylprop-1-ene)+H]$^+$. $^1$H NMR (400 MHz, CDCl$_3$) δ 6.39 (t, J=2.4 Hz, 1H), 4.76 (d, J=2.5 Hz, 2H), 3.81-3.66 (br m, 2H), 3.34-3.24 (m, 2H), 1.69-1.54 (m, 4H, assumed; partially obscured by water peak), 1.47 (s, 9H), 1.29 (s, 12H).

Step 3. Synthesis of tert-butyl 3-[6-(trifluoromethyl)pyridin-2-yl]-1-oxa-8-azaspiro[4.5]dec-3-ene-8-carboxylate (C50)

To a solution of C49 (370 mg, 1.01 mmol) in 1,4-dioxane (5 mL) were added 2-chloro-6-(trifluoromethyl)pyridine (203 mg, 1.12 mmol), cesium fluoride (392 mg, 2.58 mmol), [1,1'-bis(diphenylphosphino)ferrocene]dichloropalladium (II) (63.0 mg, 86.1 μmol), and water (0.5 mL). The reaction mixture was stirred at 80° C. for 16 hours, whereupon it was combined with a similar reaction mixture derived from C49 (30 mg, 82 μmol), concentrated in vacuo, and purified via silica gel chromatography (Gradient: 0% to 20% ethyl acetate in petroleum ether) to provide the product as a yellow solid. Combined yield: 280 mg, 0.728 mmol, 67%. LCMS m/z 328.9 [(M−2-methylprop-1-ene)+H]$^+$. $^1$H NMR (400 MHz, CDCl$_3$) δ 7.84 (dd, J=8.0, 7.8 Hz, 1H), 7.56 (d, J=7.8 Hz, 1H), 7.50 (d, J=8.0 Hz, 1H), 6.57 (t, J=2.1 Hz, 1H), 5.11 (d, J=2.0 Hz, 2H), 3.90-3.74 (br m, 2H), 3.39-3.27 (m, 2H), 1.81-1.67 (m, 4H), 1.48 (s, 9H).

Step 4. Synthesis of tert-butyl 3-[6-(trifluoromethyl)pyridin-2-yl]-1-oxa-8-azaspiro[4.5]decane-8-carboxylate (C51)

A mixture of C50 (280 mg, 0.728 mmol) and palladium on carbon (10%; 155 mg) in methanol (10 mL) was stirred for 2 hours at 28° C. under a balloon of hydrogen. The reaction mixture was filtered and the filtrate was concentrated in vacuo to afford the product as a yellow gum. This material was used directly in the following step. LCMS m/z 330.9 [(M−2-methylprop-1-ene)+H]$^+$.

Step 5. Synthesis of 3-[6-(trifluoromethyl)pyridin-2-yl]-1-oxa-8-azaspiro[4.5]decane, trifluoroacetate salt (C52)

Trifluoroacetic acid (2 mL) was added to a 0° C. solution of C51 (from the previous step; 50.728 mmol) in dichloromethane (8 mL). The reaction mixture was stirred at 25° C. for 1 hour, whereupon it was concentrated in vacuo, providing the product as a yellow gum. This material was used directly in the following step. LCMS m/z 286.9 [M+H]$^+$.

Step 6. Synthesis of (2R)-1,1,1-trifluoro-3-[(4-methoxybenzyl)oxy]propan-2-yl 3-[6-(trifluoromethyl)pyridin-2-yl]-1-oxa-8-azaspiro[4.5]decane-8-carboxylate (C53)

Triethylamine (368 mg, 3.64 mmol) was slowly added to a 0° C. solution of C52 (from the previous step; ≤0.728 mmol) in acetonitrile (10 mL). After 30 minutes, C2 (reaction solution in acetonitrile, containing 1.09 mmol) was added to the cold solution, and the reaction mixture was stirred at 25° C. for 15 hours. Volatiles were then removed under reduced pressure, and the residue was purified using chromatography on silica gel (Gradient: 0% to 25% ethyl acetate in petroleum ether) to afford the product as a colorless gum. Yield: 240 mg, 0.427 mmol, 59% over 3 steps. LCMS m/z 585.1 [M+Na$^+$].

Step 7. Isolation of (2R)-1,1,1-trifluoro-3-[(4-methoxybenzyl)oxy]propan-2-yl 3-[6-(trifluoromethyl)pyridin-2-yl]-1-oxa-8-azaspiro[4.5]decane-8-carboxylate, DIAST 1 (C54) and (2R)-1,1,1-trifluoro-3-[(4-methoxybenzyl)oxy]propan-2-yl 3-[6-(trifluoromethyl)pyridin-2-yl]-1-oxa-8-azaspiro[4.5]decane-8-carboxylate, DIAST 2 (C55)

Separation of C53 (240 mg, 0.427 mmol) into its component diastereomers was carried out using supercritical fluid chromatography [Column: Phenomenex Lux Cellulose-2, 10 μm; Mobile phase: 4:1 carbon dioxide/(methanol containing 0.1% ammonium hydroxide)]. The first-eluting diastereomer was C54, obtained as a colorless gum. Yield: 110 mg, 0.196 mmol, 46%.
LCMS m/z 585.1 [M+Na$^+$].
The second-eluting diastereomer was further purified using the same supercritical fluid chromatography conditions, affording C55 as a colorless gum. Yield: 80 mg, 0.142 mmol, 33%.
LCMS m/z 585.1 [M+Na$^+$].

Step 8. Synthesis of (2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 1 [From C54, DIAST 1] (14)

Trifluoroacetic acid (1.5 mL) was added to a 0° C. solution of C54 (110 mg, 0.196 mmol) in dichloromethane (6 mL). The reaction mixture was stirred at 0° C. for 1 hour, whereupon it was concentrated in vacuo. The residue was partitioned between ethyl acetate (10 mL) and saturated aqueous sodium bicarbonate solution (15 mL), and the aqueous layer was extracted with ethyl acetate (2×15 mL). The combined organic layers were dried over sodium sulfate, filtered, and concentrated under reduced pressure. Purification was effected via reversed-phase HPLC (Column: Waters XBridge C18 OBD, 5 μm; Mobile phase A: water containing 0.225% formic acid; Mobile phase B: acetonitrile; Gradient: 25% to 95% B), followed by a second reversed-phase purification (Column: Agela Durashell C18, 5 μm; Mobile phase A: 0.225% formic acid in water; Mobile phase B: acetonitrile; Gradient: 40% to 60% B). The product was isolated as a brown gum. Yield: 33.5 mg, 75.7 μmol, 39%. LCMS m/z 443.0 [M+H]$^+$. $^1$H NMR (400 MHz, CDCl$_3$) δ 7.80 (dd, J=7.9, 7.9 Hz, 1H), 7.54 (d, J=7.9 Hz, 1H), 7.39 (d, J=7.9 Hz, 1H), 5.32-5.21 (br m, 1H), 4.29 (dd, J=8.6, 7.7 Hz, 1H), 4.04-3.98 (m, 1H), 4.00 (dd, J=8.8, 8.8 Hz, 1H), 3.92-3.72 (m, 4H), 3.52-3.34 (m, 2H), 2.66-2.35 (br s, 1H), 2.25 (dd, half of ABX pattern, J=12.5, 8.6 Hz, 1H), 2.21-2.12 (m, 1H), 1.93-1.56 (m, 4H, assumed; partially obscured by water peak).

Step 9. Synthesis of (2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 2 [From C55, DIAST 2] (15)

Conversion of C55 to the product was effected using the method employed for synthesis of 14 from C54. Purification in this case was carried out via a single reversed-phase HPLC separation (Column: Agela Durashell C18, 5 μm; Mobile phase A: 0.225% formic acid in water; Mobile phase B: acetonitrile; Gradient: 40% to 60% B). The product was isolated as a brown gum. Yield: 9.66 mg, 21.8 μmol, 15%. LCMS m/z 443.0 [M+H]$^+$. $^1$H NMR (400 MHz, CDCl$_3$) δ 7.81 (dd, J=8.0, 7.5 Hz, 1H), 7.54 (d, J=7.5 Hz, 1H), 7.39 (d, J=8.0 Hz, 1H), 5.33-5.20 (br m, 1H), 4.29 (dd, J=8.5, 8.0 Hz, 1H), 4.05-3.96 (m, 2H), 3.92-3.72 (m, 4H), 3.51-3.33 (m, 2H), 2.58-2.36 (br s, 1H), 2.25 (br dd, half of ABX pattern, J=12.6, 8.5 Hz, 1H), 2.16 (dd, half of ABX pattern, J=12.6, 9.0 Hz, 1H), 1.93-1.6 (m, 4H, assumed; partially obscured by water peak).

Examples 16 and 17

(2R)-1,1,1-Trifluoro-3-hydroxypropan-2-yl 3-(5-fluoropyridin-2-yl)-1-oxa-8-azaspiro[4.5]decane-8-carboxylate, DIAST 1 [From C59, DIAST 1] (16) and (2R)-1,1,1-Trifluoro-3-hydroxypropan-2-yl 3-(5-fluoropyridin-2-yl)-1-oxa-8-azaspiro[4.5]decane-8-carboxylate, DIAST 2 [From C60, DIAST 2] (17)

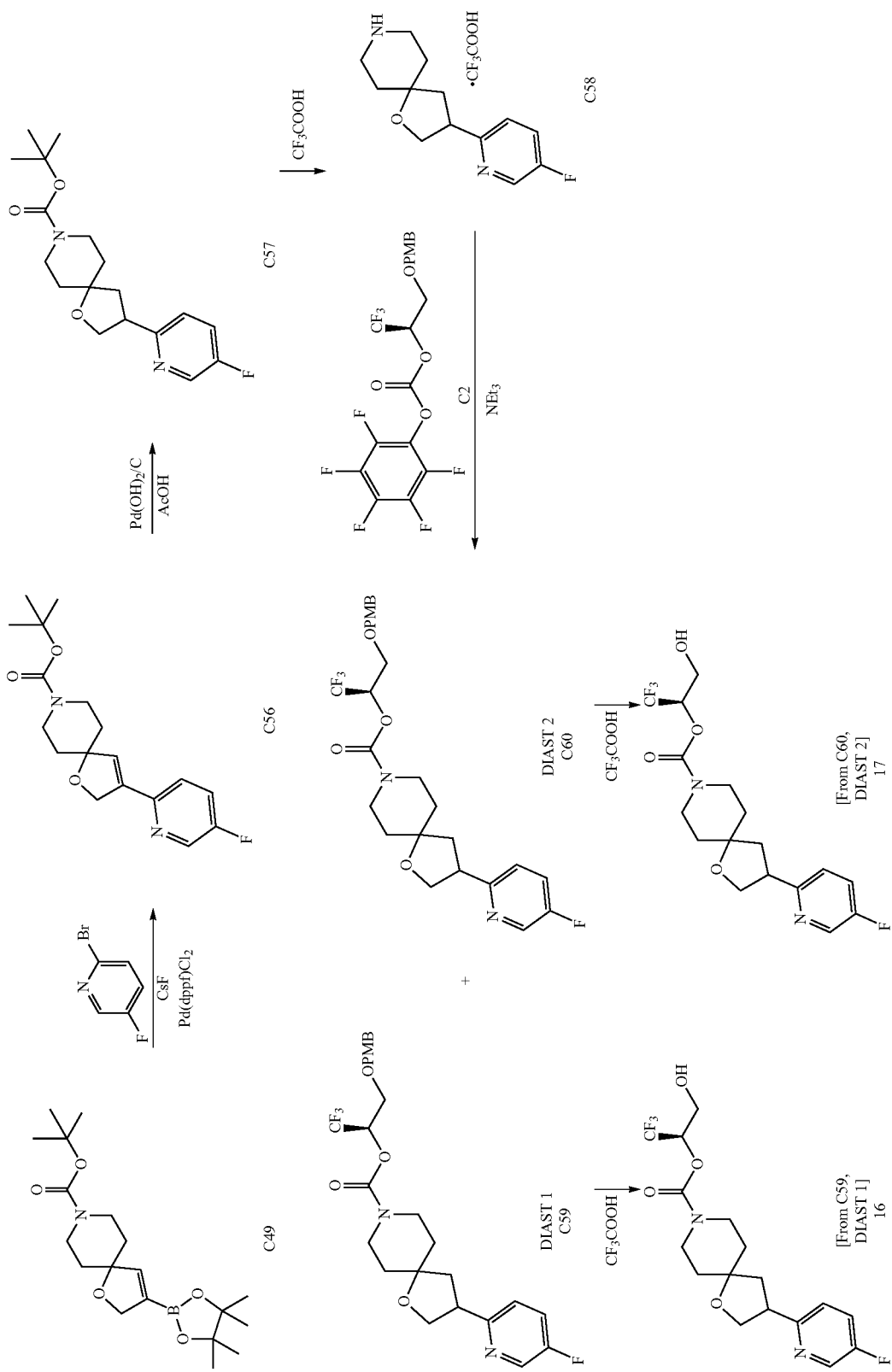

Step 1. Synthesis of tert-butyl 3-(5-fluoropyridin-2-yl)-1-oxa-8-azaspiro[4.5]dec-3-ene-8-carboxylate (C56)

2-Bromo-5-fluoropyridine (1.35 g, 7.67 mmol), cesium fluoride (2.69 g, 17.7 mmol), [1,1'-bis(diphenylphosphino)ferrocene]dichloropalladium(II) (432 mg, 0.590 mmol) and water (5 mL) were added to C49 [crude reaction mixture from preparation of C49 from C48; 5.9 mmol of C49 in 1,4-dioxane (50 mL)]. The reaction mixture was stirred at 80° C. for 16 hours, whereupon it was concentrated in vacuo. The residue was dissolved in ethyl acetate (200 mL) and filtered, and the filtrate was concentrated under reduced pressure and purified via silica gel chromatography (Gradient: 0% to 25% of ethyl acetate in petroleum ether), affording the product as an off-white solid. By $^1$H NMR analysis, this product was somewhat impure. Yield: 1.23 g, <3.68 mol, <62%. LCMS m/z 278.9 [(M−2-methylprop-1-ene)+H]$^+$. $^1$H NMR (400 MHz, CDCl$_3$), characteristic product peaks only: δ 8.42 (d, J=2.5 Hz, 1H), 7.42-7.34 (m, 2H), 6.37 (t, J=2.2 Hz, 1H), 5.08 (d, J=2.0 Hz, 2H), 3.86-3.73 (br m, 2H), 3.39-3.27 (m, 2H), 1.48 (s, 9H).

Step 2. Synthesis of tert-butyl/3-(5-fluoropyridin-2-yl)-1-oxa-8-azaspiro[4.5]decane-8-carboxylate (C57)

A solution of C56 (295 mg, 0.882 mmol) in a mixture of acetic acid and methanol (1:20 ratio; 25 mL) was added to a slurry of palladium hydroxide on carbon [20% Pd (50% wet with water); 30 mg] in methanol (2 mL) in a Parr reactor. The reaction mixture was hydrogenated at 50 psi at room temperature until LCMS analysis indicated that the reaction was essentially complete, whereupon the reaction mixture was filtered through diatomaceous earth. The filter pad was rinsed with methanol, and the combined filtrates were concentrated in vacuo, providing the product as a clear golden oil (375 mg). By $^1$H NMR, this product contained some impurities; it was taken directly to the following step. LCMS m/z 281.4 [(M−2-methylprop-1-ene)+H]$^+$. $^1$H NMR (400 MHz, CD$_3$OD), product peaks only: δ 8.39 (d, J=2.7 Hz, 1H), 7.53 (ddd, J=8.6, 8.6, 3.0 Hz, 1H), 7.39 (dd, J=8.8, 4.5 Hz, 1H), 4.22 (dd, J=8.2, 7.8 Hz, 1H), 3.92 (dd, J=9.0, 8.6 Hz, 1H), 3.79-3.69 (m, 1H), 3.67-3.56 (m, 2H), 3.42-3.3 (m, 2H), 2.28 (dd, J=12.5, 8.2 Hz, 1H), 2.05 (dd, J=12.5, 9.8 Hz, 1H), 1.78-1.69 (m, 3H), 1.68-1.57 (m, 1H), 1.46 (s, 9H).

Step 3. Synthesis of 3-(5-fluoropyridin-2-yl)-1-oxa-8-azaspiro[4.5]decane, trifluoroacetate salt (C58)

Trifluoroacetic acid (2 mL) was added to a 0° C. solution of C57 (from the previous step; 50.882 mmol) in dichloromethane (10 mL), and the reaction mixture was allowed to warm to room temperature. After 2 hours at room temperature, it was concentrated in vacuo, affording the product as an oil (395 mg). This material was taken directly to the following step. LCMS m/z 237.4 [M+H]$^+$. $^1$H NMR (400 MHz, CDCl$_3$), characteristic peaks: δ 8.64 (d, J=2.0 Hz, 1H), 7.76-7.69 (m, 1H), 7.51 (dd, J=9.2, 4.9 Hz, 1H), 4.31 (dd, J=9.0, 7.4 Hz, 1H), 4.01 (dd, J=8.6, 8.2 Hz, 1H), 3.97-3.87 (m, 1H), 2.44 (dd, J=13.1, 8.4 Hz, 1H), 2.09 (dd, J=13.1, 9.2 Hz, 1H).

Step 4. Synthesis of (2R)-1,1,1-trifluoro-3-[(4-methoxybenzyl)oxy]propan-2-yl 3-(5-fluoropyridin-2-yl)-1-oxa-8-azaspiro[4.5]decane-8-carboxylate, DIAST 1 (C59) and (2R)-1,1,1-trifluoro-3-[(4-methoxybenzyl)oxy]propan-2-yl 3-(5-fluoropyridin-2-yl)-1-oxa-8-azaspiro[4.5]decane-8-carboxylate, DIAST 2 (C60)

Conversion of C58 to a mixture of C59 and C60 was carried out using the method described for synthesis of C5 from C4 in Example 1. In this case, silica gel chromatography was carried out using eluents of 5% followed by 10%, 20%, and 30% ethyl acetate in heptane, affording the product as a thick, colorless oil. Yield of diastereomeric mixture: 231 mg, 0.451 mmol, 51% over three steps.

Separation of C59 and C60 was carried out via supercritical fluid chromatography [Column: Chiral Technologies Chiralcel OJ, 5 μm; Mobile phase: 9:1 carbon dioxide/(methanol containing 0.2% ammonium hydroxide)]. The first-eluting diastereomer was C59, obtained as a colorless oil. Yield: 70.3 mg, 0.137 mmol, 30% for the separation. LCMS m/z 558.6 [M+HCOOH+H]$^+$. $^1$H NMR (400 MHz, CDCl$_3$) δ 8.42 (d, J=2.7 Hz, 1H), 7.34 (ddd, J=8.6, 8.2, 2.7 Hz, 1H), 7.25 (br d, J=8.6 Hz, 2H), 7.18 (dd, J=8.6, 4.7 Hz, 1H), 6.88 (br d, J=7.4 Hz, 2H), 5.54-5.43 (m, 1H), 4.51 (AB quartet, upfield doublet is broadened, J$_{AB}$=11.7 Hz, Δv$_{AB}$=27.7 Hz, 2H), 4.24 (dd, J=8.2, 7.8 Hz, 1H), 3.95 (dd, J=9.0, 8.6 Hz, 1H), 3.87-3.62 (m, 5H), 3.81 (br s, 3H), 3.48-3.35 (m, 2H), 2.26-2.13 (m, 1H), 2.13-2.00 (m, 1H), 1.88-1.65 (m, 3H), 1.67-1.54 (m, 1H). The second-eluting diastereomer was C60, also isolated as a colorless oil. Yield: 69.3 mg, 0.135 mmol, 30% for the separation. LCMS m/z 535.7 [M+Na$^+$]. $^1$H NMR (400 MHz, CDCl$_3$) δ 8.41 (d, J=2.7 Hz, 1H), 7.34 (ddd, J=8.6, 8.2, 3.1 Hz, 1H), 7.25 (br d, J=8.6 Hz, 2H), 7.18 (dd, J=8.6, 4.3 Hz, 1H), 6.88 (br d, J=8.2 Hz, 2H), 5.55-5.43 (br m, 1H), 4.51 (AB quartet, upfield doublet is broadened, J$_{AB}$=11.5 Hz, Δv$_{AB}$=27.5 Hz, 2H), 4.24 (dd, J=8.2, 7.8 Hz, 1H), 4.00-3.90 (br m, 1H), 3.88-3.61 (m, 5H), 3.81 (br s, 3H), 3.47-3.34 (m, 2H), 2.27-2.12 (m, 1H), 2.12-2.00 (m, 1H), 1.87-1.50 (m, 4H).

Step 5. Synthesis of (2R)-1,1,1-trifluoro-3-hydroxypropan-2-yl 3-(5-fluoropyridin-2-yl)-1-oxa-8-azaspiro[4.5]decane-8-carboxylate, DIAST 1 [From C59, DIAST 1] (16)

Trifluoroacetic acid (1 mL) was added to a 0° C. solution of C59 (70 mg, 0.14 mmol) in dichloromethane (4 mL). The reaction mixture was allowed to stir at room temperature for 2 hours, whereupon it was concentrated in vacuo. The residue was partitioned between saturated aqueous sodium bicarbonate solution and dichloromethane, and the aqueous layer was extracted with dichloromethane. The combined organic layers were dried over sodium sulfate, filtered, concentrated under reduced pressure, and purified via silica gel chromatography (Eluents: 10% followed by 25% and 50% ethyl acetate in heptane), providing the product as a colorless oil that contained some solvent. Yield: 60 mg. LCMS m/z 393.2 [M+H]$^+$. $^1$H NMR (400 MHz, CDCl$_3$) δ 8.46 (d, J=2.7 Hz, 1H), 7.42 (ddd, J=8.4, 8.2, 2.9 Hz, 1H), 7.26 (dd, J=8.6, 4.3 Hz, 1H), 5.31-5.20 (br m, 1H), 4.25 (dd, J=8.6, 7.8 Hz, 1H), 4.00 (dd, half of ABX pattern, J=12.5, 3.1 Hz, 1H), 3.96 (dd, J=8.6, 8.6 Hz, 1H), 3.92-3.68 (m, 4H), 3.51-3.33 (m, 2H), 2.26 (dd, half of ABX pattern, J=12.5, 8.6

Hz, 1H), 2.05 (dd, half of ABX pattern, J=12.5, 9.8 Hz, 1H), 1.87-1.70 (m, 3H), 1.70-1.55 (m, 1H).

Step 6. Synthesis of (2R)-1,1,1-trifluoro-3-hydroxypropan-2-yl 3-(5-fluoropyridin-2-yl)-1-oxa-8-azaspiro[4.5]decane-8-carboxylate, DIAST 2 [From C60, DIAST 2] (17)

Conversion of C60 to the product was effected using the method employed for synthesis of 16 from C59. The product was obtained as a colorless oil. Yield, corrected for solvent: 48 mg, 0.12 mmol, 92%. LCMS m/z 415.0 [M+Na⁺]. $^1$H NMR (400 MHz, CDCl$_3$) δ 8.41 (d, J=2.7 Hz, 1H), 7.34 (ddd, J=8.6, 8.2, 2.7 Hz, 1H), 7.18 (dd, J=8.6, 4.7 Hz, 1H), 5.31-5.20 (br m, 1H), 4.24 (dd, J=8.2, 8.2 Hz, 1H), 4.04-3.91 (m, 2H), 3.91-3.73 (m, 3H), 3.73-3.63 (m, 1H), 3.51-3.31 (m, 2H), 2.8-2.3 (v br s, 1H), 2.22 (dd, half of ABX pattern, J=12.7, 8.4 Hz, 1H), 2.08 (dd, half of ABX pattern, J=12.5, 9.4 Hz, 1H), 1.89-1.58 (m, 4H).

Example 18

(2R)-1,1,1-Trifluoro-3-hydroxypropan-2-yl 2-{[(cyclopropylmethyl)sulfonyl](methyl)amino}-7-azaspiro[3.5]nonane-7-carboxylate (18)

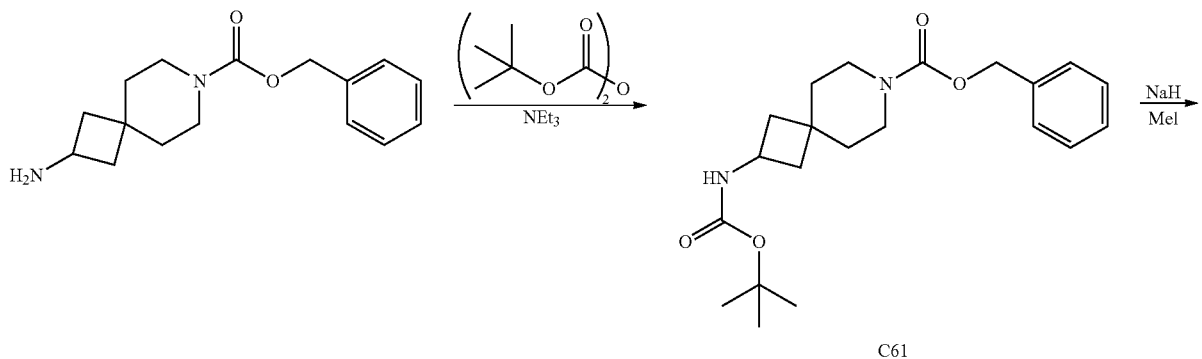

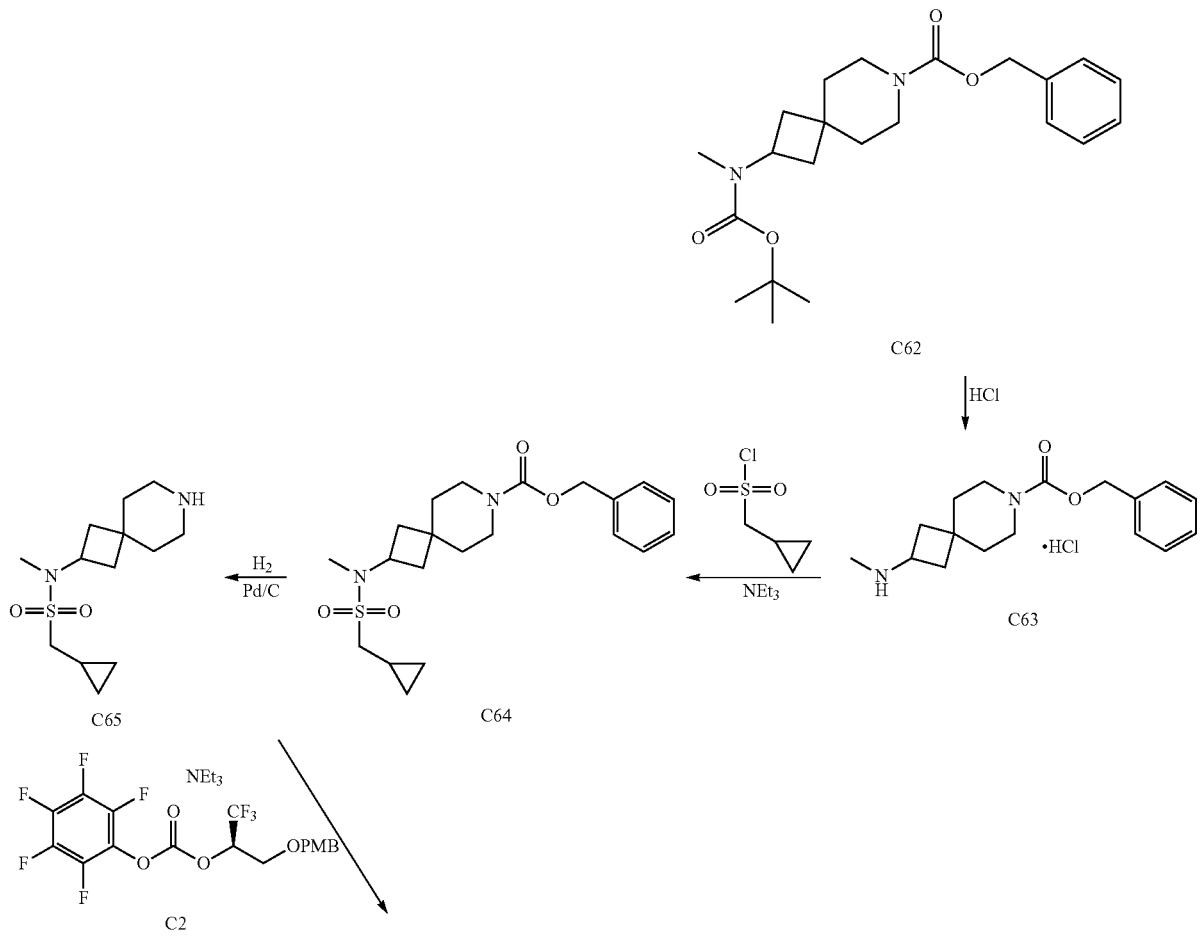

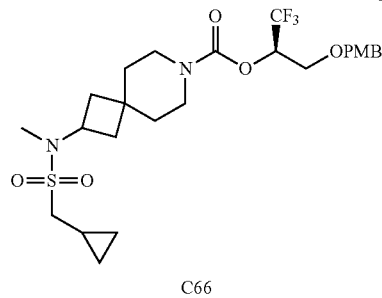

C66

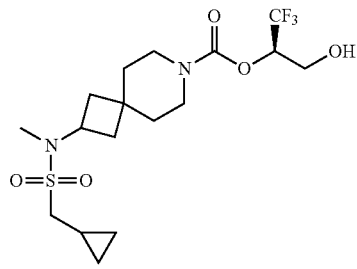

18

Step 1. Synthesis of benzyl 2-[(tert-butoxycarbonyl)amino]-7-azaspiro[3.5]nonane-7-carboxylate (C61)

To a solution of benzyl 2-amino-7-azaspiro[3.5]nonane-7-carboxylate (17.8 g, 64.9 mmol) and triethylamine (9.86 g, 97.4 mmol) in methanol (300 mL) was added di-tert-butyl dicarbonate (15.6 g, 71.5 mmol), and the reaction mixture was stirred at room temperature overnight. It was then concentrated in vacuo and purified using silica gel chromatography, affording the product as a white solid. Yield: 13.0 g, 34.7 mmol, 53%. $^1$H NMR (400 MHz, CDCl$_3$) δ 7.39-7.28 (m, 5H), 5.12 (s, 2H), 4.75-4.60 (br m, 1H), 4.19-4.04 (br m, 1H), 3.48-3.40 (m, 2H), 3.40-3.30 (m, 2H), 2.37-2.22 (m, 2H), 1.64-1.37 (m, 6H, assumed; partially obscured by water peak), 1.44 (s, 9H).

Step 2. Synthesis of benzyl 2-[(tert-butoxycarbonyl)(methyl)amino]-7-azaspiro[3.5]nonane-7-carboxylate (C62)

Sodium hydride (60% dispersion in mineral oil; 320 mg, 8.0 mmol) was added to a 0° C. solution of C61 (2.00 g, 5.34 mmol) in tetrahydrofuran (25 mL), and the reaction mixture was stirred at 0° C. for 30 minutes. Iodomethane (985 mg, 6.94 mmol) was added drop-wise to the 0° C. reaction mixture, which was then allowed to stir at 30° C. for 16 hours. Water (15 mL) was slowly added, the resulting mixture was extracted with ethyl acetate (2×30 mL), and the combined organic layers were dried over sodium sulfate, filtered, and concentrated in vacuo to provide the product as a yellow gum (2.36 g). This material was used directly in the following step. LCMS m/z 411.2 [M+Na$^+$]. $^1$H NMR (400 MHz, CDCl$_3$) δ 7.40-7.29 (m, 5H), 5.12 (s, 2H), 4.67-4.35 (v br m, 1H), 3.48-3.42 (m, 2H), 3.41-3.35 (m, 2H), 2.80 (s, 3H), 2.15-2.06 (m, 2H), 1.89-1.80 (m, 2H), 1.67-1.56 (m, 2H, assumed; partially obscured by water peak), 1.56-1.47 (m, 2H), 1.46 (s, 9H).

Step 3. Synthesis of benzyl 2-(methylamino)-7-azaspiro[3.5]nonane-7-carboxylate, hydrochloride salt (C63)

Compound C62 (from the previous step, 55.34 mmol) was dissolved in methanolic hydrogen chloride (0.2 M, 25 mL) and stirred at 30° C. for 2 hours. The reaction mixture was then concentrated in vacuo to afford the product as a pale yellow gum (3.1 g), a portion of which was used directly in the following step. LCMS m/z 289.1 [M+H]$^+$.

Step 4. Synthesis of benzyl 2-{[(cyclopropylmethyl)sulfonyl](methyl)amino}-7-azaspiro[3.5]nonane-7-carboxylate (C64)

Cyclopropylmethanesulfonyl chloride (134 mg, 0.867 mmol) was added in a drop-wise manner to a 0° C. solution of C63 [from the previous step; 400 mg (impure), <0.69 mmol] and triethylamine (202 mg, 2.00 mmol) in dichloromethane (8 mL). The reaction mixture was stirred at room temperature (28° C.) for 2.5 hours, whereupon it was concentrated in vacuo. The residue was purified via chromatography on silica gel (Gradient: 17% to 33% ethyl acetate in petroleum ether), providing the product as a pale yellow gum. Yield: 90 mg, 0.22 mmol, 32% over three steps.

Step 5. Synthesis of N-(7-azaspiro[3.5]non-2-yl)-1-cyclopropyl-N-methylmethanesulfonamide (C65)

A mixture of C64 (140 mg, 0.344 mmol) and Pd/C (20 mg) in methanol (10 mL) was stirred at room temperature (26° C.) under hydrogen (15 psi) for 16 hours. The catalyst was removed via filtration, and the collected solid was washed with methanol (10 mL). The combined filtrates were concentrated in vacuo to afford the product as a pale yellow gum (80 mg), which by $^1$H NMR analysis was not pure. This material was taken directly into the following step. $^1$H NMR (400 MHz, CD$_3$OD), product peaks only: δ 4.38-4.26 (m, 1H), 2.90 (d, J=7.0 Hz, 2H), 2.87 (s, 3H), 2.78-2.72 (m, 2H), 2.70-2.64 (m, 2H), 2.14-1.95 (m, 4H), 1.64-1.59 (m, 2H), 1.56-1.50 (m, 2H), 1.10-0.97 (m, 1H), 0.69-0.60 (m, 2H), 0.40-0.33 (m, 2H).

Step 6. Synthesis of (2R)-1,1,1-trifluoro-3-[(4-methoxybenzyl)oxy]propan-2-yl 2-{[(cyclopropylmethyl)sulfonyl](methyl)amino}-7-azaspiro[3.5]nonane-7-carboxylate (C66)

Conversion of C65 to C66 was carried out using the method described for synthesis of the mixture of C13 and C14 from C12 in Examples 3 and 4. In this case, purification was effected via silica gel chromatography (Gradient: 9% to 25% ethyl acetate in petroleum ether) followed by reversed-phase HPLC (Column: Waters XBridge C18 OBD, 5 μm; Mobile phase A: water containing 0.05% ammonium hydroxide; Mobile phase B: acetonitrile; Gradient: 45% to 75% B). Yield: 43 mg, 78 μmol, 23% over two steps. LCMS m/z 571.1 [M+Na$^+$].

Step 7. Synthesis of (2R)-1,1,1-trifluoro-3-hydroxypropan-2-yl 2-{[(cyclopropylmethyl)sulfonyl](methyl)amino}-7-azaspiro[3.5]nonane-7-carboxylate (18)

Trifluoroacetic acid (1 mL) was added to a solution of C66 (42 mg, 77 μmol) in dichloromethane (3 mL), and the reaction mixture was stirred at room temperature (28° C.) for 3 hours. After dilution with dichloromethane (20 mL), the mixture was washed with saturated aqueous sodium bicarbonate solution (3×10 mL), concentrated in vacuo, and purified by reversed-phase HPLC (Column: Agela Durashell C18, 5 μm; Mobile phase A: 0.225% formic acid in water; Mobile phase B: acetonitrile; Gradient: 30% to 50% B). The product was isolated as a yellow gum. Yield: 7.13 mg, 16.6 μmol, 22%. LCMS m/z 429.1 [M+H]⁺. ¹H NMR (400 MHz, CDCl₃) δ 5.30-5.18 (m, 1H), 4.46-4.31 (m, 1H), 4.00 (dd, half of ABX pattern, J=12.5, 2.9 Hz, 1H), 3.87 (dd, half of ABX pattern, J=12.3, 6.6 Hz, 1H), 3.56-3.30 (br m, 4H), 2.89 (s, 3H), 2.83 (d, J=7.0 Hz, 2H), 2.19-2.09 (m, 2H), 2.01 (dd, J=11.9, 9.2 Hz, 2H), 1.71-1.51 (br m, 4H, assumed; partially obscured by water peak), 1.14-1.02 (m, 1H), 0.73-0.66 (m, 2H), 0.39-0.32 (m, 2H).

Example 19

(2R)-1,1,1-Trifluoro-3-hydroxypropan-2-yl 2-{[6-(difluoromethyl)pyridin-3-yl]oxy}-7-azaspiro[3.5]nonane-7-carboxylate (19)

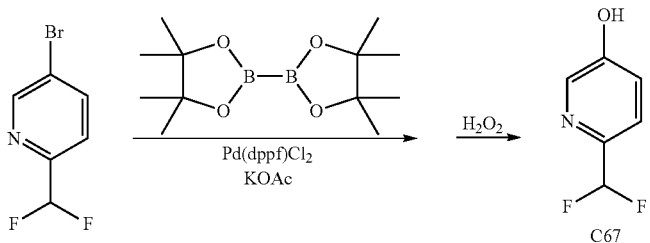

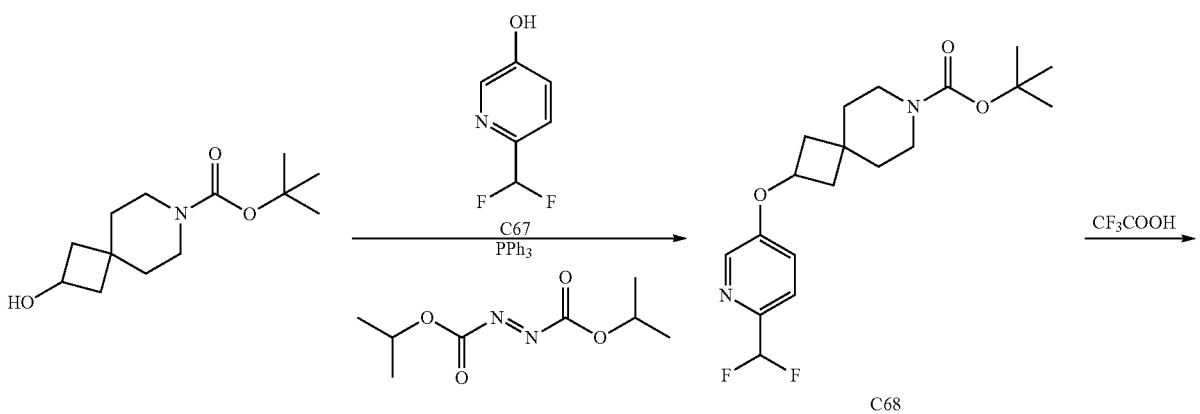

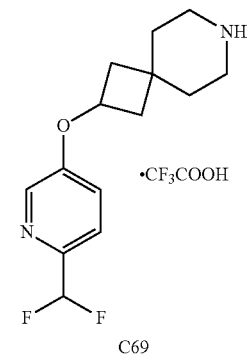

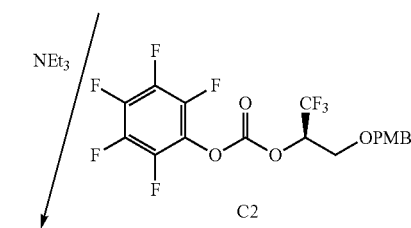

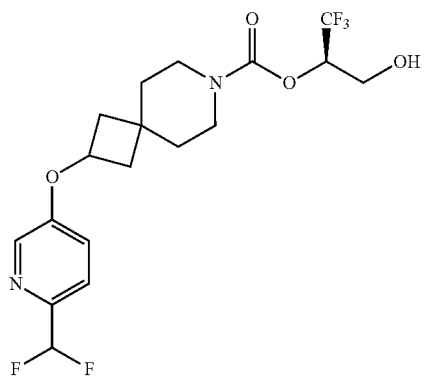

19

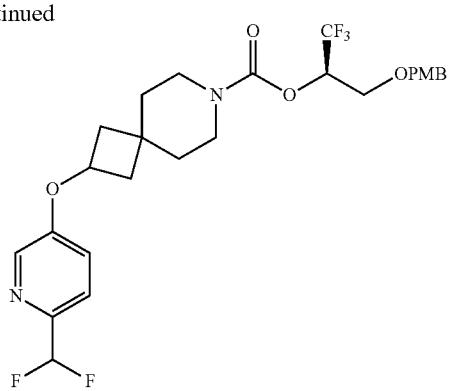

C70

CF₃COOH

Step 1. Synthesis of 6-(difluoromethyl)pyridin-3-ol (C67)

4,4,4',4',5,5,5',5'-Octamethyl-2,2'-bi-1,3,2-dioxaborolane (537 mg, 2.11 mmol), [1,1'-bis(diphenylphosphino)ferrocene]dichloropalladium(II) (141 mg, 0.193 mmol), and potassium acetate (377 mg, 3.84 mmol) were added to a 30° C. solution of 5-bromo-2-(difluoromethyl)pyridine (400 mg, 1.92 mmol) in 1,4-dioxane (5 mL). After the reaction mixture had been degassed with nitrogen for 5 minutes, it was stirred for 18 hours at 115° C., whereupon it was filtered. Concentration of the filtrate provided a black solid (1.17 g), which was divided into two portions for addition of the next reagent. One portion of this material (870 mg, 51.43 mmol) was dissolved in a mixture of tetrahydrofuran (10 mL) and water (10 mL) and treated with hydrogen peroxide (30% aqueous solution; 487 mg, 4.29 mmol) at 28° C. The reaction mixture was stirred for 15 hours at 28° C., whereupon it was combined with the reaction mixture from the second portion, and the oxidant was quenched via addition of saturated aqueous sodium sulfite solution (5 mL) (until the resulting mixture tested negative with potassium iodide-starch test paper). The resulting mixture was extracted with ethyl acetate (2×20 mL), and the combined organic layers were dried over sodium sulfate, filtered, and concentrated in vacuo. Silica gel chromatography (Gradient: 0% to 25% ethyl acetate in petroleum ether) provided the product as a white solid. Yield: 148 mg, 1.02 mmol, 53%. LCMS m/z 145.9 [M+H]⁺. ¹H NMR (400 MHz, CDCl₃) δ 8.28 (d, J=2.5 Hz, 1H), 7.56 (d, J=8.5 Hz, 1H), 7.30 (dd, J=8.5, 2.5 Hz, 1H), 6.62 (t, $J_{HF}$=55.7 Hz, 1H).

Step 2. Synthesis of tert-butyl 2-{[6-(difluoromethyl)pyridin-3-yl]oxy}-7-azaspiro[3.5]nonane-7-carboxylate (C68)

To a 0° C. mixture of tert-butyl 2-hydroxy-7-azaspiro[3.5]nonane-7-carboxylate (50 mg, 0.21 mmol), C67 (39.1 mg, 0.269 mmol), and triphenylphosphine (109 mg, 0.416 mmol) in tetrahydrofuran (1.5 mL) was added diisopropyl azodicarboxylate (83.8 mg, 0.414 mmol) in a drop-wise manner, and the reaction mixture was stirred at 28° C. for 15 hours. It was then directly purified via preparative thin-layer chromatography on silica gel (Eluent: 3:1 petroleum ether/ethyl acetate), providing the product as a yellow gum (100 mg), which by ¹H NMR analysis was contaminated with material derived from diisopropyl azodicarboxylate. ¹H NMR (400 MHz, CDCl₃), product peaks only: δ 8.22 (d, J=2.5 Hz, 1H), 7.56 (d, J=8.5 Hz, 1H), 7.18 (dd, J=8.5, 3.0 Hz, 1H), 6.61 (t, $J_{HF}$=55.7 Hz, 1H), 4.80-4.72 (m, 1H), 3.42-3.36 (m 2H), 3.36-3.30 (m, 2H), 2.49-2.41 (m, 2H), 2.03-1.95 (m, 2H), 1.65-1.56 (m, 4H, assumed; partially obscured by water peak), 1.46 (s, 9H).

Step 3. Synthesis of 2-{[6-(difluoromethyl)pyridin-3-yl]oxy}-7-azaspiro[3.5]nonane, trifluoroacetate salt (C69)

Trifluoroacetic acid (1 mL) was added to a 0° C. solution of C68 (256 mg, 0.695 mmol) in dichloromethane (4 mL). The reaction mixture was stirred at 28° C. for 2 hours, whereupon it was concentrated under reduced pressure to afford the product as a yellow gum. This material was taken directly to the following step. LCMS m/z 268.9 [M+H]⁺.

Step 4. Synthesis of (2R)-1,1,1-trifluoro-3-[(4-methoxybenzyl)oxy]propan-2-yl 2-{[6-(difluoromethyl)pyridin-3-yl]oxy}-7-azaspiro[3.5]nonane-7-carboxylate (C70)

Conversion of C69 to C70 was carried out using the method described for synthesis of the mixture of C13 and C14 from C12 in Examples 3 and 4. The product was obtained as a yellow gum. Yield: 259 mg, 0.476 mmol, 68% over 2 steps. LCMS m/z 545.1 [M+H]⁺. ¹H NMR (400 MHz, CDCl₃), characteristic peaks: δ 8.21 (d, J=3.0 Hz, 1H), 7.57 (d, J=8.5 Hz, 1H), 7.24 (d, J=8.5 Hz, 2H), 7.19 (dd, J=8.5, 3.0 Hz, 1H), 6.88 (d, J=8.5 Hz, 2H), 6.62 (t, $J_{HF}$=55.7 Hz, 1H), 5.53-5.42 (m, 1H), 4.82-4.72 (m, 1H), 4.51 (AB quartet, $J_{AB}$=11.8 Hz, $\Delta v_{AB}$=28.5 Hz, 2H), 3.81 (s, 3H), 3.79-3.65 (m, 2H), 3.54-3.35 (br m, 4H), 2.52-2.41 (m, 2H), 2.05-1.95 (m, 2H).

Step 5. Synthesis of (2R)-1,1,1-trifluoro-3-hydroxypropan-2-yl 2-{[6-(difluoromethyl)pyridin-3-yl]oxy}-7-azaspiro[3.5]nonane-7-carboxylate (19)

Trifluoroacetic acid (1 mL) was added to a 10° C. solution of C70 (259 mg, 0.476 mmol) in dichloromethane (4 mL). The reaction mixture was stirred at 30° C. for 1 hour, whereupon it was washed with saturated aqueous sodium bicarbonate solution (2×3 mL), and concentrated in vacuo. The residue was purified by reversed-phase HPLC (Column: Agela Durashell, 5 μm; Mobile phase A: 0.225% formic acid in water; Mobile phase B: acetonitrile; Gradient: 42% to 62% B), followed by supercritical fluid chromatography (Column: Chiral Technologies Chiralpak AD, 5 μm; Mobile phase: 3:2 carbon dioxide/ethanol) to provide the product as a brown gum. Yield: 27.7 mg, 65.3 μmol, 14%. LCMS m/z 425.2 [M+H]+. 1H NMR (400 MHz, CDCl$_3$) δ 8.21 (d, J=3.0 Hz, 1H), 7.56 (d, J=8.5 Hz, 1H), 7.18 (dd, J=8.8, 2.8 Hz, 1H), 6.61 (t, J$_{HF}$=55.7 Hz, 1H), 5.30-5.21 (m, 1H), 4.82-4.73 (m, 1H), 4.00 (dd, half of ABX pattern, J=12.6, 3.0 Hz, 1H), 3.86 (dd, half of ABX pattern, J=12.3, 6.8 Hz, 1H), 3.59-3.34 (m, 4H), 2.53-2.42 (m, 2H), 2.07-1.98 (m, 2H), 1.75-1.6 (br m, 4H, assumed; partially obscured by water peak).

Alternate Synthesis of Example 11

(2R)-1,1,1-Trifluoro-3-hydroxypropan-2-yl (3R)-3-(4-fluoro-1H-pyrazol-1-yl)-1-oxa-8-azaspiro[4.5]decane-8-carboxylate (11)

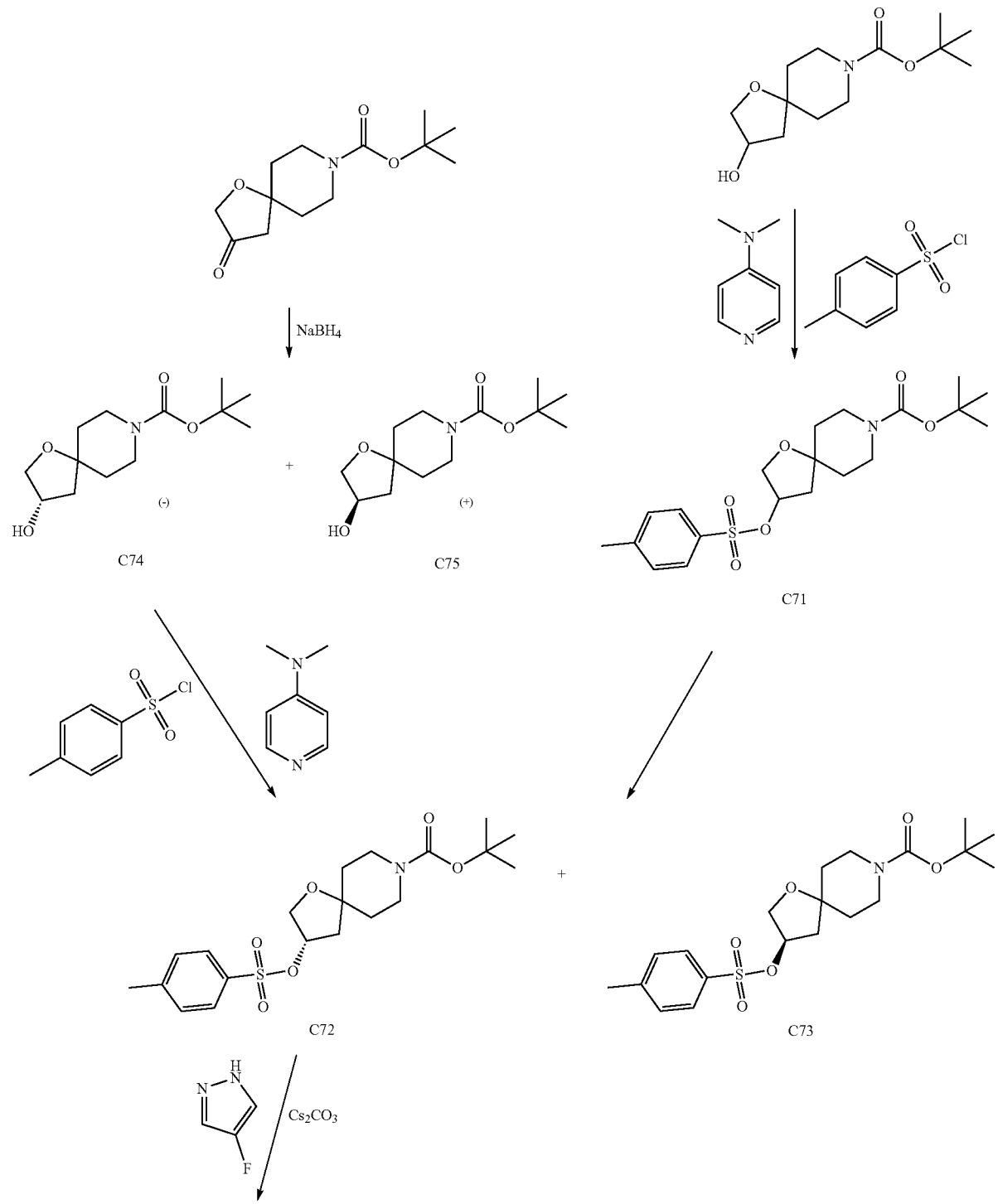

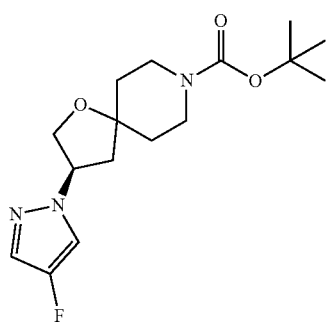
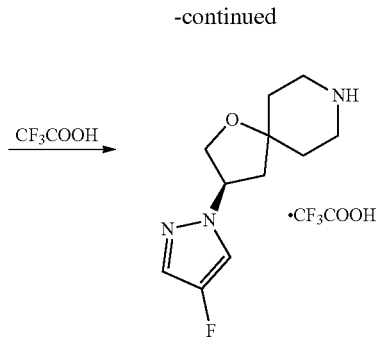
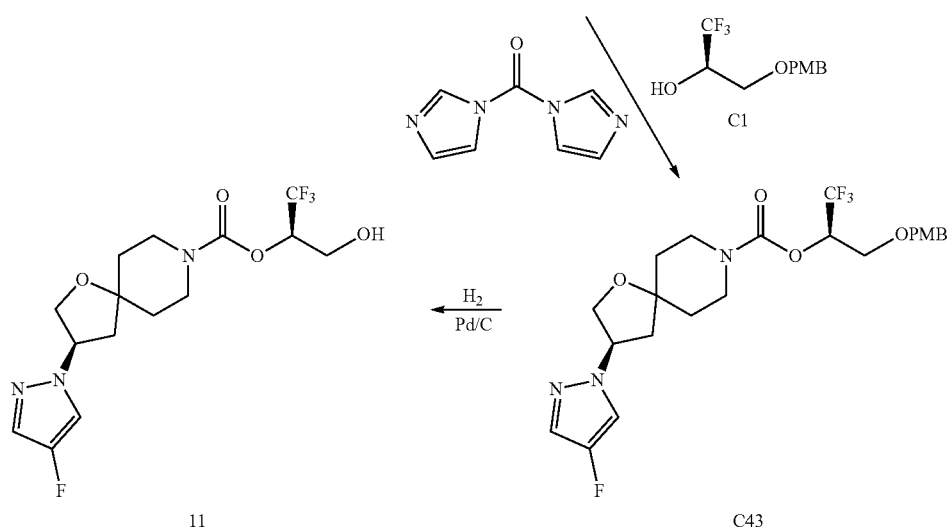

Step 1. Synthesis of tert-butyl 3-{[(4-methylphenyl)sulfonyl]oxy}-1-oxa-8-azaspiro[4.5]decane-8-carboxylate (C71)

p-Toluenesulfonyl chloride (359 mg, 1.88 mmol) and 4-(dimethylamino)pyridine (558 mg, 4.57 mmol) were added to a 27° C. solution of tert-butyl 3-hydroxy-1-oxa-8-azaspiro[4.5]decane-8-carboxylate (440 mg, 1.71 mmol) in dichloromethane (10 mL). The reaction mixture was stirred at 25° C. for 16 hours, whereupon it was combined with a similar reaction carried out with tert-butyl 3-hydroxy-1-oxa-8-azaspiro[4.5]decane-8-carboxylate (30 mg, 0.12 mmol) and concentrated in vacuo. The residue was purified using chromatography on silica gel (Gradient: 0% to 30% ethyl acetate in petroleum ether) to provide the product as a colorless gum. Combined yield: 640 mg, 1.56 mmol, 85%. LCMS m/z 434.0 [M+Na+]. $^1$H NMR (400 MHz, CDCl$_3$) δ 7.79 (d, J=8.4 Hz, 2H), 7.36 (d, J=8.4 Hz, 2H), 5.13-5.06 (br m, 1H), 3.97-3.88 (m, 2H), 3.67-3.53 (br m, 2H), 3.31-3.19 (m, 2H), 2.46 (s, 3H), 2.01 (br dd, half of ABX pattern, J=14.3, 2.0 Hz, 1H), 1.93 (dd, half of ABX pattern, J=14.5, 6.6 Hz, 1H), 1.82-1.74 (m, 1H), 1.61-1.48 (m, 3H), 1.45 (s, 9H).

Step 2. Isolation of tert-butyl (3S)-3-{[(4-methylphenyl)sulfonyl]oxy}-1-oxa-8-azaspiro[4.5]decane-8-carboxylate (C72) and tert-butyl (3R)-3-{[(4-methylphenyl)sulfonyl]oxy}-1-oxa-8-azaspiro[4.5]decane-8-carboxylate (C73)

Supercritical fluid chromatography was used to separate C71 (from the previous step; 640 mg, 1.56 mmol) into its component enantiomers [Column: Chiral Technologies Chiralpak AD, 5 μm; Mobile phase: 3:2 carbon dioxide/(ethanol containing 0.1% ammonium hydroxide)]. The first-eluting product, obtained as a colorless gum that exhibited a positive (+) rotation, was designated as C72. The indicated absolute stereochemistry of C72 was established on the basis of an X-ray crystal structure determined on its enantiomer C73 (see below). Yield: 259 mg, 0.629 mmol, 40%. LCMS m/z 434.0 [M+Na+]. $^1$H NMR (400 MHz, CDCl$_3$) δ 7.79 (br d, J=8.0 Hz, 2H), 7.36 (d, J=8.0 Hz, 2H), 5.14-5.06 (br m, 1H), 3.97-3.89 (m, 2H), 3.67-3.54 (br m, 2H), 3.31-3.20 (m, 2H), 2.47 (s, 3H), 2.01 (br dd, half of ABX pattern, J=14.3, 1.8 Hz, 1H), 1.93 (dd, half of ABX pattern, J=14.6, 6.5 Hz, 1H), 1.82-1.74 (m, 1H), 1.60-1.48 (m, 3H), 1.45 (s, 9H).

The second-eluting product, also obtained as a colorless gum, exhibited a negative (−) rotation and was designated as C73. Yield: 263 mg, 0.639 mmol, 41%. LCMS m/z 434.1 [M+Na+]. $^1$H NMR (400 MHz, CDCl$_3$) δ 7.79 (br d, J=8.0 Hz, 2H), 7.36 (d, J=8.0 Hz, 2H), 5.13-5.06 (br m, 1H), 3.97-3.89 (m, 2H), 3.68-3.53 (br m, 2H), 3.31-3.20 (m, 2H), 2.46 (s, 3H), 2.01 (br dd, half of ABX pattern, J=14.3, 1.8 Hz, 1H), 1.93 (dd, half of ABX pattern, J=14.6, 6.5 Hz, 1H), 1.82-1.74 (m, 1H), 1.61-1.48 (m, 3H), 1.45 (s, 9H).

A sample of C73 was recrystallized from tert-butyl methyl ether/pentane and used to determine the absolute configuration via X-ray crystallography:

Single-crystal X-ray structural determination of C73

Single Crystal X-Ray Analysis

Data collection was performed on a Bruker D8 Quest diffractometer at room temperature. Data collection consisted of omega and phi scans.

The structure was solved by direct methods using SHELX software suite in the orthorhombic space group $P2_12_12_1$. The structure was subsequently refined by the full-matrix least squares method. All non-hydrogen atoms were found and refined using anisotropic displacement parameters.

The hydrogen atoms were placed in calculated positions and were allowed to ride on their carrier atoms. The final refinement included isotropic displacement parameters for all hydrogen atoms.

Analysis of the absolute structure using likelihood methods (Hooft 2008) was performed using PLATON (Spek 2010). Assuming the sample is enantiopure, the results indicate that the absolute structure has been correctly assigned. The method calculates that the probability that the structure is correctly assigned is 100.0. The Hooft parameter is reported as 0.04 with an esd of 0.002.

The final R-index was 6.0%. A final difference Fourier revealed no missing or misplaced electron density.

Pertinent crystal, data collection, and refinement information is summarized in Table 14. Atomic coordinates, bond lengths, bond angles, and displacement parameters are listed in Tables 15-17.

SOFTWARE AND REFERENCES

SHELXTL, Version 5.1, Bruker AXS, 1997.
PLATON, A. L. Spek, *J. Appl. Cryst.* 2003, 36, 7-13.
MERCURY, C. F. Macrae, P. R. Edington, P. McCabe, E. Pidcock, G. P. Shields, R. Taylor, M. Towler, and J. van de Streek, *J. Appl. Cryst.* 2006, 39, 453-457.
OLEX2, O. V. Dolomanov, L. J. Bourhis, R. J. Gildea, J. A. K. Howard, and H. Puschmann, *J. Appl. Cryst.* 2009, 42, 339-341.
R. W. W. Hooft, L. H. Straver, and A. L. Spek, *J. Appl. Cryst.* 2008, 41, 96-103.
H. D. Flack, *Acta Cryst.* 1983, A39, 867-881.

TABLE 14

Crystal data and structure refinement for C73.

| | |
|---|---|
| Empirical formula | $C_{20}H_{29}NO_6S$ |
| Formula weight | 411.51 |
| Temperature | 296(2) K |
| Wavelength | 1.54178 Å |
| Crystal system | Orthorhombic |
| Space group | $P2_12_12_1$ |
| Unit cell dimensions | a = 6.0597(12) Å   α = 90° |
| | b = 9.7363(17) Å   β = 90° |
| | c = 36.602(6) Å   γ = 90° |
| Volume | 2159.5(7) Å³ |
| Z | 4 |
| Density (calculated) | 1.266 Mg/m³ |
| Absorption coefficient | 1.627 mm⁻¹ |
| F(000) | 880 |
| Crystal size | 0.16 × 0.06 × 0.02 mm³ |
| Theta range for data collection | 2.414 to 70.149° |
| Index ranges | -6 <= h <= 6, -11 <= k <= 11, -37 <= l <= 38 |
| Reflections collected | 19628 |
| Independent reflections | 3492 [$R_{int}$ = 0.0878] |
| Completeness to theta = 67.679° | 88.4% |
| Absorption correction | Empirical |
| Refinement method | Full-matrix least-squares on $F^2$ |
| Data/restraints/parameters | 3492/0/257 |
| Goodness-of-fit on $F^2$ | 1.089 |
| Final R indices [I > 2σ(I)] | R1 = 0.0596, wR2 = 0.1092 |
| R indices (all data) | R1 = 0.1215, wR2 = 0.1263 |
| Absolute structure parameter | 0.051(15) |
| Largest diff. peak and hole | 0.174 and -0.149 e · Å⁻³ |

TABLE 15

Atomic coordinates (×10⁴) and equivalent isotropic displacement parameters (Å² × 10³) for C73. U(eq) is defined as one-third of the trace of the orthogonalized $U^{ij}$ tensor.

| | x | y | z | U(eq) |
|---|---|---|---|---|
| S(1) | 5947(3) | 9247(2) | 4251(1) | 82(1) |
| N(1) | 7765(7) | 7309(4) | 2389(1) | 65(1) |
| O(1) | 7264(8) | 10289(4) | 4410(1) | 98(1) |
| O(2) | 3603(7) | 9332(5) | 4263(1) | 106(1) |
| O(3) | 6491(6) | 9126(4) | 3835(1) | 74(1) |
| O(4) | 9650(6) | 7625(3) | 3283(1) | 80(1) |
| O(5) | 4826(7) | 7516(4) | 2018(1) | 95(1) |
| O(6) | 8242(5) | 8058(4) | 1823(1) | 67(1) |
| C(1) | 8816(11) | 7478(7) | 4584(1) | 79(2) |
| C(2) | 9399(12) | 6205(8) | 4717(1) | 88(2) |
| C(3) | 7981(15) | 5107(7) | 4702(2) | 98(2) |
| C(4) | 8699(18) | 3713(8) | 4844(2) | 159(4) |
| C(5) | 5973(15) | 5321(9) | 4549(2) | 111(2) |
| C(6) | 5312(12) | 6579(8) | 4415(2) | 92(2) |
| C(7) | 6761(9) | 7668(6) | 4427(1) | 70(2) |
| C(8) | 8759(10) | 9334(6) | 3703(1) | 72(2) |
| C(9) | 9928(13) | 8002(7) | 3642(2) | 103(2) |
| C(10) | 8621(8) | 8694(5) | 3072(1) | 56(1) |
| C(11) | 8632(10) | 9931(5) | 3328(2) | 74(2) |
| C(12) | 10002(8) | 8919(5) | 2733(1) | 61(1) |
| C(13) | 10002(9) | 7693(6) | 2482(1) | 67(2) |
| C(14) | 6421(10) | 6993(6) | 2707(1) | 76(2) |
| C(15) | 6345(9) | 8214(5) | 2959(1) | 65(2) |
| C(16) | 6789(10) | 7629(5) | 2073(2) | 61(1) |
| C(17) | 7526(9) | 8625(6) | 1472(2) | 66(2) |
| C(18) | 6298(12) | 7567(6) | 1249(2) | 95(2) |
| C(19) | 9684(11) | 9020(7) | 1295(2) | 99(2) |
| C(20) | 6135(12) | 9903(6) | 1540(2) | 93(2) |

TABLE 16

Bond lengths [Å] and angles [°] for C73.

| | |
|---|---|
| S(1)—O(1) | 1.416(4) |
| S(1)—O(2) | 1.424(4) |
| S(1)—O(3) | 1.562(4) |
| S(1)—C(7) | 1.738(6) |
| N(1)—C(16) | 1.336(6) |
| N(1)—C(13) | 1.447(7) |
| N(1)—C(14) | 1.453(6) |
| O(3)—C(8) | 1.471(7) |
| O(4)—C(9) | 1.372(6) |
| O(4)—C(10) | 1.438(5) |
| O(5)—C(16) | 1.212(6) |
| O(6)—C(16) | 1.337(6) |
| O(6)—C(17) | 1.463(6) |
| C(1)—C(2) | 1.378(8) |
| C(1)—C(7) | 1.384(8) |
| C(1)—H(1) | 0.9300 |
| C(2)—C(3) | 1.372(9) |
| C(2)—H(2) | 0.9300 |
| C(3)—C(5) | 1.356(10) |
| C(3)—C(4) | 1.517(9) |
| C(4)—H(4A) | 0.9600 |
| C(4)—H(4B) | 0.9600 |
| C(4)—H(4C) | 0.9600 |
| C(5)—C(6) | 1.379(9) |
| C(5)—H(5) | 0.9300 |
| C(6)—C(7) | 1.378(8) |
| C(6)—H(6) | 0.9300 |
| C(8)—C(11) | 1.493(7) |
| C(8)—C(9) | 1.496(7) |
| C(8)—H(8) | 0.9800 |
| C(9)—H(9A) | 0.9700 |
| C(9)—H(9B) | 0.9700 |
| C(10)—C(12) | 1.513(6) |
| C(10)—C(15) | 1.514(7) |
| C(10)—C(11) | 1.526(6) |
| C(11)—H(11A) | 0.9700 |
| C(11)—H(11B) | 0.9700 |
| C(12)—C(13) | 1.506(7) |

TABLE 16-continued

Bond lengths [Å] and angles [°] for C73.

| | |
|---|---|
| C(12)—H(12A) | 0.9700 |
| C(12)—H(12B) | 0.9700 |
| C(13)—H(13A) | 0.9700 |
| C(13)—H(13B) | 0.9700 |
| C(14)—C(15) | 1.507(7) |
| C(14)—H(14A) | 0.9700 |
| C(14)—H(14B) | 0.9700 |
| C(15)—H(15A) | 0.9700 |
| C(15)—H(15B) | 0.9700 |
| C(17)—C(19) | 1.510(7) |
| C(17)—C(18) | 1.511(7) |
| C(17)—C(20) | 1.523(7) |
| C(18)—H(18A) | 0.9600 |
| C(18)—H(18B) | 0.9600 |
| C(18)—H(18C) | 0.9600 |
| C(19)—H(19A) | 0.9600 |
| C(19)—H(19B) | 0.9600 |
| C(19)—H(19C) | 0.9600 |
| C(20)—H(20A) | 0.9600 |
| C(20)—H(20B) | 0.9600 |
| C(20)—H(20C) | 0.9600 |
| O(1)—S(1)—O(2) | 120.5(3) |
| O(1)—S(1)—O(3) | 109.6(2) |
| O(2)—S(1)—O(3) | 104.1(2) |
| O(1)—S(1)—C(7) | 108.8(3) |
| O(2)—S(1)—C(7) | 108.9(3) |
| O(3)—S(1)—C(7) | 103.5(2) |
| C(16)—N(1)—C(13) | 123.9(5) |
| C(16)—N(1)—C(14) | 119.6(5) |
| C(13)—N(1)—C(14) | 113.1(4) |
| C(8)—O(3)—S(1) | 120.5(3) |
| C(9)—O(4)—C(10) | 111.9(4) |
| C(16)—O(6)—C(17) | 121.6(4) |
| C(2)—C(1)—C(7) | 119.8(6) |
| C(2)—C(1)—H(1) | 120.1 |
| C(7)—C(1)—H(1) | 120.1 |
| C(3)—C(2)—C(1) | 121.7(6) |
| C(3)—C(2)—H(2) | 119.1 |
| C(1)—C(2)—H(2) | 119.1 |
| C(5)—C(3)—C(2) | 117.3(7) |
| C(5)—C(3)—C(4) | 122.4(7) |
| C(2)—C(3)—C(4) | 120.2(7) |
| C(3)—C(4)—H(4A) | 109.5 |
| C(3)—C(4)—H(4B) | 109.5 |
| H(4A)—C(4)—H(4B) | 109.5 |
| C(3)—C(4)—H(4C) | 109.5 |
| H(4A)—C(4)—H(4C) | 109.5 |
| H(4B)—C(4)—H(4C) | 109.5 |
| C(3)—C(5)—C(6) | 122.9(7) |
| C(3)—C(5)—H(5) | 118.5 |
| C(6)—C(5)—H(5) | 118.5 |
| C(7)—C(6)—C(5) | 119.2(6) |
| C(7)—C(6)—H(6) | 120.4 |
| C(5)—C(6)—H(6) | 120.4 |
| C(6)—C(7)—C(1) | 119.0(6) |
| C(6)—C(7)—S(1) | 119.2(5) |
| C(1)—C(7)—S(1) | 121.8(5) |
| O(3)—C(8)—C(11) | 108.0(5) |
| O(3)—C(8)—C(9) | 111.9(5) |
| C(11)—C(8)—C(9) | 102.9(5) |
| O(3)—C(8)—H(8) | 111.3 |
| C(11)—C(8)—H(8) | 111.3 |
| C(9)—C(8)—H(8) | 111.3 |
| O(4)—C(9)—C(8) | 108.5(5) |
| O(4)—C(9)—H(9A) | 110.0 |
| C(8)—C(9)—H(9A) | 110.0 |
| O(4)—C(9)—H(9B) | 110.0 |
| C(8)—C(9)—H(9B) | 110.0 |
| H(9A)—C(9)—H(9B) | 108.4 |
| O(4)—C(10)—C(12) | 107.8(4) |
| O(4)—C(10)—C(15) | 108.5(4) |
| C(12)—C(10)—C(15) | 109.0(4) |
| O(4)—C(10)—C(11) | 103.8(4) |
| C(12)—C(10)—C(11) | 112.8(4) |
| C(15)—C(10)—C(11) | 114.5(4) |
| C(8)—C(11)—C(10) | 105.0(4) |
| C(8)—C(11)—H(11A) | 110.8 |
| C(10)—C(11)—H(11A) | 110.8 |
| C(8)—C(11)—H(11B) | 110.8 |
| C(10)—C(11)—H(11B) | 110.8 |
| H(11A)—C(11)—H(11B) | 108.8 |
| C(13)—C(12)—C(10) | 112.7(4) |
| C(13)—C(12)—H(12A) | 109.0 |
| C(10)—C(12)—H(12A) | 109.0 |
| C(13)—C(12)—H(12B) | 109.0 |
| C(10)—C(12)—H(12B) | 109.0 |
| H(12A)—C(12)—H(12B) | 107.8 |
| N(1)—C(13)—C(12) | 110.4(4) |
| N(1)—C(13)—H(13A) | 109.6 |
| C(12)—C(13)—H(13A) | 109.6 |
| N(1)—C(13)—H(13B) | 109.6 |
| C(12)—C(13)—H(13B) | 109.6 |
| H(13A)—C(13)—H(13B) | 108.1 |
| N(1)—C(14)—C(15) | 110.0(4) |
| N(1)—C(14)—H(14A) | 109.7 |
| C(15)—C(14)—H(14A) | 109.7 |
| N(1)—C(14)—H(14B) | 109.7 |
| C(15)—C(14)—H(14B) | 109.7 |
| H(14A)—C(14)—H(14B) | 108.2 |
| C(14)—C(15)—C(10) | 112.5(4) |
| C(14)—C(15)—H(15A) | 109.1 |
| C(10)—C(15)—H(15A) | 109.1 |
| C(14)—C(15)—H(15B) | 109.1 |
| C(10)—C(15)—H(15B) | 109.1 |
| H(15A)—C(15)—H(15B) | 107.8 |
| O(5)—C(16)—O(6) | 124.1(5) |
| O(5)—C(16)—N(1) | 123.9(5) |
| O(6)—C(16)—N(1) | 112.0(5) |
| O(6)—C(17)—C(19) | 102.6(4) |
| O(6)—C(17)—C(18) | 111.3(5) |
| C(19)—C(17)—C(18) | 111.5(5) |
| O(6)—C(17)—C(20) | 109.3(4) |
| C(19)—C(17)—C(20) | 110.0(5) |
| C(18)—C(17)—C(20) | 111.8(5) |
| C(17)—C(18)—H(18A) | 109.5 |
| C(17)—C(18)—H(18B) | 109.5 |
| H(18A)—C(18)—H(18B) | 109.5 |
| C(17)—C(18)—H(18C) | 109.5 |
| H(18A)—C(18)—H(18C) | 109.5 |
| H(18B)—C(18)—H(18C) | 109.5 |
| C(17)—C(19)—H(19A) | 109.5 |
| C(17)—C(19)—H(19B) | 109.5 |
| H(19A)—C(19)—H(19B) | 109.5 |
| C(17)—C(19)—H(19C) | 109.5 |
| H(19A)—C(19)—H(19C) | 109.5 |
| H(19B)—C(19)—H(19C) | 109.5 |
| C(17)—C(20)—H(20A) | 109.5 |
| C(17)—C(20)—H(20B) | 109.5 |
| H(20A)—C(20)—H(20B) | 109.5 |
| C(17)—C(20)—H(20C) | 109.5 |
| H(20A)—C(20)—H(20C) | 109.5 |
| H(20B)—C(20)—H(20C) | 109.5 |

Symmetry transformations used to generate equivalent atoms.

TABLE 17

Anisotropic displacement parameters (Å$^2$ × 10$^3$) for C73. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| S(1) | 86(1) | 94(1) | 66(1) | −7(1) | 4(1) | 3(1) |
| N(1) | 48(3) | 88(3) | 59(3) | 3(3) | −3(2) | −14(2) |
| O(1) | 117(4) | 94(3) | 84(3) | −29(2) | 3(2) | −13(3) |
| O(2) | 74(3) | 141(4) | 105(3) | 13(3) | 12(2) | 20(3) |
| O(3) | 78(3) | 83(3) | 63(3) | 2(2) | −3(2) | −4(2) |
| O(4) | 113(3) | 60(2) | 66(3) | 2(2) | −17(2) | 26(2) |
| O(5) | 52(3) | 150(4) | 83(3) | −3(2) | −5(2) | −27(3) |
| O(6) | 50(2) | 87(2) | 63(3) | 7(2) | 7(2) | −2(2) |
| C(1) | 81(4) | 98(5) | 56(4) | −1(3) | −8(3) | −19(4) |
| C(2) | 92(5) | 112(6) | 61(4) | 6(4) | −22(3) | 1(5) |

TABLE 17-continued

Anisotropic displacement parameters (Å² × 10³) for C73. The anisotropic displacement factor exponent takes the form: $-2\pi^2[h^2 a^{*2}U^{11} + \ldots + 2 h k a^* b^* U^{12}]$.

| | $U^{11}$ | $U^{22}$ | $U^{33}$ | $U^{23}$ | $U^{13}$ | $U^{12}$ |
|---|---|---|---|---|---|---|
| C(3) | 139(8) | 89(5) | 66(5) | 0(4) | −19(4) | −22(5) |
| C(4) | 229(11) | 99(6) | 148(7) | 36(5) | −64(7) | −15(6) |
| C(5) | 122(7) | 109(6) | 102(5) | −2(5) | −29(5) | −43(5) |
| C(6) | 85(5) | 103(5) | 90(5) | −6(4) | −18(3) | −18(4) |
| C(7) | 68(4) | 94(4) | 48(3) | −9(3) | −4(3) | −9(3) |
| C(8) | 72(4) | 75(4) | 69(4) | −9(3) | −4(3) | −7(4) |
| C(9) | 125(6) | 116(5) | 69(5) | −6(4) | −17(4) | 45(5) |
| C(10) | 57(4) | 53(3) | 57(3) | 8(3) | 1(2) | 7(3) |
| C(11) | 94(5) | 47(3) | 80(5) | −7(3) | 14(3) | 0(3) |
| C(12) | 44(3) | 65(3) | 75(4) | 4(3) | 1(2) | −3(3) |
| C(13) | 47(3) | 85(4) | 68(4) | −4(3) | 1(2) | 4(3) |
| C(14) | 69(4) | 94(4) | 65(4) | 1(3) | 10(3) | −27(3) |
| C(15) | 52(4) | 80(4) | 64(4) | 11(3) | 12(3) | 0(3) |
| C(16) | 50(4) | 66(4) | 67(4) | −6(3) | 4(3) | −9(3) |
| C(17) | 67(4) | 71(4) | 59(4) | 4(3) | 3(3) | 0(3) |
| C(18) | 117(6) | 88(4) | 82(5) | −13(3) | −10(4) | −3(4) |
| C(19) | 89(5) | 110(5) | 98(5) | 15(4) | 33(4) | −4(4) |
| C(20) | 97(5) | 76(4) | 105(5) | −1(3) | −2(4) | 22(4) |

Step 3. Synthesis of tert-butyl (3S)-3-hydroxy-1-oxa-8-azaspiro[4.5]decane-8-carboxylate (C74) and tert-butyl (3R)-3-hydroxy-1-oxa-8-azaspiro[4.5]decane-8-carboxylate (C75)

Sodium borohydride (445 mg, 11.8 mmol) was added to a 0° C. solution of tert-butyl 3-oxo-1-oxa-8-azaspiro[4.5]decane-8-carboxylate (1.50 g, 5.88 mmol) in methanol (59 mL) and the reaction mixture was stirred at 23° C. for 2 hours. After removal of solvent in vacuo, the residue was partitioned between ethyl acetate and water. The aqueous layer was extracted with ethyl acetate, and the combined organic layers were dried over magnesium sulfate, filtered, and concentrated under reduced pressure to provide a mixture of C74 and C75 as a colorless oil. Yield of racemic product: 1.45 g, 5.63 mmol, 96%. GCMS m/z 257.1 [M+]. $^1$H NMR (400 MHz, CDCl$_3$) δ 4.54-4.48 (br m, 1H), 3.93 (dd, half of ABX pattern, J=10.2, 4.3 Hz, 1H), 3.85-3.79 (m, 1H), 3.67-3.53 (br m, 2H), 3.40-3.28 (m, 2H), 1.97 (dd, half of ABX pattern, J=13.7, 6.2 Hz, 1H), 1.89-1.48 (m, 6H, assumed; partially obscured by water peak), 1.46 (s, 9H). A portion of this racemic material (1.30 g, 5.05 mmol) was separated into its component enantiomers via supercritical fluid chromatography [Column: Phenomenex Lux Amylose-1, 5 μm; Mobile phase: 85:15 carbon dioxide/(methanol containing 0.2% ammonium hydroxide)].

The first-eluting product, obtained as a gum that exhibited a negative (−) rotation, was designated as C74. Yield: 650 mg, 2.53 mmol, 50% for the separation.

The second-eluting product, obtained as a solid that exhibited a positive (+) rotation, was designated as C75. Yield: 620 mg, 2.41 mmol, 48% for the separation. The indicated absolute stereochemistries of C74 and C75 were assigned on the basis of conversion of C74 to C72 (see step 4).

Step 4. Alternate synthesis of tert-butyl (3S)-3-{[(4-methylphenyl)sulfonyl]oxy}-1-oxa-8-azaspiro[4.5]decane-8-carboxylate (C72)

p-Toluenesulfonyl chloride (244 mg, 1.28 mmol) was added to a solution of C74 (300 mg, 1.17 mmol) in dichloromethane (12 mL). 4-(Dimethylamino)pyridine (285 mg, 2.33 mmol) was then added, and the reaction mixture was stirred overnight. After addition of water, the mixture was extracted with dichloromethane, and the combined organic layers were concentrated in vacuo and purified via silica gel chromatography (Gradient: 10% to 55% ethyl acetate in heptane). The product was obtained as a gum that exhibited a positive (+) rotation.

Yield: 426 mg, 1.04 mmol, 89%. LCMS m/z 412.5 [M+H]+. $^1$H NMR (400 MHz, CDCl$_3$) δ 7.76 (d, J=8.2 Hz, 2H), 7.34 (d, J=7.8 Hz, 2H), 5.10-5.03 (m, 1H), 3.94-3.86 (m, 2H), 3.62-3.53 (m, 2H), 3.27-3.17 (m, 2H), 2.43 (s, 3H), 1.98 (dd, half of ABX pattern, J=14.4, 2.0 Hz, 1H), 1.90 (dd, half of ABX pattern, J=14.6, 6.4 Hz, 1H), 1.79-1.71 (m, 1H), 1.59-1.45 (m, 3H), 1.42 (s, 9H). This sample, derived from C74, was established as possessing the indicated absolute stereochemistry via comparison of its optical rotation with that of the C72 sample synthesized in step 2 above.

Step 5. Synthesis of tert-butyl (3R)-3-(4-fluoro-1H-pyrazol-1-yl)-1-oxa-8-azaspiro[4.5]decane-8-carboxylate (C76)

To a solution of C72 (222 mg, 0.539 mmol) in N,N-dimethylformamide (3 mL) were added cesium carbonate (528 mg, 1.62 mmol) and 4-fluoro-1H-pyrazole (69.6 mg, 0.809 mmol). The reaction mixture was stirred overnight at room temperature, and then at 50° C. for 3 hours, whereupon it was diluted with water and extracted with ethyl acetate (3×50 mL). The combined organic layers were dried over magnesium sulfate, filtered, concentrated in vacuo, and purified via chromatography on silica gel (Gradient: 10% to 65% ethyl acetate in heptane) to provide the product as a colorless oil. Yield: 148 mg, 0.455 mmol, 84%. LCMS m/z 326.4 [M+H]+. $^1$H NMR (400 MHz, CDCl$_3$) δ 7.37 (d, J=5.1 Hz, 1H), 7.32 (d, J=4.3 Hz, 1H), 4.88-4.80 (m, 1H), 4.15 (dd, half of ABX pattern, J=10.0, 6.0 Hz, 1H), 4.10 (dd, half of ABX pattern, J=10.2, 4.7 Hz, 1H), 3.68-3.56 (br m, 2H), 3.37-3.26 (m, 2H), 2.28 (dd, half of ABX pattern, J=13.7, 8.6 Hz, 1H), 2.17 (dd, half of ABX pattern, J=13.5, 5.3 Hz, 1H), 1.80-1.59 (m, 3H), 1.59-1.49 (m, 1H), 1.44 (s, 9H).

Step 6. Synthesis of (3R)-3-(4-fluoro-1H-pyrazol-1-yl)-1-oxa-8-azaspiro[4.5]decane, trifluoroacetate salt (C77)

Trifluoroacetic acid (0.70 mL) was added to a 0° C. solution of C76 (148 mg, 0.455 mmol) in dichloromethane (4.6 mL), and the reaction mixture was stirred at 0° C. for 35 minutes. It was then concentrated in vacuo, and azeotroped repeatedly with heptane (3×25 mL) to afford the product as an oil. This material was taken directly into the following step. LCMS m/z 226.4 [M+H]+. $^1$H NMR (400 MHz, CDCl$_3$) δ 8.2-7.9 (br s, 2H), 7.48 (br d, J=3.9 Hz, 1H), 7.45 (br d, J=4.7 Hz, 1H), 5.06-4.98 (m, 1H), 4.23 (dd, half of ABX pattern, J=10.6, 3.9 Hz, 1H), 4.19 (dd, half of ABX pattern, J=10.6, 5.9 Hz, 1H), 3.47-3.30 (br m, 4H), 2.44 (dd, half of ABX pattern, J=14.1, 8.2 Hz, 1H), 2.27 (dd, half of ABX pattern, J=14.1, 4.7 Hz, 1H), 2.12-1.93 (m, 4H).

Step 7. Synthesis of (2R)-1,1,1-trifluoro-3-[(4-methoxybenzyl)oxy]propan-2-yl (3R)-3-(4-fluoro-1H-pyrazol-1-yl)-1-oxa-8-azaspiro[4.5]decane-8-carboxylate (C43)

1,1'-Carbonyldiimidazole (75.6 mg, 0.466 mmol) was added to a solution of C1 (111 mg, 0.444 mmol) in acetonitrile (2 mL). After 1 hour, a solution of C77 (from the previous step; ≤0.455 mmol) in acetonitrile (3 mL) was added, and the reaction mixture was stirred overnight. Solvent was then removed in vacuo, and the residue was dissolved in ethyl acetate (20 mL), washed with water, dried over magnesium sulfate, filtered, and concentrated under reduced pressure. Silica gel chromatography (Gradient: 10% to 50% ethyl acetate in heptane) afforded the product as an oil, which by $^1$H NMR analysis contained a contaminant. Yield: 80 mg, 0.16 mmol, 36%. LCMS m/z 502.5 [M+H]$^+$. $^1$H NMR (400 MHz, CDCl$_3$), product peaks only: δ 7.37 (d, J=4.7 Hz, 1H), 7.34 (d, J=4.3 Hz, 1H), 7.24 (br d, J=8.6 Hz, 2H), 6.90-6.84 (m, 2H), 5.53-5.42 (m, 1H), 4.89-4.80 (m, 1H), 4.50 (AB quartet, upfield doublet is broad, $J_{AB}$=11.7 Hz, $\Delta v_{AB}$=28.5 Hz, 2H), 4.17 (dd, half of ABX pattern, J=9.8, 5.8 Hz, 1H), 4.12 (br dd, half of ABX pattern, J=10, 5 Hz, 1H), 3.84-3.72 (m, 3H), 3.80 (s, 3H), 3.68 (dd, half of ABX pattern, J=11.1, 7.2 Hz, 1H), 3.43-3.29 (br m, 2H), 2.34-2.13 (m, 2H), 1.89-1.61 (m, 3H), 1.56 (ddd, J=13.5, 10.9, 4.5 Hz, 1H).

Step 8. Synthesis of (2R)-1,1,1-trifluoro-3-hydroxypropan-2-yl (3R)-3-(4-fluoro-1H-pyrazol-1-yl)-1-oxa-8-azaspiro[4.5]decane-8-carboxylate (11)

A mixture of C43 (40 mg, 80 μmol) and palladium on carbon [10% Pd (50% wet with water); 4 mg] in ethanol (8 mL) was hydrogenated at 50 psi and 23° C. for 60 hours. The reaction mixture was then charged with additional palladium on carbon [10% Pd (50% wet with water); 17 mg] and hydrogenation at 50 psi was continued for 7 hours, whereupon the reaction mixture was filtered. The filtrate was concentrated in vacuo to provide the product as a solid. This material proved to be identical to an authentic sample of 11 by chiral supercritical fluid chromatographic analysis [Column: Phenomenex Lux Amylose-1, 5 μm; Mobile phase A: carbon dioxide; Mobile phase B: ethanol; Gradient: 5% B for 1 minute, then 5% to 60% B over 8.0 minutes; Flow rate: 3.0 mL/minute]. Retention times: 6.96 minutes versus 6.97 minutes. Yield: 25 mg, 66 μmol, 82%. LCMS m/z 382.4 [M+H]$^+$. $^1$H NMR (400 MHz, CDCl$_3$) δ 7.38 (d, J=4.7 Hz, 1H), 7.35 (d, J=3.9 Hz, 1H), 5.31-5.20 (br m, 1H), 4.91-4.82 (m, 1H), 4.18 (dd, half of ABX pattern, J=9.8, 6.2 Hz, 1H), 4.14 (dd, half of ABX pattern, J=10.2, 5.1 Hz, 1H), 4.00 (dd, half of ABX pattern, J=12.5, 3.1 Hz, 1H), 3.91-3.74 (m, 3H), 3.50-3.28 (m, 2H), 2.31 (dd, half of ABX pattern, J=13.7, 8.6 Hz, 1H), 2.23 (br dd, half of ABX pattern, J=13.5, 4.5 Hz, 1H), 1.90-1.53 (m, 4H).

TABLE 18

Method of preparation, structure, and physicochemical data for Examples 20-90.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 20 | Examples 8 and 9$^{1,2}$; C35 | 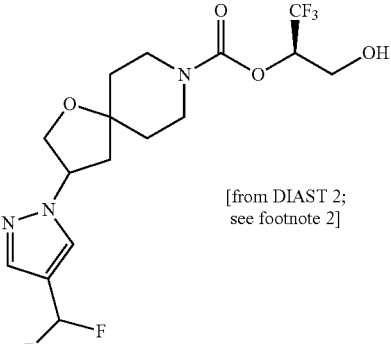 [from DIAST 2; see footnote 2] | 7.69 (s, 1H), 7.66 (s, 1H), 6.70 (t, $J_{HF}$ = 56.8 Hz, 1H), 5.31-5.20 (br m, 1H), 5.02-4.94 (m, 1H), 4.26-4.15 (m, 2H), 4.04-3.96 (m, 1H), 3.92-3.74 (m, 3H), 3.49-3.30 (m, 2H), 2.60-2.46 (br m, 1H), 2.35 (dd, half of ABX pattern, J = 13.2, 8.4 Hz, 1H), 2.27 (br dd, half of ABX pattern, J = 13.6, 5.3 Hz, 1H), 1.94-1.82 (br m, 1H), 1.82-1.54 (br m, 3H, assumed; partially obscured by water peak); 414.0 |
| 21 | Examples 8 and 9$^3$; C35 | 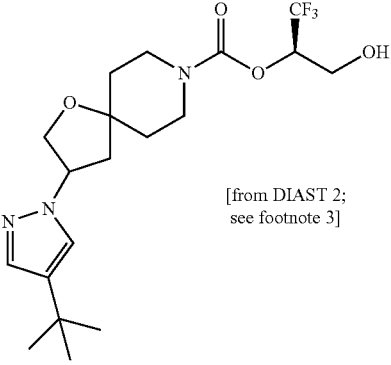 [SMILES: CC(C)(C)c1cnn(C2COC3(CCN(C(=O)O[C@H](CO)C(F)(F)F)CC3)C2)c1] [from DIAST 2; see footnote 3] | 7.40 (s, 1H), 7.24 (s, 1H), 5.31-5.20 (br m, 1H), 4.96-4.87 (m, 1H), 4.21 (dd, half of ABX pattern, J = 9.7, 6.6 Hz, 1H), 4.16 (dd, half of ABX pattern, J = 9.7, 5.7 Hz, 1H), 4.00 (br dd, half of ABX pattern, J = 12.8, 3.1 Hz, 1H), 3.92-3.72 (m, 3H), 3.51-3.32 (m, 2H), 2.35-2.23 (m, 2H), 1.94-1.83 (br m, 1H), 1.82-1.69 (br m, 2H), 1.69-1.53 (m, 2H, assumed; largely obscured by water peak), 1.25 (s, 9H); 420.1 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 22 | Examples 8 and 9[4]; C35 | 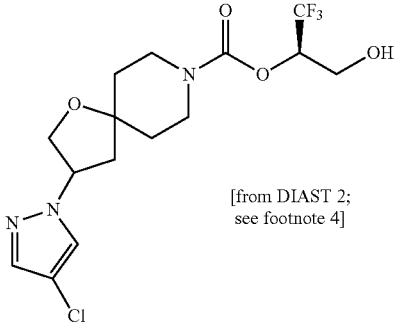 [SMILES: O=C(O[C@H](CO)C(F)(F)F)N1CCC2(CC1)CC(n1cc(Cl)cn1)CO2] [from DIAST 2; see footnote 4] | 7.49 (s, 1H), 7.45 (s, 1H), 5.31-5.20 (br m, 1H), 4.96-4.87 (m, 1H), 4.20 (dd, half of ABX pattern, J = 10.1, 6.2 Hz, 1H), 4.15 (dd, half of ABX pattern, J = 10.1, 4.8 Hz, 1H), 4.00 (dd, half of ABX pattern, J = 12.8, 3.1 Hz, 1H), 3.92-3.74 (m, 3H), 3.49-3.30 (m, 2H), 2.32 (dd, half of ABX pattern, J = 13.4, 8.1 Hz, 1H), 2.25 (br dd, half of ABX pattern, J = 13.6, 4.8 Hz, 1H), 1.92-1.81 (br m, 1H), 1.81-1.52 (br m, 4H); 398.1 (chlorine isotope pattern observed) |
| 23 | Example 1; C45 | 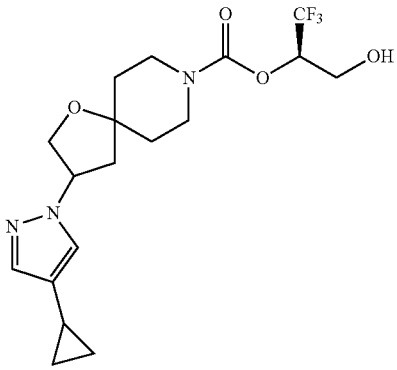 [SMILES: O=C(O[C@H](CO)C(F)(F)F)N1CCC2(CC1)CC(n1cc(C3CC3)cn1)CO2] | 3.22 minutes[5]; 404.3 |
| 24 | Examples 8 and 9[6]; C35 | 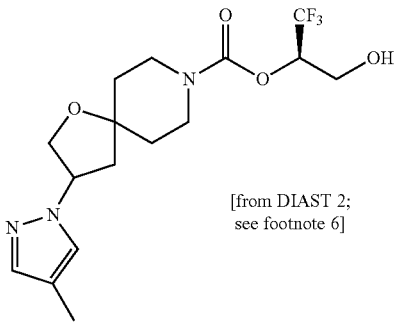 [SMILES: Cc1cnn(C2COC3(CCN(C(=O)O[C@H](CO)C(F)(F)F)CC3)C2)c1] [from DIAST 2; see footnote 6] | 7.32 (s, 1H), 7.25 (s, 1H), 5.32-5.20 (br m, 1H), 4.96-4.86 (m, 1H), 4.23-4.10 (m, 2H), 3.99 (br dd, half of ABX pattern, J = 12.5, 2.4 Hz, 1H), 3.91-3.71 (br m, 3H), 3.50-3.30 (m, 2H), 2.35-2.20 (m, 2H), 2.07 (s, 3H), 1.92-1.81 (br m, 1H), 1.81-1.53 (br m, 3H); 378.3 |
| 25 | Examples 14 and 15[7,8]; C48 | 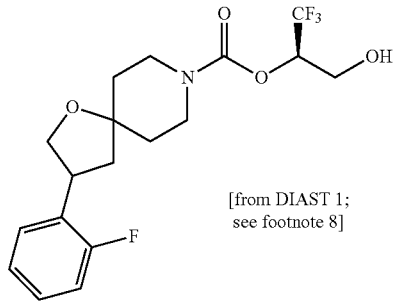 [SMILES: O=C(O[C@H](CO)C(F)(F)F)N1CCC2(CC1)CC(c1ccccc1F)CO2] [from DIAST 1; see footnote 8] | 7.30-7.24 (m, 1H, assumed; partially obscured by solvent peak), 7.24-7.19 (m, 1H), 7.11 (ddd, J = 7.5, 7.5, 1 Hz, 1H), 7.04 (ddd, J = 10.6, 8.4, 1.3 Hz, 1H), 5.31-5.21 (br m, 1H), 4.24 (dd, J = 7.9, 7.5 Hz, 1H), 4.05-3.96 (br m, 1H), 3.93-3.71 (m, 5H), 3.50-3.32 (m, 2H), 2.54-2.42 (br m, 1H), 2.25 (dd, half of ABX pattern, J = 12.8, 7.9 Hz, 1H), 1.90 (dd, half of ABX pattern, J = 12.5, 9.9 Hz, 1H), 1.89-1.63 (br m, 4H); 392.1 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 26 | Examples 14 and 15[7,8]; C48 | [from DIAST 2; see footnote 8] | 7.31-7.24 (m, 1H, assumed; partially obscured by solvent peak), 7.24-7.19 (m, 1H), 7.11 (br dd, J = 7.5, 7.5 Hz, 1H), 7.07-7.00 (m, 1H), 5.32-5.20 (br m, 1H), 4.25 (dd, J = 7.9, 7.5 Hz, 1H), 4.05-3.96 (m, 1H), 3.93-3.71 (m, 5H), 3.52-3.34 (m, 2H), 2.54-2.42 (m, 1H), 2.30-2.20 (m, 1H), 1.90 (dd, J = 12.5, 9.9 Hz, 1H), 1.87-1.71 (br m, 3H); 392.1 |
| 27 | Examples 10 and 11[9,10]; C35 | [from DIAST 2; see footnote 8] | 7.58 (dd, J = 7.7, 6.8 Hz, 1H), 7.18-7.08 (m, 2H), 5.32-5.21 (br m, 1H), 4.24 (dd, J = 8.4, 7.9 Hz, 1H), 4.01 (br dd, J = 12.3, 2.6 Hz, 1H), 3.94-3.77 (m, 4H), 3.63-3.52 (m, 1H), 3.49-3.30 (m, 2H), 2.31 (dd, J = 12.5, 8.6 Hz, 1H), 1.86-1.72 (m, 4H), 1.7-1.53 (m, 1H, assumed; partially obscured by water peak); 417.0 |
| 28 | Example 27[11]; C35 | [from DIAST 2; see footnote 11] | 7.52-7.45 (m, 2H), 7.18 (br dd, J = 9, 8 Hz, 1H), 5.32-5.21 (br m, 1H), 4.23 (dd, J = 7.9, 7.9 Hz, 1H), 4.06-3.96 (br m, 1H), 3.95-3.77 (m, 3H), 3.77 (dd, J = 8.8, 8.4 Hz, 1H), 3.59-3.47 (m, 1H), 3.47-3.31 (m, 2H), 2.50-2.37 (br s, 1H), 2.30 (dd, J = 12.5, 8.6 Hz, 1H), 1.86-1.71 (m, 4H), 1.69-1.54 (m, 1H, assumed; partially obscured by water peak); 417.0 |
| 29 | Examples 10 and 11[12,13]; C35 | [from DIAST 1; see footnote 13] | characteristic peaks: 7.62 (dd, J= 7.0, 2.0 Hz, 1H), 7.57 (ddd, J = 8.5, 4.8, 2.3 Hz, 1H), 7.16 (dd, J = 10.0, 8.5 Hz, 1H), 5.32-5.21 (br m, 1H), 4.25 (dd, J = 8.0, 7.5 Hz, 1H), 4.06-3.97 (m, 1H), 3.95-3.71 (m, 5H), 3.48-3.29 (m, 2H), 2.28 (dd, J = 12.6, 8.0 Hz, 1H); 417.0 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 30 | Examples 10 and 11[12,13]; C35 | [from DIAST 2; see footnote 13] | 7.62 (dd, J = 6.5, 2.0 Hz, 1H), 7.57 (ddd, J = 8.4, 4.6, 2.1 Hz, 1H), 7.16 (dd, J = 9.5, 8.5 Hz, 1H), 5.32-5.21 (br m, 1H), 4.26 (dd, J = 7.5, 7.5 Hz, 1H), 4.06-3.97 (m, 1H), 3.95-3.71 (m, 5H), 3.51-3.31 (m, 2H), 2.42-2.24 (m, 2H), 1.88-1.72 (m, 3H), 1.86 (dd, J = 12.6, 9.5 Hz, 1H), 1.70-1.52 (m, 1H, assumed; partially obscured by water peak); 417.0 |
| 31 | Example 27[14]; C35 | [from DIAST 2; see footnote 14] | 7.62 (d, J = 8.4 Hz, 2H), 7.35 (d, J = 8.4 Hz, 2H), 5.32-5.21 (br m, 1H), 4.24 (dd, J = 8.4, 7.9 Hz, 1H), 4.06-3.95 (m, 1H), 3.94-3.75 (m, 4H), 3.64-3.51 (m, 1H), 3.51-3.31 (m, 2H), 2.59-2.46 (br s, 1H), 2.30 (dd, J = 12.3, 8.4 Hz, 1H), 1.88-1.72 (m, 4H), 1.7-1.54 (m, 1H, assumed; partially obscured by water peak); 399.0 |
| 32 | Example 26[15]; C48 | [from DIAST 1; see footnote 15] | 7.23-7.14 (m, 1H), 6.92-6.83 (m, 2H), 5.32-5.21 (br m, 1H), 4.13 (dd, J = 8.0, 8.0 Hz, 1H), 4.07-3.96 (m, 2H), 3.94-3.73 (m, 4H), 3.54-3.36 (m, 2H), 2.48-2.33 (br m, 1H), 2.13 (d, J = 10.0 Hz, 2H), 1.93-1.71 (m, 3H), 1.71-1.54 (m, 1H, assumed; partially obscured by water peak); 410.1 |
| 33 | Example 26[16]; C48 | [from DIAST 2; see footnote 16] | 7.23 (ddd, J = 8.8, 8.4, 6.6 Hz, 1H), 6.89-6.76 (m, 2H), 5.32-5.20 (br m, 1H), 4.22 (dd, J = 7.9, 7.9 Hz, 1H), 4.05-3.96 (m, 1H), 3.93-3.66 (m, 5H), 3.51-3.33 (m, 2H), 2.52-2.40 (br m, 1H), 2.23 (br dd, J = 12, 8 Hz, 1H), 1.86 (dd, J = 12.5, 9.9 Hz, 1H), 1.85-1.69 (m, 3H), 1.69-1.53 (m, 1H, assumed; largely obscured by water peak); 410.0 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 34 | Example 26[17]; C48 | 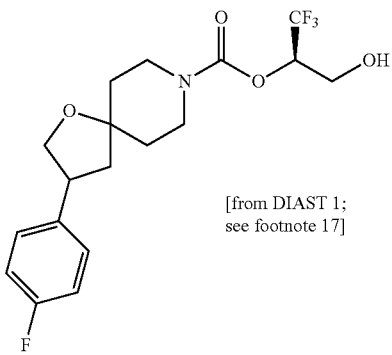 [SMILES: O=C(O[C@H](CO)C(F)(F)F)N1CCC2(CC1)CC(c1ccc(F)cc1)CO2]  [from DIAST 1; see footnote 17] | 7.20 (br dd, J = 8.4, 5.3 Hz, 2H), 7.01 (br dd, J = 8.8, 8.4 Hz, 2H), 5.32-5.20 (br m, 1H), 4.22 (dd, J = 7.9, 7.9 Hz, 1H), 4.05-3.96 (br m, 1H), 3.92-3.75 (m, 3H), 3.76 (dd, J = 9.2, 8.8 Hz, 1H), 3.57-3.30 (m, 3H), 2.55-2.43 (br m, 1H), 2.26 (dd, J = 12.5, 8.1 Hz, 1H), 1.86-1.69 (m, 4H), 1.69-1.58 (m, 1H, assumed; partially obscured by water peak); 392.1 |
| 35 | Examples 14 and 15[18]; C49 | 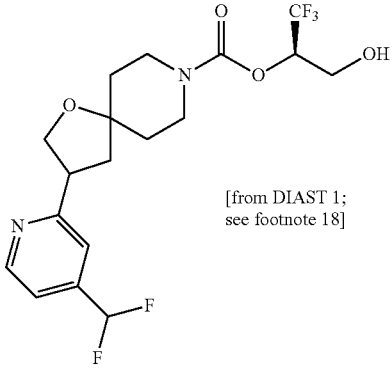 [SMILES: O=C(O[C@H](CO)C(F)(F)F)N1CCC2(CC1)CC(c1cc(C(F)F)ccn1)CO2]  [from DIAST 1; see footnote 18] | 8.69 (d, J = 4.5 Hz, 1H), 7.31 (s, 1H), 7.29-7.26 (m, 1H, assumed; partially obscured by solvent peak), 6.62 (t, J$_{HF}$ = 55.7 Hz, 1H), 5.32-5.20 (br m, 1H), 4.29 (dd, J = 8.0, 8.0 Hz, 1H), 4.04-3.98 (m, 1H), 4.02 (dd, J = 9.0, 8.5 Hz, 1H), 3.92-3.69 (m, 4H), 3.52-3.34 (m, 2H), 2.26 (br dd, half of ABX pattern, J = 12, 9 Hz, 1H), 2.14 (dd, half of ABX pattern, J = 12.6, 9.5 Hz, 1H), 1.92-1.71 (br m, 3H), 1.71-1.5 (br m, 2H, assumed; partially obscured by water peak); 425.1 |
| 36 | Examples 14 and 15[19]; C49 | 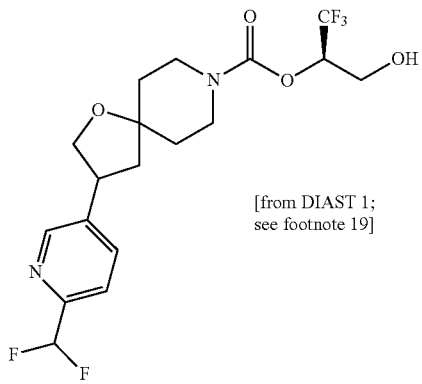 [SMILES: O=C(O[C@H](CO)C(F)(F)F)N1CCC2(CC1)CC(c1ccc(C(F)F)nc1)CO2]  [from DIAST 1; see footnote 19] | 8.54 (d, J = 2.0 Hz, 1H), 7.73 (dd, half of ABX pattern, J = 8.0, 2.0 Hz, 1H), 7.61 (d, half of AB quartet, J = 8.0 Hz, 1H), 6.64 (t, J$_{HF}$ = 55.5 Hz, 1H), 5.32-5.21 (br m, 1H), 4.28 (dd, J = 8.0, 8.0 Hz, 1H), 4.05-3.97 (m, 1H), 3.95-3.78 (m, 4H), 3.66-3.54 (m, 1H), 3.48-3.29 (m, 2H), 2.34 (dd, J = 12.8, 8.3 Hz, 1H), 1.89-1.71 (m, 3H), 1.85 (dd, J = 12.6, 9.5 Hz, 1H), 1.71-1.55 (m, 1H, assumed; partially obscured by water peak); 425.1 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 37 | Examples 14 and 15[19]; C49 | 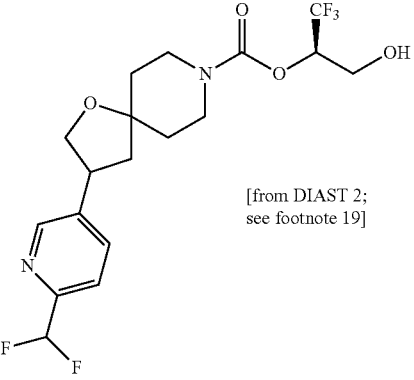 [from DIAST 2; see footnote 19] | 8.54 (d, J = 2.0 Hz, 1H), 7.73 (dd, half of ABX pattern, J = 8.0, 2.0 Hz, 1H), 7.61 (d, half of AB quartet, J = 8.0 Hz, 1H), 6.64 (t, $J_{HF}$ = 55.5 Hz, 1H), 5.32-5.21 (br m, 1H), 4.28 (dd, J = 8.5, 8.0 Hz, 1H), 4.01 (br dd, half of ABX pattern, J = 12.3, 3.3 Hz, 1H), 3.95-3.78 (m, 4H), 3.66-3.54 (m, 1H), 3.50-3.32 (m, 2H), 2.38-2.29 (m, 1H), 1.89-1.73 (m, 3H), 1.85 (dd, J = 12.0, 10.0 Hz, 1H), 1.70-1.55 (m, 1H, assumed; partially obscured by water peak); 425.0 |
| 38 | Examples 14 and 15[20]; C49 | 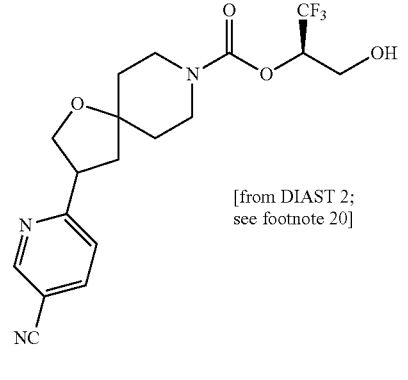 [SMILES: N#Cc1ccc(C2COC3(CCN(C(=O)O[C@H](CO)C(F)(F)F)CC3)C2)nc1] [from DIAST 2; see footnote 20] | 8.83 (d, J = 1.5 Hz, 1H), 7.89 (dd, J = 8.0, 2.0 Hz, 1H), 7.33 (d, J = 8.0 Hz, 1H), 5.31-5.21 (br m, 1H), 4.27 (dd, J = 8.0, 8.0 Hz, 1H), 4.04-3.96 (m, 2H), 3.92-3.69 (m, 4H), 3.50-3.32 (m, 2H), 2.55-2.42 (br s, 1H), 2.25 (br dd, half of ABX pattern, J = 12.8, 8.8 Hz, 1H), 2.12 (dd, half of ABX pattern, J = 12.8, 9.3 Hz, 1H), 1.90-1.70 (br m, 3H), 1.70-1.56 (m, 1H, assumed; partially obscured by water peak); 400.0 |
| 39 | Examples 16 and 17[21,22]; C48 | 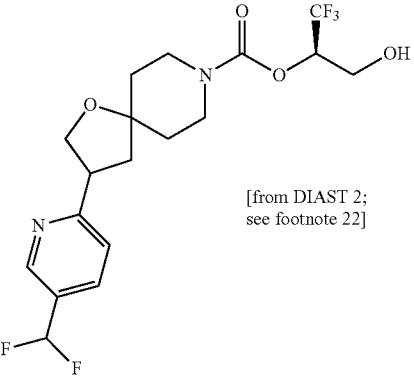 [SMILES: O=C(O[C@H](CO)C(F)(F)F)N1CCC2(CC1)CC(c1ccc(C(F)F)cn1)CO2] [from DIAST 2; see footnote 22] | 8.69 (br s, 1H), 7.79 (br d, J = 8 Hz, 1H), 7.30 (d, J = 7.8 Hz, 1H), 6.70 (d, $J_{HF}$ = 55.8 Hz, 1H), 5.32-5.20 (br m, 1H), 4.28 (dd, J = 8.2, 7.8 Hz, 1H), 4.05-3.97 (m, 2H), 3.93-3.69 (m, 4H), 3.52-3.34 (m, 2H), 2.25 (br dd, half of ABX pattern, J = 12.5, 8.6 Hz, 1H), 2.13 (dd, half of ABX pattern, J = 12.5, 9.4 Hz, 1H), 1.91-1.71 (br m, 3H; assumed; partially obscured by water peak), 1.71-1.56 (br m, 1H); 425.5 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 40 | Examples 14 and 15[23]; C49 | 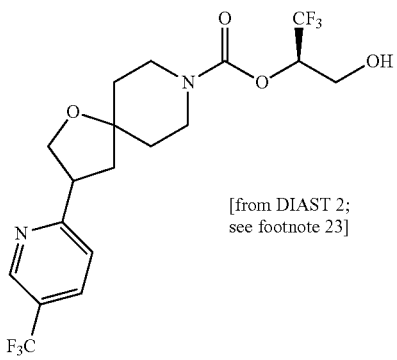 [SMILES: O=C(O[C@H](CO)C(F)(F)F)N1CCC2(CC1)CC(c1ccc(C(F)(F)F)cn1)CO2]<br>[from DIAST 2; see footnote 23] | 8.83 (br s, 1H), 7.86 (dd, J = 8.3, 2.3 Hz, 1H), 7.33 (d, J = 8.0 Hz, 1H), 5.32-5.21 (br m, 1H), 4.28 (dd, J = 8.0, 8.0 Hz, 1H), 4.06-3.97 (m, 2H), 3.93-3.70 (m, 4H), 3.51-3.34 (m, 2H), 2.54-2.39 (br s, 1H), 2.26 (br dd, half of ABX pattern, J = 12.3, 8.8 Hz, 1H), 2.14 (dd, half of ABX pattern, J = 12.6, 9.5 Hz, 1H), 1.91-1.71 (br m, 3H), 1.71-1.5 (m, 1H, assumed; obscured by water peak); 443.0 |
| 41 | Examples 14 and 15[24,25]; C2 | 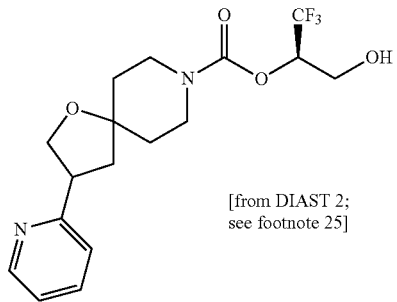 [SMILES: O=C(O[C@H](CO)C(F)(F)F)N1CCC2(CC1)CC(c1ccccn1)CO2]<br>[from DIAST 2; see footnote 25] | 8.57 (br d, J = 4.8 Hz, 1H), 7.63 (ddd, J = 7.7, 7.5, 2.0 Hz, 1H), 7.20 (br d, J = 7.9 Hz, 1H), 7.16 (ddd, J = 7.5, 4.8, 0.9 Hz, 1H), 5.31-5.20 (br m, 1H), 4.27 (dd, J = 8.4, 7.9 Hz, 1H), 4.04-3.96 (m, 2H), 3.92-3.64 (m, 4H), 3.53-3.35 (m, 2H), 2.25 (dd, half of ABX pattern, J = 12.8, 8.4 Hz, 1H), 2.13 (dd, half of ABX pattern, J = 12.3, 9.7 Hz, 1H), 1.90-1.52 (m, 4H, assumed; partially obscured by water peak); 375.1 |
| 42 | Example 18; C63 | 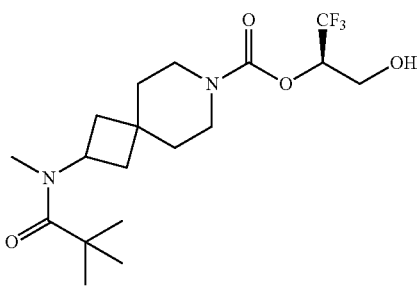 [SMILES: CN(C(=O)C(C)(C)C)C1CC2(CCN(C(=O)O[C@H](CO)C(F)(F)F)CC2)C1] | 5.29-5.20 (m, 1H), 4.81-4.69 (m, 1H), 4.00 (dd, half of ABX pattern, J = 12.3, 3.1 Hz, 1H), 3.87 (dd, half of ABX pattern, J = 12.5, 6.8 Hz, 1H), 3.58-3.32 (m, 4H), 2.95 (s, 3H), 2.22-2.09 (br m, 2H), 2.00-1.89 (m, 2H), 1.73-1.49 (br m, 4H, assumed; partially obscured by water peak), 1.29 (s, 9H); 395.2 |
| 43 | Example 18[26]; C63 | 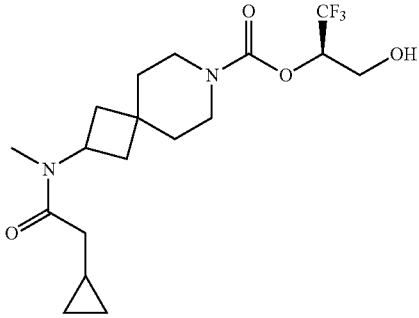 [SMILES: CN(C(=O)CC1CC1)C1CC2(CCN(C(=O)O[C@H](CO)C(F)(F)F)CC2)C1] | From analysis of the $^1$H NMR, this material was presumed to exist as a mixture of rotamers. 5.31-5.19 (br m, 1H), [5.10-4.94 (br m) and 4.46-4.33 (m), total 1H], 4.00 (br d, half of AB quartet, J = 12 Hz, 1H), 3.87 (br dd, half of ABX pattern, J = 12.5, 7.0 Hz, 1H), 3.59-3.30 (br m, 4H), [2.93 (s) and 2.92 (s), total 3H], 2.31-2.23 (m, 2H), 2.22-2.10 (br m, 2H), 2.09-1.99 (m, 1H), [1.92-1.82 (br m) and 1.75-1.51 (br m), total 6H, assumed; partially obscured by water peak], 1.13-0.99 (br m, 1H), 0.61-0.53 (m, 2H), 0.20-0.13 (m, 2H); 393.3 |

TABLE 18-continued

*Method of preparation, structure, and physicochemical data for Examples 20-90.*

| Example Number | Method of Preparation; Non-commercial starting materials | Structure | ¹H NMR (400 MHz, CDCl₃) δ; Mass spectrum, observed ion m/z [M + H]⁺ or HPLC retention time; Mass spectrum m/z [M + H]⁺ (unless otherwise indicated) |
|---|---|---|---|
| 44 | Example 43; C63 | 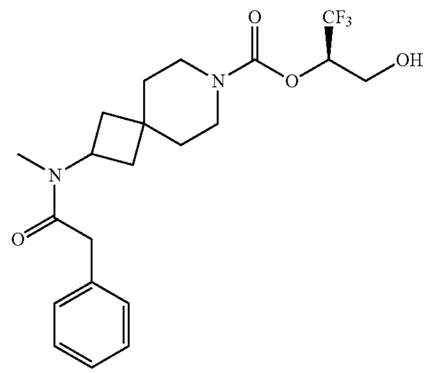 [SMILES: CN(C(=O)Cc1ccccc1)C1CC2(CCN(C(=O)O[C@H](CO)C(F)(F)F)CC2)C1] | From analysis of the ¹H NMR, this material was presumed to exist as a mixture of rotamers. 7.36-7.29 (m, 2H), 7.29-7.18 (m, 3H), 5.29-5.19 (m, 1H), [5.07-4.92 (br m) and 4.47-4.34 (m), total 1H], 3.99 (dd, half of ABX pattern, J = 12.3, 3.1 Hz, 1H), 3.86 (dd, half of ABX pattern, J = 12.1, 6.8 Hz, 1H), [3.77 (s) and 3.72 (s), total 2H], 3.58-3.26 (br m, 4H), [2.94 (s) and 2.93 (s), total 3H], 2.54-2.24 (v br s, 1H), 2.23-2.10 (br m, 1H), 1.96-1.77 (m, 3H), 1.77-1.44 (m, 4H, assumed; partially obscured by water peak); 429.3 |
| 45 | Example 18; C63 | 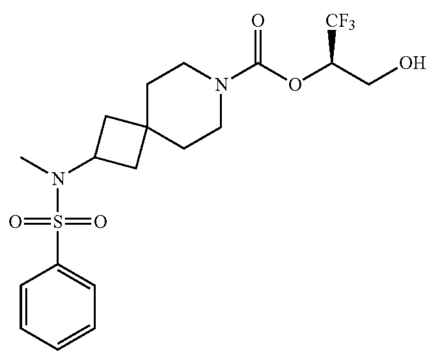 [SMILES: CN(C1CC2(CCN(C(=O)O[C@H](CO)C(F)(F)F)CC2)C1)S(=O)(=O)c1ccccc1] | 7.77-7.72 (m, 2H), 7.62-7.56 (m, 1H), 7.56-7.49 (m, 2H), 5.28-5.18 (m, 1H), 4.12-3.90 (m, 2H), 3.87-3.77 (br m, 1H) 3.52-3.23 (m, 4H), 2.76-2.69 (m, 1H), 2.67 (s, 3H), 2.08-1.94 (m, 2H), 1.93-1.81 (m, 2H), 1.64-1.53 (br m, 2H), 1.53-1.43 (br m, 2H); 451.0 |
| 46 | Examples 12 and 13; C5 | 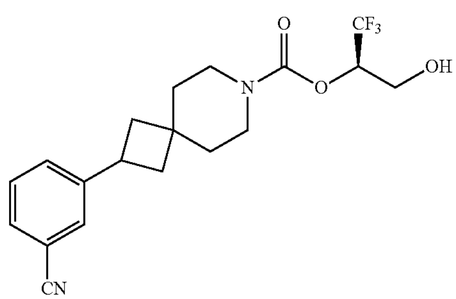 [SMILES: N#Cc1cccc(C2CC3(CCN(C(=O)O[C@H](CO)C(F)(F)F)CC3)C2)c1] | 7.52-7.38 (m, 4H), 5.31-5.21 (m, 1H), 4.06-3.96 (m, 1H), 3.93-3.83 (br m, 1H), 3.64-3.33 (m, 5H), 2.43-2.29 (m, 3H), 1.99-1.87 (m, 2H), 1.85-1.73 (br m, 2H), 1.66-1.52 (m, 2H, assumed; largely obscured by water peak); 383.5 |
| 47 | Examples 12 and 13; C5 | 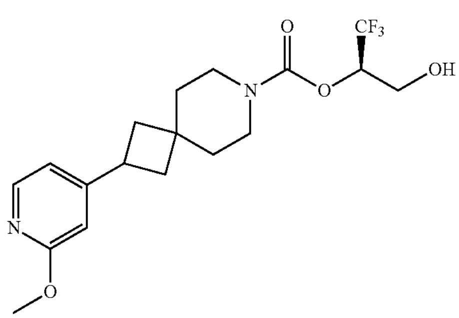 [SMILES: COc1cc(C2CC3(CCN(C(=O)O[C@H](CO)C(F)(F)F)CC3)C2)ccn1] | 8.08 (d, J = 5.1 Hz, 1H), 6.71 (dd, J = 5.5, 1.2 Hz, 1H), 6.57 (br s, 1H), 5.30-5.21 (m, 1H), 4.01 (br dd, half of ABX pattern, J = 12.5, 2.7 Hz, 1H), 3.94 (s, 3H), 3.87 (br dd, half of ABX pattern, J = 12.3, 6.8 Hz, 1H), 3.61-3.31 (m, 5H), 2.37-2.26 (m, 2H), 1.98-1.88 (m, 2H), 1.82-1.72 (br m, 2H), 1.61-1.50 (br m, 2H, assumed; partially obscured by water peak); 389.5 |

TABLE 18-continued

Method of preparation, structure, and physicochemical data for Examples 20-90.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 48 | Example 2; C5 | 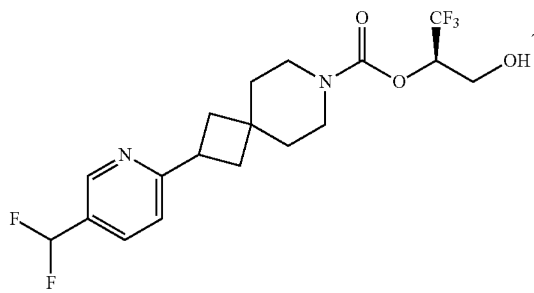 | 8.70 (s, 1H), 7.77 (br d, J = 8 Hz, 1H), 7.25 (d, J = 7.8 Hz, 1H), 6.70 (t, J$_{HF}$ = 56.0 Hz, 1H), 5.30-5.20 (m, 1H), 4.00 (br dd, half of ABX pattern, J = 12.5, 2.7 Hz, 1H), 3.87 (dd, half of ABX pattern, J = 12.1, 6.6 Hz, 1H), 3.70 (quint, J = 9.0 Hz, 1H), 3.62-3.33 (m, 4H), 2.37-2.27 (m, 2H), 2.17 (br dd, J = 12, 9 Hz, 2H), 1.84-1.74 (m, 2H), 1.68-1.58 (m, 2H); 409.5 |
| 49 | Example 1; C5 | •CF$_3$COOH | 7.39 (s, 1H), 7.22 (s, 1H), 5.30-5.21 (m, 1H), 4.83-4.69 (br m, 1H), 4.00 (dd, half of ABX pattern, J = 12.7, 3.3 Hz, 1H), 3.87 (dd, half of ABX pattern, J = 12.5, 7.0 Hz, 1H), 3.60-3.34 (m, 4H), 2.51-2.40 (m, 2H), 2.39-2.28 (m, 2H), 1.77-1.63 (m, 5H), 0.89-0.83 (m, 2H), 0.55-0.48 (m, 2H); 388.5 |
| 50 | Example 18[27,28] | [from DIAST 2; see footnote 28] | 5.30-5.19 (br m, 1H), 4.21-4.09 (m, 1H), 4.05-3.95 (m, 1H), 3.95-3.79 (m, 4H), 3.72-3.59 (m, 1H), 3.40-3.22 (m, 1H), 3.20-3.05 (m, 1H), 2.87 (d, J = 7.5 Hz, 2H), 2.81 (s, 3H), 2.44-2.3 (br s, 1H), 2.27 (br d, J = 14 Hz, 1H), 1.87-1.74 (m, 1H), 1.72-1.5 (m, 5H, assumed; partially obscured by water peak), 1.48-1.31 (m, 1H), 1.16-1.04 (m, 1H), 0.74-0.66 (m, 2H), 0.42-0.33 (m, 2H); 459.3 |
| 51 | Example 19 | 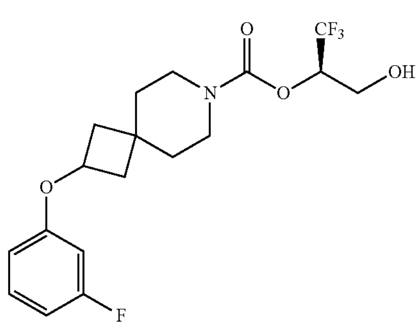 [SMILES: O=C(O[C@H](CO)C(F)(F)F)N1CCC2(CC1)CC(Oc1cccc(F)c1)C2] | 7.21 (ddd, J = 8.5, 8.0, 7.0 Hz, 1H), 6.65 (dddd, J = 8.5, 7.5, 2.5, 1.0 Hz, 1H), 6.58 (br dd, J = 8.0, 2.0 Hz, 1H), 6.50 (ddd, J = 11, 2.5, 2 Hz, 1H), 5.30-5.20 (m, 1H), 4.67 (br quint, J = 6.5 Hz, 1H), 4.00 (br d, half of AB quartet, J = 12 Hz, 1H), 3.86 (br dd, half of ABX pattern, J = 12.5, 7 Hz, 1H), 3.58-3.34 (m, 4H), 2.51-2.38 (m, 3H), 2.04-1.94 (m, 2H), 1.73-1.58 (m, 4H, assumed; partially obscured by water peak); 392.2 |

TABLE 18-continued

*Method of preparation, structure, and physicochemical data for Examples 20-90.*

| Example Number | Method of Preparation; Non-commercial starting materials | Structure | 1H NMR (400 MHz, CDCl3) δ; Mass spectrum, observed ion m/z [M + H]+ or HPLC retention time; Mass spectrum m/z [M + H]+ (unless otherwise indicated) |
|---|---|---|---|
| 52 | Examples 8 and 9[29]; C35 | 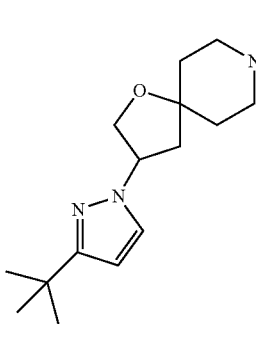 [from DIAST 2; see footnote 29] | 7.36 (d, J = 2.0 Hz, 1H), 6.10 (d, J = 2.0 Hz, 1H), 5.31-5.20 (br m, 1H), 5.00-4.91 (m, 1H), 4.20 (dd, half of ABX pattern, J = 9.8, 6.3 Hz, 1H), 4.14 (br dd, half of ABX pattern, J = 9.8, 4.8 Hz, 1H), 4.05-3.96 (m, 1H), 3.92-3.71 (m, 3H), 3.50-3.31 (m, 2H), 2.58-2.40 (br s, 1H), 2.30 (dd, half of ABX pattern, J = 13.6, 8.0 Hz, 1H), 2.25 (dd, half of ABX pattern, J = 13.6, 5.5 Hz, 1H), 1.93-1.83 (br m, 1H), 1.81-1.58 (br m, 3H, assumed; partially obscured by water peak), 1.29 (s, 9H); 420.1 |
| 53 | Examples 8 and 9[30]; C45 | 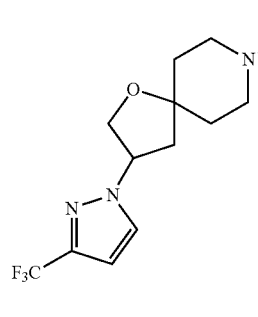 [from DIAST 2; see footnote 30] | 7.56 (br s, 1H), 6.55 (d, J = 2.2 Hz, 1H), 5.31-5.21 (br m, 1H), 5.07-4.99 (m, 1H), 4.24 (dd, half of ABX pattern, J = 10.1, 6.2 Hz, 1H), 4.20 (dd, half of ABX pattern, J = 10.1, 4.8 Hz, 1H), 4.01 (dd, half of ABX pattern, J = 12.5, 3.3 Hz, 1H), 3.93-3.75 (m, 3H), 3.49-3.29 (m, 2H), 2.37 (dd, half of ABX pattern, J = 13.6, 8.4 Hz, 1H), 2.35-2.25 (m, 1H), 1.91-1.55 (br m, 4H, assumed; partially obscured by water peak); 432.0 |
| 54 | Examples 8 and 9[31]; C35 | 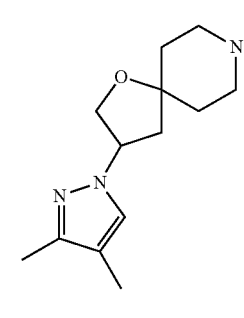 [from DIAST 2; see footnote 31] | 7.18 (s, 1H), 5.31-5.20 (br m, 1H), 4.90-4.81 (m, 1H), 4.17 (dd, half of ABX pattern, J = 9.7, 6.6 Hz, 1H), 4.11 (br dd, half of ABX pattern, J = 9.5, 5.5 Hz, 1H), 4.00 (dd, half of ABX pattern, J = 12.3, 3.1 Hz, 1H), 3.92-3.71 (brm, 3H), 3.50-3.31 (m, 2H), 2.28 (dd, half of ABX pattern, J = 13.2, 8.4 Hz, 1H), 2.25-2.15 (m, 1H), 2.18 (s, 3H), 1.98 (s, 3H), 1.91-1.52 (br m, 4H, assumed; partially obscured by water peak); 392.1 |
| 55 | Example 43; C63 | 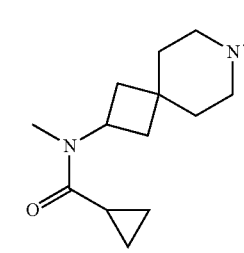 | From analysis of the 1H NMR, this material was presumed to exist as a mixture of rotamers. 5.31-5.19 (m, 1H), [5.05-4.87 (br m) and 4.78-4.64 (br m), total 1H], 4.00 (br dd, half of ABX pattern, J = 13, 2 Hz, 1H), 3.86 (dd, half of ABX pattern, J = 12.6, 6.5 Hz, 1H), 3.58-3.31 (br m, 4H), [3.10 (br s) and 2.94 (br s), total 3H], 2.52-1.81 (br m, 5H), 1.76-1.50 (br m, 5H, assumed; partially obscured by water peak), 1.02-0.94 (br m, 2H), 0.81-0.73 (m, 2H); 379.2 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 56 | Example 1; C5 | 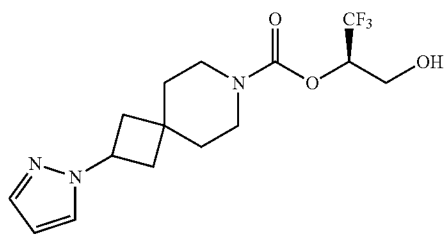 [SMILES: O=C(O[C@H](CO)C(F)(F)F)N1CCC2(CC1)CC(n1cccn1)C2] | 7.68 (br s, 1H), 7.49 (br s, 1H), 6.33 (br dd, J = 2.0, 2.0 Hz, 1H), 5.31-5.21 (m, 1H), 4.95-4.83 (br m, 1H), 4.01 (dd, half of ABX pattern, J = 12.5, 3.5 Hz, 1H), 3.87 (dd, half of ABX pattern, J = 12.5, 7.0 Hz, 1H), 3.62-3.34 (m, 4H), 2.57-2.45 (m, 2H), 2.41-2.29 (m, 2H), 1.79-1.64 (br m, 4H); 348.5 |
| 57 | C23[32] | 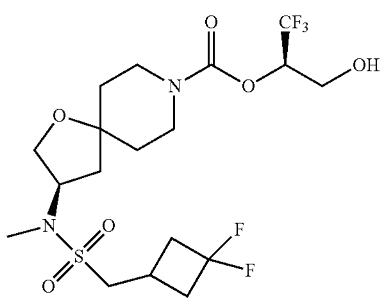 [SMILES: CN([C@H]1COC2(CCN(C(=O)O[C@H](CO)C(F)(F)F)CC2)C1)S(=O)(=O)CC1CC(F)(F)C1] | 5.31-5.20 (br m, 1H), 4.69-4.59 (m, 1H), 4.05-3.93 (m, 2H), 3.93-3.74 (m, 4H), 3.46-3.24 (m, 2H), 3.06 (d, J = 7.5 Hz, 2H), 2.94-2.80 (m, 2H), 2.85 (s, 3H), 2.71-2.58 (br m, 1H), 2.53-2.27 (m, 3H), 2.14-2.04 (m, 1H), 1.81-1.68 (m, 4H), 1.57-1.41 (m, 1H); 495.1 |
| 58 | Example 5; C23 | 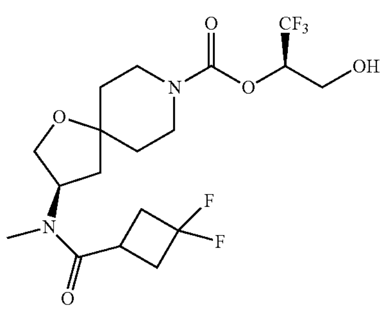 [SMILES: CN(C(=O)C1CC(F)(F)C1)[C@H]1COC2(CCN(C(=O)O[C@H](CO)C(F)(F)F)CC2)C1] | From analysis of the $^1$H NMR, this material was presumed to exist as a mixture of rotamers. [5.43-5.33 (m) and 4.53-4.43 (m), total 1H], 5.31-5.20 (br m, 1H), 4.05-3.71 (m, 6H), 3.48-3.25 (m, 2H), 3.14-3.00 (m, 1H), 2.98-2.81 (m, 2H), [2.92 (s) and 2.90 (s), total 3H], 2.81-2.67 (m, 2H), 2.55-2.2 (v br s, 1H), 2.19-2.01 (m, 1H), 1.85-1.42 (m, 5H, assumed; partially obscured by water peak); 445.1 |
| 59 | Example 19 | 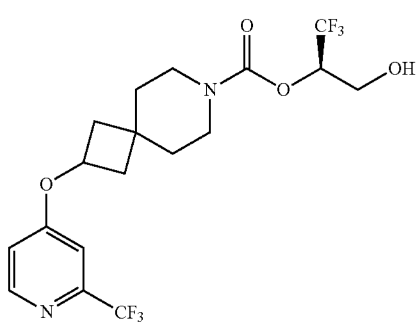 [SMILES: O=C(O[C@H](CO)C(F)(F)F)N1CCC2(CC1)CC(Oc1ccnc(C(F)(F)F)c1)C2] | 8.53 (d, J = 5.5 Hz, 1H), 7.08 (d, J = 2.5 Hz, 1H), 6.85 (dd, J = 5.5, 2.5 Hz, 1H), 5.30-5.21 (m, 1H), 4.85-4.77 (m, 1H), 4.05-3.97 (m, 1H), 3.92-3.84 (m, 1H), 3.61-3.36 (m, 4H), 2.56-2.45 (m, 2H), 2.35-2.22 (br s, 1H), 2.09-2.00 (m, 2H), 1.74-1.64 (br m, 4H); 443.2 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 60 | Example 19[33] | 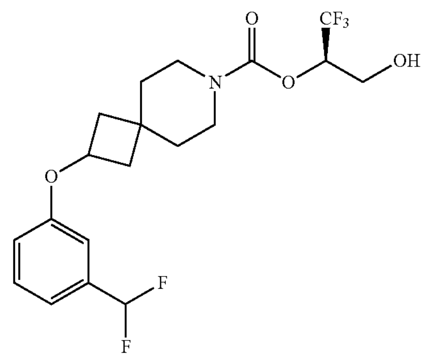 [SMILES: O=C(O[C@H](CO)C(F)(F)F)N1CCC2(CC1)CC(Oc1cccc(C(F)F)c1)C2] | 7.35 (dd, J = 8.0, 8.0 Hz, 1H), 7.08 (br d, J = 7.5 Hz, 1H), 6.94-6.87 (m, 2H), 6.60 (t, J$_{HF}$ = 56.5 Hz, 1H), 5.30-5.20 (m, 1H), 4.73 (quint, J = 6.6 Hz, 1H), 4.00 (br dd, half of ABX pattern, J = 12.0, 2.5 Hz, 1H), 3.86 (dd, half of ABX pattern, J = 12.6, 7.0 Hz, 1H), 3.59-3.34 (m, 4H), 2.59-2.40 (m, 3H), 2.05-1.95 (m, 2H), 1.74-1.59 (m, 4H, assumed; largely obscured by water peak); 424.1 |
| 61 | Example 6[34,35] | 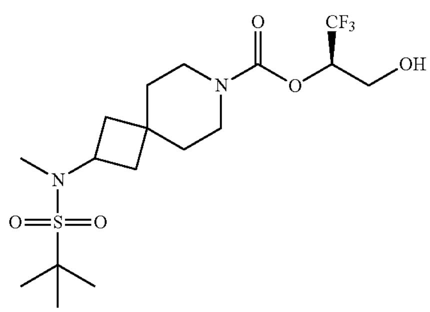 [SMILES: CN(C1CC2(CCN(C(=O)O[C@H](CO)C(F)(F)F)CC2)C1)S(=O)(=O)C(C)(C)C] | 5.29-5.20 (m, 1H), 4.50 (quint, J = 8.8 Hz, 1H), 4.04-3.96 (m, 1H), 3.91-3.82 (m, 1H), 3.56-3.31 (m, 4H), 2.95 (s, 3H), 2.29 (br t, J = 6.2 Hz, 1H), 2.17-1.98 (m, 4H), 1.70-1.51 (m, 4H, assumed; partially obscured by water peak), 1.36 (s, 9H); 431.2 |
| 62 | Examples 8 and 9[36]; C35 | [from DIAST 1; see footnote 36] | 8.03 (s, 1H), 7.75 (ddd, J = 8.0, 1.0, 1.0 Hz, 1H), 7.49-7.45 (m, 1H), 7.43-7.38 (m, 1H), 7.20-7.15 (m, 1H), 5.39-5.21 (m, 2H), 4.36-4.25 (m, 2H), 4.01 (dd, half of ABX pattern, J = 12.6, 3.0 Hz, 1H), 3.93-3.76 (m, 3H), 3.56-3.38 (m, 2H), 2.49 (dd, half of ABX pattern, J = 13.0, 6.5 Hz, 1H), 2.38 (dd, half of ABX pattern, J = 13.0, 9.0 Hz, 1H), 2.14-2.03 (m, 1H), 1.91-1.78 (m, 2H), 1.76-1.5 (m, 2H, assumed; partially obscured by water peak); 414.0 |
| 63 | Example 60 | 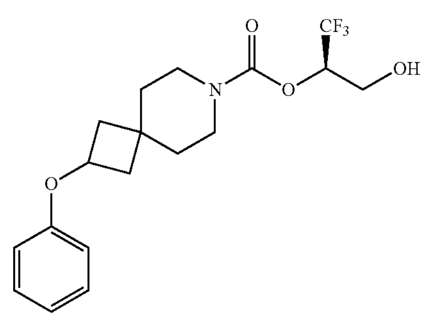 [SMILES: O=C(O[C@H](CO)C(F)(F)F)N1CCC2(CC1)CC(Oc1ccccc1)C2] | 7.31-7.24 (m, 2H, assumed; partially obscured by solvent peak), 6.95 (br dd, J = 8, 8 Hz, 1H), 6.83-6.77 (m, 2H), 5.29-5.20 (m, 1H), 4.75-4.66 (m, 1H), 4.04-3.95 (m, 1H), 3.91-3.82 (m, 1H), 3.59-3.34 (m, 4H), 2.49-2.32 (m, 3H), 2.05-1.94 (m, 2H), 1.73-1.5 (m, 4H, assumed; partially obscured by water peak); 374.2 |

TABLE 18-continued

Method of preparation, structure, and physicochemical data for Examples 20-90.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 64 | Example 1; C5 | 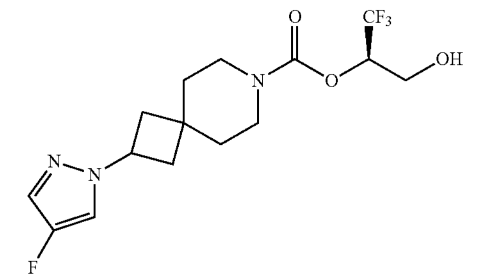 [SMILES: O=C(O[C@H](CO)C(F)(F)F)N1CCC2(CC1)CC(n1cc(F)cn1)C2] | 7.39 (d, J = 4.3 Hz, 1H), 7.32 (d, J = 4.7 Hz, 1H), 5.30-5.21 (m, 1H), 4.74-4.63 (m, 1H), 4.01 (dd, half of ABX pattern, J = 12.5, 3.1 Hz, 1H), 3.87 (dd, half of ABX pattern, J = 12.5, 7.0 Hz, 1H), 3.61-3.34 (m, 4H), 2.49-2.40 (m, 2H), 2.38-2.29 (m, 2H), 1.77-1.64 (br m, 4H); 366.6 |
| 65 | Example 1; C5 | 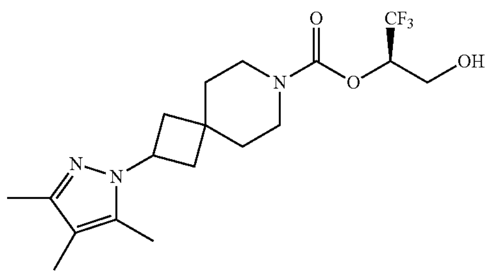 [SMILES: Cc1nn(C2CC3(CCN(C(=O)O[C@H](CO)C(F)(F)F)CC3)C2)c(C)c1C] | 5.31-5.20 (m, 1H), 4.65-4.55 (m, 1H), 4.00 (br dd, half of ABX pattern, J = 12.6, 2.5 Hz, 1H), 3.87 (dd, half of ABX pattern, J = 12.6, 7.0 Hz, 1H), 3.60-3.34 (m, 4H), 2.53-2.41 (m, 2H), 2.38-2.28 (m, 2H), 2.19 (s, 3H), 2.11 (s, 3H), 1.89 (s, 3H), 1.77-1.67 (br m, 4H); 390.0 |
| 66 | Example 1[37]; C3 | 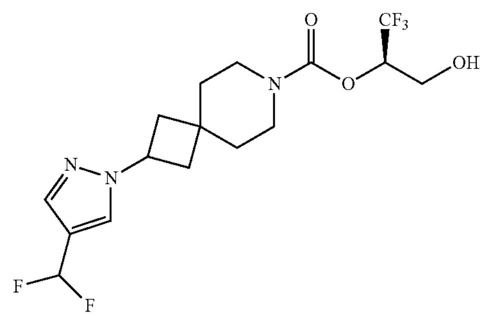 [SMILES: O=C(O[C@H](CO)C(F)(F)F)N1CCC2(CC1)CC(n1cc(C(F)F)cn1)C2] | 7.68 (s, 1H), 7.61 (s, 1H), 6.70 (t, J$_{HF}$ = 57.0 Hz, 1H), 5.31-5.21 (m, 1H), 4.84-4.74 (m, 1H), 4.01 (br dd, half of ABX pattern, J = 12.6, 3.0 Hz, 1H), 3.87 (dd, half of ABX pattern, J = 12.6, 7.0 Hz, 1H), 3.62-3.35 (m, 4H), 2.53-2.43 (m, 2H), 2.43-2.35 (m, 2H), 1.78-1.68 (br m, 4H); 398.1 |
| 67 | Examples 14 and 15[38] | 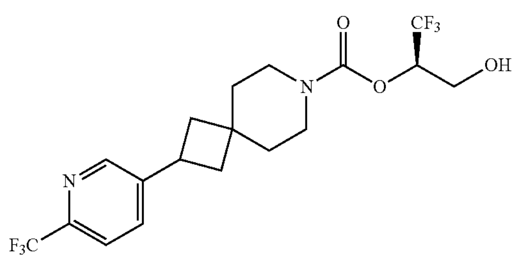 [SMILES: O=C(O[C@H](CO)C(F)(F)F)N1CCC2(CC1)CC(c1ccc(C(F)(F)F)nc1)C2] | 8.57 (br d, J = 1.5 Hz, 1H), 7.70 (br d, half of AB quartet, J = 8 Hz, 1H), 7.64 (d, half of AB quartet, J = 8.5 Hz, 1H), 5.31-5.21 (m, 1H), 4.05-3.97 (m, 1H), 3.93-3.84 (m, 1H), 3.72-3.33 (m, 5H), 2.50-2.27 (m, 3H), 2.03-1.93 (m, 2H), 1.87-1.76 (m, 2H), 1.69-1.53 (m, 2H, assumed; partially obscured by water peak); 427.3 |
| 68 | Examples 14 and 15[38] | 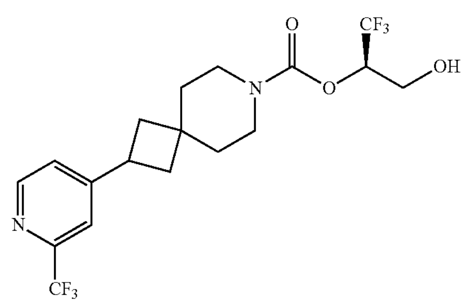 [SMILES: O=C(O[C@H](CO)C(F)(F)F)N1CCC2(CC1)CC(c1ccnc(C(F)(F)F)c1)C2] | 8.64 (d, J = 5.0 Hz, 1H), 7.50 (s, 1H), 7.31 (d, J = 5.0 Hz, 1H), 5.31-5.21 (m, 1H), 4.06-3.97 (m, 1H), 3.93-3.83 (m, 1H), 3.68-3.33 (m, 5H), 2.47-2.35 (m, 3H), 2.03-1.93 (m, 2H), 1.86-1.76 (m, 2H), 1.67-1.55 (m, 2H, assumed; partially obscured by water peak); 427.3 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 69 | Examples 8 and 9[39,40] | 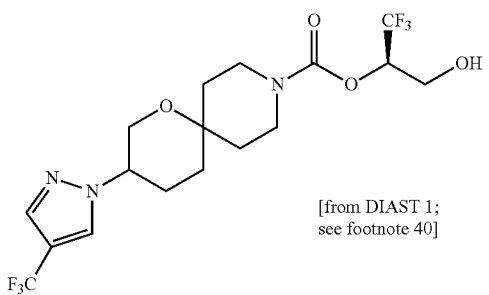 [SMILES: O=C(O[C@H](CO)C(F)(F)F)N1CCC2(CCC(n3cc(C(F)(F)F)cn3)CO2)CC1] [from DIAST 1; see footnote 40] | 7.89-7.83 (m, 1H), 7.73 (s, 1H), 5.32-5.21 (br m, 1H), 4.36-4.27 (m, 1H), 4.05-3.83 (m, 6H), 3.36-3.10 (m, 2H), 2.34-2.23 (m, 1H), 2.23-2.08 (m, 2H), 1.94-1.80 (m, 1H), 1.72-1.52 (m, 3H, assumed; partially obscured by water peak), 1.47 (ddd, J = 14.0, 12.5, 4.5 Hz, 1H); 446.2 |
| 70 | Examples 8 and 9[39,41] | 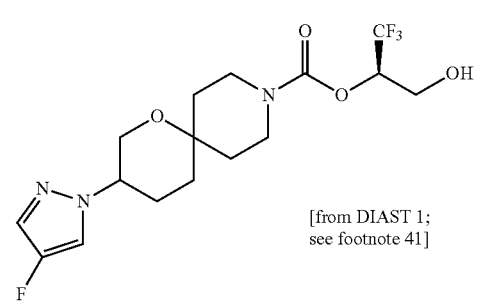 [SMILES: O=C(O[C@H](CO)C(F)(F)F)N1CCC2(CCC(n3cc(F)cn3)CO2)CC1] [from DIAST 1; see footnote 41] | $^1$H NMR (400 MHz, CD$_3$OD) δ 7.78 (d, J = 4.0 Hz, 1H), 7.39 (d, J = 4.0 Hz, 1H), 5.34-5.24 (m, 1H), 4.26-4.17 (m, 1H), 3.97-3.82 (m, 5H), 3.77 (dd, half of ABX pattern, J = 12.3, 6.8 Hz, 1H), 3.38-3.11 (m, 2H, assumed; partially obscured by solvent peak), 2.29-2.15 (m, 2H), 2.13-2.03 (m, 1H), 1.85-1.77 (m, 1H), 1.75-1.66 (m, 1H), 1.65-1.41 (m, 3H); 396.0 |
| 71 | Examples 12 and 13[42,43]; C45 | 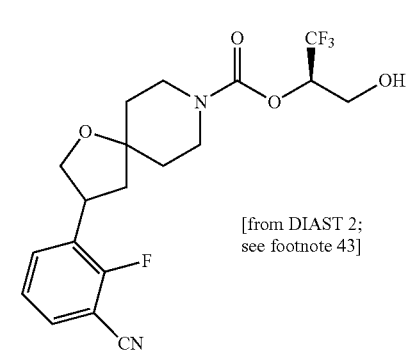 [SMILES: N#Cc1cccc(C2COC3(CCN(C(=O)O[C@H](CO)C(F)(F)F)CC3)C2)c1F] [from DIAST 2; see footnote 43] | 7.60-7.50 (m, 2H), 7.28-7.22 (m, 1H, assumed; partially obscured by solvent peak), 5.32-5.21 (br m, 1H), 4.25 (dd, J = 8.0, 7.5 Hz, 1H), 4.05-3.97 (m, 1H), 3.94-3.74 (m, 5H), 3.50-3.31 (m, 2H), 2.47-2.25 (m, 2H), 1.90-1.79 (m, 2H), 1.79-1.71 (br m, 2H), 1.70-1.56 (m, 1H, assumed; partially obscured by water peak); 417.0 |
| 72 | Examples 12 and 13[42,44]; C45 | 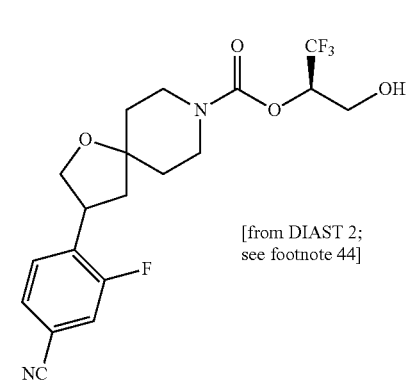 [SMILES: N#Cc1ccc(C2COC3(CCN(C(=O)O[C@H](CO)C(F)(F)F)CC3)C2)c(F)c1] [from DIAST 2; see footnote 44] | 7.47-7.39 (m, 2H), 7.35 (br d, J = 10 Hz, 1H), 5.32-5.21 (br m, 1H), 4.25 (dd, J = 7.8, 7.8 Hz, 1H), 4.05-3.96 (m, 1H), 3.93-3.74 (m, 5H), 3.50-3.30 (m, 2H), 2.57-2.44 (br m, 1H), 2.29 (dd, J = 12.2, 8.3 Hz, 1H), 1.90-1.78 (m, 2H), 1.78-1.70 (br m, 2H), 1.69-1.55 (m, 1H, assumed; partially obscured by water peak); 417.0 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 73 | Examples 14 and 15[45,46] | [from DIAST 2; see footnote 46] | 7.55-7.49 (m, 2H), 7.49-7.40 (m, 2H), 5.31-5.21 (br m, 1H), 4.05-3.83 (m, 5H), 3.78-3.66 (m, 1H), 3.44-3.26 (m, 1H), 3.26-3.11 (m, 1H), 3.05-2.93 (m, 1H), 2.50-2.35 (m, 2H), 1.85-1.52 (m, 6H, assumed; partially obscured by water peak), 1.46-1.30 (m, 1H); 413.3 |
| 74 | Examples 14 and 15[47] | [from DIAST 2; see footnote 47] | 8.40 (d, J= 3.0 Hz, 1H), 7.34 (ddd, J = 8.5, 8.5, 3.0 Hz, 1H), 7.19 (dd, J = 8.5, 4.5 Hz, 1H), 5.32-5.20 (br m, 1H), 4.05-3.96 (m, 1H), 3.96-3.81 (m, 4H), 3.81-3.71 (m, 1H), 3.41-3.27 (m, 1H), 3.27-3.07 (m, 1H), 3.02-2.92 (m, 1H), 2.45-2.32 (m, 1H), 2.13-1.99 (m, 1H), 1.94-1.84 (m, 1H), 1.7-1.53 (m, 4H), 1.44-1.33 (m, 1H); 407.1 |
| 75 | Examples 8 and 9[39,48,49] | [from DIAST 2; see footnote 49] | 7.76 (br s, 1H), 7.66 (s, 1H), 6.71 (t, $J_{HF}$ = 56.7 Hz, 1H), 5.32-5.21 (br m, 1H), 4.35-4.26 (m, 1H), 4.06-3.82 (m, 6H), 3.37-3.12 (m, 2H), 2.58-2.3 (v br s, 1H), 2.34-2.07 (m, 3H), 1.91-1.78 (m, 1H), 1.74-1.52 (m, 3H, assumed; partially obscured by water peak), 1.52-1.36 (m, 1H); 428.1 |
| 76 | Examples 14 and 15[50] | 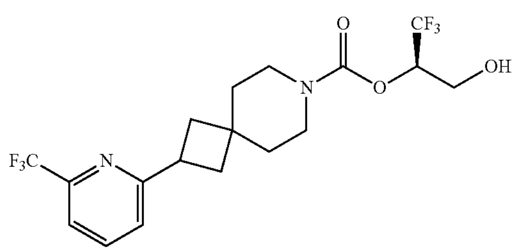 [SMILES: O=C(O[C@H](CO)C(F)(F)F)N1CCC2(CC1)CC(c1cccc(C(F)(F)F)n1)C2] | 7.77 (dd, J = 8.0, 7.5 Hz, 1H), 7.50 (d, J = 8.0 Hz, 1H), 7.37-7.30 (m, 1H), 5.30-5.20 (m, 1H), 4.05-3.96 (m, 1H), 3.92-3.83 (m, 1H), 3.76-3.66 (m, 1H), 3.62-3.34 (m, 4H), 2.45-2.37 (br s, 1H), 2.36-2.27 (m, 2H), 2.23-2.13 (m, 2H), 1.83-1.73 (m, 2H), 1.70-1.60 (m, 2H); 427.0 |
| 77 | Examples 14 and 15[38] | 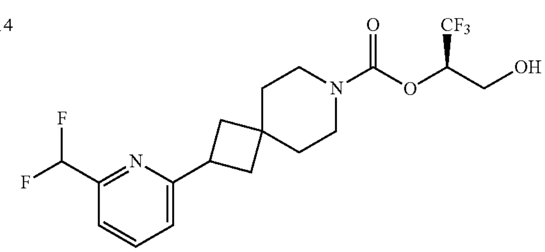 | 7.75 (dd, J = 8.0, 7.5 Hz, 1H), 7.46 (d, J = 7.5 Hz, 1H), 7.30-7.22 (m, 1H, assumed; partially obscured by solvent peak), 6.62 (t, $J_{HF}$ = 55.7 Hz, 1H), 5.30-5.20 (m, 1H), 4.05-3.97 (m, 1H), 3.92-3.84 (m, 1H), 3.67 (quintet, J = 9.0 Hz, 1H), 3.62-3.34 (m, 4H), 2.43-2.34 (br s, 1H), 2.34-2.26 (m, 2H), 2.16 (dd, J = 12.0, 9.0 Hz, 2H), 1.83-1.73 (m, 2H), 1.68-1.60 (m, 2H); 409.0 |

TABLE 18-continued

Method of preparation, structure, and physicochemical data for Examples 20-90.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 78 | Examples 14 and 15$^{38}$ | 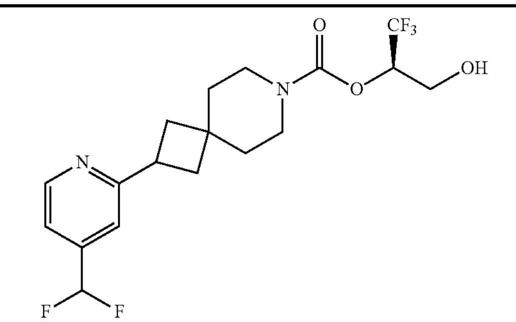 | 8.70 (d, J = 4.9 Hz, 1H), 7.29-7.21 (m, 2H, assumed; partially obscured by solvent peak), 6.62 (t, J$_{HF}$ = 55.8 Hz, 1H), 5.30-5.21 (m, 1H), 4.05-3.97 (m, 1H), 3.92-3.83 (m, 1H), 3.76-3.65 (m, 1H), 3.62-3.34 (m, 4H), 2.52-2.37 (br s, 1H), 2.37-2.27 (m, 2H), 2.17 (dd, J = 11.7, 9.3 Hz, 2H), 1.84-1.74 (m, 2H), 1.69-1.55 (m, 2H, assumed; partially obscured by water peak); 409.0 |
| 79 | | 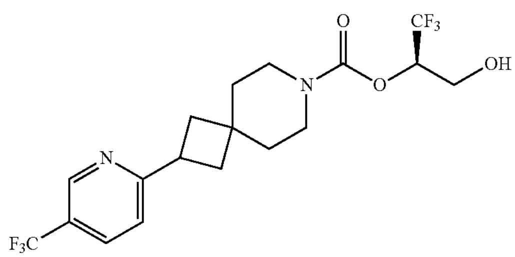 [SMILES: O=C(O[C@H](CO)C(F)(F)F)N1CCC2(CC1)CC(c1ccc(C(F)(F)F)cn1)C2] | 8.84 (br s, 1H), 7.83 (dd, J = 8.3, 2.0 Hz, 1H), 7.30-7.23 (m, 1H, assumed; partially obscured by solvent peak), 5.30-5.21 (m, 1H), 4.05-3.96 (m, 1H), 3.92-3.83 (m, 1H), 3.71 (quintet, J = 8.8 Hz, 1H), 3.62-3.34 (m, 4H), 2.37-2.27 (m, 2H), 2.18 (dd, J = 11.7, 8.8 Hz, 2H), 1.84-1.74 (m, 2H), 1.69-1.6 (m, 2H, assumed; partially obscured by water peak); 427.0 |
| 80 | Examples 14 and 15$^{38}$ | 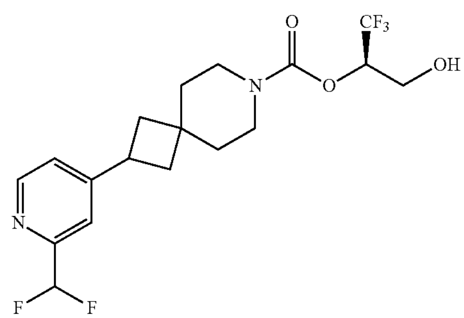 [SMILES: O=C(O[C@H](CO)C(F)(F)F)N1CCC2(CC1)CC(c1ccnc(C(F)F)c1)C2] | 8.56 (d, J = 4.5 Hz, 1H), 7.47 (s, 1H), 7.23 (br d, J = 5 Hz, 1H), 6.64 (t, J$_{HF}$ = 55.7 Hz, 1H), 5.31-5.21 (m, 1H), 4.05-3.97 (m, 1H), 3.93-3.84 (m, 1H), 3.66-3.33 (m, 5H), 2.45-2.35 (m, 2H), 2.03-1.93 (m, 2H), 1.85-1.76 (m, 2H), 1.67-1.52 (m, 2H, assumed; obscured by water peak); 409.0 |
| 81 | Examples 14 and 15$^{38}$ | 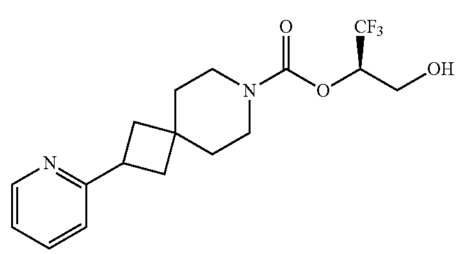 [SMILES: O=C(O[C@H](CO)C(F)(F)F)N1CCC2(CC1)CC(c1ccccn1)C2] | Characteristic peaks: 8.58 (br d, J = 4.0 Hz, 1H), 7.64 (ddd, J = 7.8, 7.5, 1.8 Hz, 1H), 7.18 (br d, J = 8.0 Hz, 1H), 7.14 (ddd, J = 7.5, 5.0, 1.0 Hz, 1H), 5.30-5.21 (m, 1H), 4.04-3.97 (m, 1H), 3.91-3.83 (m, 1H), 3.67 (quintet, J = 9.0 Hz, 1H), 3.61-3.33 (m, 4H), 2.18-2.10 (m, 2H), 1.83-1.74 (m, 2H), 1.67-1.58 (m, 2H); 359.3 |
| 82 | Examples 14 and 15$^{38}$ | 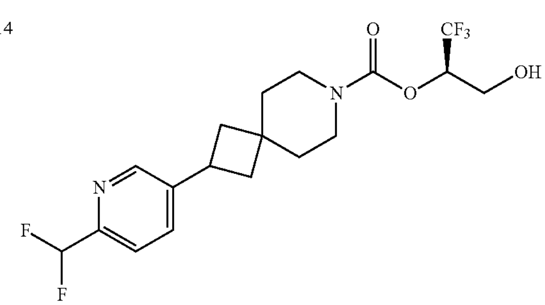 | 8.50 (s, 1H), 7.64 (AB quartet, downfield doublet is broadened, J$_{AB}$ =8.0 Hz, Δν$_{AB}$ = 34.7 Hz, 2H), 6.64 (t, J$_{HF}$ = 55.7 Hz, 1H), 5.32-5.22 (m, 1H), 4.07-3.97 (m, 1H), 3.94-3.83 (m, 1H), 3.70-3.33 (m, 5H), 2.51-2.35 (m, 3H), 2.04-1.93 (m, 2H), 1.88-1.76 (m, 2H), 1.68-1.55 (m, 2H, assumed; obscured by water peak); 409.3 |

TABLE 18-continued

*Method of preparation, structure, and physicochemical data for Examples 20-90.*

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 83 | Examples 14 and 15[38] | 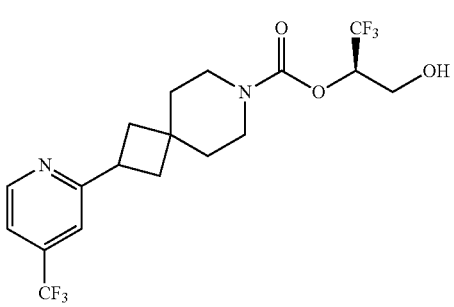 [SMILES: O=C(O[C@H](CO)C(F)(F)F)N1CCC2(CC1)CC(c1cc(C(F)(F)F)ccn1)C2] | 8.77-8.74 (m, 1H), 7.36-7.33 (m, 2H), 5.30-5.21 (m, 1H), 4.05-3.97 (m, 1H), 3.92-3.84 (m, 1H), 3.72 (quintet, J = 9.0 Hz, 1H), 3.62-3.35 (m, 4H), 2.51-2.35 (br s, 1H), 2.38-2.29 (m, 2H), 2.18 (dd, J = 11.8, 9.3 Hz, 2H), 1.85-1.75 (m, 2H), 1.70-1.6 (m, 2H, assumed; partially obscured by water peak); 427.3 |
| 84 | Examples 14 and 15[38,51] | 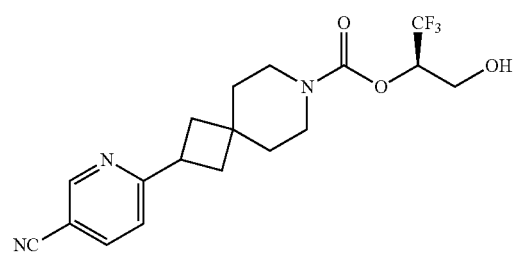 [SMILES: N#Cc1ccc(C2CC3(CCN(C(=O)O[C@H](CO)C(F)(F)F)CC3)C2)nc1] | 8.85 (d, J = 2 Hz, 1H), 7.86 (dd, J = 8.0, 2.5 Hz, 1H), 7.26 (d, J = 8.5 Hz, 1H), 5.30-5.21 (m, 1H), 4.05-3.96 (m, 1H), 3.92-3.83 (m, 1H), 3.70 (quintet, J = 9.0 Hz, 1H), 3.62-3.33 (m, 4H), 2.51-2.40 (br s, 1H), 2.36-2.26 (m, 2H), 2.17 (dd, J = 12.0, 9.0 Hz, 2H), 1.83-1.73 (m, 2H), 1.69-1.59 (m, 2H, assumed; obscured by water peak); 384.2 |
| 85 | C2[52] | 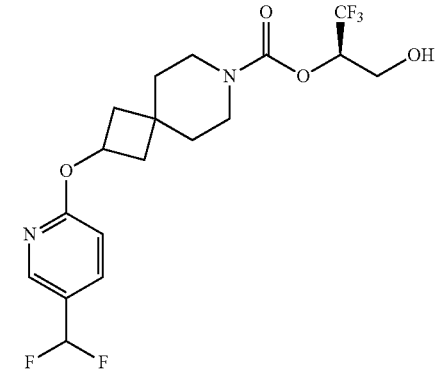 [SMILES: O=C(O[C@H](CO)C(F)(F)F)N1CCC2(CC1)CC(Oc1ccc(C(F)F)cn1)C2] | 8.25 (br s, 1H), 7.76-7.71 (m, 1H), 6.82-6.76 (m, 1H), 6.64 (t, J$_{HF}$ = 55.7 Hz, 1H), 5.31-5.19 (m, 2H), 4.04-3.96 (m, 1H), 3.91-3.83 (m, 1H), 3.58-3.33 (m, 4H), 2.54-2.44 (m, 2H), 2.4-2.25 (br s, 1H), 2.00-1.91 (m, 2H), 1.76-1.6 (m, 4H, assumed; partially obscured by water peak); 425.3 |
| 86 | Example 19 | 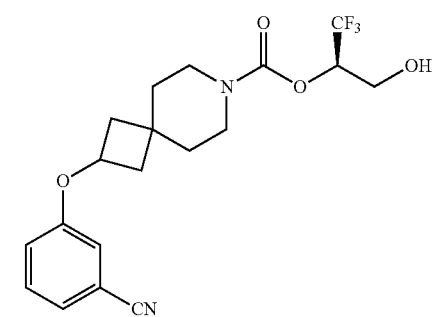 [SMILES: N#Cc1cccc(OC2CC3(CCN(C(=O)O[C@H](CO)C(F)(F)F)CC3)C2)c1] | 7.37 (dd, J = 8.0, 8.0 Hz, 1H), 7.25 (br d, J = 7.5 Hz, 1H), 7.06-7.00 (m, 2H), 5.30-5.21 (m, 1H), 4.75-4.66 (m, 1H), 4.05-3.97 (m, 1H), 3.92-3.83 (m, 1H), 3.59-3.35 (m, 4H), 2.52-2.42 (m, 2H), 2.37 (br t, J = 6 Hz, 1H), 2.05-1.96 (m, 2H), 1.72-1.63 (m, 4H); 399.2 |

TABLE 18-continued

Method of preparation, structure, and physicochemical data for Examples 20-90.

| Example Number | Method of Preparation; Non-commercial starting materials | Structure | $^1$H NMR (400 MHz, CDCl$_3$) δ; Mass spectrum, observed ion m/z [M + H]$^+$ or HPLC retention time; Mass spectrum m/z [M + H]$^+$ (unless otherwise indicated) |
|---|---|---|---|
| 87 | C2[53] | 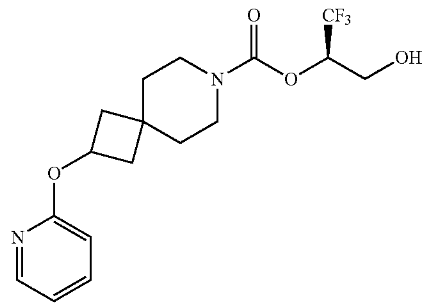 [SMILES: O=C(O[C@H](CO)C(F)(F)F)N1CCC2(CC1)CC(Oc1ccccn1)C2] | 8.14 (br d, J = 4.5 Hz, 1H), 7.57 (br dd, J = 8.0, 7.5 Hz, 1H), 6.86 (br dd, J = 6, 6 Hz, 1H), 6.71 (d, J = 8.5 Hz, 1H), 5.30-5.18 (m, 2H), 4.04-3.96 (m, 1H), 3.92-3.83 (m, 1H), 3.58-3.34 (m, 4H), 2.55-2.31 (m, 3H), 2.01-1.90 (m, 2H), 1.74-1.52 (m, 4H, assumed; partially obscured by water peak); 375.1 |
| 88 | Example 87 | 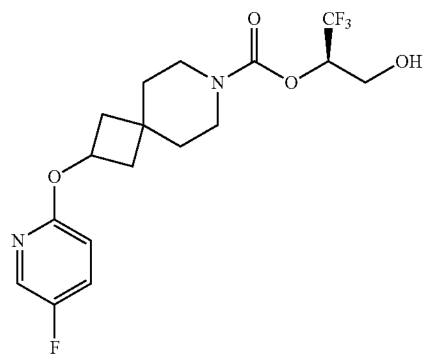 [SMILES: O=C(O[C@H](CO)C(F)(F)F)N1CCC2(CC1)CC(Oc1ccc(F)cn1)C2] | 7.96 (d, J = 2.5 Hz, 1H), 7.38-7.30 (m, 1H), 6.68 (br dd, J = 9, 3.5 Hz, 1H), 5.29-5.20 (m, 1H), 5.16 (quintet, J = 7 Hz, 1H), 4.05-3.96 (m, 1H), 3.92-3.83 (m, 1H), 3.59-3.33 (m, 4H), 2.52-2.41 (m, 2H), 2.41-2.33 (m, 1H), 1.98-1.88 (m, 2H), 1.73-1.55 (m, 4H, assumed; partially obscured by water peak); 393.2 |
| 89 | Example 19[54] | 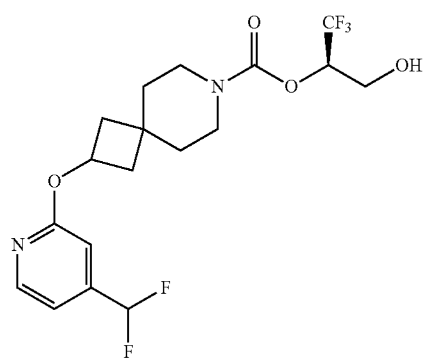 [SMILES: O=C(O[C@H](CO)C(F)(F)F)N1CCC2(CC1)CC(Oc1cc(C(F)F)ccn1)C2] | 8.24 (d, J = 5.5 Hz, 1H), 6.98 (br d, J = 5.0 Hz, 1H), 6.83 (br s, 1H), 6.57 (t, J$_{HF}$ = 55.7 Hz, 1H), 5.29-5.20 (m, 2H), 4.05-3.96 (m, 1H), 3.92-3.83 (m, 1H), 3.59-3.34 (m, 4H), 2.54-2.44 (m, 2H), 2.36 (dd, J = 7.0, 6.0 Hz, 1H), 2.00-1.91 (m, 2H), 1.74-1.62 (m, 4H); 425.3 |
| 90 | Example 87 | 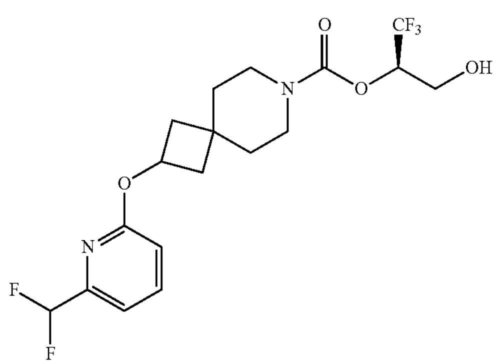 [SMILES: O=C(O[C@H](CO)C(F)(F)F)N1CCC2(CC1)CC(Oc1cccc(C(F)F)n1)C2] | 7.69 (dd, J = 8.0, 7.5 Hz, 1H), 7.19 (d, J = 7.0 Hz, 1H), 6.80 (d, J = 8.5 Hz, 1H), 6.48 (t, J$_{HF}$ = 55.5 Hz, 1H), 5.30-5.18 (m, 2H), 4.05-3.96 (m, 1H), 3.92-3.82 (m, 1H), 3.60-3.34 (m, 4H), 2.53-2.43 (m, 2H), 2.43-2.35 (m, 1H), 2.00-1.90 (m, 2H), 1.74-1.61 (m, 4H); 425.3 |

1. Compound C35 was reacted with 1H-pyrazole-4-carbaldehyde to afford tert-butyl 3-(4-form) 1H-pyrazol-1-yl)-1-oxa-8-azaspiro[4.5]decane-8-carboxylate; this was converted into the requisite tert-butyl 3-[4-(difluoromethyl)-1H-pyrazol-1-yl]-1-oxa-8-azaspiro[4.5]decane-8-carboxylate via treatment with (diethylamino)sulfur trifluoride.

2. Prior to the final deprotection, intermediate (2R)-1,1,1-trifluoro-3-[(4-methoxybenzyl)oxy]propan-2-yl 3-[4-(difluoromethyl)-1H-pyrazol-1-yl]-1-oxa-8-azaspiro[4.5]decane-8-carboxylate was separated into its component diastereomers via supercritical fluid chromatography [Column: Chiral Technologies Chiralpak AD, 10 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 20, LCMS m/z 414.0 [M+H]$^+$, which exhibited the following biological data: MAGL (T=30 min) IC$_{50}$=0.065 µM.

3. Prior to the final deprotection, intermediate (2R)-1,1,1-trifluoro-3-[(4-methoxybenzyl)oxy]propan-2-yl 3-(4-tert-butyl-1H-pyrazol-1-yl)-1-oxa-8-azaspiro[4.5]decane-8-carboxylate was separated into its component diastereomers via supercritical fluid chromatography [Column: Chiral Technologies Chiralpak AD, 10 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 21, LCMS m/z 420.1 [M+H]$^+$, which exhibited the following biological data: MAGL (T=30 min) IC$_{50}$=0.007 µM.

4. Prior to the final deprotection, intermediate (2R)-1,1,1-trifluoro-3-[(4-methoxybenzyl)oxy]propan-2-yl 3-(4-chloro-1H-pyrazol-1-yl)-1-oxa-8-azaspiro[4.5]decane-8-carboxylate was separated into its component diastereomers via supercritical fluid chromatography [Column: Chiral Technologies Chiralpak AD, 10 µm; Mobile phase: 1:1 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 22, LCMS m/z 398.0 (chlorine isotope pattern observed) [M+H]$^+$, which exhibited the following biological data: MAGL (T=30 min) IC$_{50}$=0.023 µM.

5. Conditions for analytical HPLC. Column: Waters Atlantis dC18, 4.6×50 mm, 5 µm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

6. Prior to the final deprotection, intermediate (2R)-1,1,1-trifluoro-3-[(4-methoxybenzyl)oxy]propan-2-yl 3-(4-methyl-1H-pyrazol-1-yl)-1-oxa-8-azaspiro[4.5]decane-8-carboxylate was separated into its component diastereomers via supercritical fluid chromatography [Column: Chiral Technologies Chiralpak AD, 5 µm; Mobile phase: 7:3 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 24, LCMS m/z 378.1 [M+H]$^+$, which exhibited the following biological data: MAGL (T=30 min) IC$_{50}$=0.060 µM.

7. Reaction of C48 with (2-fluorophenyl)boronic acid in the presence of [1,1'-bis(diphenylphosphino)ferrocene]dichloropalladium(II) and sodium carbonate at 95° C. provided the requisite tert-butyl 3-(2-fluorophenyl)-1-oxa-8-azaspiro[4.5]dec-3-ene-8-carboxylate.

8. Prior to the final deprotection, intermediate (2R)-1,1,1-trifluoro-3-[(4-methoxybenzyl)oxy]propan-2-yl 3-(2-fluorophenyl)-1-oxa-8-azaspiro[4.5]decane-8-carboxylate was separated into its component diastereomers via supercritical fluid chromatography [Column: Chiral Technologies Chiralpak AD, 10 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. Example 25 was synthesized from DIAST 1, and Example 26 was synthesized from DIAST 2.

9. tert-Butyl 3-(4-cyano-3-fluorophenyl)-1-oxa-8-azaspiro[4.5]decane-8-carboxylate was synthesized via reaction of C35 with (4-cyano-3-fluorophenyl)boronic acid, using the procedure described for synthesis of C46 and C47 from C45 in Examples 12 and 13.

10. Prior to the final deprotection, intermediate (2R)-1,1,1-trifluoro-3-[(4-methoxybenzyl)oxy]propan-2-yl 3-(4-cyano-3-fluorophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. DIAST 2 was used to synthesize Example 27, which was crystallized from ethyl acetate/pentane via vapor diffusion; this crystal was used to determine the indicated absolute configuration via X-ray crystallography. DIAST 1 was used to synthesize the diastereomer of Example 27, (2R)-1,1,1-trifluoro-3-hydroxypropan-2-yl (3R)-3-(4-cyano-3-fluorophenyl)-1-oxa-8-azaspiro[4.5]decane-8-carboxylate, LCMS m/z 417.0 [M+H]$^+$, which exhibited the following biological data: MAGL (T=30 min) IC$_{50}$=0.017 µM.

11. Prior to the final deprotection, intermediate (2R)-1,1,1-trifluoro-3-[(4-methoxybenzyl)oxy]propan-2-yl 3-(3-cyano-4-fluorophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 28, LCMS m/z 417.0 [M+H]$^+$, which exhibited the following biological data: MAGL (T=30 min) IC$_{50}$=0.014 µM.

12. tert-Butyl 3-(5-cyano-2-fluorophenyl)-1-oxa-8-azaspiro[4.5]decane-8-carboxylate was synthesized from C35 via reaction with 3-bromo-4-fluorobenzonitrile in the presence of nickel(II) iodide, zinc, and pyridine.

13. Prior to the final deprotection, intermediate (2R)-1,1,1-trifluoro-3-[(4-methoxybenzyl)oxy]propan-2-yl 3-(5-cyano-2-fluorophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(ethanol containing 0.1% ammonium hydroxide)]. The first-eluting diastereomer was assigned as DIAST 1, and the second-eluting diastereomer as DIAST 2. Example 29 was synthesized from DIAST 1, and Example 30 was synthesized from DIAST 2.

14. Prior to the final deprotection, intermediate (2R)-1,1,1-trifluoro-3-[(4-methoxybenzyl)oxy]propan-2-yl 3-(4-cyanophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 3:1 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 31, LCMS m/z 399.0 [M+H]$^+$, which exhibited the following biological data: MAGL (T=30 min) IC$_{50}$=0.023 µM.

15. Prior to the final deprotection, intermediate (2R)-1,1,1-trifluoro-3-[(4-methoxybenzyl)oxy]propan-2-yl 3-(2,6-difluorophenyl)-1-oxa-8-azaspiro[4.5]decane-8-carboxylate was separated into its component diastereomers via supercritical fluid chromatography [Column: Chiral Technologies Chiralcel OJ, 5 µm; Mobile phase: 85:15 carbon dioxide/(ethanol containing 0.1% ammonium hydroxide)]. The first-eluting diastereomer was assigned as DIAST 1, and the second-eluting diastereomer as DIAST 2. DIAST 2 was used to synthesize the diastereomer of Example 32, LCMS m/z 410.0 [M+H]$^+$, which exhibited the following biological data: MAGL (T=30 min) IC$_{50}$=0.001 µM.

16. Prior to the final deprotection, intermediate (2R)-1,1,1-trifluoro-3-[(4-methoxybenzyl)oxy]propan-2-yl 3-(2,4-difluorophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 7:3 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 33, LCMS m/z 410.1 [M+H]$^+$, which exhibited the following biological data: MAGL (T=30 min) IC$_{50}$=0.002 µM.

17. Prior to the final deprotection, intermediate (2R)-1,1,1-trifluoro-3-[(4-methoxybenzyl)oxy]propan-2-yl 3-(4-fluorophenyl)-1-oxa-8-azaspiro[4.5]decane-8-carboxylate was separated into its component diastereomers via supercritical fluid chromatography [Column: Chiral Technologies Chiralpak AD, 5 µm; Mobile phase: 7:3 carbon dioxide/(methanol containing 0.1% ammonium hydroxide)]. The first-eluting diastereomer was assigned as DIAST 1, and the second-eluting diastereomer as DIAST 2. DIAST 2 was used to synthesize the diastereomer of Example 34, LCMS m/z 392.1 [M+H]$^+$, which exhibited the following biological data: MAGL (T=30 min) IC$_{50}$=0.001 µM.

18. Prior to the final deprotection, intermediate (2R)-1,1,1-trifluoro-3-[(4-methoxybenzyl)oxy]propan-2-yl 3-[4-(difluoromethyl)pyridin-2-yl]-1-oxa-8-azaspiro[4.5]decane-8-carboxylate was separated into its component diastereomers via supercritical fluid chromatography [Column: Phenomenex Lux Cellulose-2, 10 µm; Mobile phase: 3:1 carbon dioxide/(methanol containing 0.1% ammonium hydroxide)]. The first-eluting diastereomer was assigned as DIAST 1, and the second-eluting diastereomer as DIAST 2. DIAST 2 was used to synthesize the diastereomer of Example 35, LCMS m/z 425.0 [M+H]$^+$, which exhibited the following biological data: MAGL (T=30 min) IC$_{50}$=0.019 µM.

19. Prior to the final deprotection, intermediate (2R)-1,1,1-trifluoro-3-[(4-methoxybenzyl)oxy]propan-2-yl 3-[6-(difluoromethyl)pyridin-3-yl]-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. Example 36 was synthesized from DIAST 1, and Example 37 was synthesized from DIAST 2.

20. Prior to the final deprotection, intermediate (2R)-1,1,1-trifluoro-3-[(4-methoxybenzyl)oxy]propan-2-yl 3-(5-cyanopyridin-2-yl)-1-oxa-8-azaspiro[4.5]decane-8-carboxylate was separated into its component diastereomers via supercritical fluid chromatography [Column: Chiral Technologies Chiralpak AD, 5 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 38, LCMS m/z 400.0 [M+H]$^+$, which exhibited the following biological data: MAGL (T=30 min) IC$_{50}$=0.336 µM.

21. Reaction of C48 with hexamethyldistannane, in the presence of tetrakis(triphenylphosphine)palladium(0) and lithium chloride, afforded tert-butyl 3-(trimethylstannanyl)-1-oxa-8-azaspiro[4.5]dec-3-ene-8-carboxylate. This material was subjected to a Stille coupling with 2-bromo-5-(difluoromethyl)pyridine, mediated via dichlorobis(triphenylphosphine)palladium(II), to provide the requisite tert-butyl 3-[5-(difluoromethyl)pyridin-2-yl]-1-oxa-8-azaspiro[4.5]dec-3-ene-8-carboxylate.

22. Prior to the final deprotection, intermediate (2R)-1,1,1-trifluoro-3-[(4-methoxybenzyl)oxy]propan-2-yl 3-[5-(difluoromethyl)pyridin-2-yl]-1-oxa-8-azaspiro[4.5]decane-8-carboxylate was separated into its component diastereomers via supercritical fluid chromatography {Column: Chiral Technologies Chiralpak 1A, 5 µm; Mobile phase 7:3 carbon dioxide/[methanol containing 0.2% (7 M ammonia in methanol)]}. The first-eluting diastereomer was assigned as DIAST 1, and the second-eluting diastereomer as DIAST 2. DIAST 1 was used to synthesize the diastereomer of Example 39, LCMS m/z 425.5 [M+H]$^+$, which exhibited the following biological data: MAGL (T=30 min) IC$_{50}$=0.031 µM.

23. Prior to the final deprotection, intermediate (2R)-1,1,1-trifluoro-3-[(4-methoxybenzyl)oxy]propan-2-yl 3-[5-(trifluoromethyl)pyridin-2-yl]-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 40, LCMS m/z 443.0 [M+H]$^+$, which exhibited the following biological data: MAGL (T=30 min) IC$_{50}$=0.009 µM.

24. In this case, the order of assembly was reversed: 1-oxa-8-azaspiro[4.5]decan-3-one was converted to (2R)-1,1,1-trifluoro-3-[(4-methoxybenzyl)oxy]propan-2-yl 3-oxo-1-oxa-8-azaspiro[4.5]decane-8-carboxylate via reaction with C2, and this material was converted to the boronate intermediate (2R)-1,1,1-trifluoro-3-[(4-methoxybenzyl)oxy]propan-2-yl 3-(4,4,5,5-tetramethyl-1,3,2-dioxaborolan-2-yl)-1-oxa-8-azaspiro[4.5]dec-3-ene-8-carboxylate.

25. Prior to the final deprotection, intermediate (2R)-1,1,1-trifluoro-3-[(4-methoxybenzyl)oxy]propan-2-yl 3-(pyridin-2-yl)-1-oxa-8-azaspiro[4.5]decane-8-carboxylate was separated into its component diastereomers via supercritical fluid chromatography [Column: Chiral Technologies Chiralpak AD, 5 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 41, LCMS m/z 375.2 [M+H]$^+$, which exhibited the following biological data: MAGL (T=30 min) IC$_{50}$=0.020 µM.

26. Synthesis of benzyl 2-[(cyclopropylacetyl)(methyl)amino]-7-azaspiro[3.5]nonane-7-carboxylate was carried 27. The requisite tert-butyl 4-oxo-1-oxa-9-azaspiro[5.5]undecane-9-carboxylate may be prepared using the method described by T. Cernak et al., Tetrahedron Lett. 2011, 52, 6457-6459. This material was subjected to reductive amination with methylamine hydrochloride, using sodium cyanoborohydride in the presence of triethylamine and magnesium sulfate, to afford tert-butyl 4-(methylamino)-1-oxa-9-azaspiro[5.5]undecane-9-carboxylate.

28. Prior to the final deprotection, intermediate (2R)-1,1,1-trifluoro-3-[(4-methoxybenzyl)oxy]propan-2-yl 4-{[(cyclopropylmethyl)sulfonyl](methyl)amino}-1-oxa-9-azaspiro[5.5]undecane-9-carboxylate was separated into its component diastereomers via supercritical fluid chromatography [Column: Chiral Technologies Chiralpak AD, 5 μm; Mobile phase: 3:1 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 50, LCMS m/z 459.1 [M+H]$^+$, which exhibited the following biological data: MAGL (T=30 min) IC$_{50}$=0.284 μM.

29. Prior to the final deprotection, intermediate (2R)-1,1,1-trifluoro-3-[(4-methoxybenzyl)oxy]propan-2-yl 3-(3-tert-butyl-1H-pyrazol-1-yl)-1-oxa-8-azaspiro[4.5]decane-8-carboxylate was separated into its component diastereomers via supercritical fluid chromatography [Column: Chiral Technologies Chiralcel OJ, 5 μm; Mobile phase: 85:15 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 52, LCMS m/z 420.1 [M+H]$^+$, which exhibited the following biological data: MAGL (T=30 min) IC$_{50}$=0.004 μM.

30. Prior to the final deprotection, intermediate (2R)-1,1,1-trifluoro-3-[(4-methoxybenzyl)oxy]propan-2-yl 3-[3-(trifluorom ethyl)-1H-pyrazol-1-yl]-1-oxa-8-azaspiro[4.5]decane-8-carboxylate was separated into its component diastereomers via supercritical fluid chromatography [Column: Chiral Technologies Chiralpak AD, 5 μm; Mobile phase: 85:15 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 53, LCMS m/z 432.0 [M+H]$^+$, which exhibited the following biological data: MAGL (T=30 min) IC$_{50}$=0.009 μM.

31. Prior to the final deprotection, intermediate (2R)—,1,1,1-trifluoro-3-[(4-methoxybenzyl)oxy]propan-2-yl 3-(3,4-dimethyl-1H-pyrazol-1-yl)-1-oxa-8-azaspiro[4.5]decane-8-carboxylate was separated into its component diastereomers via supercritical fluid chromatography (Column: Chiral Technologies Chiralpak AD, 5 μm; Mobile phase: 4:1 carbon dioxide/methanol). The first-eluting diastereomer was assigned as DIAST 1, and the second-eluting diastereomer as DIAST 2. DIAST 1 was used to synthesize the diastereomer of Example 54, LCMS m/z 392.1 [M+H]$^+$, which exhibited the following biological data: MAGL (T=30 min) IC$_{50}$=0.020 μM.

32. Triphenylphosphine-mediated reaction of (3,3-difluorocyclobutyl)methanol and 2,2'-disulfanediylbis(1,3-benzothiazole) provided 2-{[(3,3-difluorocyclobutyl)methyl]sulfanyl}-1,3-benzothiazole, which was oxidized with 3-chloroperoxybenzoic acid to afford the corresponding sulfone. This material was reacted with sodium borohydride, and the resulting (3,3-difluorocyclobutyl)methanesulfinic acid was reacted with 1-chloromethyl-4-fluoro-1,4-diazoniabicyclo[2.2.2]octane bis(tetrafluoroborate) [Selectfluor®] to give (3,3-difluorocyclobutyl)methanesulfonyl fluoride. Sulfonamide formation with C23 was effected using barium bis(trifluoromethanesulfonimide), and the product (2R)-1,1,1-trifluoro-3-[(4-methoxybenzyl)oxy]propan-2-yl (3R)-3-[{[(3,3-difluorocyclobutyl)methyl]sulfonyl}(methyl)amino]-1-oxa-8-azaspiro[4.5]decane-8-carboxylate was deprotected with trifluoroacetic acid to afford Example 57.

33. In this case, the Mitsunobu reaction was effected using 1,1'-(azodicarbonyl)dipiperidine and tributylphosphine.

34. In this case, the intermediate sulfinamide was oxidized to the corresponding sulfonamide using 3-chloroperoxybenzoic acid rather than Oxone.

35. Reductive amination of tert-butyl 2-oxo-7-azaspiro[3.5]nonane-7-carboxylate with methylamine hydrochloride and sodium cyanoborohydride afforded tert-butyl 2-(methylamino)-7-azaspiro[3.5]nonane-7-carboxylate. This material was converted to (2R)-1,1,1-trifluoro-3-[(4-methoxybenzyl)oxy]propan-2-yl 2-(methylamino)-7-azaspiro[3.5]nonane-7-carboxylate using the general procedure described for synthesis of C23 from C18 in Example 5.

36. Prior to the final deprotection, intermediate (2R)-1,1,1-trifluoro-3-[(4-methoxybenzyl)oxy]propan-2-yl 3-(1H-indazol-1-yl)-1-oxa-8-azaspiro[4.5]decane-8-carboxylate was separated into its component diastereomers via supercritical fluid chromatography [Column: Chiral Technologies Chiralcel OD, 5 μm; Mobile phase: 7:3 carbon dioxide/(ethanol containing 0.05% ammonium hydroxide)]. The first-eluting diastereomer was assigned as DIAST 1, and the second-eluting diastereomer as DIAST 2. DIAST 2 was used to synthesize the diastereomer of Example 62, LCMS m/z 414.0 [M+H]$^+$, which exhibited the following biological data: MAGL (T=30 min) IC$_{50}$=0.049 μM.

37. In this case, C3 was reacted with 1H-pyrazole-4-carbaldehyde and cesium carbonate to afford tert-butyl 2-(4-formyl-1H-pyrazol-1-yl)-7-azaspiro[3.5]nonane-7-carboxylate. This material was treated with (diethylamino)sulfur trifluoride to provide the requisite tert-butyl 2-[4-(difluoromethyl)-1H-pyrazol-1-yl]-7-azaspiro[3.5]nonane-7-carboxylate.

38. The requisite tert-butyl 2-(4,4,5,5-tetramethyl-1,3,2-dioxaborolan-2-yl)-7-azaspiro[3.5]non-1-ene-7-carboxylate was synthesized from tert-butyl 2-oxo-7-azaspiro[3.5]nonane-7-carboxylate, using the general method described for synthesis of C49 in Examples 14 and 15. In this case, N-(5-chloropyridin-2-yl)-1,1,1-trifluoro-N-[(trifluoromethyl)sulfonyl]methanesulfonamide was used for preparation of the enol trifluoromethanesulfonate, rather than 1,1,1-trifluoro-N-phenyl-N-[(trifluoromethyl)sulfonyl]methanesulfonamide.

39. tert-Butyl 3-hydroxy-1-oxa-9-azaspiro[5.5]undecane-9-carboxylate was treated with methanesulfonyl chloride and triethylamine, affording tert-butyl 3-[(methylsulfonyl)oxy]-1-oxa-9-azaspiro[5.5]undecane-9-carboxylate. This material, rather than the corresponding bromide, was used in synthesis of the Example.

40. Prior to the final deprotection, intermediate (2R)-1,1,1-trifluoro-3-[(4-methoxybenzyl)oxy]propan-2-yl 3-[4-(trifluoromethyl)-1H-pyrazol-1-yl]-1-oxa-9-azaspiro[5.5]undecane-9-carboxylate was separated into its component diastereomers via supercritical fluid chromatography [Column: Chiral Technologies Chiralpak AD, 10 μm; Mobile phase: 4:1 carbon dioxide/(methanol containing 0.1% ammonium hydroxide)]. The first-eluting diastereomer was assigned as DIAST 1, and the second-eluting diastereomer as DIAST 2. DIAST 2 was used to synthesize the diastereomer of Example 69, LCMS m/z 446.2 [M+H]$^+$, which exhibited the following biological data: MAGL (T=30 min) IC$_{50}$=0.003 µM.

41. Prior to the final deprotection, intermediate (2R)—,1,1,1-trifluoro-3-[(4-methoxybenzyl)oxy]propan-2-yl 3-(4-fluoro-1H-pyrazol-1-yl)-1-oxa-9-azaspiro[5.5]undecane-9-carboxylate was separated into its component diastereomers via supercritical fluid chromatography [Column: Chiral Technologies Chiralpak AD, 5 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 2 was used to synthesize the diastereomer of Example 70, LCMS m/z 396.1 [M+H]$^+$, which exhibited the following biological data: MAGL (T=30 min) IC$_{50}$=0.014 µM.

42. In this case, C45 was coupling with the appropriate aryl bromide in the presence of nickel(II) iodide, 4,4'-di-tert-butyl-2,2'-bipyridine, zinc powder, and pyridine.

43. Prior to the final deprotection, intermediate (2R)-1,1,1-trifluoro-3-[(4-methoxybenzyl)oxy]propan-2-yl 3-(3-cyano-2-fluorophenyl)-1-oxa-8-azaspiro[4.5]decane-8-carboxylate was separated into its component diastereomers via supercritical fluid chromatography [Column: Chiral Technologies Chiralpak AD, 10 µm; Mobile phase: 65:35 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 71, LCMS m/z 417.0 [M+H]$^+$, which exhibited the following biological data: MAGL (T=30 min) IC$_{50}$=0.008 µM.

44. Prior to the final deprotection, intermediate (2R)-1,1,1-trifluoro-3-[(4-methoxybenzyl)oxy]propan-2-yl 3-(4-cyano-2-fluorophenyl)-1-oxa-8-azaspiro[4.5]decane-8-carboxylate was separated into its component diastereomers via supercritical fluid chromatography [Column: Chiral Technologies Chiralpak AD, 10 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 72, LCMS m/z 417.0 [M+H]$^+$, which exhibited the following biological data: MAGL (T=30 min) IC$_{50}$=0.012 µM.

45. Swern oxidation of tert-butyl 4-hydroxy-1-oxa-9-azaspiro[5.5]undecane-9-carboxylate provided tert-butyl 4-oxo-1-oxa-9-azaspiro[5.5]undecane-9-carboxylate, which was converted to tert-butyl 4-{[(trifluoromethyl)sulfonyl]oxy}-1-oxa-9-azaspiro[5.5]undec-4-ene-9-carboxylate using the method employed for synthesis of C48 in Examples 14 and 15. This was then reacted with (3-carbamoylphenyl)boronic acid in the presence of sodium carbonate to afford tert-butyl 4-(3-carbamoylphenyl)-1-oxa-9-azaspiro[5.5]undec-4-ene-9-carboxylate. After hydrogenation of the double bond, the amide functional group was converted to a nitrile via treatment with trifluoroacetic anhydride and triethylamine.

46. Prior to the final deprotection, intermediate (2R)-1,1,1-trifluoro-3-[(4-methoxybenzyl)oxy]propan-2-yl 4-(3-cyanophenyl)-1-oxa-9-azaspiro[5.5]undecane-9-carboxylate was separated into its component diastereomers via supercritical fluid chromatography [Column: Chiral Technologies Chiralpak AD, 10 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 73, LCMS m/z 413.3 [M+H]$^+$, which exhibited the following biological data: MAGL (T=30 min) IC$_{50}$=0.074 µM.

47. Prior to the final deprotection, intermediate (2R)-1,1,1-trifluoro-3-[(4-methoxybenzyl)oxy]propan-2-yl 3-(5-fluoropyridin-2-yl)-1-oxa-9-azaspiro[5.5]undecane-9-carboxylate was separated into its component diastereomers via supercritical fluid chromatography [Column: Chiral Technologies ChiralCel OD, 5 µm; Mobile phase: 3:1 carbon dioxide/(ethanol containing 0.1% ammonium hydroxide)]. The first-eluting diastereomer was assigned as DIAST 1, and the second-eluting diastereomer as DIAST 2. DIAST 1 was used to synthesize the diastereomer of Example 74, LCMS m/z 407.1 [M+H]$^+$, which exhibited the following biological data: MAGL (T=30 min) IC$_{50}$=0.015 µM.

48. tert-Butyl 3-[(methylsulfonyl)oxy]-1-oxa-9-azaspiro[5.5]undecane-9-carboxylate was reacted with 1H-pyrazole-4-carbaldehyde and cesium carbonate to afford tert-butyl 3-(4-formyl-1H-pyrazol-1-yl)-1-oxa-9-azaspiro[5.5]undecane-9-carboxylate. This material was treated with (diethylamino)sulfur trifluoride to provide the requisite tert-butyl 3-[4-(difluoromethyl)-1H-pyrazol-1-yl]-1-oxa-9-azaspiro[5.5]undecane-9-carboxylate.

49. Prior to the final deprotection, (2R)-1,1,1-trifluoro-3-[(4-methoxybenzyl)oxy]propan-2-yl 3-[4-(difluoromethyl)-1H-pyrazol-1-yl]-1-oxa-9-azaspiro[5.5]undecane-9-carboxylate was separated into its component diastereomers via supercritical fluid chromatography [Column: Chiral Technologies Chiralpak AD, 5 µm; Mobile phase: 3:2 carbon dioxide/(methanol containing 0.1% ammonium hydroxide)]. The first-eluting diastereomer was assigned as DIAST 1, and the second-eluting diastereomer as DIAST 2. DIAST 1 was used to synthesize the diastereomer of Example 75, LCMS m/z 428.1 [M+H]$^+$, which exhibited the following biological data: MAGL (T=30 min) IC$_{50}$=0.003 µM.

50. 2-Bromo-6-(trifluoromethyl)pyridine was lithiated by reaction with n-butyllithium and then combined with tert-butyl 2-oxo-7-azaspiro[3.5]nonane-7-carboxylate; the resulting tert-butyl 2-hydroxy-2-[6-(trifluoromethyl)pyridin-2-yl]-7-azaspiro[3.5]nonane-7-carboxylate was dehydrated via exposure to thionyl chloride, pyridine and 4-(dimethylamino)pyridine to provide tert-butyl 2-[6-(trifluoromethyl)pyridin-2-yl]-7-azaspiro[3.5]non-1-ene-7-carboxylate. This material was converted to Example 76 using the method described for synthesis of Examples 14 and 15 from C50.

51. In this case, the Suzuki coupling was carried out between tert-butyl 2-(4,4,5,5-tetramethyl-1,3,2-dioxaborolan-2-yl)-7-azaspiro[3.5]non-1-ene-7-carboxylate and 6-bromopyridine-3-carboxamide. After hydrogenation of the double bond, the amide functional group was converted to the corresponding nitrile via treatment with trifluoroacetic anhydride and triethylamine, affording tert-butyl 2-(5-cyanopyridin-2-yl)-7-azaspiro[3.5]nonane-7-carboxylate.

52. Reaction of 7-azaspiro[3.5]nonan-2-ol with triethylamine and C2 provided (2R)-1,1,1-trifluoro-3-[(4-methoxybenzyl)oxy]propan-2-yl 2-hydroxy-7-azaspiro[3.5]nonane-7-carboxylate. Ether formation with 2-bromo-5-(difluoromethyl)pyridine was carried out using sodium hydride to afford (2R)-1,1,1-trifluoro-3-[(4-methoxybenzyl)oxy]propan-2-yl 2-{[5-(difluoromethyl)pyridin-2-yl]oxy}-7-azaspiro[3.5]nonane-7-carboxylate; subsequent deprotection using trifluoroacetic acid yielded Example 85.

53. Reaction of 7-azaspiro[3.5]nonan-2-ol with triethylamine and C2 provided (2R)-1,1,1-trifluoro-3-[(4-methoxybenzyl)oxy]propan-2-yl 2-hydroxy-7-azaspiro[3.5]nonane-7-carboxylate. This material was treated with 2-bromopyridine in the presence of (R)-1-[(S$_P$)-2-(diphenylphosphino)ferrocenyl]ethyldi-tert-butylphosphine (Josiphos SL-J002-1), tris(dibenzylideneacetone)dipalladium(0), and cesium carbonate to afford (2R)-1,1,1-trifluoro-3-[(4-methoxybenzyl)oxy]propan-2-yl 2-(pyridin-2-yloxy)-7-azaspiro[3.5]nonane-7-carboxylate, which was deprotected with trifluoroacetic acid to yield Example 87.

54. In this case, the first step was carried out via reaction of tert-butyl 2-hydroxy-7-azaspiro[3.5]nonane-7-carboxylate with 2-bromo-4-(difluoromethyl)pyridine in the presence of (R)-1-[(Sp)-2-(diphenylphosphino)ferrocenyl]ethyldi-tert-butylphosphine (Josiphos SL-J002-1), tris(dibenzylideneacetone)dipalladium(0), and cesium carbonate, to provide tert-butyl 2-{[4-(difluoromethyl)pyridin-2-yl]oxy}-7-azaspiro[3.5]nonane-7-carboxylate.

Example AA: MAGL Enzymatic Assay

Assessment of MAGL inhibition utilizes human recombinant Monoacylglycerol Lipase and the fluorogenic substrate 7-hydroxycoumarinyl arachidonate (7-HCA, Biomol ST-502). 400 nL of a test compound at decreasing concentration (ranging from 150 μM down to 1.5 nM) was spotted into a 384-well back plate (PerkinElmer, 6007279) using a Labcyte Echo, followed by addition of 10 μL of MAGL enzyme in assay buffer (50 mM HEPES, pH 7.4, 100 mM NaCl, 5 mM $MgCl_2$, 0.1% Triton X-100 and 25% glycerin). An equal volume of 7-HCA in assay buffer with 10% DMSO was added either immediately (T=0 min) or after a 30 minute incubation (T=30 min) to initiate the reaction. The final concentration of MAGL enzyme was 88 μM and 7-HCA substrate was 5 μM. After these dilutions, the final concentration of the test compound ranged from 3 μM to 0.03 nM. The reaction was allowed to progress for 60 minutes, after which the plate was read at an Ex/Em of 340/465. Percent inhibitions were calculated based on control wells containing no compound (0% inhibition) and a control compound (e.g., a MAGL inhibitor whose activity is known or was previously reported in the literature, such as one with about 100% inhibition). $IC_{50}$ values were generated based on a four parameter fit model using ABASE software from IDBS. See e.g., Wang, Y. et al., "A Fluorescence-Based Assay for Monoacylglycerol Lipase Compatible with Inhibitor Screening," *Assay and Drug Development Technologies*, 2008, Vol. 6 (3) pp 387-393 (reporting an assay for measuring MAGL activity).

To measure MAGL inactivation, the same protocol for the (T=0 min) MAGL inhibition $IC_{50}$ assay was performed with data collected every minute to acquire enzyme progress curves at decreasing concentrations of compound. $K_{obs}$ values were calculated from this data and $k_{inact}/K_I$ ratios were determined from a plot of $K_{obs}$ values vs. compound concentrations.

TABLE 19

Biological Data (MAGL $IC_{50}$, and MAGL $k_{inact}/K_I$) for Examples 1-90.

| Example Number | MAGL (T = 0 min) $IC_{50}$ (μM)$^a$ | MAGL (T = 30 min) $IC_{50}$ (μM)$^a$ | MAGL $k_{inact}/K_I$ (1/s per M)$^a$ | Compound Name |
|---|---|---|---|---|
| 1 | 0.012 | 0.002 | 22200 | (2R)-1,1,1-trifluoro-3-hydroxypropan-2-yl 2-[4-(trifluoromethyl)-1H-pyrazol-1-yl]-7-azaspiro[3.5]nonane-7-carboxylate |
| 2 | 0.021 | 0.002 | 33800 | (2R)-1,1,1-trifluoro-3-hydroxypropan-2-yl 2-(5-fluoropyridin-2-yl)-7-azaspiro[3.5]nonane-7-carboxylate |
| 3 | 0.047 | 0.007 | 10300 | (2R)-1,1,1-trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 1 [From C13, DIAST 1] |
| 4 | 0.065 | 0.008 | 4710 | (2R)-1,1,1-trifluoro-3-hydroxypropan-2-yl 3-{[4-(trifluoromethyl)-1H-pyrazol-1-yl]methyl}-1-oxa-8-azaspiro[4.5]decane-8-carboxylate, DIAST 2 [From C14, DIAST 2] |
| 5 | 0.067 | 0.007 | 5530 | (2R)-1,1,1-trifluoro-3-hydroxypropan-2-yl (3R)-3-[(cyclopentylcarbonyl)(methyl)amino]-1-oxa-8-azaspiro[4.5]decane-8-carboxylate |
| 6 | 0.098 | 0.008 | 6630$^b$ | (2R)-1,1,1-trifluoro-3-hydroxypropan-2-yl (3R)-3-[(tert-butylsulfonyl)(methyl)amino]-1-oxa-8-azaspiro[4.5]decane-8-carboxylate |
| 7 | 0.037 | 0.003 | 19700 | (2R)-1,1,1-trifluoro-3-hydroxypropan-2-yl (3R)-3-[(2,2-dimethylpropanoyl)(methyl)amino]-1-oxa-8-azaspiro[4.5]decane-8-carboxylate |
| 8 | 0.172 | 0.016 | 2880 | (2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 1 [From C39, DIAST 1] |
| 9 | 0.016 | 0.003 | 32800 | (2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 2 [From C40, DIAST 2] |
| 10 | 0.563 | 0.049 | N.D.$^c$ | (2R)-1,1,1-trifluoro-3-hydroxypropan-2-yl (3S)-3-(4-fluoro-1H-pyrazol-1-yl)-1-oxa-8-azaspiro[4.5]decane-8-carboxylate |
| 11 | 0.211 | 0.015 | 4210 | (2R)-1,1,1-trifluoro-3-hydroxypropan-2-yl (3R)-3-(4-fluoro-1H-pyrazol-1-yl)-1-oxa-8-azaspiro[4.5]decane-8-carboxylate |
| 12 | 0.282 | 0.030 | 1680 | (2R)-1,1,1-trifluoro-3-hydroxypropan-2-yl (3R)-3-(3-cyanophenyl)-1-oxa-8-azaspiro[4.5]decane-8-carboxylate |

TABLE 19-continued

Biological Data (MAGL IC$_{50}$, and MAGL k$_{inact}$/K$_I$) for Examples 1-90.

| Example Number | MAGL (T = 0 min) IC$_{50}$ (μM)$^a$ | MAGL (T = 30 min) IC$_{50}$ (μM)$^a$ | MAGL k$_{inact}$/K$_I$ (1/s per M)$^a$ | Compound Name |
|---|---|---|---|---|
| 13 | 0.035 | 0.003 | 12300 | (2R)-1,1,1-trifluoro-3-hydroxypropan-2-yl (3S)-3-(3-cyanophenyl)-1-oxa-8-azaspiro[4.5]decane-8-carboxylate |
| 14 | 0.005 | 0.001 | 124000$^b$ | (2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 1 [From C54, DIAST 1] |
| 15 | 0.067 | 0.007 | 8230 | (2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 2 [From C55, DIAST 2] |
| 16 | 0.092 | 0.009 | 5010$^b$ | (2R)-1,1,1-trifluoro-3-hydroxypropan-2-yl 3-(5-fluoropyridin-2-yl)-1-oxa-8-azaspiro[4.5]decane-8-carboxylate, DIAST 1 [From C59, DIAST 1] |
| 17 | 0.297 | 0.026 | 1390$^b$ | (2R)-1,1,1-trifluoro-3-hydroxypropan-2-yl 3-(5-fluoropyridin-2-yl)-1-oxa-8-azaspiro[4.5]decane-8-carboxylate, DIAST 2 [From C60, DIAST 2] |
| 18 | 0.052 | 0.004 | 14900 | (2R)-1,1,1-trifluoro-3-hydroxypropan-2-yl 2-{[(cyclopropylmethyl)sulfonyl](methyl)amino}-7-azaspiro[3.5]nonane-7-carboxylate |
| 19 | 0.008 | 0.001 | 78900 | (2R)-1,1,1-trifluoro-3-hydroxypropan-2-yl 2-{[6-(difluoromethyl)pyridin-3-yl]oxy}-7-azaspiro[3.5]nonane-7-carboxylate |
| 20 | 0.107 | 0.011 | 7170 | (2R)-1,1,1-trifluoro-3-hydroxypropan-2-yl 3-[4-(difluoromethyl)-1H-pyrazol-1-yl]-1-oxa-8-azaspiro[4.5]decane-8-carboxylate [From DIAST 2 in footnote 2, Table 18] |
| 21 | 0.009 | 0.002 | 24400 | (2R)-1,1,1-trifluoro-3-hydroxypropan-2-yl 3-(4-tert-butyl-1H-pyrazol-1-yl)-1-oxa-8-azaspiro[4.5]decane-8-carboxylate, DIAST 2 [From DIAST 2 in footnote 3, Table 18] |
| 22 | 0.049 | 0.004 | 9780 | (2R)-1,1,1-trifluoro-3-hydroxypropan-2-yl 3-(4-chloro-1H-pyrazol-1-yl)-1-oxa-8-azaspiro[4.5]decane-8-carboxylate, DIAST 2 [From DIAST 2 in footnote 4, Table 18] |
| 23 | 0.068 | 0.009 | 9650 | (2R)-1,1,1-trifluoro-3-hydroxypropan-2-yl 3-(4-cyclopropyl-1H-pyrazol-1-yl)-1-oxa-8-azaspiro[4.5]decane-8-carboxylate, mixture of diastereomers |
| 24 | 0.115 | 0.012 | 7840 | (2R)-1,1,1-trifluoro-3-hydroxypropan-2-yl 3-(4-methyl-1H-pyrazol-1-yl)-1-oxa-8-azaspiro[4.5]decane-8-carboxylate, DIAST 2 [From DIAST 2 in footnote 6, Table 18] |
| 25 | 0.020 | 0.002 | 25500 | (2R)-1,1,1-trifluoro-3-hydroxypropan-2-yl 3-(2-fluorophenyl)-1-oxa-8-azaspiro[4.5]decane-8-carboxylate, DIAST 1 [From DIAST 1 in footnote 8, Table 18] |
| 26 | 0.008 | 0.001 | 87700 | (2R)-1,1,1-trifluoro-3-hydroxypropan-2-yl 3-(2-fluorophenyl)-1-oxa-8-azaspiro[4.5]decane-8-carboxylate, DIAST 2 [From DIAST 2 in footnote 8, Table 18] |
| 27 | 0.017 | 0.003 | 22800 | (2R)-1,1,1-trifluoro-3-hydroxypropan-2-yl (3S)-3-(4-cyano-3-fluorophenyl)-1-oxa-8-azaspiro[4.5]decane-8-carboxylate |
| 28 | 0.027 | 0.003 | 16900 | (2R)-1,1,1-trifluoro-3-hydroxypropan-2-yl 3-(3-cyano-4-fluorophenyl)-1-oxa-8-azaspiro[4.5]decane-8-carboxylate, DIAST 2 [From DIAST 2 in footnote 11, Table 18] |
| 29 | 0.184 | 0.017 | 3250 | (2R)-1,1,1-trifluoro-3-hydroxypropan-2-yl 3-(5-cyano-2-fluorophenyl)-1-oxa-8-azaspiro[4.5]decane-8-carboxylate, DIAST 1 [From DIAST 1 in footnote 13, Table 18] |
| 30 | 0.054 | 0.004 | 14400 | (2R)-1,1,1-trifluoro-3-hydroxypropan-2-yl 3-(5-cyano-2-fluorophenyl)-1-oxa-8-azaspiro[4.5]decane-8-carboxylate, DIAST 2 [From DIAST 2 in footnote 13, Table 18] |
| 31 | 0.033 | 0.004 | 8060 | (2R)-1,1,1-trifluoro-3-hydroxypropan-2-yl 3-(4-cyanophenyl)-1-oxa-8-azaspiro[4.5]decane-8-carboxylate, DIAST 2 [From DIAST 2 in footnote 14, Table 18] |

TABLE 19-continued

Biological Data (MAGL IC$_{50}$, and MAGL k$_{inact}$/K$_I$) for Examples 1-90.

| Example Number | MAGL (T = 0 min) IC$_{50}$ (μM)$^a$ | MAGL (T = 30 min) IC$_{50}$ (μM)$^a$ | MAGL k$_{inact}$/K$_I$ (1/s per M)$^a$ | Compound Name |
|---|---|---|---|---|
| 32 | 0.005 | 0.0004 | 233000 | (2R)-1,1,1-trifluoro-3-hydroxypropan-2-yl 3-(2,6-difluorophenyl)-1-oxa-8-azaspiro[4.5]decane-8-carboxylate, DIAST 1 [From DIAST 1 in footnote 15, Table 18] |
| 33 | 0.010 | 0.001 | 53400 | (2R)-1,1,1-trifluoro-3-hydroxypropan-2-yl 3-(2,4-difluorophenyl)-1-oxa-8-azaspiro[4.5]decane-8-carboxylate, DIAST 2 [From DIAST 2 in footnote 16, Table 18] |
| 34 | 0.048 | 0.004 | 7920 | (2R)-1,1,1-trifluoro-3-hydroxypropan-2-yl 3-(4-fluorophenyl)-1-oxa-8-azaspiro[4.5]decane-8-carboxylate, DIAST 1 [From DIAST 1 in footnote 17, Table 18] |
| 35 | 0.031 | 0.003 | 23000 | (2R)-1,1,1-trifluoro-3-hydroxypropan-2-yl 3-[4-(difluoromethyl)pyridin-2-yl]-1-oxa-8-azaspiro[4.5]decane-8-carboxylate, DIAST 1 [From DIAST 1 in footnote 18, Table 18] |
| 36 | 0.239 | 0.027 | 1440 | (2R)-1,1,1-trifluoro-3-hydroxypropan-2-yl 3-[6-(difluoromethyl)pyridin-3-yl]-1-oxa-8-azaspiro[4.5]decane-8-carboxylate, DIAST 1 [From DIAST 1 in footnote 19, Table 18] |
| 37 | 0.057 | 0.008 | 3840 | (2R)-1,1,1-trifluoro-3-hydroxypropan-2-yl 3-[6-(difluoromethyl)pyridin-3-yl]-1-oxa-8-azaspiro[4.5]decane-8-carboxylate, DIAST 2 [From DIAST 2 in footnote 19, Table 18] |
| 38 | 0.200 | 0.024 | 1610 | (2R)-1,1,1-trifluoro-3-hydroxypropan-2-yl 3-(5-cyanopyridin-2-yl)-1-oxa-8-azaspiro[4.5]decane-8-carboxylate, DIAST 2 [From DIAST 2 in footnote 20, Table 18] |
| 39 | 0.043 | 0.005 | 5180 | (2R)-1,1,1-trifluoro-3-hydroxypropan-2-yl 3-[5-(difluoromethyl)pyridin-2-yl]-1-oxa-8-azaspiro[4.5]decane-8-carboxylate, DIAST 2 [From DIAST 2 in footnote 22, Table 18] |
| 40 | 0.009 | 0.003 | 21800 | (2R)-1,1,1-trifluoro-3-hydroxypropan-2-yl 3-[5-(trifluoromethyl)pyridin-2-yl]-1-oxa-8-azaspiro[4.5]decane-8-carboxylate, DIAST 2 [From DIAST 2 in footnote 23, Table 18] |
| 41 | 0.076 | 0.007 | 13200 | (2R)-1,1,1-trifluoro-3-hydroxypropan-2-yl 3-(pyridin-2-yl)-1-oxa-8-azaspiro[4.5]decane-8-carboxylate, DIAST 2 [From DIAST 2 in footnote 25, Table 18] |
| 42 | 0.004 | 0.0004 | 309000 | (2R)-1,1,1-trifluoro-3-hydroxypropan-2-yl 2-[(2,2-dimethylpropanoyl)(methyl)amino]-7-azaspiro[3.5]nonane-7-carboxylate |
| 43 | 0.029 | 0.002 | 18500 | (2R)-1,1,1-trifluoro-3-hydroxypropan-2-yl 2-[(cyclopropylacetyl)(methyl)amino]-7-azaspiro[3.5]nonane-7-carboxylate |
| 44 | 0.040 | 0.004 | 13800 | (2R)-1,1,1-trifluoro-3-hydroxypropan-2-yl 2-[methyl(phenylacetyl)amino]-7-azaspiro[3.5]nonane-7-carboxylate |
| 45 | 0.009 | 0.001 | 63200 | (2R)-1,1,1-trifluoro-3-hydroxypropan-2-yl 2-[methyl(phenylsulfonyl)amino]-7-azaspiro[3.5]nonane-7-carboxylate |
| 46 | 0.004 | 0.001 | 167000 | (2R)-1,1,1-trifluoro-3-hydroxypropan-2-yl 2-(3-cyanophenyl)-7-azaspiro[3.5]nonane-7-carboxylate |
| 47 | 0.017 | 0.002 | 17100 | (2R)-1,1,1-trifluoro-3-hydroxypropan-2-yl 2-(2-methoxypyridin-4-yl)-7-azaspiro[3.5]nonane-7-carboxylate |
| 48 | 0.018 | 0.002 | 26000 | (2R)-1,1,1-trifluoro-3-hydroxypropan-2-yl 2-[5-(difluoromethyl)pyridin-2-yl]-7-azaspiro[3.5]nonane-7-carboxylate |
| 49 | 0.013 | 0.001 | 77400 | (2R)-1,1,1-trifluoro-3-hydroxypropan-2-yl 2-(4-cyclopropyl-1H-pyrazol-1-yl)-7-azaspiro[3.5]nonane-7-carboxylate, trifluoroacetate salt |
| 50 | 0.752 | 0.067 | N.D.$^c$ | (2R)-1,1,1-trifluoro-3-hydroxypropan-2-yl 4-{[(cyclopropylmethyl)sulfonyl](methyl)amino}-1-oxa-9-azaspiro[5.5]undecane-9-carboxylate, DIAST 2 [From DIAST 2 in footnote 28, Table 18] |
| 51 | 0.004 | 0.0003 | 128000 | (2R)-1,1,1-trifluoro-3-hydroxypropan-2-yl 2-(3-fluorophenoxy)-7-azaspiro[3.5]nonane-7-carboxylate |
| 52 | 0.004 | 0.001 | 200000 | (2R)-1,1,1-trifluoro-3-hydroxypropan-2-yl 3-(3-tert-butyl-1H-pyrazol-1-yl)-1-oxa-8-azaspiro[4.5]decane-8-carboxylate, DIAST 2 [From DIAST 2 in footnote 29, Table 18] |

TABLE 19-continued

Biological Data (MAGL IC$_{50}$, and MAGL k$_{inact}$/K$_I$) for Examples 1-90.

| Example Number | MAGL (T = 0 min) IC$_{50}$ (μM)$^a$ | MAGL (T = 30 min) IC$_{50}$ (μM)$^a$ | MAGL k$_{inact}$/K$_I$ (1/s per M)$^a$ | Compound Name |
|---|---|---|---|---|
| 53 | 0.009 | 0.001 | 66900 | (2R)-1,1,1-trifluoro-3-hydroxypropan-2-yl 3-[3-(trifluoromethyl)-1H-pyrazol-1-yl]-1-oxa-8-azaspiro[4.5]decane-8-carboxylate, DIAST 2 [From DIAST 2 in footnote 30, Table 18] |
| 54 | 0.021 | 0.004 | 26500 | (2R)-1,1,1-trifluoro-3-hydroxypropan-2-yl 3-(3,4-dimethyl-1H-pyrazol-1-yl)-1-oxa-8-azaspiro[4.5]decane-8-carboxylate, DIAST 2 [From DIAST 2 in footnote 31, Table 18] |
| 55 | 0.030 | 0.002 | 15700 | (2R)-1,1,1-trifluoro-3-hydroxypropan-2-yl 2-[(cyclopropylcarbonyl)(methyl)amino]-7-azaspiro[3.5]nonane-7-carboxylate |
| 56 | 0.310 | 0.030 | 1420 | (2R)-1,1,1-trifluoro-3-hydroxypropan-2-yl 2-(1H-pyrazol-1-yl)-7-azaspiro[3.5]nonane-7-carboxylate |
| 57 | 0.113 | 0.013 | 2770 | (2R)-1,1,1-trifluoro-3-hydroxypropan-2-yl (3R)-3-[{[(3,3-difluorocyclobutyl)methyl]sulfonyl}(methyl)amino]-1-oxa-8-azaspiro[4.5]decane-8-carboxylate |
| 58 | 0.169 | 0.021 | 1810 | (2R)-1,1,1-trifluoro-3-hydroxypropan-2-yl (3R)-3-{[(3,3-difluorocyclobutyl)carbonyl](methyl)amino}-1-oxa-8-azaspiro[4.5]decane-8-carboxylate |
| 59 | 0.005 | 0.001 | 137000 | (2R)-1,1,1-trifluoro-3-hydroxypropan-2-yl 2-{[2-(trifluoromethyl)pyridin-4-yl]oxy}-7-azaspiro[3.5]nonane-7-carboxylate |
| 60 | 0.002 | 0.0003 | 267000 | (2R)-1,1,1-trifluoro-3-hydroxypropan-2-yl 2-[3-(difluoromethyl)phenoxy]-7-azaspiro[3.5]nonane-7-carboxylate |
| 61 | 0.009 | 0.001 | 66900 | (2R)-1,1,1-trifluoro-3-hydroxypropan-2-yl 2-[(tert-butylsulfonyl)(methyl)amino]-7-azaspiro[3.5]nonane-7-carboxylate |
| 62 | 0.010 | 0.001 | 18100 | (2R)-1,1,1-trifluoro-3-hydroxypropan-2-yl 3-(1H-indazol-1-yl)-1-oxa-8-azaspiro[4.5]decane-8-carboxylate, DIAST 1 [From DIAST 1 in footnote 36, Table 18] |
| 63 | 0.011 | 0.001 | 34100 | (2R)-1,1,1-trifluoro-3-hydroxypropan-2-yl 2-phenoxy-7-azaspiro[3.5]nonane-7-carboxylate |
| 64 | 0.096 | 0.009 | 6260 | (2R)-1,1,1-trifluoro-3-hydroxypropan-2-yl 2-(4-fluoro-1H-pyrazol-1-yl)-7-azaspiro[3.5]nonane-7-carboxylate |
| 65 | 0.044 | 0.004 | 10600 | (2R)-1,1,1-trifluoro-3-hydroxypropan-2-yl 2-(3,4,5-trimethyl-1H-pyrazol-1-yl)-7-azaspiro[3.5]nonane-7-carboxylate |
| 66 | 0.040 | 0.004 | 15700 | (2R)-1,1,1-trifluoro-3-hydroxypropan-2-yl 2-[4-(difluoromethyl)-1H-pyrazol-1-yl]-7-azaspiro[3.5]nonane-7-carboxylate |
| 67 | 0.014 | 0.002 | 60600 | (2R)-1,1,1-trifluoro-3-hydroxypropan-2-yl 2-[6-(trifluoromethyl)pyridin-3-yl]-7-azaspiro[3.5]nonane-7-carboxylate |
| 68 | 0.009 | 0.0009 | 88300 | (2R)-1,1,1-trifluoro-3-hydroxypropan-2-yl 2-[2-(trifluoromethyl)pyridin-4-yl]-7-azaspiro[3.5]nonane-7-carboxylate |
| 69 | 0.010 | 0.001 | 71900 | (2R)-1,1,1-trifluoro-3-hydroxypropan-2-yl 3-[4-(trifluoromethyl)-1H-pyrazol-1-yl]-1-oxa-9-azaspiro[5.5]undecane-9-carboxylate, DIAST 1 [From DIAST 1 in footnote 40, Table 18] |
| 70 | 0.022 | 0.002 | 40400 | (2R)-1,1,1-trifluoro-3-hydroxypropan-2-yl 3-(4-fluoro-1H-pyrazol-1-yl)-1-oxa-9-azaspiro[5.5]undecane-9-carboxylate, DIAST 1 [From DIAST 1 in footnote 41, Table 18] |
| 71 | 0.029 | 0.003 | 17800 | (2R)-1,1,1-trifluoro-3-hydroxypropan-2-yl 3-(3-cyano-2-fluorophenyl)-1-oxa-8-azaspiro[4.5]decane-8-carboxylate, DIAST 2 [From DIAST 2 in footnote 43, Table 18] |
| 72 | 0.032 | 0.004 | 17000 | (2R)-1,1,1-trifluoro-3-hydroxypropan-2-yl 3-(4-cyano-2-fluorophenyl)-1-oxa-8-azaspiro[4.5]decane-8-carboxylate, DIAST 2 [From DIAST 2 in footnote 44, Table 18] |
| 73 | 0.026 | 0.003 | 8870 | (2R)-1,1,1-trifluoro-3-hydroxypropan-2-yl 4-(3-cyanophenyl)-1-oxa-9-azaspiro[5.5]undecane-9-carboxylate, DIAST 2 [From DIAST 2 in footnote 46, Table 18] |
| 74 | 0.069 | 0.006 | 7140 | (2R)-1,1,1-trifluoro-3-hydroxypropan-2-yl 3-(5-fluoropyridin-2-yl)-1-oxa-9-azaspiro[5.5]undecane-9-carboxylate [From DIAST 2 in footnote 47, Table 18] |

TABLE 19-continued

Biological Data (MAGL IC$_{50}$, and MAGL k$_{inact}$/K$_I$) for Examples 1-90.

| Example Number | MAGL (T = 0 min) IC$_{50}$ (μM)$^a$ | MAGL (T = 30 min) IC$_{50}$ (μM)$^a$ | MAGL k$_{inact}$/K$_I$ (1/s per M)$^a$ | Compound Name |
|---|---|---|---|---|
| 75 | 0.115 | 0.012 | 7370 | (2R)-1,1,1-trifluoro-3-hydroxypropan-2-yl 3-[4-(difluoromethyl)-1H-pyrazol-1-yl]-1-oxa-9-azaspiro[5.5]undecane-9-carboxylate, DIAST 2 [From DIAST 2 in footnote 49, Table 18] |
| 76 | 0.002 | 0.0002 | 206000 | (2R)-1,1,1-trifluoro-3-hydroxypropan-2-yl 2-[6-(trifluoromethyl)pyridin-2-yl]-7-azaspiro[3.5]nonane-7-carboxylate |
| 77 | 0.004 | 0.0006 | 82100 | (2R)-1,1,1-trifluoro-3-hydroxypropan-2-yl 2-[6-(difluoromethyl)pyridin-2-yl]-7-azaspiro[3.5]nonane-7-carboxylate |
| 78 | 0.009 | 0.001 | 75400 | (2R)-1,1,1-trifluoro-3-hydroxypropan-2-yl 2-[4-(difluoromethyl)pyridin-2-yl]-7-azaspiro[3.5]nonane-7-carboxylate |
| 79 | 0.008 | 0.001 | 63500 | (2R)-1,1,1-trifluoro-3-hydroxypropan-2-yl 2-[5-(trifluoromethyl)pyridin-2-yl]-7-azaspiro[3.5]nonane-7-carboxylate |
| 80 | 0.013 | 0.001 | 46200 | (2R)-1,1,1-trifluoro-3-hydroxypropan-2-yl 2-[2-(difluoromethyl)pyridin-4-yl]-7-azaspiro[3.5]nonane-7-carboxylate |
| 81 | 0.045 | 0.004 | 20400 | (2R)-1,1,1-trifluoro-3-hydroxypropan-2-yl 2-(pyridin-2-yl)-7-azaspiro[3.5]nonane-7-carboxylate |
| 82 | 0.024 | 0.002 | 19300 | (2R)-1,1,1-trifluoro-3-hydroxypropan-2-yl 2-[6-(difluoromethyl)pyridin-3-yl]-7-azaspiro[3.5]nonane-7-carboxylate |
| 83 | 0.005 | 0.0006 | 156000 | (2R)-1,1,1-trifluoro-3-hydroxypropan-2-yl 2-[4-(trifluoromethyl)pyridin-2-yl]-7-azaspiro[3.5]nonane-7-carboxylate |
| 84 | 0.143 | 0.015 | 4000 | (2R)-1,1,1-trifluoro-3-hydroxypropan-2-yl 2-(5-cyanopyridin-2-yl)-7-azaspiro[3.5]nonane-7-carboxylate |
| 85 | 0.004 | 0.0006 | 42100 | (2R)-1,1,1-trifluoro-3-hydroxypropan-2-yl 2-{[5-(difluoromethyl)pyridin-2-yl]oxy}-7-azaspiro[3.5]nonane-7-carboxylate |
| 86 | 0.009 | 0.0007 | 50100 | (2R)-1,1,1-trifluoro-3-hydroxypropan-2-yl 2-(3-cyanophenoxy)-7-azaspiro[3.5]nonane-7-carboxylate |
| 87 | 0.026 | 0.002 | 32600 | (2R)-1,1,1-trifluoro-3-hydroxypropan-2-yl 2-(pyridin-2-yloxy)-7-azaspiro[3.5]nonane-7-carboxylate |
| 88 | 0.016 | 0.001 | 33000 | (2R)-1,1,1-trifluoro-3-hydroxypropan-2-yl 2-[(5-fluoropyridin-2-yl)oxy]-7-azaspiro[3.5]nonane-7-carboxylate |
| 89 | 0.008 | 0.0008 | 31900 | (2R)-1,1,1-trifluoro-3-hydroxypropan-2-yl 2-{[4-(difluoromethyl)pyridin-2-yl]oxy}-7-azaspiro[3.5]nonane-7-carboxylate |
| 90 | 0.009 | 0.0005 | 71700 | (2R)-1,1,1-trifluoro-3-hydroxypropan-2-yl 2-{[6-(difluoromethyl)pyridin-2-yl]oxy}-7-azaspiro[3.5]nonane-7-carboxylate |

$^a$Reported IC$_{50}$ values or k$_{inact}$/K$_I$ values are the geometric mean of 2-5 determinations, unless otherwise indicated.
$^b$The reported IC$_{50}$ value or k$_{inact}$/K$_I$ value is the geometric mean of ≥6 determinations.
$^c$N.D. = not determined Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A compound of Formula I:

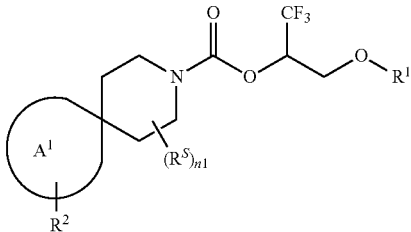

or a pharmaceutically acceptable salt thereof, wherein:
$R^1$ is H, —P(=O)(OR$^{81}$)(OR$^{82}$); or —S(=O)$_2$OR$^{90}$;
each of $R^{81}$, $R^{82}$, and $R^{90}$ is independently selected from the group consisting of H and $C_{1-6}$ alkyl, wherein each of the $C_{1-6}$ alkyl is optionally substituted with one or more substituents each independently selected from the group consisting of —NH$_2$, —NH($C_{1-4}$ alkyl), and —N($C_{1-4}$ alkyl)$_2$;
each $R^S$ is independently selected from the group consisting of OH, oxo, halogen, $C_{1-4}$ alkyl, $C_{1-4}$ haloalkyl, $C_{3-4}$ cycloalkyl, $C_{3-4}$ cycloalkyl-$C_{1-2}$ alkyl-, $C_{1-4}$ alkoxy, and $C_{1-4}$ haloalkoxy;
n1 is 0, 1, 2, 3, 4, 5, or 6;
the moiety of Formula M-1 of Formula I

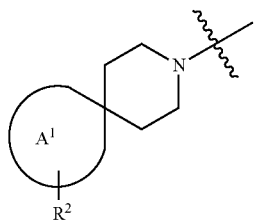

is a moiety of Formula M-1a, M-1b, or M-1c:

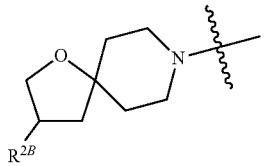

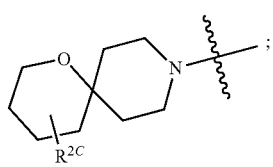

each of $R^{2A}$ and $R^{2C}$ is, independently, —NR$^3$S(=O)$_2$R$^4$, —NR$^3$C(=O)R$^4$; R$^5$, or —OR$^5$;

$R^{2B}$ is selected from the group consisting of [4-(trifluoromethyl)-1H-pyrazol-1-yl]methyl-, (cyclopentylcarbonyl)(methyl)amino-, (tert-butylsulfonyl)(methyl)amino-, (2,2-dimethylpropanoyl)(methyl)amino-, 4-(trifluoromethyl)-1H-pyrazol-1-yl-, 4-fluoro-1H-pyrazol-1-yl-, 3-cyanophenyl-, 6-(trifluoromethyl)pyridin-2-yl-, 5-fluoropyridin-2-yl-, 4-(difluoromethyl)-1H-pyrazol-1-yl-, 4-tert-butyl-1H-pyrazol-1-yl-, 4-chloro1-1H-pyrazol-1-yl-, 4-cyclopropyl-1H-pyrazol-1-yl-, 4-methyl-1H-pyrazol-1-yl-, 2-fluorophenyl-, 4-cyano-3-fluorophenyl-, 3-cyano-4-fluorophenyl-, 5-cyano-2-fluorophenyl-, 4-cyanophenyl-, 2,6-difluorophenyl-, 2,4-difluorophenyl-, 4-fluorophenyl-, 4-(difluoromethyl)pyridin-2-yl-, 6-(difluoromethyl)pyridin-3-yl-, 5-cyanopyridin-2-yl-, 5-(difluoromethyl)pyridin-2-yl-, 5-(trifluoromethyl)pyridin-2-yl-, pyridin-2-yl-, 3-tert-butyl-1H-pyrazol-1-yl-, 3-(trifluoromethyl)-1H-pyrazol-1-yl-, 3,4-dimethyl-1H-pyrazol-1-yl-, {[(3,3-difluorocyclobutyl)methyl]sulfonyl}(methyl)amino-, [(3,3-difluorocyclobutyl)carbonyl](methyl)amino-, 1H-indazol-1-yl-, 3-cyano-2-fluorophenyl-, and 4-cyano-2-fluorophenyl-;
each $R^3$ is independently $C_{1-3}$ alkyl;
each $R^4$ is independently selected from $C_{1-6}$ alkyl, $C_{3-7}$ cycloalkyl, ($C_{3-7}$ cycloalkyl)-$C_{1-2}$ alkyl-, ($C_{6-10}$ aryl)-$C_{1-2}$ alkyl-, (5- or 10-membered heteroaryl)-$C_{1-2}$ alkyl-, 5- or 10-membered heteroaryl, and $C_{6-10}$ aryl, wherein each of the selections is substituted with 0, 1, 2, or 3 halogen;
or $R^3$ and $R^4$, together with the intervening moiety of "—NS(=O)$_2$—" or "—NC(=O)—" to which they are attached, form a 4- to 10-membered heterocycloalkyl that is substituted with 0, 1, 2, 3, 4, or 5 substituents each independently selected from the group consisting of OH, oxo, halogen, $C_{1-4}$ alkyl, $C_{1-4}$ haloalkyl, $C_{1-4}$ alkoxy, and $C_{1-4}$ haloalkoxy, and wherein each of the ring-forming atoms of the 4- to 10-membered heterocycloalkyl is C, N, O, or S; and
each $R^5$ is phenyl or 5- or 6-membered heteroaryl, wherein each of the phenyl or 5- or 6-membered heteroaryl is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy, and wherein each of the ring-forming atoms of the 5- or 6-membered heteroaryl is a carbon atom or a nitrogen atom.

2. The compound of claim 1 or a pharmaceutically acceptable salt thereof, wherein each $R^S$ is independently selected from the group consisting of halogen, $C_{1-2}$ alkyl, $C_{1-2}$ haloalkyl, $C_{1-2}$ alkoxy, and $C_{1-2}$ haloalkoxy.

3. The compound of claim 2 or a pharmaceutically acceptable salt thereof, wherein n1 is 0.

4. The compound of claim 3, or a pharmaceutically acceptable salt thereof, wherein each $R^3$ is independently $C_{1-3}$ alkyl; and each $R^4$ is independently selected from $C_{1-6}$ alkyl, $C_{3-7}$ cycloalkyl, ($C_{3-7}$ cycloalkyl)-$C_{12}$ alkyl-, ($C_{6-10}$ aryl)-$C_{1-2}$ alkyl-, (5- or 10-membered heteroaryl)-$C_{1-2}$ alkyl-, 5- or 10-membered heteroaryl, and $C_{6-10}$ aryl, wherein each of the selections is substituted with 0, 1, 2, or 3 halogen.

5. The compound of claim 3, or a pharmaceutically acceptable salt thereof, wherein each $R^3$ is independently $C_{1-3}$ alkyl; and each $R^4$ is independently selected from $C_{1-6}$ alkyl, $C_{3-7}$ cycloalkyl, ($C_{3-7}$ cycloalkyl)-$C_{1-2}$ alkyl-, ($C_{6-10}$ aryl)-$C_{1-2}$ alkyl-, and $C_{6-10}$ aryl, wherein each of the selections is substituted with 0, 1, 2, or 3 halogen.

6. The compound of claim 3 or a pharmaceutically acceptable salt thereof, wherein the compound is a compound of Formula I-1, I-2, or I-3:

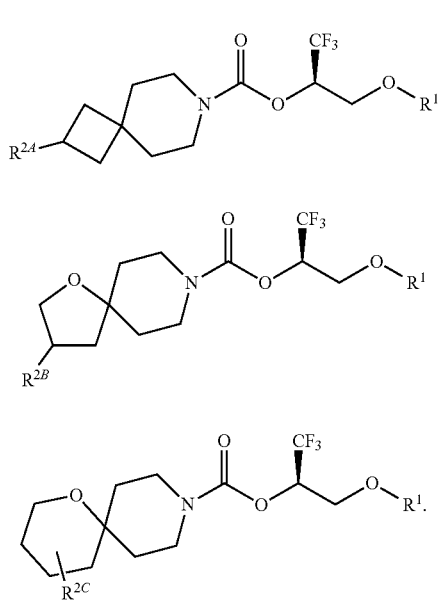

7. The compound of claim 6, or a pharmaceutically acceptable salt thereof, wherein $R^1$ is H or —P(=O)(OH)(OH).

8. The compound of claim 7, or a pharmaceutically acceptable salt thereof, wherein $R^1$ is H.

9. The compound of claim 6, or a pharmaceutically acceptable salt thereof, wherein the compound is a compound of Formula I-1.

10. The compound of claim 6, or a pharmaceutically acceptable salt thereof, wherein $R^{2A}$ is $R^5$ or —$OR^5$.

11. The compound of claim 6, or a pharmaceutically acceptable salt thereof, wherein $R^{2A}$ is $R^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

12. The compound of claim 6, or a pharmaceutically acceptable salt thereof, wherein $R^{2A}$ is $R^5$; and $R^5$ is selected from the group consisting of phenyl, 1H-pyrazol-1-yl-, pyridin-2-yl-, pyridin-3-yl-, and pyridin-4-yl, wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

13. The compound of claim 6, or a pharmaceutically acceptable salt thereof, wherein $R^{2A}$ is —$OR^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

14. The compound of claim 6, or a pharmaceutically acceptable salt thereof, wherein $R^{2A}$ is —$OR^5$; and $R^5$ is selected from the group consisting of phenyl, 1H-pyrazol-1-yl-, pyridin-2-yl-, pyridin-3-yl-, and pyridin-4-yl, wherein each of the selections is substituted with 0 or 1 substituent selected from the group consisting of —CN, halogen, $C_{1-2}$ alkyl, $C_{3-4}$ cycloalkyl, $C_{1-2}$ alkoxy, $C_{1-2}$ haloalkyl, and $C_{1-2}$ haloalkoxy.

15. The compound of claim 6, or a pharmaceutically acceptable salt thereof, wherein $R^{2A}$ is —$NR^3S(=O)_2R^4$ or —$NR^3C(=O)R^4$; $R^3$ is methyl; each $R^4$ is independently selected from the group consisting of $C_{1-6}$ alkyl, $C_{3-7}$ cycloalkyl, ($C_{3-7}$ cycloalkyl)-$C_{1-2}$ alkyl-, (phenyl)-$C_{1-2}$ alkyl-, and phenyl.

16. The compound of claim 6, or a pharmaceutically acceptable salt thereof, wherein the compound is a compound of Formula I-2.

17. The compound of claim 6, or a pharmaceutically acceptable salt thereof, wherein $R^{2B}$ is 4-(trifluoromethyl)-1H-pyrazol-1-yl-, 4-fluoro-1H-pyrazol-1-yl-, 3-cyanophenyl-, 6-(trifluoromethyl)pyridin-2-yl-, 5-cyano-2-fluorophenyl-, or 4-(difluoromethyl)pyridin-2-yl-.

18. The compound of claim 6, or a pharmaceutically acceptable salt thereof, wherein the compound is a compound of Formula I-3.

19. The compound of claim 18, or a pharmaceutically acceptable salt thereof, wherein the compound is a compound of Formula I-3a or Formula I-3b:

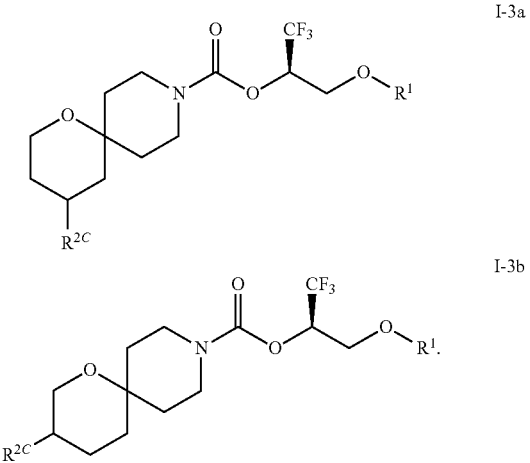

20. The compound of claim 19, or a pharmaceutically acceptable salt thereof, wherein $R^{2C}$ is —$NR^3S(=O)_2R^4$ or $R^5$; and $R^5$ is selected from the group consisting of phenyl, 1H-pyrazolyl, and pyridinyl, wherein each of the selections is substituted with 0, 1, 2, or 3 substituents each independently selected from the group consisting of —CN, halogen, $C_{1-4}$ alkyl, $C_{3-6}$ cycloalkyl, $C_{1-4}$ alkoxy, $C_{1-4}$ haloalkyl, and $C_{1-4}$ haloalkoxy.

21. The compound of claim 20 or a pharmaceutically acceptable salt thereof, wherein $R^3$ is methyl; and $R^4$ is selected from the group consisting of $C_{1-6}$ alkyl, $C_{3-7}$ cycloalkyl, and ($C_{3-7}$ cycloalkyl)-$C_{1-2}$ alkyl-.

22. A compound of claim 1 selected from the group consisting of:
- (2R)-1,1,1-trifluoro-3-hydroxypropan-2-yl 3-[4-(trifluoromethyl)-1H-pyrazol-1-yl]-1-oxa-8-azaspiro[4.5]decane-8-carboxylate, DIAST 2;
- (2R)-1,1,1-trifluoro-3-hydroxypropan-2-yl (3R)-3-(4-fluoro-1H-pyrazol-1-yl)-1-oxa-8-azaspiro[4.5]decane-8-carboxylate;
- (2R)-1,1,1-trifluoro-3-hydroxypropan-2-yl (3S)-3-(3-cyanophenyl)-1-oxa-8-azaspiro[4.5]decane-8-carboxylate;

(2R)-1,1,1-trifluoro-3-hydroxypropan-2-yl 3-[6-(trifluoromethyl)pyridin-2-yl]-1-oxa-8-azaspiro[4.5]decane-8-carboxylate, DIAST 1;

(2R)-1,1,1-trifluoro-3-hydroxypropan-2-yl 2-{[6-(difluoromethyl)pyridin-3-yl]oxy}-7-azaspiro[3.5]nonane-7-carboxylate;

(2R)-1,1,1-trifluoro-3-hydroxypropan-2-yl 3-(5-cyano-2-fluorophenyl)-1-oxa-8-azaspiro[4.5]decane-8-carboxylate, DIAST 2;

(2R)-1,1,1-trifluoro-3-hydroxypropan-2-yl 3-[4-(difluoromethyl)pyridin-2-yl]-1-oxa-8-azaspiro[4.5]decane-8-carboxylate, DIAST 1;

(2R)-1,1,1-trifluoro-3-hydroxypropan-2-yl 2-[5-(difluoromethyl)pyridin-2-yl]-7-azaspiro[3.5]nonane-7-carboxylate;

(2R)-1,1,1-trifluoro-3-hydroxypropan-2-yl 2-(4-cyclopropyl-1H-pyrazol-1-yl)-7-azaspiro[3.5]nonane-7-carboxylate; and (2R)-1,1,1-trifluoro-3-hydroxypropan-2-yl 2-(3-fluorophenoxy)-7-azaspiro[3.5]nonane-7-carboxylate, or a pharmaceutically acceptable salt thereof.

23. A pharmaceutical composition comprising a compound or pharmaceutically acceptable salt according to claim 1, and a pharmaceutically acceptable carrier.

* * * * *